(12) United States Patent
LaFever et al.

(10) Patent No.: US 10,572,684 B2
(45) Date of Patent: *Feb. 25, 2020

(54) SYSTEMS AND METHODS FOR ENFORCING CENTRALIZED PRIVACY CONTROLS IN DE-CENTRALIZED SYSTEMS

(71) Applicant: Anonos Inc., New York, NY (US)

(72) Inventors: Malcolm Gary LaFever, Lyons, CO (US); Ted N. Myerson, New York, NY (US); Steven Mason, Las Vegas, NV (US)

(73) Assignee: Anonos Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/963,609

(22) Filed: Apr. 26, 2018

(65) Prior Publication Data

US 2018/0307859 A1 Oct. 25, 2018

Related U.S. Application Data

(63) Continuation-in-part of application No. 15/483,997, filed on Apr. 10, 2017, now Pat. No. 10,043,035,
(Continued)

(51) Int. Cl.
*H04L 9/00* (2006.01)
*G06F 21/62* (2013.01)
*H04L 29/06* (2006.01)

(52) U.S. Cl.
CPC ...... *G06F 21/6254* (2013.01); *H04L 63/0407* (2013.01); *G06F 2221/2115* (2013.01); *H04L 63/068* (2013.01)

(58) Field of Classification Search
CPC .................................................. G06F 21/6254
See application file for complete search history.

(56) References Cited

U.S. PATENT DOCUMENTS 7,430,755 B1 9/2008 Hughes
7,454,356 B2 11/2008 Fields
(Continued)

FOREIGN PATENT DOCUMENTS

DE 19638072 A1 3/1998
EP 1154624 A2 11/2001
(Continued)

OTHER PUBLICATIONS

"We'll see you, anon: Can big databases be kept both anonymous and useful?" The Economist, Apr. 15, 2015, available at http://www.economist.com/news/science-and-technology/21660966-can-big-databases-be-kept-both-anonymous-and-useful-well-see-you-anon?fsrc=scn/tw/te/pe/ed/Wellseeyouanon.
(Continued)

*Primary Examiner* — Josnel Jeudy
(74) *Attorney, Agent, or Firm* — Blank Rome LLP

(57) ABSTRACT

Systems, computer-readable media, and methods for improving both data privacy/anonymity and data value, wherein data related to a data subject can be used and stored, e.g., in a distributed ledger data structure, such as a blockchain, while minimizing re-identification risk by unauthorized parties and enabling data, including quasi-identifiers, related to the data subject to be disclosed to any authorized party by granting access only to the data relevant to that authorized party's purpose, time period, place and/or other criterion via the obfuscation of specific data values, e.g., pursuant to the European Union's General Data Protection Regulation (GDPR) or other similar regulatory schemes. The techniques described herein maintain this level of privacy/anonymity while still satisfying the immutability, auditability, and verification mandated by blockchain and other distributed ledger technologies (DLTs) for the decentralized storage of transactional data. Such systems, media,
(Continued)

and methods may be implemented on both classical and quantum computing devices.

20 Claims, 63 Drawing Sheets

Related U.S. Application Data which is a continuation-in-part of application No. 15/174,797, filed on Jun. 6, 2016, now Pat. No. 9,619,669, which is a continuation-in-part of application No. 14/846,167, filed on Sep. 4, 2015, now Pat. No. 9,361,481, which is a continuation-in-part of application No. 14/530,304, filed on Oct. 31, 2014, now Pat. No. 9,129,133, which is a continuation of application No. 14/529,960, filed on Oct. 31, 2014, now Pat. No. 9,087,215.

(60) Provisional application No. 61/899,096, filed on Nov. 1, 2013, provisional application No. 61/938,631, filed on Feb. 11, 2014, provisional application No. 61/941,242, filed on Feb. 18, 2014, provisional application No. 61/944,565, filed on Feb. 25, 2014, provisional application No. 61/945,821, filed on Feb. 27, 2014, provisional application No. 61/948,575, filed on Mar. 6, 2014, provisional application No. 61/969,194, filed on Mar. 23, 2014, provisional application No. 61/974,442, filed on Apr. 3, 2014, provisional application No. 61/988,373, filed on May 5, 2014, provisional application No. 61/992,441, filed on May 13, 2014, provisional application No. 61/994,076, filed on May 15, 2014, provisional application No. 61/994,715, filed on May 16, 2014, provisional application No. 61/994,721, filed on May 16, 2014, provisional application No. 62/001,127, filed on May 21, 2014, provisional application No. 62/015,431, filed on Jun. 21, 2014, provisional application No. 62/019,987, filed on Jul. 2, 2014, provisional application No. 62/037,703, filed on Aug. 15, 2014, provisional application No. 62/043,238, filed on Aug. 28, 2014, provisional application No. 62/045,321, filed on Sep. 3, 2014, provisional application No. 62/051,270, filed on Sep. 16, 2014, provisional application No. 62/055,669, filed on Sep. 26, 2014, provisional application No. 62/059,882, filed on Oct. 4, 2014, provisional application No. 62/491,294, filed on Apr. 28, 2017, provisional application No. 62/535,601, filed on Jul. 21, 2017, provisional application No. 62/554,000, filed on Sep. 4, 2017, provisional application No. 62/580,628, filed on Nov. 2, 2017, provisional application No. 62/644,463, filed on Mar. 17, 2018, provisional application No. 62/649,103, filed on Mar. 28, 2018.

(56) References Cited

U.S. PATENT DOCUMENTS

| | | | |
|---|---|---|---|
| 7,455,218 | B2 | 11/2008 | Shafer |
| 8,112,405 | B2 | 2/2012 | Shiloh |
| 8,306,845 | B2 | 11/2012 | Dmporzano |
| 8,364,969 | B2 | 1/2013 | King |
| 8,549,579 | B2 | 10/2013 | Dixon |
| 8,881,019 | B2 | 11/2014 | Gupta |
| 9,129,133 | B2 | 9/2015 | Lafever |
| 2001/0054155 | A1 | 12/2001 | Hagan |
| 2003/0204592 | A1 | 10/2003 | Crouse-Kemp |
| 2004/0059952 | A1 | 3/2004 | Newport |
| 2004/0153908 | A1 | 8/2004 | Schiavone |
| 2005/0010536 | A1 | 1/2005 | Cochran |
| 2006/0015358 | A1 | 1/2006 | Chua |
| 2006/0020542 | A1 | 1/2006 | Litle |
| 2006/0168111 | A1 | 7/2006 | Gidwani |
| 2006/0174037 | A1 | 8/2006 | Bernardi |
| 2006/0282662 | A1 | 12/2006 | Whitcomb |
| 2007/0027974 | A1 | 2/2007 | Lee |
| 2007/0118419 | A1 | 5/2007 | Maga |
| 2007/0150568 | A1 | 6/2007 | Ruiz |
| 2007/0198432 | A1 | 8/2007 | Pitroda |
| 2008/0069341 | A1 | 3/2008 | Relyea |
| 2008/0195965 | A1 | 8/2008 | Pomerantz |
| 2009/0083367 | A1 | 3/2009 | Li |
| 2009/0132366 | A1 | 5/2009 | Lam |
| 2009/0254971 | A1 | 10/2009 | Herz |
| 2009/0323937 | A1 | 12/2009 | Teng |
| 2010/0114776 | A1 | 5/2010 | Weller |
| 2010/0145960 | A1 | 6/2010 | Casteel |
| 2010/0199098 | A1 | 8/2010 | King |
| 2010/0199356 | A1 | 8/2010 | Krishnamurthy |
| 2010/0205448 | A1 | 8/2010 | Tarhan |
| 2011/0010563 | A1 | 1/2011 | Lee |
| 2011/0035414 | A1 | 2/2011 | Barton |
| 2011/0055548 | A1 | 3/2011 | Varghese |
| 2011/0208599 | A1 | 8/2011 | Sen |
| 2011/0241825 | A1 | 10/2011 | Kitamura |
| 2011/0302598 | A1 | 12/2011 | Lundgren |
| 2011/0311049 | A1 | 12/2011 | Amaudruz |
| 2012/0047530 | A1 | 2/2012 | Shkedi |
| 2012/0053987 | A1 | 3/2012 | Satyavolu |
| 2012/0054680 | A1 | 3/2012 | Moonka |
| 2012/0278876 | A1 | 11/2012 | McDonald |
| 2012/0296829 | A1 | 11/2012 | Camenisch |
| 2012/0316992 | A1 | 12/2012 | Oborne |
| 2012/0323656 | A1 | 12/2012 | Leach |
| 2012/0324242 | A1 | 12/2012 | Kirsch |
| 2013/0042313 | A1 | 2/2013 | Lambert |
| 2013/0091452 | A1 | 4/2013 | Sorden |
| 2013/0219481 | A1 | 8/2013 | Voltz |
| 2014/0025753 | A1 | 1/2014 | Gronowski |
| 2014/0032723 | A1 | 1/2014 | Nema |
| 2014/0287723 | A1 | 9/2014 | LaFever |
| 2015/0249679 | A1* | 9/2015 | Villegas .............. H04L 9/003 713/159 |
| 2017/0039330 | A1 | 2/2017 | Tanner, Jr. |
| 2017/0208041 | A1 | 7/2017 | Kho |
| 2018/0089041 | A1* | 3/2018 | Smith .............. G06F 11/1474 |

FOREIGN PATENT DOCUMENTS

| | | |
|---|---|---|
| WO | 2013097886 A1 | 7/2013 |
| WO | 2014082648 A1 | 6/2014 |
| WO | 2017027900 A1 | 2/2017 |
| WO | 2018009979 A1 | 1/2018 |

OTHER PUBLICATIONS

ACXIOM, Acxiom Data FAQ, About Acxiom, available at http://www.acxiom.com/about-acxiom/privacy/acxiom-data-faq/, Apr. 12, 2019.

Bort, Julie, MasterCard Just Took a Stake in a Hot Big Data Startup, Business Insider, Feb. 11, 2013, available at http://www.businessinsider.com/mastercard-big-data-for-shopping-habits-2013-2#comments.

Bowdish, Lawrence, "The Risks of Data Minimization," U.S. Chamber of Commerce Foundation, Apr. 2, 2015, available at http://www.uschamberfoundation.org/blog/post/risks-data-minimization/42945.

Brill, Julie, Reclaim Your Name, Keynote Address at the 23rd Computers Freedom and Privacy Conference Mar. 26, 2013, available at http://www.ftc.gov/speeches/brill/130626computersfreedom.pdf.

Bustos, Linda, How Data Brokers Track Consumers [Infographic], Get Elastic, Jun. 14, 2013, available at http://www.getelastic.com/how-data-brokers-track-consumers-infographic/.

Calo, Professor Ryan, Digital Market Manipulation—Legal Studies Research Paper No. 2013-27, University of Washington School of

(56) References Cited

OTHER PUBLICATIONS

Law, Aug. 15, 203, available at http://papers.ssrn.com/sol3/JELJOUR_Results.cfm?form_name=journalbrowse&journal_id=1884304.
Carr, Austin, Will Foursquare CEO Dennis Crowley Finally Get It Right?, Fast Company, Sep. 2013, available at http://www.fastcompany.com/3014821/will-foursquare-ceo-dennis-crowley-finally-get-it-right.
D. Morikawa et al, "A Proposal of User Profile Management Framework for Context-Aware Service," Proceedings. The 2005 Symposium on Applications and the Internet Workshop—Jan. 31-Feb. 4, 2005—Trento, Italy, Jan. 1, 2005 (Jan. 1, 2005), pp. 184-187, XP055242960, DOI: 10.1109/SAINTW.2005.1620007 ISBN: 978-0-7695-2263-0.
Dickey, Megan Rose, How Facebook Gets You to Buy Products Even If You Never Click on Ads, Business Insider, Mar. 20, 2013, available at http://www.businessinsider.com/why-facebook-ads-work-2013-3.
Dunning, L., et al., "Privacy Preserving Data Sharing With Anonymous ID Assignment," IEEE Transactions on Information Forensics and Security, vol. 8, No. 2, Feb. 2013, entire document, http://ieeexplore.ieee.org/stamp/stamp.jsp?arnumber=6389771.
Dyche, Jill, "The CRM Handbook: a business guide to customer relationship management," Addison Wesley Professional, Aug. 9, 2001 [this reference can be found in the List of references on May 23, 2013, in commonly-assigned U.S. Appl. No. 13/764,773].
Electronic Frontier Foundation, About EFF, Electronic Frontier Foundation available at http://www.eff.org/about, Apr. 12, 2019.
Electronic Frontier Foundation, Panopticlick How Unique—and Trackable—Is Your Browser?, Research Project of the Electronic Frontier Foundation, available at https://panopticlick.eff.org/, Apr. 12, 2019.
ERN Global, Big data startup ERN secures further $1 million funding, Finextra, Aug. 2, 2013, available at http://www.finextra.com/News/Announcement.aspx?pressreleaseid=51023.
Federal Trade Commission, "Internet of Things: Privacy & Security in a Connected World," FTC Staff Report, Jan. 2015, available at https://www.ftc.gov/system/files/documents/reports/federal-trade-commission-staff-report-november-2013-workshop-entitled-internet-things-privacy/150127iotrpt.pdf.
Federal Trade Commission, Protecting Consumer Privacy in an Era of Rapid Change—Recommendations for Businesses and Policymakers, FTC Report, Mar. 2012, available at http://ftc.gov/os/2012/03/120326privacyreport.pdf.
Gage, Deborah, The New Shape of Big Data, The Wall Street Journal, Mar. 8, 2013, available at http://online.wsj.com/article/SB10001424127887323452204578288264046780392.html.
Garfinkel, Simson L., "De-Identification of Personally Identifiable Information," National Institute of Standards and Technology (NIST), Apr. 2015, available at http://csrc.nist.gov/publications/drafts/nistir-8053/nistir_8053_draft.pdf.
Gartenstein-Ross, Daveed and Kelsey D. Atherton, How We Killed Privacy—in 4 Easy Steps, Foreign Policy, Aug. 23, 2013, available at http://www.foreignpolicy.com/articles/2013/08/23/now_we_killed_privacy_nsa_surveillance?print=yes&hidecomments=yes&page=full.
Gillette, Felix, Snapchat and the Erasable Future of Social Media, Bloomberg Businessweek, Feb. 7, 2013, available at http://www.businessweek.com/printer/articles/95976-snapchat-and-the-erasable-future-of-social-media.
Gulyas, G., et al., "Comprehensive Analysis of Web Privacy and Anonymous Web Browsers: Are Next Generation Services Based on Collaborative Filtering?," Joint Space and Time International Workshops, Jun. 17, 2008, entire document, http://ieeexplore.ieee.org/stamp/stamp.jsp?tp=&arnumber=5211017.
Ingram, Mathew, Remember, Facebook isn't a platform for you to use—you are a platform for Facebook to use, GIGAOM, Mar. 4, 2013, available at http://gigao.com/2013/03/04/remember-facebook-isnt-a-platform-for-you-to-use-you-are-a-platform-for-facebook-to-use/.

Jayson, Sharon, Facebook 'Likes' reveal more about you than you think, USA Today, Mar. 11, 2013, available at http://www.usatoday.com/story/news/nation/2013/03/11/facebook-likes-predictions-privacy/1975777/.
Journal Reports by Joel R Reidenberg and Thomas H. Davenport, Should the U.S. Adopt European-Style Data-Privacy Protections?, The Wall Street Journal, Mar. 8, 2013, available at http://online.wsj.com/article/SB10001424127887324338604578328393797127094.html.
Kaye, Kate, FTC's Brill Calls for Congress to Legislate New Data Privacy, Stuns Marketers, Ad Age dataworks, Jun. 26, 2013, available at http://adage.com/article/privacy-and-regulaton/ftc-s-call-legislate-data-privacy-stuns-marketers/242848/.
Kissmetrics, Note: document included in IDS is a previous version of their home page, KISSmetrics Website, available at https://www.kissmetrics.com, Apr. 12, 2019.
Knibbs, Kate, The Snapchat Identity Crisis and Why Impermanence No Longer Matters for the App, Digital Trends, Aug. 21, 2013, available at http://www.digitaltrends.com/social-media/snapchats-identity-crisis-why-impermanence-no-longer-matters-for-the-app/.
Kroes, Neelie, Statement by Vice President Neelie Kroes "on the consequences of living in an age of total information," European Comission Memo, Jul. 4, 2013, Brussels, available at http://europa.eu/rapid/press-release_MEMO-13-654_en.htm.
Leber, Jessica, A Stock Exchange for Your Personal Data, MIT Technology Review, May 1, 2013, available at http://www.technologyreview.cm/new/427796/a-stock-exchange-for-your-personal-data/.
Li, Wen-Syan, "Knowledge gathering and matching in heterogeneous databases," Working Notes of the AAAI Spring Symposium on Information Gathering from Heterogeneous, Distributed Environments, 1995.
Lifelock, How LifeLock Works, available at http://www.lifelock.com/how-it-works/, Apr. 12, 2019.
Linden, Sheri, Review: 'Terms and Conditions May Apply' explores loss of privacy, Los Angeles Times, Jul. 17, 2013, available at http://articles.latimes.com/2013/jul/17/entertainment/la-et-mn-terms-conditions-revie-20130717.
Lohr, Steve, Big Data is Opening Doors, but Maybe Too Many, The New York Times, Mar. 23, 2013, available at http://www.nytimes.com/2013/03/24/technology/big-data-and-a-renewed-debate-over-privacy.html?pagewanted=print.
Magid, Larry, Magid: A much-needed national debate about privacy is now underway, Mercury News, Aug. 16, 2013, available at http://www.mercurynews.com/larry-magid/ci_23877563/magid-much-needed-national-debate-about-privacy-is#.
Maul, Kimberly, Survey: How Marketing Data Connects to Loyalty, ad exchanger, Apr. 18, 2013, available at http://www.adexchanger.com/data-nugget/in-an-effort-to-build-loyalty-marketers-must-turn-to-company-wide-data/.
Mielikainen, Taneli, "Privacy problems with anonymized transaction databases," Discovery Science, Springer Berline Heidelberg, 2004.
Moss, Frank, How Small Businesses Are Innovating With 'Big Data,' Fox Business: Small Business Center, Oct. 6, 2011, available at http://smallbusiness.foxbusiness.com/biz-on-main/2011/10/06/how-small-businesses-are-innovating-with-big-data/.
Nice, Nice to Acquire Causata to Enable a Seamless Customer Experience across the Web and Contact Center, Mar. 7, 2013, available at http://www.nice.com/nice-acquire-causata-enable-seamless-customer-experience-across-web-and-contact-center.
O'Hara, John, Your Customers Know You're Watching Them, Harvard Business Review Blog Network, Apr. 5, 2013, available at http://blogs.hbr.org/cs/2013/04/your_customers_know_youre_watching_them.html.
Ohm, Paul, "Broken Promises of Privacy: Responding to the Surprising Failure of Anonymization," UCLA Law Review, Aug. 2009 [retrieved from http://www.uclalawreview.org/?p=1353].
Peter Schartner et al, "Unique User-Generated Digital Pseudonyms," Jan. 1, 2005 (Jan. 1, 2005), Computer Network Security Lecture Notices in Computer Science; LNCS, Springer, Berlin, DE, pp. 194-205, XP019020295, ISBN: 978-3-540-29113-8.

(56) References Cited

OTHER PUBLICATIONS

Podesta, John, et al., "Big Data: Seizing Opportunities, Preserving Values," Executive Office of the President, May 2014, available at https://www.whitehouse.gov/sites/default/files/docs/big_data_privacy_report_may_1_2014.pdf.

Rao, Leena, The Ecommerce Revolution Is All About You, TechCrunch, Jan. 29, 2012, available at http://techcrunch.com/2012/01/29/the-ecommerce-revolution-is-all-about-you/.

Reding, Viviane, Q. and A. With Viviane Reding, The New York Times Business Day, Feb. 2, 2013, available at http://www.nytimes.com/2013/02/03/business/q-and-a-with-viviane-reding.html.

Reitman, Rainey, New California "Right to Know" Act Would Let Consumers Find Out Who Has Their Personal Data—And Ge a Copy of It, Electronic Frontier Foundation, Apr. 2, 2013, available at http://www.eff.org/deeplinks/2013/04/new-califomia-right-know-act-would-let-consumers-find-out-who-has-their-personal.

Singer, Natasha, A Data Broker Offers a Peek Behind the Curtain, The New York Times Business Day, Aug. 31, 2013, available at http://www.nytimes.com/2013/09/01/business/a-data-broker-offers-a-peek-behind-the-curtain.html?pagewanted=all&r=1&.

Singer, Natasha, A Game That Deals in Personal Data, The New York Times Bits, Jul. 10, 2013, available at http://bits.blogs.nytimes.com/2013/07/10/a-game-that-deals-in-personal-data/?pagewanted=print&_r=0.

Singer, Natasha, Acxiom, the Quiet Giant of Consumer Database Marketing—Mapping, and Sharing, the Consumer Genome, The New York Times, Jun. 16, 2013, available at http://www.nytimes.com/2012/06/17/technology/acxiom-the-quiet-gian...-consumer-database-maketing.html?pagewanted=all&pagewanted=print.

Singer, Natasha, FTC Member Starts 'Reclaim Your Name' Campaign for Personal Data, The New York Times Bits, Jun. 26, 2013, available at http://bits.blogs.nytimes.com/2013/06/26/reclaim-your-name/pagewanted=print.

International Search Report and Written Opinion received in PCT Patent Application No. PCT/US2018/029890, dated Jul. 12, 2018.

Singer, Natasha, Your Online Attention, Bought in an Instant, The New York Times, Nov. 17, 2012, available at http://www.nytimes.com/2012/11/18/technology/your-online-attention-bought-in-an-instant-by-advertisers.html?pagewanted=all.

Stampler, Laura, Facebook Ads Are About to Get Even More Personal [The Brief], Business Insider, Feb. 25, 2013, available at http://www.businesinsider.com/facebook-ads-will-get-even-more-personal-the-brief-2013-2.

Stengel, Richard, Editor's Desk: Making Sense of Our Wireless World, Time, Aug. 27, 2013, available at http://content.time.com/time/magazine/article/0,9171,2122243,00.html.

Sterling, Greg, FTC Commissioner Surprises Marketers With "Reclaim Your Name" Proposal, Marketing Land, Mar. 27, 2013, available at http://marketingland.com/ftc-commission-surprises-marketers-with-reclaim-your-name-proposal-49874

Tanner, Adam, Data Brokers Don't Know You From a Naked Man Stumbling on the Beach, Forbes, Aug. 6, 2013, available at http://www.forbes.com/sites/adamtanner/2013/08/06/data-brokers-dont-know-you-from-a-naked-man-stumbling-on-the-beach/print/.

WSJ Staff, Readers Weigh in on Privacy Protection [Pie Chart], Wall Street Journal, Mar. 5, 2013, available at http://blogs.wsj.com/digits/2013/03/05/vote-the-governments-role-in-data-privacy/

Zahid Iqbal et al, "Toward User-Centric Privacy-Aware User Profile Ontology for Future Services," Communication Theory, Reliability, and Quality of Service (CTRQ), 2010 Third International Conference on, IEEE, Piscataway, NJ, USA, Jun. 13, 2010 (Jun. 13, 2010), pp. 249-254, XP031720703, ISBN: 978-1-4244-7273-4.

\* cited by examiner

FIG. 1B

ASSIGNMENT, APPLICATION, EXPIRATION AND RECYCLING OF DDIDS WITH RESPECT TO DATA ATTRIBUTES AND/OR ATTRIBUTE COMBINATIONS MAY OCCUR IN ANY OF THE FOLLOWING, OR COMBINATION OF THE FOLLOWING, WAYS:

1. PURPOSE BASED
   A. BROWSE
   B. DATA SUBJECT
   C. TRANSACTION
   D. OTHER

2. PHYSICAL LOCATION BASED
   A. ENTER
   B. EXIT
   C. CHANGE
   D. GENERAL
   E. SPECIFIC
   F. OTHER

3. VIRTUAL LOCATION BASED
   A. ENTER
   B. EXIT
   C. CHANGE
   D. PAGE
   E. SITE
   F. OTHER

4. TEMPORALLY BASED
   A. RANDOM
   B. SET
   C. INTERVAL
   D. OTHER

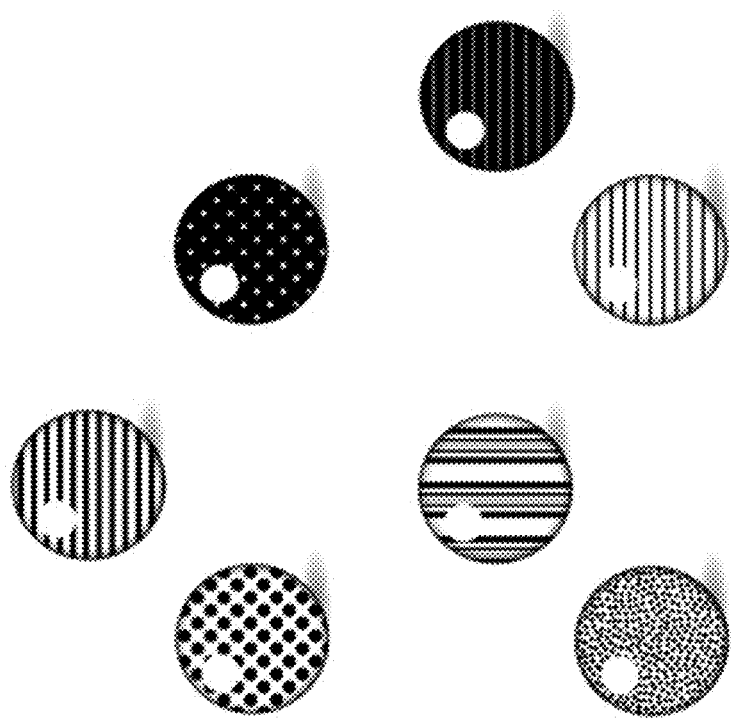
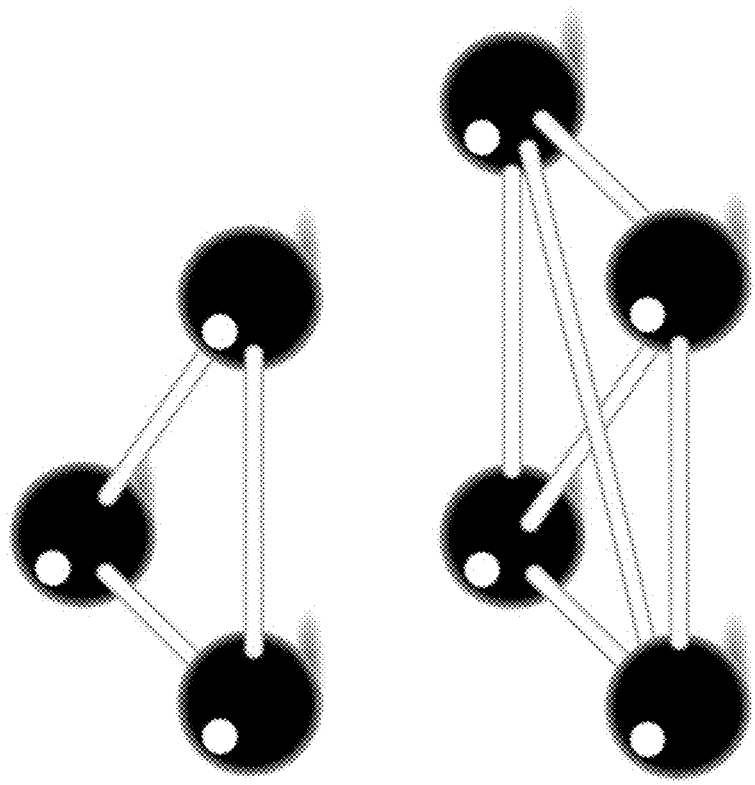
FIG. 1H
1H-B. Obscured Data Elements
1H-A. Non-Obscured Data Elements

|  | Non-Disassociated /Replaced | Disassociation / Replacement Level 1 | Disassociation / Replacement Level 2 | Disassociation / Replacement Level 3 |
|---|---|---|---|---|
| Social Security Number | 100 | 90 | 81 | 40.5 |
| Credit Card Number | 75 | 67.5 | 60.75 | 30.375 |
| First Name | 25 | 22.5 | 20.25 | 10.125 |
| Last Name | 25 | 22.5 | 20.25 | 10.125 |
| Birthdate | 25 | 22.5 | 20.25 | 10.125 |
| Age | 20 | 18 | 16.2 | 8.1 |
| Sex | 10 | 9 | 8.1 | 4.05 |

Level 1 = DDIDs are assigned for purposes of disassociation and/or replacement and retain their initially assigned value(s) — i.e., permanent assignments Level 2 = DDIDs are assigned for purposes of disassociation and/or replacement and retain their initially assigned value(s) until the value(s) are changed on an ad hoc basis — i.e., ad hoc changeability.

Level 3 = DDIDs are assigned for purposes of disassociation and/or replacement and retain their initially assigned value(s) until the value(s) are changed based on a random, fixed, variable or other dynamic basis — i.e., dynamic changeability.

Category A = Aggregated score of 75+
Category B = Aggregated score of 40 to 74.9
Category C = Aggregated score of 39.9 and lower Category A = Data set may be used only with current, express and unambiguous consent of data subject.

Category B = Data set may be used with (i) current or (ii) prior, express consent of data subject.

Category C = Data set may be used without requiring consent of data subject.

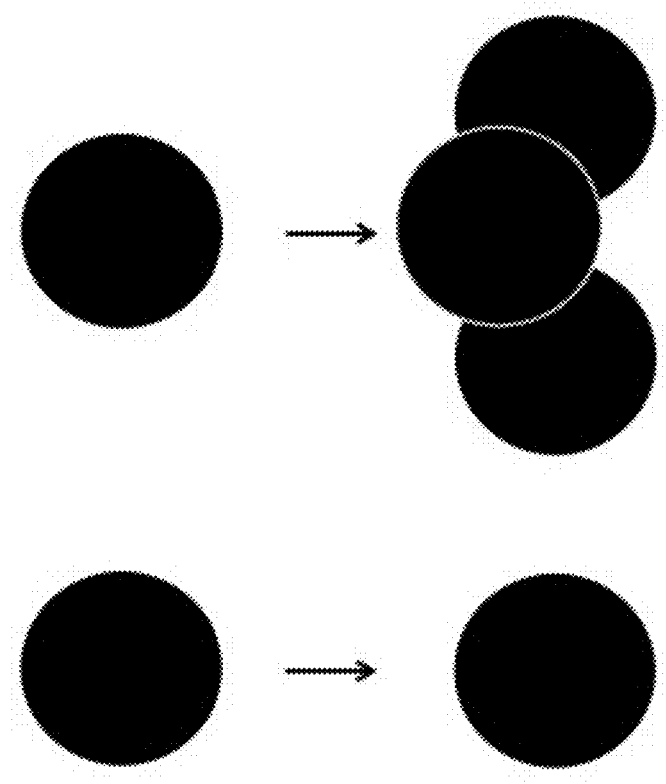
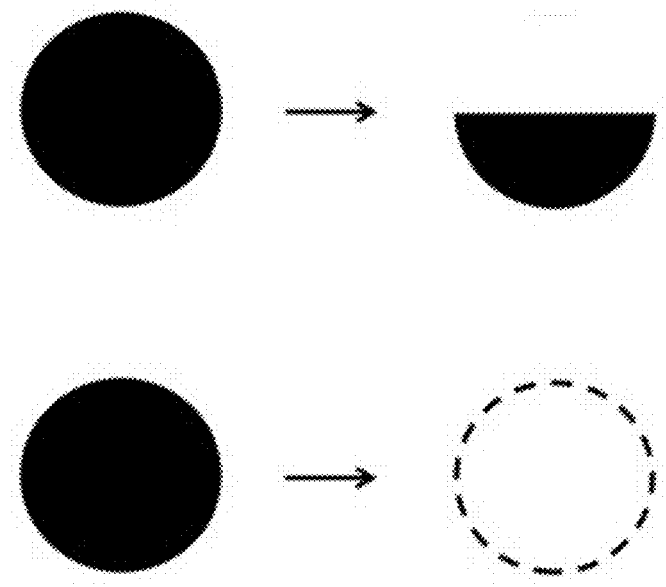
FIG. 1M

'Static' Anonymity Example. Financial traces in a simply anonymized data set such as the one we use for this work. Arrows represent the temporal sequence of transactions for user 7abc1a23 and the prices are grouped in bins of increasing size.

| shop | user_id | time | price | price_bin |
|---|---|---|---|---|
| 🏔️ | 7abc1a23 | 09/23 | $97.30 | $49 - $146 |
| ❤️ | 7abc1a23 | 09/23 | $15.13 | $5 - $16 |
| 🏢 | 3092fc10 | 09/23 | $43.78 | $16 - $49 |
| 🌿 | 7abc1a23 | 09/23 | $4.33 | $2 - $5 |
| 🏃 | 4c7af72a | 09/23 | $12.29 | $5 - $16 |
| 🌿 | 89c0829c | 09/24 | $3.66 | $2 - $5 |
| 🍴 | 7abc1a23 | 09/24 | $35.81 | $16 - $49 |

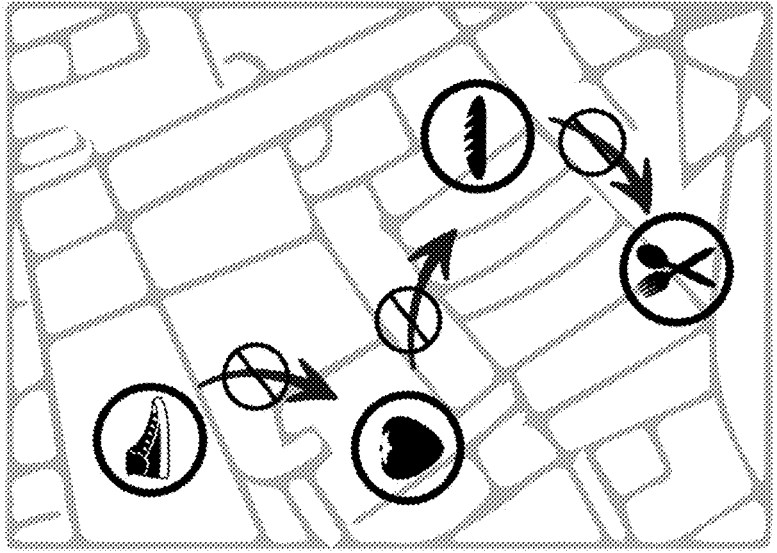

FIG. 1P-2

Just-In-Time-Identity (JITI) enables dynamic protection at the data element level. The universal 'no' symbols highlight that dynamically obscuring data linkages that could be aggregated by parsing recognizable static 'anonymous' identifiers breaks the assumptions necessary for re-identification.

| shop | user_id | time | price | price_bin |
|---|---|---|---|---|
| | 7abc1a23 | 09/23 | $97.30 | $49 - $146 |
| | 54ಐ | 09/23 | $15.13 | $5 - $16 |
| | 3092fc10 | 09/23 | $43.78 | $16 - $49 |
| | DeTym321 | 09/23 | $4.33 | $2 - $5 |
| | 4c7af72a | 09/23 | $12.29 | $5 - $16 |
| | 89c0829c | 09/24 | $3.66 | $2 - $5 |
| | HHyargLM | 09/24 | $35.81 | $16 - $49 |

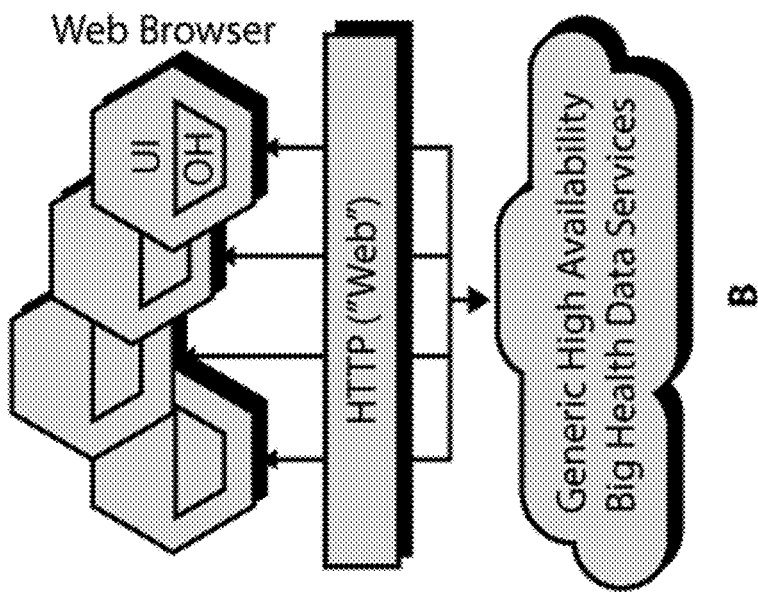
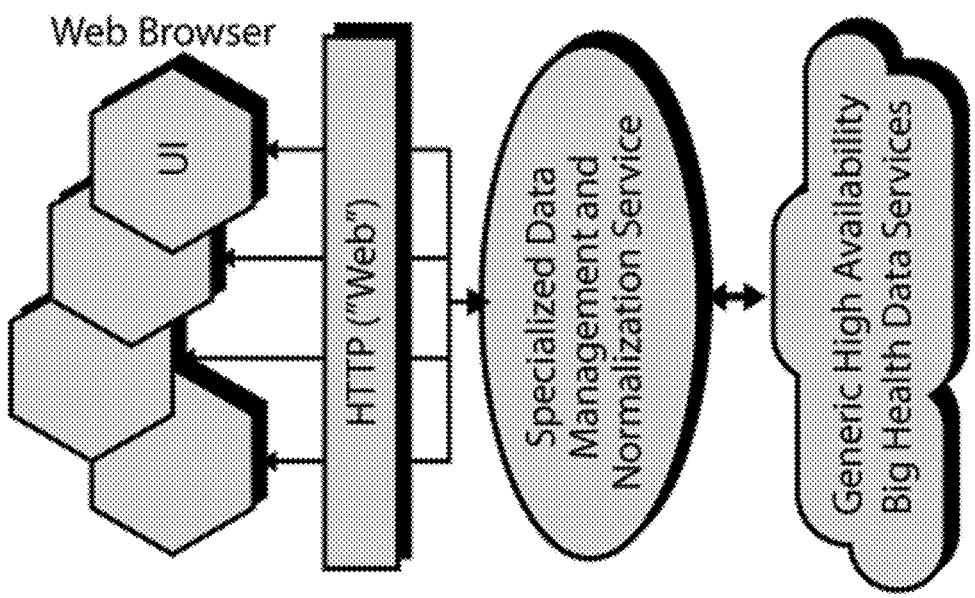
FIG. 1S

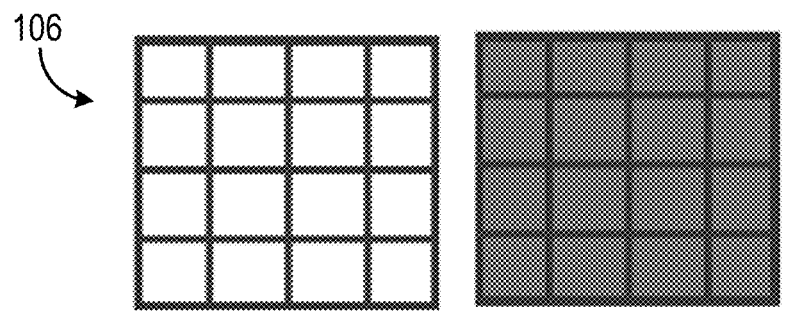
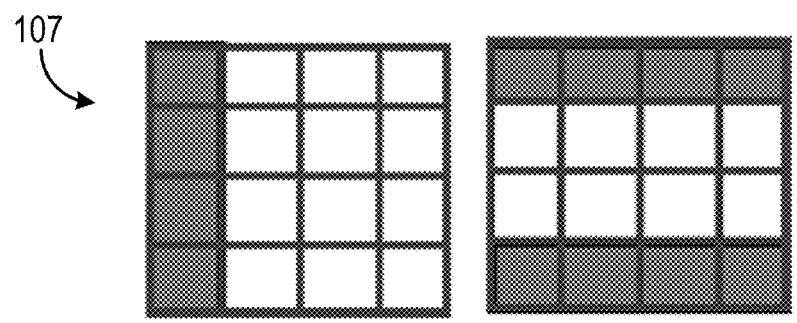
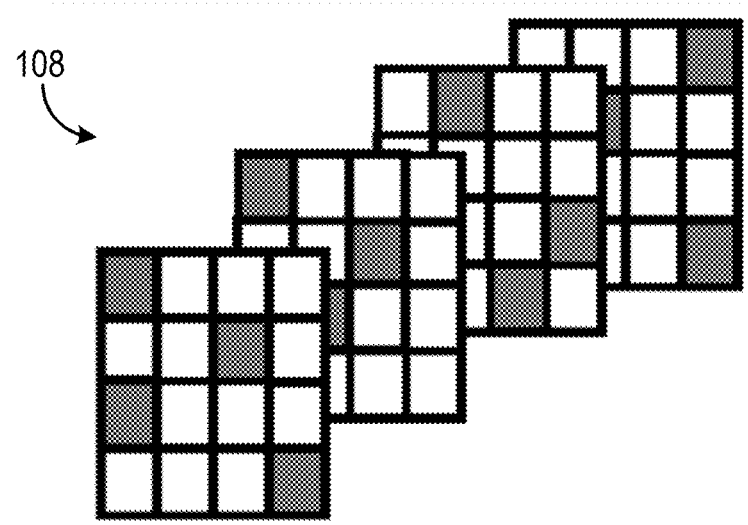
FIG. 1U

| | Subject Area | Accuracy Rating | Privacy Rating | Price Per Run |
|---|---|---|---|---|
| DB276921 Policy | HIPAA | 87.3 | 92.54 | $1.10 |
| CT209jh276 Policy | HIPAA | 54.1 | 97.3 | $0.78 |
| CT209jh299 Policy | GDPR | 49.87 | 95.3 | $5.87 |
| CT209jh371 Policy | GDPR | 51.6 | 77.64 | $2.98 |

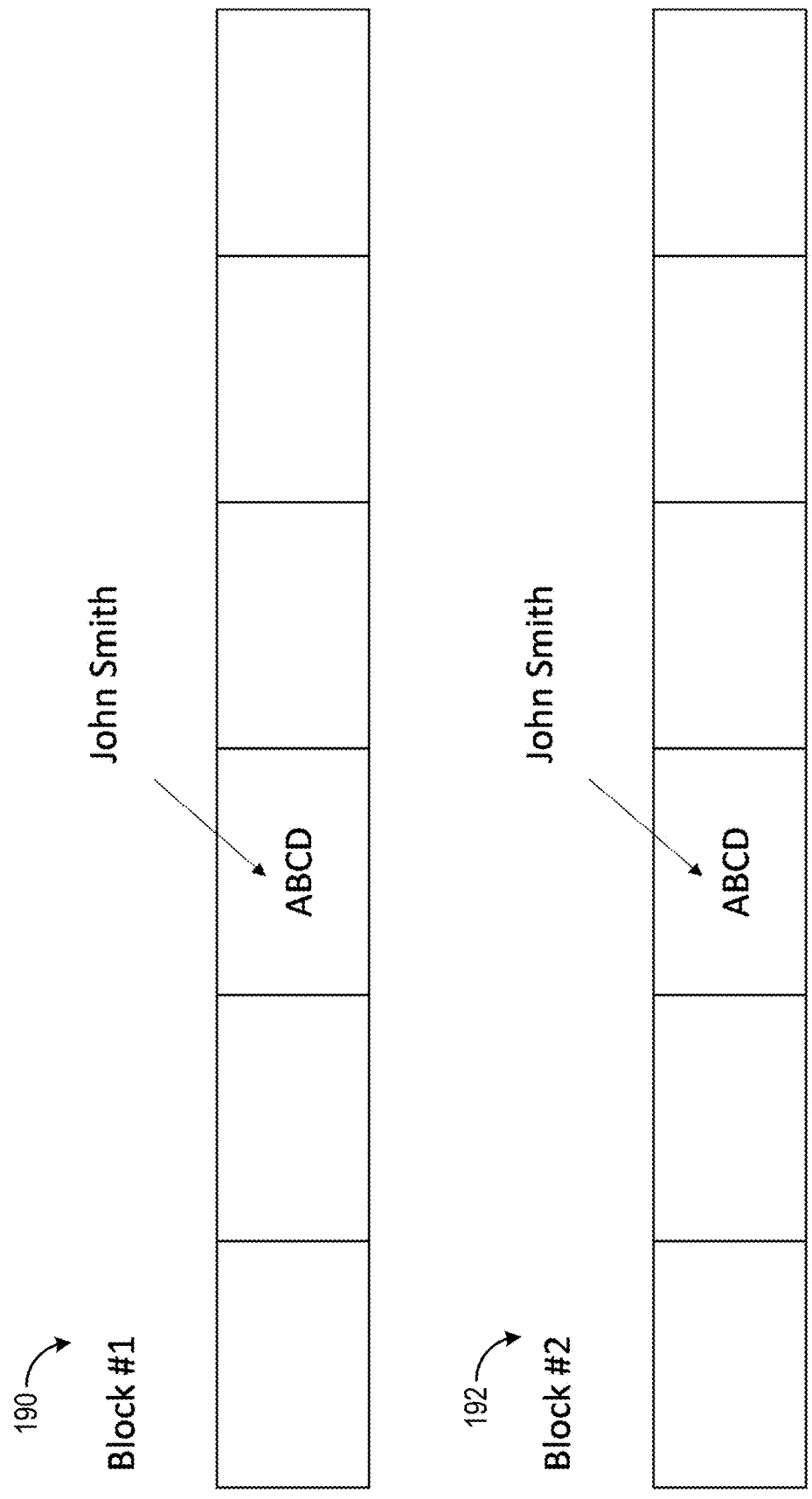

FIG. 22

| PRIVACY SERVER AND ASSOCIATED DATABASE | |
|---|---|
| ATTRIBUTE COMBINATIONS | DDIDS |
| INPUT TECHNOLOGY PROVIDER | |
| A | 1 |
| d | 4 |
| F | 7 |
| PROCESS TECHNOLOGY PROVIDER | |
| C | 2 |
| G | 5 |
| e | 8 |
| OUTPUT TECHNOLOGY PROVIDER | |
| b | 3 |
| H | 6 |
| i | 9 |

SYSTEMS AND METHODS FOR ENFORCING CENTRALIZED PRIVACY CONTROLS IN DE-CENTRALIZED SYSTEMS

CROSS-REFERENCE TO RELATED APPLICATIONS

This application is a Continuation-in-part of U.S. patent application Ser. No. 15/483,997, filed Apr. 10, 2017, entitled, "Systems and Methods for Enhancing Data Protection By Anonosizing Structured and Unstructured Data and Incorporating Machine Learning and Artificial Intelligence in Classical and Quantum Computing Environments," which is a Continuation-in-part of U.S. patent application Ser. No. 15/174,797 filed Jun. 6, 2016 entitled "Systems and Methods for Anonosizing Data," which is a Continuation-in-part of U.S. patent application Ser. No. 14/846,167 filed Sep. 4, 2015 entitled "Systems and Methods for Contextualized Data Protection," which is a Continuation-in-part of U.S. patent application Ser. No. 14/530,304 filed Oct. 31, 2014 entitled "Dynamic De-Identification and Anonymity," which is a Continuation of U.S. patent application Ser. No. 14/529, 960 filed Oct. 31, 2014 entitled "Dynamic De-Identification and Anonymity." U.S. patent application Ser. Nos. 14/530, 304 and 14/529,960 each claim the benefit under 35 U.S.C. § 119(e) of U.S. Provisional Patent Application No. 61/899, 096 filed Nov. 1, 2013 entitled "Dynamic Identity Masking and Management System and Methods"; U.S. Provisional Patent Application No. 61/938,631 filed Feb. 11, 2014 entitled "Digital Rights Management For Individuals And For De-Identification Purposes"; U.S. Provisional Patent Application No. 61/941,242 filed Feb. 18, 2014 entitled "Data Privacy And Security Systems, Methods And Devices"; U.S. Provisional Patent Application No. 61/944, 565 filed Feb. 25, 2014 entitled "Privacy And Security Systems, Methods And Devices"; U.S. Provisional Patent Application No. 61/945,821 filed Feb. 27, 2014 entitled "Photo Sharing Privacy Systems And Methods"; U.S. Provisional Patent Application No. 61/948,575 filed Mar. 6, 2014 entitled "Object Oriented Anonymity Privacy And Security Systems, Methods And Devices"; U.S. Provisional Patent Application No. 61/969,194 filed Mar. 23, 2014 entitled "Object Oriented Anonymity Data Privacy, Security And Accuracy Systems, Methods And Devices"; U.S. Provisional Patent Application No. 61/974,442 filed Apr. 3, 2014 entitled "Dynamic Object Oriented Anonymity Data Privacy, Security And Accuracy Systems, Methods And Devices"; U.S. Provisional Patent Application No. 61/988, 373 filed May 5, 2014 entitled "Controlled Dynamic Anonymity Data Privacy, Security And Accuracy Systems, Methods And Devices"; U.S. Provisional Patent Application No. 61/992,441 filed May 13, 2014 entitled "Dynamic Deidentification And Anonymity Systems, Methods And Devices"; U.S. Provisional Patent Application No. 61/994, 076 filed May 15, 2014 entitled "Anonos Consumer Privacy System"; U.S. Provisional Patent Application No. 61/994, 715 filed May 16, 2014 entitled "Dynamic De-Identification And Anonymity Systems, Methods And Devices"; U.S. Provisional Patent Application No. 61/994,721 filed May 16, 2014 entitled "Anonos Privacy Measurement Scoring Methods And Systems"; U.S. Provisional Patent Application No. 62/001,127 filed May 21, 2014 entitled "Big Data/Data Subject Privacy System"; U.S. Provisional Patent Application No. 62/015,431 filed Jun. 21, 2014 entitled "Anonos Dynamic Anonymity/Circle of Trust System"; U.S. Provisional Patent Application No. 62/019,987 filed Jul. 2, 2014 entitled "Anonos Controlled Data Fusion and Anti-Discrimination System"; U.S. Provisional Patent Application No. 62/037,703 filed Aug. 15, 2014 entitled "Anonos Dynamic Anonymity Information Risk Management Platform"; U.S. Provisional Patent Application No. 62/043,238 filed Aug. 28, 2014 entitled "Formulaic Expression of Anonos Risk Management Data Privacy System"; U.S. Provisional Patent Application No. 62/045,321 filed Sep. 3, 2014 entitled "Formulaic Expression of Dynamic De-Identification and Anonymity"; U.S. Provisional Patent Application No. 62/051,270 filed Sep. 16, 2014 entitled "Anonos Data-Privacy as-a-Service (DPaaS) System"; U.S. Provisional Patent Application No. 62/055,669 filed Sep. 26, 2014 entitled "Data Privacy as-a-Service (DPaaS) supported by Anonos Dynamic Anonymity/Circle of Trust (CoT) System based on DDIDs"; and U.S. Provisional Patent Application No. 62/059,882 filed Oct. 4, 2014 entitled "Privacy for the Interconnected World—Systems and Methods," the disclosures of which are all incorporated herein by reference in their entireties This application further claims the benefit under 35 U.S.C. § 119(e) of U.S. Provisional Patent Application No. 62/491,294, filed Apr. 28, 2017, entitled, "Anonosizing the Collection and Sharing of Healthcare Data"; U.S. Provisional Patent Application No. 62/535,601, filed Jul. 21, 2017, entitled, "Anonos Format Preserving Dynamic Pseudonymization"; U.S. Provisional Patent Application No. 62/554,000, filed Sep. 4, 2017, entitled, "Anonos Global Data Protection Regulation Compliant Analytics"; U.S. Provisional Patent Application No. 62/580,628, filed Nov. 2, 2017, entitled, "Anonos BigPrivacy Compressible Dynamic De-Identifiers"; U.S. Provisional Patent Application No. 62/644,463, filed Mar. 17, 2018, entitled, "Anonos BigPrivacy GDPR Compliant Block Chain Systems and Methods"; and U.S. Provisional Patent Application No. 62/649,103, filed Mar. 28, 2018, entitled, "BigPrivacy Data Compliance in the Cloud," the disclosures of which are all incorporated herein by reference in their entireties.

FIELD OF THE INVENTION

This disclosure relates generally to improving data security, privacy, and accuracy, and, in particular, to using dynamically changing identifiers to render elements of data, which may, e.g., be stored in a Distributed Ledger Technology (DLT), such as a blockchain, to be anonymous. (Note: The words "privacy" and "anonymity" are used interchangeably herein to refer to data protection, privacy, anonymity, pseudonymity, obscurity and/or other actions available to a legal entity, which entity may be a natural person and/or an artificial person, like a business entity or a corporate entity or group of legal entities, in order to seclude, sequester or redact information about themselves from unauthorized parties, and thereby provide information about themselves selectively. The words "Distributed Ledger Technology" or "DLT" are used herein to refer to a data storage element comprising a consensus of replicated, shared, and/or synchronized digital data, e.g., which may be geographically spread across multiple sites, countries, or institutions. With DLT, there is typically no central administrator or centralized data storage. Examples of the use of DLT include: blockchains, cryptocurrencies, smart contracts, and even decentralized file storage.)

BACKGROUND

This section is intended to provide a background or context to the invention that is recited in the claims. The description herein may include concepts that could be pursued, but are not necessarily ones that have been previously conceived, implemented or described. Therefore, unless otherwise indicated herein, what is described in this section is not prior art to the description and claims in this application and is not admitted to be prior art by inclusion in this section.

There are certain inherent conflicts between: (i) the goal of parties to maximize the value of data and their goal of respecting privacy rights of individuals; (ii) the goal of individuals' to protect their privacy rights and their goal of benefiting from highly personalized offerings; and (iii) the goal of U.S. and international government agencies to facilitate research and commerce and their goal of safeguarding rights of citizens.

One goal of non-healthcare-related parties is to reach the most "highly qualified" prospects, i.e., prospective buyers who have the requisite financial resources, motivation, and authority to make a purchase. Commercial parties will pay much more to reach qualified prospects than to reach undifferentiated prospects because the chances of consummating a transaction with a qualified prospect is significantly higher, given their interest, predisposition, and means to close transactions. The level of personalization/customization of offerings for prospective customers—which is directly related to the likelihood of consummating transactions—is enhanced by the depth and scope of information available about each individual prospect. One goal of healthcare-related parties is to conduct research pertaining to health and/or disease with the goal of advancing discoveries in applications that may improve human health.

The development, emergence and widespread adoption of computer networks, internets, intranets and supporting technologies has resulted in the wide-spread availability of cost-effective technology to collect, transmit, store, analyze and use information in electronic formats. As a result, entities now have the ability to readily collect and analyze vast amounts of information. This has created tensions between: (a) the increasing quantity of information available to qualify prospects, develop personalized/customized offerings for potential customers and/or conduct health-related or other research; and (b) decreasing security, anonymity and privacy for individuals who often are not aware of the existence of many data elements that may be traced back to them, and over which they often have little or no effective control.

Data elements may be collected both online and offline (both "born digital" and "born analog" and converted into digital format at a later date) through a variety of sources including, but not limited to, activity on social networking sites, electronic or digital records, emails, participation in rewards or bonus card programs that track purchases and locations, browsing or other activity on the Internet, and activity and purchases at brick-and-mortar stores and/or on e-commerce websites. Merchants, medical-related and other service providers, governments, and other entities use this tremendous amount of data that is collected, stored, and analyzed to suggest or find patterns and correlations and to draw useful conclusions. This data is sometimes referred to as "big data," due to the extensive amount of information entities may now gather. With big data analytics, entities may now unlock and maximize the value of data—one example may involve non-health related entities engaging in behavioral marketing (with materials created for distribution being customized in an attempt to increase the correlation with the preferences pertaining to a particular recipient party) and another example may involve health-related entities accessing big data to conduct medical research. However, with behavioral marketing and big data analytics, related parties now have a much lower level of privacy and anonymity.

Attempts at reconciling the conflict between privacy/anonymity and value/personalization/research have often historically involved using alternative identifiers rather than real names or identifying information. However, these alternative identifiers are generally statically assigned and persist over time. Static identifiers are more easily tracked, identified, and cross-referenced to ascertain true identities, and may be used to ascertain additional data about subjects associated with data elements without the consent of related parties. Privacy and information experts have expressed concerns that re-identification techniques may be used with data associated with static identifiers and question whether data that is identifiable with specific computers, devices or activities (i.e., through associated static identifiers) can in practice be considered anonymous or maintained in a protected state of anonymity. When an identifier does not change over time, adversarial entities have unlimited time to accrete, analyze and associate additional or even exogenous data with the persistent identifier, and thus to determine the true identity of the subject and associate other data with the true identity. In addition, unlimited time provides adversarial entities with the opportunity to perform time-consuming brute-force attacks that can be used against any encrypted data.

According to a 2011 McKinsey Global Institute report:
A retailer using big data to the full extent could increase its operating margin by more than 60 percent;
Harnessing big data in the public sector has enormous potential—if U.S. healthcare were to use big data creatively and effectively to drive efficiency and quality, the sector could create more than $300 billion in value every year—two-thirds of that would be in the form of reducing US healthcare expenditure by about 8 percent;
In the developed economies of Europe, government administrators could save more than €100 billion ($149 billion) in operational efficiency improvements from using big data, not including using big data to reduce fraud and errors and boost the collection of tax revenues; and
Users of services enabled by personal-location enabled big data could capture $600 billion in consumer surplus.

Many potential benefits from big data have not been fully realized due to ambiguity regarding ownership/usage rights of underlying data, tensions regarding privacy of underlying data, and consequences of inaccurate analysis due to erroneous data collected from secondary (versus primary) sources and/or inferred from activities of parties without active participation of, or verification by, said parties.

The recent explosion in popularity of decentralized networks or platforms (including permissionless systems and distributed ledger technologies, such as blockchain), including networks or platforms linked on a peer-to-peer basis or other non-centralized basis, has further increased the difficulty in maintaining a desired level of privacy/anonymity for users, while still allowing for the appropriate extraction of informational value and/or provision of personalized services by authorized third parties. In particular, due to the requirements of distributed ledger technologies with respect to immutability, auditability, and verification, it has heretofore been impossible to provide high levels of privacy/ anonymity, at least because of the necessarily static nature of the information that is recorded in such distributed ledgers.

What are needed are systems, methods and devices that overcome the limitations of static and/or persistent privacy/anonymity and security systems and improve the accuracy of data for exchange, collection, transactions, analysis and other uses—especially in applications that store data in a decentralized fashion, e.g., using a distributed ledger technology, such as blockchain. Put another way, privacy/anonymity-enhancing technologies, such as those described herein, can help to reconcile the tensions between auditable and immutable information stores by providing tools that enable the ability of an authorized user to unlock the "true" meaning of such information, given a particular time and context.

SUMMARY

Embodiments of the present invention may improve data privacy and security by enabling subjects to which data pertains to remain "dynamically anonymous," i.e., anonymous for as long as is desired—and to the extent that is desired. Embodiments of the present invention may include systems, methods and devices that create, access, use (e.g., collecting, processing, copying, analyzing, combining, modifying or disseminating, etc.), store and/or erase data with increased privacy, anonymity and security, thereby facilitating availability of more qualified and accurate information. And, when data is authorized to be shared with third parties, embodiments of the present invention may facilitate sharing information in a dynamically controlled manner that enables delivery of temporally-, geographically-, and/or purpose-limited information to the receiving party. Embodiments of the present invention may even be employed in decentralized networks built on blockchain or other distributed ledger technologies that require immutability and auditability of record over time.

As compared to existing systems, wherein electronic data may be readily accessible for use (e.g., collecting, processing, copying, analyzing, combining, modifying or disseminating, etc.), storing and/or erasing with few effective controls over the data, embodiments of the present invention may use temporally unique, dynamically changing de-identifiers ("DDIDs")—each associated with a subject, e.g., a person, place, or thing (e.g., an event, document, contract, or "smart contract"), to which data directly or indirectly pertains or relates (a "Data Subject"), and/or an action, activity, process and/or trait pertaining to a Data Subject, for a temporally unique period of time, thereby enabling the Data Subject to operate in a "dynamically anonymous" manner. "Dynamically anonymous" or "Dynamic Anonymity" as used herein, refers to a user's ability to remain anonymous until such time as a decision is made not to remain anonymous, at which time only the desired information is shared with one or more desired parties in connection with one or more actions, activities, processes or traits. Embodiments of the present invention may thereby enable the ability of Data Subjects to maintain flexible levels of privacy and/or anonymity under the control of a Data Subject or controlling entity that may be a trusted party or proxy.

Embodiments of the invention may use DDIDs to help prevent the retention of data, sometimes referred to as metadata, that may otherwise provide third parties with information about one or more aspects of a Data Subject and/or data attributes reflecting actions, activities, processes and/or traits pertaining to a Data Subject, such as, by way of example and not limitation, information pertaining to means of creation, purpose, time and/or date of creation, identity of the Data Subject and/or creator of the data attributes, location where data attributes were created, standards used in creating or using data attributes, etc. This is due to the fact that metadata must have something to attach itself to—or to associate itself with—in order to establish an ongoing record of information associated with one or more specific data attributes. The words "data," "attributes," "elements" or similar terms used in this application will include, any or all of the following, as applicable, (i) structured data (i.e., data in predetermined structured schemas), (ii) unstructured data, (iii) metadata (i.e., data about data), (iv) other data, and/or (v) any of the foregoing types of data initially recorded in analog format and later converted into digital format.

Embodiments of the present invention may use a first DDID at one time for a specific purpose pertaining to a first Data Subject, action, activity, process and/or trait, and then use a second DDID in association with the first Data Subject, action, activity, process and/or trait, for a different purpose, and/or use the first DDID in association with a second Data Subject, action, activity, process and/or trait, for a different purpose, etc. As a result, attempts to retain and aggregate data associated with underlying information associated with DDIDs may be ineffective since different DDIDs may be associated with the same Data Subject, action, activity, process and/or trait, and/or the same DDID may be used with different Data Subjects, actions, activities, processes and/or traits, and/or purposes—each for a temporally unique period of time.

Embodiments of the present invention may track and record different DDIDs used by, and associated with, Data Subjects at different times with respect to various actions, activities, processes or traits thereby enabling the storage, selection and retrieval of information applicable to a specific action, activity, process or trait and/or a specific Data Subject. Conversely, the system may not enable third parties external to the system to effectively retain and aggregate data due to the use of multiple DDIDs and the lack of information available external to the system to determine relationships between and among DDIDs and/or Data Subjects, actions, activities, processes and/or traits.

Each DDID may be associated with any one or more data attributes to facilitate with respect to a specific action, activity, process or trait, such as, by way of example and not limitation: (a) information reflecting an action, activity, process or trait associated with a Data Subject while associated with a current DDID (e.g., browsing information reflecting current web-based activity of a Data Subject while being associated with a current DDID) before the current DDID is replaced with a different DDID; (b) information with respect to past actions, activities, processes or traits previously associated with a Data Subject while associated with one or more previous DDIDs but with respect to which the Data Subject now desires to share information with a third party while associated with the current DDID (e.g., sharing pricing information with an e-commerce website that the Data Subject collected from said website in a previous browsing session while being associated with a previous DDID); and (c) new information that may help facilitate with respect to a desired action, activity, process or trait on behalf of the Data Subject while associated with a current DDID (e.g., indicating new desired size and color for a currently desired purchase of clothing from an e-commerce website). For purposes hereof, the combination of a DDID and any data elements associated with the DDID for a temporally unique period of time are referred to as a temporal data representation, or a "TDR." For purposes hereof, if no data is associated with a DDID, then a DDID and its temporal data representation (or "TDR") are identical.

From the perspective of an implementation of an embodiment of Dynamic Anonymity being a closed system, a DDID intended to represent the identity of a Data Subject, i.e., a "primary identifier," is required to be temporally unique during the time period of the assignment of the DDID to the Data Subject—i.e., no two extant Data Subjects can have identical primary identifier DDIDs at the same time. The requirement for temporal uniqueness of DDIDs is applicable when separateness of identity of Data Subjects is desired to be represented by DDIDs; if factors other than separateness of identity of Data Subjects are desired to be represented by DDIDs, DDID assignments can be made accordingly to represent intended associations, relationships, etc. DDIDs can be instantiated in two ways: (i) within an implementation of the present invention or (ii) by externally created identifiers, but only provided that they satisfy the "temporally unique" requirement (e.g., a "cookie" or other unique identifier assigned by a website to a first-time visitor could effectively serve as a DDID) when separateness of identity of Data Subjects is desired to be represented by DDIDs.

A cookie is a small piece of data that is generally sent from a website and stored in a Data Subject's web browser while the Data Subject is browsing the website, so that, every time the Data Subject returns to the website, the browser sends the cookie back to a server associated with the website to notify the website the Data Subject has returned to the website. However, in order for a cookie to serve as a DDID, the browser (serving as the client in this potential embodiment of the invention) may prevent any cookie submitted by the website from persisting between browsing sessions (e.g., by copying the user's cookies, cache and browsing history files to the anonymity system's servers and then deleting them off the user's computer), such that a new cookie may be assigned for each browsing session. In this manner, the various cookies (in this example embodiment, serving as DDIDs representing separateness of identity of Data Subjects) issued by the website, while being created "externally" to the system, would each be unique and would not enable the website to remember stateful information or aggregate the Data Subject's browsing activity, since each of the browsing sessions would be perceived by the website as unrelated—thereby enabling the Data Subject to remain dynamically anonymous as long as desired, to the extent desired.

As mentioned in the example potential embodiment above, the Dynamic Anonymity system, according to some embodiments, may collect and retain information related to the various actions, activities, processes or traits associated with the different browsing sessions/different cookies (in this example, serving as DDIDs representing separateness of identity of Data Subjects) and store the combined information in an aggregated data profile for the Data Subject until such time as a decision is made by, or on behalf of, the Data Subject to no longer remain anonymous, at which point only desired information from the Data Subject's aggregated data profile need be shared with one or more desired parties in connection with one or more actions, activities, processes or traits. In this exemplary embodiment of the invention, this may involve the Data Subject deciding to provide information to a website from the Data Subject's aggregated data profile as a TDR that reflects past activity of the Data Subject on the website—all at the election and control of the Data Subject (or other controlling entity). In the above exemplary embodiment of the invention, in lieu of using cookies assigned by a website visited by a Data Subject as DDIDs, the system may alternatively use globally unique identifiers (GUIDs) (i.e., unique reference numbers used as identifiers in computer software), or other temporally unique, dynamically changing proxy de-identifiers, as DDIDs whether created internally by, or externally to, implementations of the present invention. In the above examples, control over the collection of data resulting from browsing activity by a Data Subject would reside with the Data Subject or other controlling entity, rather than with the websites visited by the Data Subject. In still other exemplary embodiments of the invention, rather than the Data Subject deciding when to send, i.e., "push," information to the website from the Data Subject's aggregated data profile, a website (with proper permissions and authentication) could request, i.e., "pull" the relevant information and/or relevant DDID-to-Data Subject association information from the Data Subject's aggregated data profile at such time that the information is needed by the website.

In still other exemplary embodiments of the invention, the work to dynamically anonymize and control the sending of the relevant portions of the Data Subject's aggregated data profile may be handled by: the Data Subject's client device itself; the central Dynamic Anonymity system referred to above; or a combination of the two. For example, a complete view of a particular Data Subject's information and/or relevant DDID-to-Data Subject association information for a predetermined or flexible amount of time could be stored at the Data Subject's client device for the predetermined or flexible amount of time, before then being synchronized back to a central Dynamic Anonymity system (as well as synchronized with any other client devices that the Data Subject may have registered with the central anonymity system).

TDRs and DDIDs may comprise multiple levels of abstraction for tracking and identification purposes. A system according to some embodiments of the present invention may store the TDRs (consisting of DDID values and data elements, if any, associated with the DDIDs), as well as information regarding the time period during which each DDID was associated with a particular Data Subject, data attribute(s), action, activity, process or trait—thereby allowing the TDRs to be re-associated at a later time with the particular Data Subject, data attribute(s), action, activity, process or trait. Such a system may be utilized to facilitate the development of aggregated data profiles by reference to and with the use of keys that reveal the relationship between and among various DDIDs, Data Subjects, data attributes(s), actions, activities, processes and/or traits. In other words, "Dynamic Anonymity," as afforded by the use of TDRs and/or DDIDs, as described herein, may enable Data Subjects to benefit from ongoing technological advancements (e.g., the Internet of Things (IoT), personalized medicine, etc.) without having to relinquish privacy, anonymity, security or control. This may be accomplished by: (i) assigning unique dynamically changing DDIDs to Data Subjects, actions, activities, processes and/or traits; (ii) retaining information regarding association of DDIDs with Data Subjects, actions, activities, processes and/or traits; and (iii) providing Data Subjects and/or controlling entities, that may be trusted parties/proxies, with deterministic control over access to/use of association information. With the use of dynamically changeable, temporally unique, and re-assignable DDIDs, current systems and processes (e.g., web browsers and data analytic engines) may not be able to recognize relationships between and among disassociated and/or replaced data elements. They may still process information using existing capabilities, but will do so without creating inferences, correlations, profiles or conclusions—except as expressly authorized by Data Subjects and trusted parties/proxies. Moreover, the DDIDs employed by embodiments of the present invention can be replaced dynamically at the data element-level enabling Dynamic Anonymity—not just at the Data Subject-level or data record-level. This means that individuals may have control over what data is shared or accessed, enabling dynamic de-identification without "de-valuation" of the underlying information.

Control of information down to the data element-level makes controlled information sharing possible in the age of big data—beyond the reach of controls targeted only at the data record-level or Data Subject-level. It further enables a "one and done relationship" between a Data Subject and a website or other entity receiving information about the Data Subject. Most existing systems collect information around a unique identifier over time. Even if a DDID carries with it a certain amount of history or other information pertaining to a Data Subject, the next time the Data Subject visits the site, store, doctor, etc. the Data Subject could look like a completely different Data Subject if desired. Only when and if the DDID contained a unique identifier, a name or email address for example, could a recipient correlate a then-current DDID representing the Data Subject with a DDID previously used to represent the Data Subject, at which point the recipient could interact with the Data Subject based on the recipient's collection of data on the Data Subject. However, the next time the recipient encounters the Data Subject, the Data Subject would not be re-identifiable unless desired by the Data Subject.

Dynamic Anonymity also enables controlled "data fusion" (wherein "data fusion" is defined as being what occurs when data from different sources are brought into contact with each other and new facts emerge) by providing controlled anonymity for data, identity (of the Data Subject and/or the controlling entity) and context (e.g., time, purpose, place) by obfuscating connections between and among the foregoing. Dynamic Anonymity thus also enables the undoing or reversal of either rights granted or access to data (e.g., a particular party could be provided with access to data underlying a DDID then have their access revoked via the changing of Replacement Keys), as well as the rejuvenation of data (i.e., of the values of the data, not necessarily re-identification) of data to support additional authorized secondary uses without violating promises to Data Subjects (e.g., one or more DDIDs may initially provide access via one or more Replacement Keys to the results of an X-ray and, via the changing of Replacement Keys, later reflect the results of the X-ray as well as results of follow-on physical therapy).

The reason Dynamic Anonymity will still be attractive in the commercial marketplace is that companies often do not actually care who the Data Subjects they interact with are (i.e., their actual, "real world" identities); they instead care what the Data Subjects are; how the Data Subjects behave; and when the Data Subjects behave that way. The more accurate their targeting is and the less wasteful, the more likely an anonymous consumer will respond favorably to a personalized offering. Dynamic Anonymity thus obviates the need for companies to follow Data Subjects around the digital world to try to persuade them to buy products and/or services that they may not really need or want. Dynamic Anonymity allows for more profitable "matching" of sellers and interested customers. Currently, the best that many companies can do is to "segment" potential customers by using demographics and statistics, but they may have no idea of the actual interest of individual segment members. Dynamic Anonymity also improves upon generalized demographics and statistics by providing individualized expressions/levels of expression of interest from members of segments who are "highly qualified" prospects. The ability of Dynamic Anonymity to enable Data Subjects to directly or indirectly control use of their data in accordance with their personal privacy/anonymity preferences can support disparate treatment of data in disparate jurisdictions notwithstanding different data use/privacy/anonymity requirements in such jurisdictions (e.g., differences between European Union "fundamental right" and U.S. balancing of privacy rights/right to free expression/commerce perspectives on data privacy/anonymity).

In the context of healthcare, medical-related and other areas of research, Dynamic Anonymity will be more attractive than traditional approaches to "de-identification" that protect data privacy/anonymity by using a defensive approach—e.g., a series of masking steps are applied to direct identifiers (e.g., name, address) and masking and/or statistically-based manipulations are applied to quasi-identifiers (e.g., age, sex, profession) in order to reduce the likelihood of re-identification by unauthorized third parties. This defensive approach to protecting data privacy/anonymity results in a tradeoff between protecting against re-identification and retaining access to usable information. In comparison, with Dynamic Anonymity the value of information can be retained and leveraged/exploited for authorized purposes, all with a statistically insignificant risk of re-identification of any datum. DDIDs can be used to represent actions, activities, processes and/or traits between and among Data Subjects, the meaning of which may change over time thereby requiring the then-current appropriate key(s) to discern underlying values. Dynamic Anonymity therefore rejects the proposition and traditional dichotomy that, in order to minimize the risk of/anonymity loss, one must sacrifice information content by making it forever unrecoverable. Instead, Dynamic Anonymity minimizes both the risk of privacy/anonymity loss and the amount of information lost, enabling most—if not all—of it recoverable, but only with authorization.

Keys used by embodiments of the present invention may vary depending on the use of corresponding DDIDs. For example: time keys ("TKs") may be used to correlate the time period of association between a DDID and a Data Subject, action, activity, process and/or trait—i.e., the time period of existence of a TDR; association keys ("AKs") may be used to reveal the association between two or more data elements and/or TDRs that may not otherwise be discernibly associated one with another due to the use of different DDIDs; replacement keys ("RKs") may be used if/when DDIDs are used in replacement of one or more data attributes within a TDR, in which case look-up tables may be referenced to determine the value of the one or more data attributes replaced by the said one or more DDIDs included within the TDR.

Without access to the applicable TK(s), AK(s) and/or RK(s), in the event that a third party intercepts information pertaining to one or more Data Subjects, actions, activities, processes and/or traits, the third party would not be able to: (i) re-identify a Data Subject by means of associating DDIDs and corresponding data attributes (which together comprise TDRs) in the case of the association function of the present invention; and/or (ii) knowing the value of data elements represented by DDIDs so as to correctly understand the information in the case of the replacement function of the present invention. Conversely, embodiments of the present invention may enable a Data Subject or other controlling entity to send to one or more desired third parties only those data attributes (which the system knows relate to the Data Subject by virtue of the tracking/logging/recording functions of the system) that specifically pertain to a specific action, activity, process or trait.

The following terms may also be used in connection with anonymizing data, according to the various embodiments described herein:

"A-DDID" or "Association DDID": refers to a DDID that is used to replace an identifying data element and dereference (e.g., point) to the value of the data element, thus conveying a range/association with (or correlation between) the data element and its value, in order to impart informational value in a non-identifying manner, and optionally in accordance with specified grouping rules. Indices used to resolve dereferencing may, without limitation, include keys, schema translation tables, anonymous identifiers, pseudonymous identifiers, tokens or other representations. Dereference grouping rules for A-DDIDs may be of (at least) two kinds of groupings: Numerical and Categorical. Numerical groupings refer to ranges of numerical values represented by A-DDIDs. Categorical groupings replace "correlates" (i.e., two or more related or complementary items) with A-DDIDs selected to represent correlations between values within each grouped-category. A-DDID dereference rules may also cover multiple fields. For example, a blood test may cover a number of variables from which one can infer heart attack risk, so the rule could specify the various combinations required for assigning heart attack risk to a particular category, e.g., high, moderate, or low.

"R-DDID" or "Replacement DDID": refers to a DDID that may be used to replace an identifying data element and de-reference (e.g., point) to the value of the data element.

"Mosaic Effect" refers to the ability to re-identify a data subject by correlating data between and among seemingly anonymous data sets.

Disclosed herein are various systems, methods and devices for private and secure management and use of information pertaining to one or more Data Subjects, such as persons, places or things, and associated actions, activities, processes and/or traits. The systems, methods and devices described herein may abstract data pertaining to Data Subjects, actions, activities, processes and/or traits by linking elements pertaining to the data into independent attributes or dependent attributes, separating elements pertaining to the data into independent attributes or dependent attributes. For purposes of this disclosure, an attribute refers to any data element that can be used, independently or in combination with other data elements, to directly or indirectly identify a Data Subject, such as a person, place or thing, and associated actions, activities, processes and/or traits. It should be noted that a Data Subject may have attributes or attribute combinations that are unique to the Data Subject: for example, an individual Data Subject's social security number, as well as attributes or attribute combinations that are shared by the Data Subject with other Data Subjects: for example, an individual Data Subject's sex or affiliation with a political party. In some instances, an attribute may be an electronic or digital representation of a Data Subject or associated action, activity, process and/or trait. Similarly, attributes may be electronic or digital representations of information or data related to a Data Subject or associated action, activity, process and/or trait. Separating, linking, combining, rearranging, defining, initializing or augmenting the attributes, can form attribute combinations pertaining to any particular Data Subject or group of Data Subjects, or associated actions, activities, processes and/or traits. With respect to any Data Subject, action, activity, process and/or trait, the attribute combinations may include any combination of attributes, as well as other data that is added to or combined with the attributes. It should be further noted that an attribute or combination of data attributes may identify a Data Subject but are not themselves the Data Subject—the person or legal entity identified by an attribute or combination of data attributes may be the subject of said attribute or combination of data attributes and considered a related party with regard thereto since he/she/it has an interest in or association with said attribute or combination of data attributes. In addition, parties (other than a Data Subject identified by an attribute or combination of data attributes) who have an interest in or association with an attribute or combination of data attributes may also be considered related parties with regard to the attribute or combination of data attributes.

In some embodiments, a client—server structure or architecture may be utilized to implement one or more features or aspects of this disclosure, whether on premises in or across an enterprise, in a private or public cloud, in a private or public hybrid cloud, or in any combination of the foregoing, whereby in one example, a privacy server, which may be virtual, logical or physical, provides functions and/or services to one or more privacy clients, which themselves may be virtual, logical or physical. These privacy clients that may reside on a Data Subject device, on a service provider device, accessible via and reside in a cloud network, or reside on the same computing device as the privacy server may initiate requests for such functions and/or services by interacting with data attributes and/or data attribute-to-Data Subject association information stored in a database on a hard drive or other memory element associated with the privacy server. For example, a data attribute may be linked to independent attributes or dependent attributes or separated into independent attributes or dependent attributes by means of a privacy server coupled to the database in response to requests for functions and/or services from one or more privacy clients. It should be noted that implementations of the invention may use a single computer or computing device as both a privacy server and a privacy client whereas other implementations may use one or more computers or computing devices located in one or more locations as a privacy server and one or more computers or computing devices located in one or more locations as a privacy client. A plurality of system modules may be used to perform one or more of the features, functions and processes described herein, such as but not limited to: determining and modifying required attributes for attribute combinations; assigning DDIDs; tracking DDID use; expiring or re-assigning existing DDIDs; and enabling or providing data associations relevant to or necessary with respect to a given action, activity, process or trait.

In one embodiment, these modules may include an abstraction module of the privacy server configured to among other things: dynamically associate at least one attribute with at least one Data Subject, action, activity, process and/or trait; determine and modify required attributes relevant to or necessary for a given action, activity, process or trait; generate, store, and/or assign DDIDs to the at least one data attribute to form a TDR; and assign a predetermined expiration to a TDR by means of the DDID component of the TDR.

These system modules, and if desired other modules disclosed herein, may be implemented in program code executed by a processor in the privacy server computer, or in another computer in communication with the privacy server computer. The program code may be stored on a computer readable medium, accessible by the processor. The computer readable medium may be volatile or non-volatile, and may be removable or non-removable. The computer readable medium may be, but is not limited to, RAM, ROM, solid state memory technology, Erasable Programmable ROM ("EPROM"), Electrically Erasable Programmable ROM ("EEPROM"), CD-ROM, DVD, magnetic cassettes, magnetic tape, magnetic disk storage or other magnetic or optical storage devices. In certain embodiments, privacy clients may reside in or be implemented using "smart" devices (e.g., wearable, movable or immovable electronic devices, generally connected to other devices or networks via different protocols such as Bluetooth, NFC, WiFi, 3G, etc., that can operate to some extent interactively and autonomously), smartphones, tablets, notebooks and desktop computers, and privacy clients may communicate with one or more privacy servers that process and respond to requests for information from the privacy clients, such as requests regarding data attributes, attribute combinations and/or data attribute-to-Data Subject associations.

In one implementation of the present invention, DDIDs associated with attributes and attribute combinations may be limited in scope and duration. Further, DDIDs may be re-assignable, such that a DDID may refer to multiple Data Subjects or multiple actions, activities, processes or traits at different points in time. The DDIDs may be re-assignable on a configurable basis in order to further abstract and dilute or attenuate data trails while maintaining the timeliness and saliency of the TDRs and data contained therein.

In one example, rather than storing, transmitting or processing all data attributes pertaining to a Data Subject and/or relevant to or necessary for a given action, activity, process, or trait, embodiments of the present invention may introduce an initial layer of abstraction by means of an association function, e.g., by including only a portion of the relevant data attributes in each TDR. In this way, the data attributes pertaining to a Data Subject may be disassociated within seemingly unrelated TDRs, such that access to and use of one or more AKs are necessary in order to know which two or more TDRs must be associated with each other in order to collectively contain all the data attributes pertaining to a Data Subject and/or that are relevant to or necessary for a given action, activity, process or trait. The privacy, anonymity and security of data attributes contained or referenced within a TDR may be further improved or enhanced by means of a replacement function, e.g., by replacing one or more of said data attributes contained in one or more TDRs with DDIDs so that access to and use of one or more RKs are necessary to enable use of look-up tables to determine the value of the one or more data elements replaced by said one or more DDIDs. The privacy, anonymity and security of data attributes contained or referenced within a TDR may be further improved or enhanced by using other known protection techniques, such as encrypting, tokenizing, pseudonymizing, eliding and/or otherwise; and/or by introducing additional layers of abstraction by replacing keys with second-level or n-level DDIDs.

In the case of both: disassociation of data attributes pertaining to a Data Subject, action, activity, process and/or trait, so as to require AKs; and replacement of data attributes pertaining to a Data Subject, action, activity, process and/or trait, so as to require RKs, the effective level of privacy, anonymity and security may be enhanced based on how, and how often, the DDIDs associated with the data attribute or attributes in question are changed and/or are changeable. In one exemplary embodiment of the invention, DDIDs may be assigned for purposes of disassociation and/or replacement and retain their initially assigned value(s)—i.e., permanent assignments. In another exemplary embodiment of the invention, DDIDs may be assigned for purposes of disassociation and/or replacement and retain their initially assigned value(s) until the value(s) are changed on an ad hoc basis, i.e., "ad hoc changeability." In yet another exemplary embodiment of the invention, DDIDs may be assigned for purposes of disassociation and/or replacement and retain their initially assigned value(s) until the value(s) are changed based on a random, fixed, variable or other dynamic basis, i.e., "dynamic changeability."

Embodiments of the present invention may create additional layers of abstraction by replacing identifying references within the system to external networks, internets, intranets, and/or computing devices that may be integrated, or communicate, with one or more embodiments of the present invention with DDIDs so that one or more RKs and/or AKs are necessary to enable access to and use of look-up tables to determine the identity of the one or more external networks, internets, intranets, and/or computing devices replaced by said one or more DDIDs.

Due to the changeable, temporally unique, and re-assignable characteristics of DDIDs paired with data attributes or attribute combinations to create TDRs, recipients of TDRs may make use of information contained in TDRs specifically for intended purposes at intended times. This is due to the fact that Association Keys (which may be required to stitch TDRs together to make sense of information contained in seemingly unrelated TDRs) and/or Replacement Keys (which may be required to know the value of information represented by temporally unique DDIDs sent to third parties as part of TDRs) may only have temporally limited usefulness. In other words, the usefulness is temporally limited because the DDID components of TDRs may be changed by a Data Subject or other controlling party when the intended purpose and/or intended time is no longer applicable in such a manner that AKs and/or RKs no longer reveal relevant information. Conversely, relevant information revealed by means of AKs and/or RKs may change over time to support additional secondary uses of data.

In one example, a maintenance module may be utilized to store information regarding the association at any particular point in time of a particular DDID with a particular attribute combination in a TDR in a secure database associated with the privacy server and accessible by the system but not accessible by parties other than the controlling entity or by parties authorized by the controlling entity (this time period of association may be represented by a time key (TK) or otherwise). In one example, the maintenance module of the privacy server and associated database(s) may store and keep all associations of DDIDs with attribute combinations. Thus, the system provides for secure data exchange and non-repudiation of data attributes, attribute combinations and TDRs in order to foster safer data-related collection, use, research and/or analysis while meeting stringent privacy, anonymity and security criteria.

In one example, a verification module of the privacy server and associated database(s) may provide an authenticated data structure that permits validation and verification of the integrity of information and/or DDIDs embodied in an aggregated data profile, data attributes, attribute combinations and/or TDRs at any point in time through methodologies such as cyclic redundancy checks ("CRCs"), message authentication codes, digital watermarking, linking-based time-stamping or analogous methodologies.

In another example, an authentication module of an embodiment of the present invention may be used to verify, on an anonymous basis, the authority to proceed with respect to a Data Subject, action, activity, process or trait at a particular time and/or place via the TDR assignment. A privacy client with TDR information may request of the authentication module, which in one example is part of the privacy server, confirmation as to whether the TDR (and undisclosed Data Subject, data attributes or attribute combinations associated therewith) is authorized to participate with regard to a requested action, activity, process or trait at a particular time and/or place. In one embodiment, the authentication module may compare the DDID included in the TDR to a list of authorized DDIDs to determine the state of authorization to participate with respect to a desired action, activity, process or trait at the specified time and/or place. Optionally, the authentication module may request the party possessing the TDR to confirm it is authorized to participate with respect to a desired action, activity, process or trait at the specified time and/or place through DDID confirmation or other confirmation techniques such as password confirmation or multi-factor authentication. If an optional authorization request is made, the process continues only if the party is authorized, in one example. The authentication module may transmit the authorization status information to the party controlling the TDR via a privacy client, and the authorization status may be used to allow or deny proceeding with respect to a desired action, activity, process or trait at the specified time and/or place.

TDRs and/or DDIDs contained in TDRs can also be used as advanced keys for known protection techniques such as encrypting, tokenizing, pseudonymizing, eliding or otherwise. The authentication module may be used to withhold the key necessary to unlock protection techniques for the contents of the TDR such as encrypting, tokenizing, pseudonymizing, eliding or otherwise, unless the TDR, DDID, undisclosed associated Data Subject, attribute, attribute combination or related party is confirmed as being authorized to participate with respect to a desired action, activity, process or trait at the specified time and/or place through DDID and/or TDR confirmation and known confirmation techniques such as password confirmation, multi-factor authentication or similar means.

In another example, an access log module may be provided, wherein the access log module can collect and store information to enable post-incident forensic analysis in the event of a system or privacy server error and/or misuse.

In accordance with one aspect of one embodiment of the present invention, disclosed herein is a computer-implemented method of providing controlled distribution of electronic information. In one example, the method may include the steps or operations of receiving, at a computing device, data; identifying one or more attributes of the data; selecting, through the computing device, a DDID; associating the selected DDID with one or more of the data attributes; and creating a temporally unique data representation (TDR) from at least the selected DDID and the one or more data attributes.

In one example, the step of selecting a DDID may include generating the temporally unique, dynamically changing DDID or, in another example, accepting or modifying a temporally unique, dynamically changing value created external to the system to serve as the DDID.

For purposes hereof, the phrase "dynamically changing" means that a DDID assigned with respect to a data subject, action, activity, process or trait: (a) changes over time due to (i) passage of a predetermined amount of time, (ii) passage of a flexible amount of time, (iii) expiration of the purpose for which the DDID was created, or (iv) change in virtual or real-world location associated with the data subject, action, activity, process or trait; or (b) is different at different times (i.e., the same DDID is not used at different times) with respect to a same or similar data subject, action, activity, process or trait.

For purposes hereof, the phrase "temporally unique" means that the time period of assignment of a DDID to a data subject, action, activity, process or trait is not endless. The initial assignment of a DDID to a data subject, action, activity, process or trait starts at a point in time, and information concerning the time of assignment is known and, in certain implementations of the present invention, may be used to identify relationships or connections between the DDID and said data subject, action, activity, process or trait. If the period of assignment of a DDID to a data subject, action, activity, process or trait ends at a discrete point in time, information concerning the time of termination of assignment is known and, in certain implementations of the present invention, may be used to identify relationships or connections between the DDID and said data subject, action, activity, process or trait.

For purposes hereof, the term "policy" may mean, without limitation, a way or ways to programmatically enforce mathematical, logical, sampling, or other functions against a data set (e.g., a data set of any number of dimensions) that is equal to or greater than enforcement mechanisms for enabling any Privacy-Enhancing Technology ("PET") including, but not limited to, public key encryption, k-anonymity, l-diversity, introduction of "noise," differential privacy, homomorphic encryption, digital rights management, identity management, suppression and/or generalization of certain data by row, by column, by any other dimension, by any combination of dimensions, by discrete cell, by any combination of discrete cells and by any combination of rows, columns, and discrete cells or any portion thereof.

For purposes hereof, the term "Non-Attributing Data Element Value" (NADEV) may mean, without limitation, the value revealed when an A-DDID is re-identified or the value which would be revealed if a given A-DDID were to be re-identified. A NADEV may be produced by creating a derived or related version or subset of one or more elements of a data set to reflect the application of one or more PETs or other privacy and/or security enhancing methodologies to the data set to limit access to all of a data set, or at least to a selected portion of the data set. For example, assuming a data set contained a value for a data subject's heart rate value of 65 beats per minute, the data's value may be generalized into two NADEVs, e.g., one that specifies, "a range of 61-70 beats per minute" and one that simply specifies, "normal"—each of which NADEVs may be independently and individually suppressed or revealed without disclosing the true data value of 65 beats per minute and without disclosing the identity of the data subject.

In another example, the method may also include causing the association between the selected DDID and the one or more data attributes to expire. In yet another example, the method may include storing, in a database accessible to the computing device, information regarding the time periods during which the selected DDID was associated with different data attributes or combinations of attributes by means of time keys (TKs) or otherwise.

In another embodiment, the method may also include re-associating the selected DDID with one or more other data attributes or attribute combinations following expiration of the association between the DDID and one or more initial data attributes.

In one example, the expiration of the DDID occurs at a predetermined time, or the expiration may occur following completion of a predetermined event, purpose or activity. In another example, the DDID may be authorized for use only during a given time period and/or at a predetermined location.

In another example, the method may include changing the DDID associated with the one or more data attribute, attribute combination and/or TDR, wherein the changing the DDID may occur on a random or a scheduled basis, or may occur following the completion of a predetermined activity purpose and/or event.

According to another aspect of another embodiment of the present invention, disclosed herein is a method for facilitating transactions over a network, wherein the method may include the operations of receiving a request, at a privacy server, from a client device to conduct activity over a network; determining which of a plurality of data attributes or attribute combinations in a database is necessary to complete the requested activity; creating or accepting a DDID; associating the DDID with the determined data attributes to create a combined temporally unique data representation (TDR); making the combined temporally unique data representation (TDR) accessible to at least one network device for conducting or initiating the requesting activity; receiving a modified temporally unique data representation (TDR) that includes additional information related to the activity performed; and storing the modified temporally unique data representation (TDR) and/or DDID-to-Data Subject association information in a memory database.

In one example, the at least one network device may include an internet service provider, a server operated by a merchant or service provider, a server operated by a mobile platform provider, or a server in a cloud computing environment.

According to another aspect of another embodiment of the present invention, disclosed herein is a method of providing controlled distribution of electronic information. In one example, the method may include receiving a request at a privacy server to conduct an activity over a network; selecting attributes of data located in a database accessible to the privacy server determined to be necessary to fulfill the request, wherein other attributes of the data which are not determined to be necessary are not selected; assigning or accepting the assignment of a DDID to the selected attributes, and/or attribute combinations to which they apply with an abstraction module of the privacy server, wherein the DDID does not reveal the unselected attributes; recording the time at which the DDID is assigned; receiving an indication that the requested activity is complete; receiving the DDID and the determined attributes and/or attribute combinations to which they apply at the privacy server, wherein the attributes are modified to include information regarding the conducted activity; and recording the time at which the conducted activity is complete and the DDID and the determined attributes and/or attribute combinations to which they apply are received at the privacy server.

In one example, the method may also include assigning an additional DDID to one or more of the selected data attributes and/or attribute combinations contained within a TDR. In another example, the method may include re-associating, using time keys (TKs) reflecting recorded times, the DDID and data attributes with the true identity of the data attributes, attribute combinations, or Data Subjects. The method may also include reassigning the DDID to other data attributes, and recording the time at which the DDID is reassigned.

According to another aspect of another embodiment of the present invention, disclosed herein is a computer-implemented method of improving data security, wherein the data comprises at least one attribute. In one example, the method may include associating at least one attribute with a DDID to create a temporally unique data representation (TDR); wherein the temporally unique data representation (TDR) limits access to data attributes to only those necessary to perform a given action, such as for example completing a purchase of goods from an online website.

In one example, the method may include assigning an association key (AK) to the temporally unique data representation (TDR), wherein access to the association key (AK) is required for authorized access to the temporally unique data representation (TDR).

In another example, the method may also include causing the association between the DDID and the at least one attribute to expire, wherein the expiration occurs at a predetermined time and/or the expiration may occur following completion of a predetermined event and/or activity. In another embodiment, the method may include re-associating the DDID with the at least one different attribute following an expiration of the association between the DDID and the at least one attribute. The method may also include storing, in a database, information regarding one or more time periods during which the DDID was associated with different data attributes or combinations of attributes as reflected by applicable time keys (TKs) or otherwise.

According to another aspect of another embodiment of the present invention, disclosed herein is a system for improving electronic data security. In one example, the system may include a module configured to dynamically associate at least one attribute with at least one Data Subject, action, activity, process and/or trait; a module configured to generate or accept DDIDs, and further configured to associate DDIDs to the at least one data attribute; a module configured to track activity related to the DDIDs, and configured to associate any additional electronic data generated by the activity to the DDID; and a module for storing the DDIDs, tracked activity, and time periods during which a DDID is used for conducting the tracked activity.

According to another aspect of another embodiment of the present invention, disclosed herein is a device for conducting secure, private activity over a network. In one example, the device may include a processor configured to execute program modules, wherein the program modules include at least a privacy client; a memory connected to the processor; and a communication interface for receiving data over a network; wherein the privacy client is configured to receive temporally unique data representations (TDRs) including DDIDs and associated data attributes necessary for conducting the activity over the network from a privacy server.

In one example, the privacy client may be further configured to capture activity conducted using the device, and to relate the conducted activity to the temporally unique data representations (TDRs). In another example, the privacy client may be configured to transmit the captured activity and temporally unique data representations (TDRs) to the privacy server. The privacy client may reside on a mobile device as a mobile application, in one example. The privacy client may reside in, and be accessible via, a network as a cloud based application, in another example. The privacy client may reside on the same computing device(s) on which the privacy server(s) resides as a local application, in another example.

In another example, the device may also include a geolocation module on a mobile device, wherein the temporally unique data representations (TDRs) are modified with information from the geolocation module, and wherein the temporally unique data representations (TDRs) restrict access to information regarding the identity of the device. The device may also include a user interface configured to allow a user to modify the temporally unique data representations (TDRs), including options to change the DDID or data attributes associated with a particular temporally unique data representation (TDR). The user interface may include selectable options for sharing the temporally unique data representations (TDR) only with other network devices within a predetermined physical, virtual or logical proximity to the mobile device.

In another example, the device may, in response to the shared temporally unique representations (TDRs), receive targeted advertising or marketing information based on the physical, virtual, or logical location of the mobile device, wherein the shared temporally unique data representations (TDRs) may in one example include demographic information, temporal information, geolocation information, psychographic information and/or other forms of information related to a user of the mobile device. In another example, the shared temporally unique data representations (TDRs) may include information related to purchase transactions made or desired to be made using the mobile device, and further comprising receiving targeted advertising or marketing information based on previous or desired purchase transactions. In this way, a vendor may nearly instantly know the relevant characteristics of nearby users and potential customers—without knowing or learning the identity of such users—so that the vendor may tailor product and service offerings specifically to the interests of nearby users and potential customers in real-time without compromising the privacy/anonymity of the users/potential customers.

According to another aspect of another embodiment of the present invention, disclosed herein is a system for providing electronic data privacy and anonymity. In one example, the system may include at least one user device having a first privacy client operating on the user device; at least one service provider device having a second privacy client operating on the service provider device; and at least one privacy server coupled to the network, the privacy server communicating with the first and second privacy clients; wherein the privacy server includes an abstraction module that electronically links data attributes and attribute combinations and separates data attributes and attribute combinations, and the abstraction module associates a DDID with the data attributes and/or attribute combinations.

In one example, the privacy server may include an authentication module that generates and/or accepts one or more of said DDIDs. In another example, the privacy server may include a maintenance module that stores a combination of the DDIDs with their associated data attributes and/or attribute combinations. In another example, the privacy server may include a verification module that verifies the integrity of data attributes, attribute combinations, and DDIDs.

In another example, the privacy server may include an access log module that collects and stores information relating to the DDIDs and the data attributes for use in one or more post-incident forensic analyses in the event of one or more errors.

In one example, the DDID expires after a predetermined time, and after expiration of the DDID, the abstraction module assigns the DDID to another data attribute and/or to another Data Subject.

According to another aspect of another embodiment of the present invention, disclosed herein are methods, computer readable media, and systems for: (i) transforming multi-dimensional data sets by technologically enforcing one or more policies (at the same or at different times) against at least one of the dimensions in a given data set or at least a subset of one of said dimensions; (ii) transforming the data sets in subsection (i) above at a time prior to, during, or subsequent to the original transformations, e.g., by creating one or more A-DDIDs; (iii) technologically enforcing policies using Just-In-Time-Identity (JITI) or other types of access control-based keys to limit access to all or a portion of a data set; (iv) applying parametric or non-parametric techniques and/or mathematical methods to enable the information in transformed data sets to be ranked or rated according to various industry-appropriate or industry-relevant value metrics; (v) enforcing one or more of privacy policies down to one or more individual "cells" of data; and/or (vi) enabling an electronic marketplace for the buying, selling, licensing, and/or other transactionalizing of policies, wherein such policies may be ranked or rated in terms of quantitative and/or qualitative measures of effectiveness in providing anonymization to the data set.

According to another aspect of another embodiment of the present invention, disclosed herein are methods, computer readable media, and systems for using artificial intelligence algorithms to analyze the schemata, metadata, structure, etc., of a data set to determine algorithmic actions that may be used to obscure, generalize, or otherwise transform the data set to comply with pre-determined privacy policies.

According to another aspect of another embodiment of the present invention, disclosed herein are methods, computer readable media, and systems for providing privacy policies "as-a-service," e.g., over a network or via an application program, to one or more users, in order to help facilitate compliance with regulatory and/or contractual restrictions in a way that helps unlock the full value of data, i.e., by enabling greater data use, while simultaneously enhancing data security and privacy.

According to another aspect of another embodiment of the present invention, disclosed herein are methods, computer readable media, and systems for providing electronic data privacy and anonymity to user information stored in a decentralized fashion, e.g., across permissionless systems or using immutable and verifiable distributed ledger technologies, such as blockchain.

Other embodiments of the disclosure are described herein. The features, utilities and advantages of various embodiments of this disclosure will be apparent from the following more particular description of embodiments as illustrated in the accompanying drawings.

BRIEF DESCRIPTION OF THE DRAWINGS

FIG. 1B illustrates different ways that assignment, application, expiration and recycling of DDIDs may occur with respect to data attributes and/or attribute combinations, in accordance with differing embodiments of the invention.

FIG. 1C-1 illustrates potential input and output flows for a system including a privacy server from the perspective of a Trusted Party, in accordance with one embodiment of the invention.

FIG. 1C-2 illustrates potential input and output flows for a system including a privacy server from the perspective of a Data Subject, in accordance with one embodiment of the invention.

FIG. 1H illustrates an example using DDIDs to effect dynamic data obfuscation in connection education related information, in accordance with one embodiment of the invention.

FIG. 1J illustrates exemplary calculated Anonymity Measurement Scores, in accordance with one embodiment of the invention.

FIG. 1K illustrates exemplary categories for the level of consent/involvement required by the Data Subject for certain calculated Anonymity Measurement Scores, in accordance with one embodiment of the invention.

FIG. 1M illustrates an example of the use of Just-In-Time-Identity (JITI)-enabled security and privacy, in accordance with one embodiment of the invention.

FIG. 1P-1 illustrates an example of the use of static anonymous identifiers.

FIG. 1P-2 illustrates an example of the use of Just-In-Time-Identity (JITI)-enabled security and privacy, in accordance with one embodiment of the invention.

FIG. 1S illustrates an example of a system for implementing Just-In-Time-Identity (JITI)-enabled security and privacy to support the OpenHealth Platform (OH), in accordance with one embodiment of the invention.

FIG. 1U illustrates an example of various data de-risking schemes, in accordance with one embodiment of the invention.

FIG. 1V illustrates an example of a marketplace for various data de-risking policies made available for purchase, in accordance with one embodiment of the invention.

FIG. 1W-1 illustrates an example of an intelligent policy compliance engine, in accordance with one embodiment of the invention.

FIG. 1W-2 illustrates an exemplary flow diagram for the use of an intelligent policy compliance engine, in accordance with one embodiment of the invention.

FIG. 1X-1 illustrates an exemplary system for offering data privacy services via a shim.

FIG. 1X-2 illustrates an exemplary system for offering data privacy services via an in-line service from a web browser, device, or other sensor.

FIG. 1Y-1 illustrates a cloud-based platform and application for offering a system to de-identify data.

FIG. 1Y-2 illustrates a cloud-based platform and application for offering a system to re-identify data that has been de-identified.

FIG. 1Y-3 illustrates a cloud-based platform and application for offering a system that integrates with Extract, Transform, and Load (ETL) applications.

FIG. 1Z-1 illustrates a decentralized network built on blockchain-based technology, wherein anonymizing privacy controls may be employed, according to one or more embodiments.

FIG. 1Z-2 illustrates a decentralized network built on blockchain-based technology, according to one or more embodiments.

FIG. 1Z-3 illustrates a decentralized network built on blockchain-based technology, wherein anonymizing privacy controls may be employed, according to one or more embodiments.

FIGS. 2-4 illustrate an example of the generation and use of a TDR, in accordance with one embodiment of the invention.

FIGS. 21 and 22 illustrate how a service provider acting as the controlling entity and providing information to various vendors, may provide to each vendor only those attribute combinations necessary to perform services assigned to it, in accordance with one embodiment of the invention.

DETAILED DESCRIPTION

Disclosed herein are various systems, methods and devices for private and secure management and use of information pertaining to one or more Data Subjects, such as persons, places or things, and/or associated actions, activities, processes and/or traits. The systems, methods and devices described herein abstract data attributes pertaining to Data Subjects and/or associated actions, activities, processes and/or traits by linking data pertaining to Data Subjects and/or associated actions, activities, processes and/or traits to independent attributes and/or dependent attributes and separating elements pertaining to Data Subjects and/or associated actions, activities, processes and/or traits into independent attributes and/or dependent attributes. DDIDs can then be associated with select data attributes or select attribute combinations, thus creating TDRs. In this manner, embodiments of the present invention can be utilized to provide data security, privacy, anonymity, and accuracy for Data Subjects such as persons, places or things and/or associated actions, activities, processes and/or traits—even for data that is stored across decentralized storage systems, e.g., in the form of an immutable, verifiable, and distributed ledger, such as is provided by blockchain technology. Various embodiments of the present invention are disclosed herein.

Dynamic Anonymity/Circles of Trust (CoT)

Dynamic Anonymity is premised on the principle that static anonymity is an illusion, and that the use of static identifiers is fundamentally flawed. The Dynamic Anonymity system dynamically segments and applies re-assignable dynamic de-identifiers (DDIDs) to data stream elements at various stages (Note: while dynamic segmentation may include time lapse, it is more likely determined by activity, location and/or subject matter) thereby minimizing the risk of information being unintentionally shared in transit, in use or at rest, while maintaining the ability of Trusted Parties— and of no others—to re-stitch the data stream elements.

Figure 1:
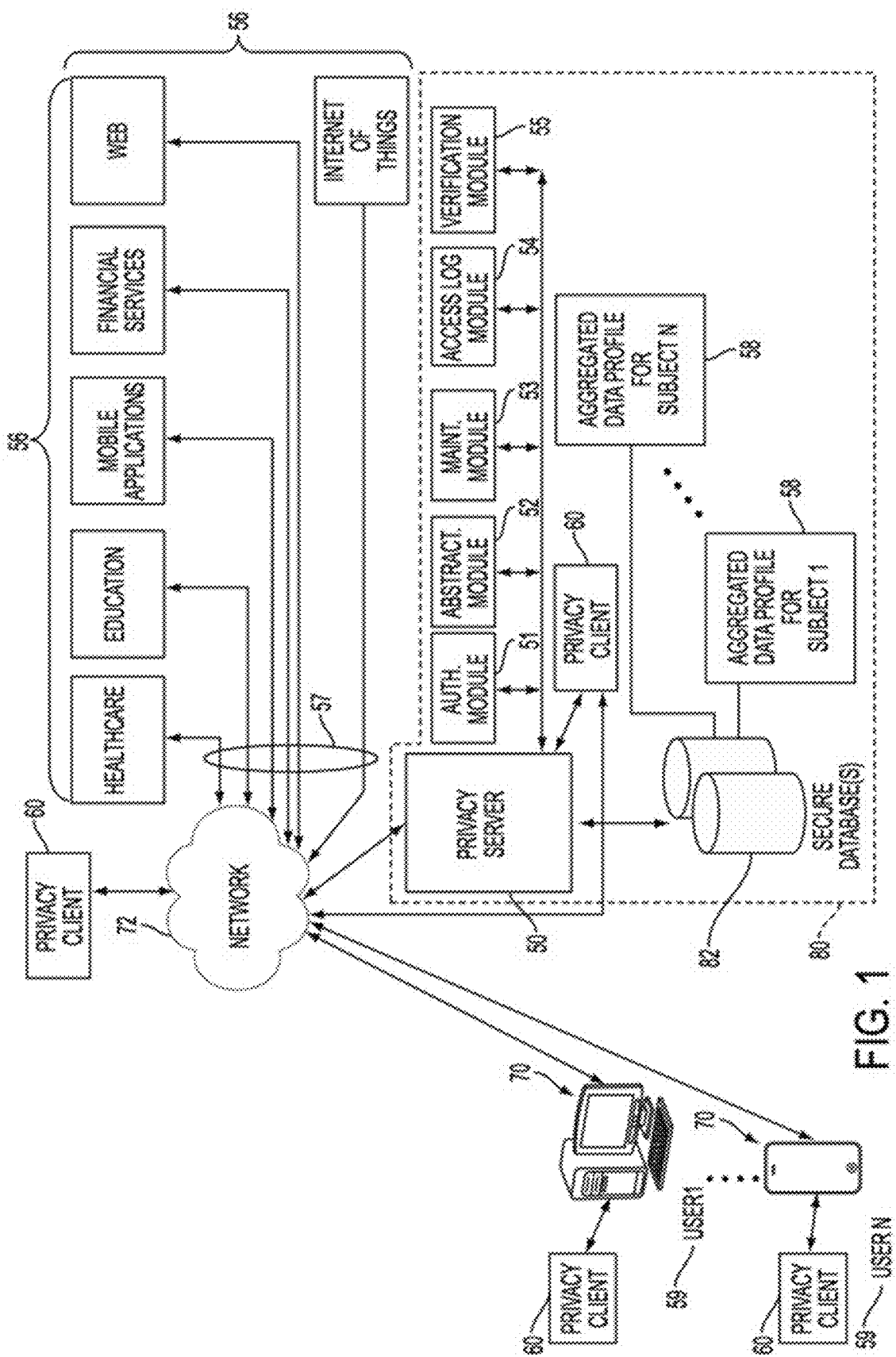
FIG. 1 illustrates an example of a block diagram of a system including a privacy server, in accordance with one embodiment of the invention.
Figure 1A:
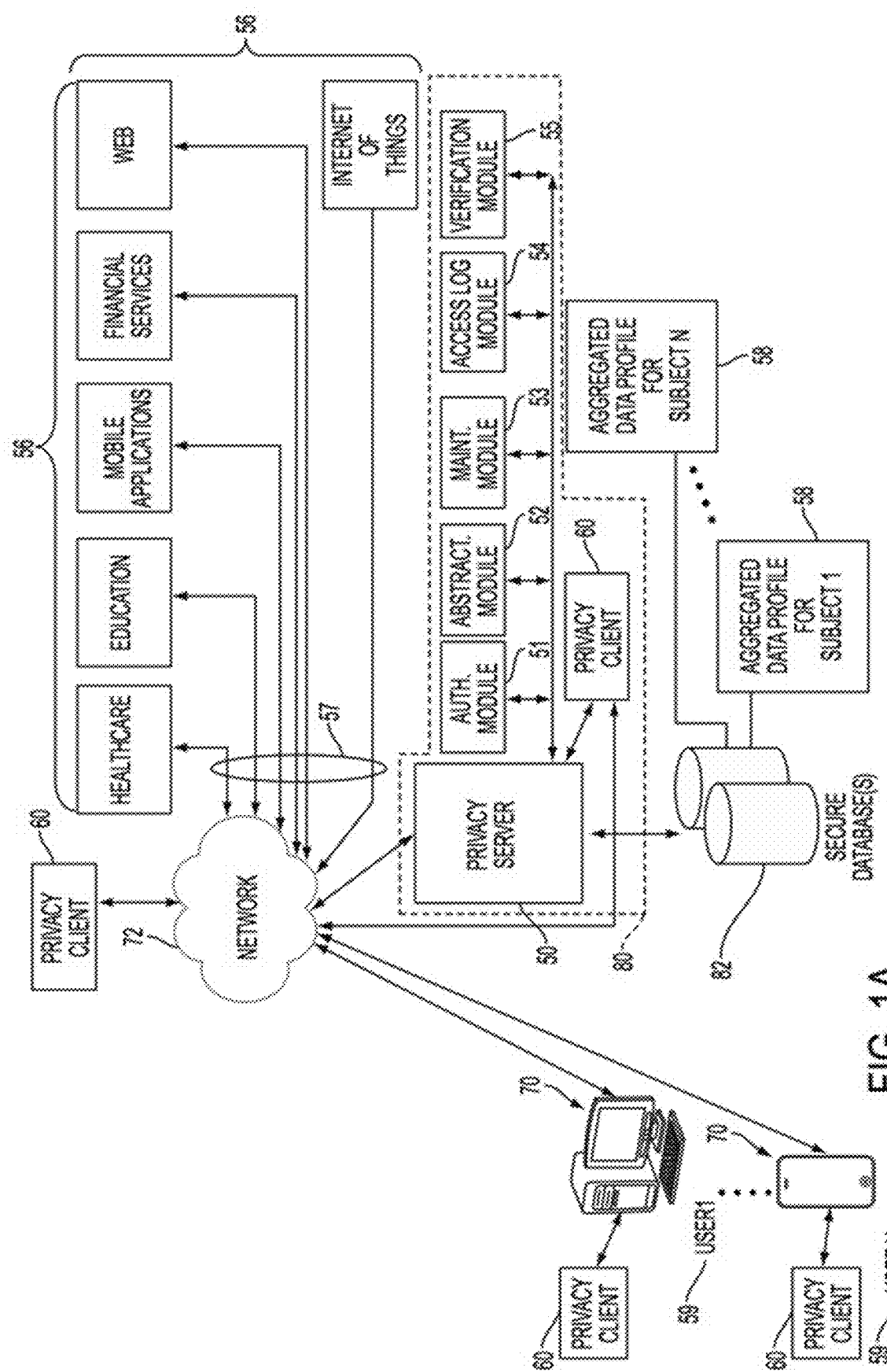
FIG. 1A illustrates an example of a block diagram of a system including a privacy server, in which the invention is offered as a service to interact with external databases in accordance with one embodiment of the invention.
Figures 1, 1C:
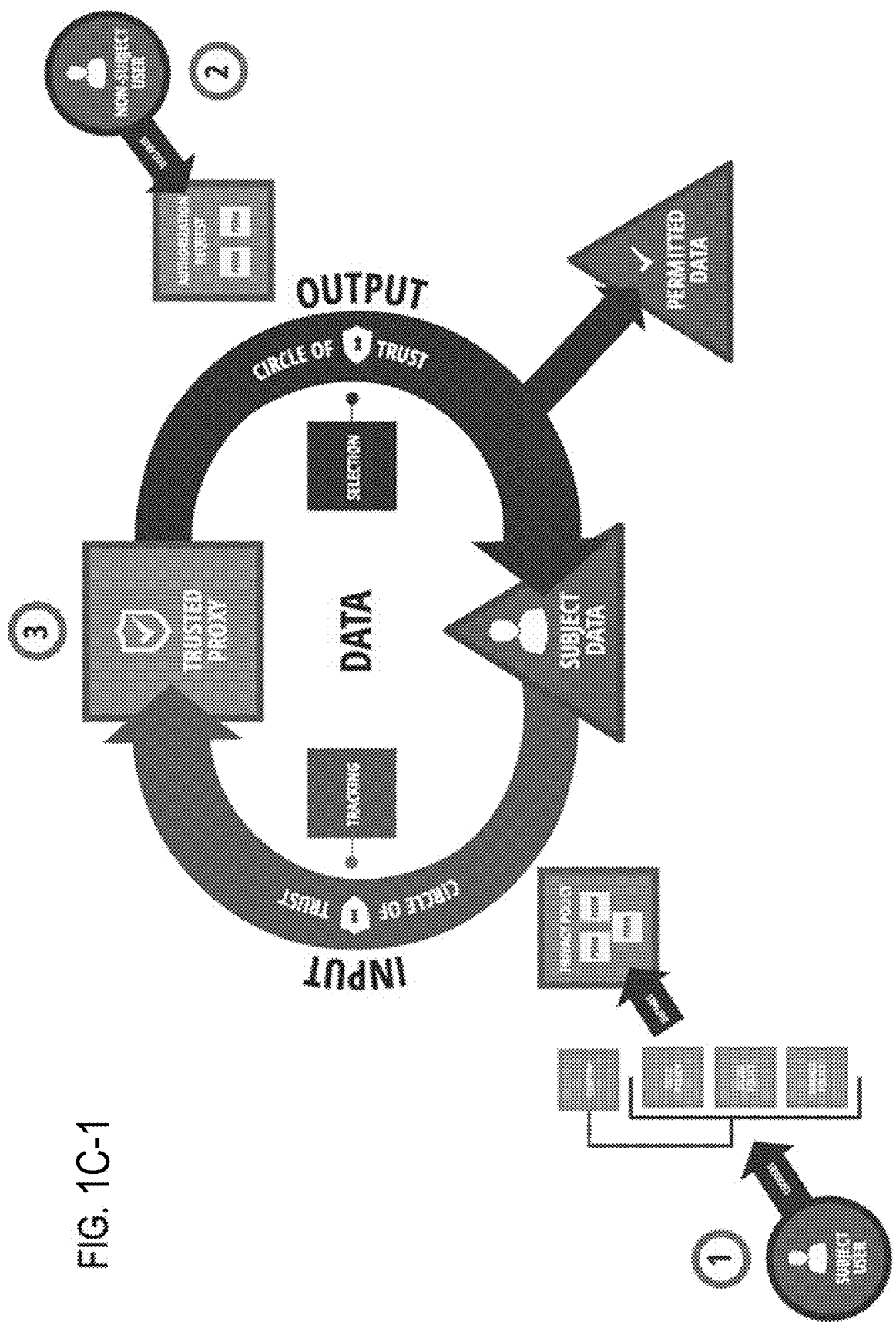

Cleartext primary keys may be used internally within a Circle of Trust ("CoT") such as shown in FIG. 1C-1 to identify Data Subjects, actions, activities, processes and/or traits; however, these keys may not be shared outside the Circle of Trust. Rather, Dynamic Anonymity uses dynamically changing and re-assignable compound keys outside of a Circle of Trust which may be comprised of: (i) a DDID; and (ii) the time period/purpose for which the DDID is associated with a Data Subject, action, activity, process and/or trait). Information regarding this association may not be made available outside of the Circle of Trust (and it may not be reconstructible if the DDID representing a connection with one or more Data Subject, action, activity, process and/or trait contains no recoverable information leading back to said one or more Data Subject, action, activity, process or trait—in each such case, the connections would be severed and are not inherently computable).

Dynamic Anonymity enhances privacy, anonymity and personal data protection capabilities in distributed platforms/fragmented ecosystems, while providing superior access to, and use of, data in accordance with policies established by, or on behalf of, Data Subjects. In this manner, everyone—including those who elect to use either closed or distributed systems—benefits from enhanced data privacy and anonymity.

Dynamic Anonymity delivers certain immediate benefits without modification to existing business and technology practices. With the use of dynamically changing and temporally unique DDIDs, current systems and processes (e.g., web browsers and data analytic engines) may not recognize relationships between and among data elements. These systems and processes can process information using existing capabilities without creating inferences, correlations, profiles or conclusions except as expressly authorized by Data Subjects and trusted parties/proxies via a Circle of Trust (CoT). However, additional significant benefits would arise from new business and technology practices that leverage specific attributes and capabilities of DDIDs, Dynamic Anonymity and/or a Circle of Trust (CoT).

Dynamic Anonymity provides benefits at four distinct points of data processing:
  A. Data Capture;
  B. Data Transmission/Storage;
  C. Data Analysis; and
  D. Data Privacy/Anonymity Control.

At each point data is protected in accordance with PERMS specified by, or on behalf of, Data Subject(s) to whom that data pertains.

A. Data Capture

In applications where a static identifier would typically be associated with capture of data pertaining to a Data Subject, Dynamic Anonymity can provide:

1. A dynamic de-identifier (or DDID) that changes over time (triggered by a lapse of time, change in purpose, temporary cessation in activity, or change in virtual or physical location) limiting the ability to track, profile or otherwise associate data with a Data Subject, action, activity, process and/or trait.

2. An association from each DDID to the applicable one or more Data Subject, action, activity, process and/or trait, stored and known only within the applicable Circle of Trust (CoT).

3. Dynamic Anonymity also offers the optional ability to store data associated with DDIDs within a CoT.

A key feature of Dynamic Anonymity is the ability to anonymize and segregate data elements at the data element level rather than at the data record level—i.e., at the level of individual data elements associated with a Data Subject, action, activity, process and/or trait rather than data elements representing the entirety or majority of information pertaining to a Data Subject, action, activity, process and/or trait. Circles of Trust retain relationship information between and among data elements and Data Subjects, actions, activities, processes and/or traits to permit re-association according to privacy/anonymity policies and/or rules established by, and/or on behalf of, Data Subjects (referred to sometimes herein as PERMS).

Example: Search Engine

Consider a person who frequently uses a particular search engine. Currently, the search engine assigns the person (via their browser) a "cookie" or other digital footprint tracker that persists for months or years, against which an ever-increasing stream of observational data (e.g. search terms, links clicked, location data) is then accumulated and, very likely, analyzed and further aggregated by multiple parties—often revealing personally identifiable information without knowing consent by the Data Subject.

Dynamic Anonymity can leverage the natural response of a search engine to create a new cookie/digital footprint tracker for each Data Subject perceived to be interacting with the search engine for the first time. Clearing history, cache, cookie/digital footprint tracker, and associated data will cause the search engine to generate a new cookie/digital footprint tracker for the Data Subject. A Circle of Trust (CoT) can store information pertaining to associations of cookies/digital footprint trackers to the Data Subject, and optionally also store a list of queries and selected links.

With this approach, the search engine would still have access to aggregate data—trending search terms, popular websites, ad clicks, etc.—but would be prevented from drawing inferences related to the Data Subject based on observational data. If/as authorized by privacy/anonymity policies and/or rules established by, and/or on behalf of, the Data Subject, the CoT could enable the search engine to perform more detailed analysis. This could be implemented using an HTTP proxy or browser extension, requiring no modification to (or cooperation from) an existing search engine.

In the past, anonymous tracking cookies were supposed to have solved the problem of how to support both privacy and analytics. However, anonymous tracking cookies failed to achieve this goal because all the data was housed together and associated with random static identifiers that made it too easy to generate information that is linked or linkable to a Data Subject ("Personal Data" or "PD"), thereby nullifying or attenuating the value of the static "anonymous" identifiers. Dynamic Anonymity overcomes these shortcomings by employing dynamically changing and re-assignable DDIDs, storing the resulting DDID associations and obscuring keys within Circles of Trust, and providing a unique interaction model enabling participation between and among Data Subjects and Trusted Parties/third-party participants.

B. Data Transmission/Storage

A CoT is composed of one or more Trusted Parties, each of which may offer one or more independent data storage facilities, as well as secure means to segment and transmit sensitive data to these data stores.

Alternatively, Dynamic Anonymity-compliant application developers could choose to only store the Data Subject-to-DDID associations within the CoT, and instead to use Dynamic Anonymity-defined procedures to obscure, encrypt, and/or segment data (or utilize Dynamic Anonymity-enabled toolkits for such procedures); allowing applications to safely store generated or collected information in their own facilities, without loss of context or business value.

In the past, analogous techniques to those employed by the present invention have been employed to:
  Segment data;
  Encrypt and obfuscate data during transmission; and
  Employ distribution, obfuscation and security during storage.

However, Dynamic Anonymity improves upon these prior approaches by:
  Employing dynamically changing and re-assignable DDIDs to obscure data at the data element (versus data record) level;
  Storing resulting DDID associations/obscuring keys within a Circles of Trust; and
  Providing a unique interaction model for enabling participation between and among Data Subjects and Trusted Parties/third-party participants.

C. Data Analysis

Traditional techniques for data "cleansing" (also referred to as data cleaning and data scrubbing) paradoxically suffer from two different and antithetical kinds of problems.

1. A given data cleansing technique can simply be ineffective. Despite earnest efforts, or even use of legally sanctioned techniques to obscure Personal Data, it may be still possible to identify the Data Subjects and Personal Data from "cleansed" data. Three famous examples:

a. In the mid-1990s, the Massachusetts Group Insurance Commission (GIC) released data on individual hospital visits by state employees in order to aid important research. Latanya Sweeney, then an MIT graduate student, purchased the Cambridge voter-registration records, and by linking the two data sets, which individually were completely innocuous, she was able to re-identify then-Massachusetts Governor Bill Weld's GIC entry despite the fact that it had been "anonymized," with all obvious identifiers, such as name, address, and Social Security number, removed.

b. In 2006, Arvind Narayanan, then a graduate student at UT-Austin, together with his advisor, showed that by linking the "anonymized" Netflix dataset to the Internet Movie Database (IMDb), in which viewers review movies, often under their own names, many Netflix users could be re-identified.

c. In 2013, a team led by Dr. Yaniv Erlich, of the Whitehead Institute for Biomedical Research, re-identified men who had participated in the 1000 Genomes Project—an international consortium to place, in an open online database, the sequenced genomes of (as it turns out, 2500) "unidentified" people—who had also participated in a study of Mormon families in Utah.

2. More effective data cleansing techniques may reduce the business value of that data—that is, many obfuscation techniques are lossy.

The Dynamic Anonymity approach to data privacy/anonymity provides a way to avoid both pitfalls, simultaneously.

D. Data Privacy/Anonymity Control

In order to protect Personal Data, Dynamic Anonymity may employ a multiple means of measuring, specifying, and enforcing data privacy/anonymity:

1. A system for determining a privacy/anonymity level for each potential kind of exposure for data associated with a Data Subject, action, activity, process and/or trait. These privacy/anonymity levels may consist of a continuum of discrete values (between the extremes of complete privacy/anonymity and complete public exposure), and/or a mathematical specification of such (an "Anonymity Measure Score" or "AMS").
2. PERMS that specify actions allowed or limited by policies regarding data. (For example: "share," "update.")
3. PERMS that associate access levels, permissions and data with each other, thus granting or denying certain levels of access to data on the basis of one or more criteria, including data type, time, organization seeking access, etc.

A Data Subject's PERMS may also be combined with, or limited by, statutory policies. (For example, medical data in the US must be protected in accordance with the US Health Insurance Portability and Accountability Act (HIPAA.)

Additionally, if allowed by the Trusted Party and with the data owner's consent, offers to modify or grant specific and limited permissions may be presented to, and accepted by, Data Subjects.

Dynamic Anonymity may also improve upon existing frameworks by using privacy/anonymity level determinations to prevent inappropriate use of data, which is obscured and only analyzed, whether from inside or outside a Circle of Trust, in a manner consistent with each Data Subject's specified privacy/anonymity levels.

Dynamic De-Identifiers (DDIDs)

A dynamic de-identifier DDID is a temporally-bounded pseudonym which both refers to and obscures the value of (i) a primary key referencing a Data Subject, action, activity, process and/or trait, (ii) the value of an attribute of that Data Subject, action, activity, process and/or trait (e.g. a ZIP code), and/or (iii) the kind or type of data being associated with the Data Subject, action, activity, process and/or trait (e.g. the fact that some encoded value was a ZIP code).

DDIDs may additionally protect data if there is no discernable, inherent, nor computable relationship between their content and the values (cleartext) to which they refer. Additionally, the association between any given DDID and its cleartext value may not be exposed outside the Circle of Trust (CoT). Unlike static identifiers, an obscured value or key need not have the same associated DDID when used in a different context, for a different purpose, or at a different time.

DDIDs can be either generated within the Circle of Trust, or if the above criteria are satisfied, external IDs can be used as DDIDs.

DDIDs are Time-Bounded

As mentioned, DDID associations are temporally-bounded, by which we mean that, even within the same context, and with regard to a single type of data (e.g. ZIP code), a particular DDID may refer to one value at one time, but may (if desired) also refer to another value at a different time.

This necessarily implies that in order to decode or expose the meaning of a particular DDID, an application must also retain knowledge of the time to which that DDID applied.

This knowledge may be explicit—that is, the assignment time may also be part of the record or document in which the DDID was stored—or it may be implicit—for example, an entire data set may have been obscured as a batch, and presumed (regardless of how long processing actually takes) to have occupied the same instant—and thus have only one consistent set of DDID mappings per field type. In order to reconstitute such data, one would also need to supply some reference to the corresponding set of DDID/value associations (stored within the CoT).

DDIDs are Purpose-Bounded

Note that DDIDs are also bounded by context or purpose—meaning the same DDID can recur in multiple contexts, even at the same time. For example, consider a stream of records, each of which contain a Social Security Number (SSN) and ZIP code, and which all occupy a single time block. In such a case, a particular DDID may be used both as a replacement for a ZIP code, and also as a replacement for an SSN.

As above, this implies that some indication of that context (e.g. was this a ZIP code or SSN?) will be necessary to obtain the cleartext to which that DDID referred.

Replacing Data with DDIDs

Consider the task of replacing a single stream of data—the same kind of data (e.g. ZIP codes or SSNs), occupying the same time block—with DDIDs. A (Java-like) "pseudo-code" description of an Application Programming Interface (API) that carries out such behavior in one potential embodiment of the invention might look like this:

```
interface DDIDMap {
    DDID protect(Value cleartext);
    Value expose(DDID ddid);
}
```

In English, "interface" means that we're defining a collection of functions (named "DDIDMap") that operate on the same underlying data. Data types are here denoted with initial upper-case letters (e.g. "DDID"), and variable or function parameter names are denoted with initial lower-case letters (e.g. the "cleartext" function parameter must be data of type "Value"—where "Value" is just a stand-in for any kind of data which can be obscured: IDs, quantities, names, ZIP codes, etc.).

One function, "protect( )", accepts some cleartext value and returns a corresponding DDID. If that value has been seen previously, its previously-assigned DDID will be returned. If it has not been encountered before, a new DDID (so-far unique to this data set) will be generated, associated with that value, and then returned.

The other function, "expose( )", reverses this process: when a DDID is passed to it, it looks up and returns the cleartext value, which was previously encoded as that DDID. If the given DDID has never been seen before, it fails with an indication of error.

The data managed by these operations, then, is a two-way mapping from each cleartext value to the DDID that replaced it, and from the DDID back to the original value.

Note that although we've said that a given DDID can only refer to a single value, it is possible, if desired, to implement a variant version of this algorithm that allows a value to be associated with more than one DDID.

Managing DDID Maps by Time and Purpose

Recall that the above bidirectional DDID-to-value map operates (i) upon a single kind of data (that is, having the same type, context, and purpose), and (ii) within the same time block. In order to support operations across multiple times and contexts, we can posit another potential API which gives us the an appropriate DDID-to-value map for a given time and purpose:

```
interface DDIDMapManager {
    DDIDMap getMap(Context context, Time time);
}
```

Here, "context" is (or emits) a key that refers to a particular kind of data being obscured. (Elsewhere in this document, sometimes also called the "association key" or "A_K".) For example, the context might be the name of the table and column in which data to be obscured will reside (e.g. "employee.salary"). It could also include other non-other chronological indications of purpose or scope.

The "time" parameter indicates the instant at which the DDID is being (or was) associated with its cleartext value. Since DDID-to-value maps span a block of time, and there are many time instances within a block, this implies there exists some function (used internally, within this API, thus not shown above) that finds the time block associated which each given time. (More on this in a moment.)

DDID Generation and Time-Blocking Strategies

Note that different kinds of data can employ different DDID replacement strategies. In addition to those mentioned in the next two sections, DDIDs can vary in size, whether they're universally unique or just unique to that data set (or time block), what kind of encoding they use (e.g., integers or text), etc. And although DDID generation should typically be random, one might also wish to employ deterministic or pseudo-random DDID generators for demonstration, testing, or debugging purposes.

Unique or Reused DDIDs

One potential strategy may allow a particular DDID to be assigned to two different Data Subjects in the same context, but during two different time blocks. For example, within the same collection of time-anchored records, the DDID "X3Q" might at one moment (in one time block) refer to (for example) "80228", and later (in another time block), "12124". (We'll call this strategy "DDID reuse.")

An alternative is to disallow such "reuse"—and stipulate that a given DDID, in the same context, can only refer to a single Subject. (Although the subject may still receive different DDIDs over time.)

The choice between these two strategies involves a tradeoff between increased obscurity and the ease with which one may perform aggregation queries on obscured data.

Imagine we wish to count patients per postal code. If postal codes DDIDs are unique, we can aggregate counts per DDID, and then ask the CoT to finish the query by resolving those DDIDs to their corresponding postal codes, and aggregating again. But if we have "reused" DDIDs, then we must send the entire list of DDIDs and corresponding times to the CoT for resolution (and aggregation)—because we can't be sure that two instances of the same DDID refer to the same value.

DDID Time Blocks

Implementations also have freedom to choose different strategies for segmenting DDID maps by time. Blocks of time may vary by size and/or time offset; sizes can be fixed, random, or determined by number of records assigned per time. (Note that employing an infinite-sized time block (for a given context) gives behavior equivalent to using "static" identifiers.)

Implementation

Although there may be many strategies for creating new DDIDs, the API for generating such DDIDs may look (essentially) identical, regardless of which strategy is implemented "under the hood".

For example:

```
interface DDIDFactory {
    DDID createDDID( );
}
```

Next, consider the task of determining what time block was associated with a given DDID assignment. Since a time block can contain many instances of time, we'll need some kind of a "time key" (sometimes abbreviated "T_K" in elsewhere in this document) to each time block. This implies the need for a function to obtain the appropriate key for any time instant:

TimeKey timeKey=getTimeKey(Time time);

Further, note that both time-blocking and DDID-generation strategies depend upon the kind of data which are being obscured. In short, they are both associated with a given "context" (which includes or implies a notion of data type and usage), meaning that the "Context" API must offer at least one function supporting each:

```
interface Context {
    TimeKey getTimeKey(Time time);
    DDIDFactory createDDIDFactory( );
}
```

Given these two additional functions, we can imagine that the implementation of "getMap( )" in "DDIDManager" (shown previously) may look something like this:

```
DDIDMap getMap(Context context, Time time) {
    TimeKey timeKey = context.getTimeKey(time);
    DDIDMap map = getExistingMap(context, timeKey);
    if (map was not found) then
    DDIDFactory factory = context.createDDIDFactory( );
    map = createMap(factory);
    storeNewMap(context, timeKey, map);
    endif
    return map;
}
```

Here, "getExistingMap( )" is some function that finds the map assigned to the given context and time key, "create Map( )" creates a map which will use the given DDID factory, and "storeNewMap( )" associates a newly-created map with the context and time key by which it will be retrieved later.)

Using Context to Obscure Data and Attribute Types

Dynamic Anonymity may define the following different kinds of data to be protected: (i) primary keys which refer to Data Subjects, actions, activities, processes and/or traits (e.g. employee ID), (ii) attribute data associated with, but not unique to, Data Subjects, actions, activities, processes and/or traits (e.g. employee postal code), and (iii) the indication of a disassociated (obscured) data element's type, itself (an "association key", or "A_K").

Each of these can be achieved by defining a different context: first we'll discuss (i) and (ii), which are both achieved by obscuring data values (replacing them with "replacement key" DDIDs, abbreviated as "R_K" elsewhere). We will address (iii) the indication of a disassociated (obscured) data element's type, below.

Consider a trivial example: an order table recording which customers bought products on a given day. Each record has a day number, a customer ID, and a product ID. We want to obscure this data for use or analysis by some third party, who is outside the CoT. In particular, we wish to obscure the customer and product IDs, but leave the day numbers intact.

To do so, we could create two "Context" instances: one for "Customer ID", and one for "Product ID". Although DDIDs, should ideally be random, for our purposes, let's assume that our "DDIDFactory" will create integer DDIDs sequentially, starting from 0. Further, assume that each DDID map spans only three days, so after three days, a new set of DDID mappings will be used. This also implies that DDIDs will be "reused"—the same DDID can refer to different values when used different blocks. (This is not an ideal encoding strategy and is used here only for illustration purposes.)

TABLE 1 Show Some Cleartext Sample Data:

TABLE 1

| Day | Customer ID | Product ID |
| --- | --- | --- |
| 1 | 500 | ZZZ |
| 2 | 600 | XXX |
| 3 | 600 | YYY |
| 4 | 700 | TTT |
| 5 | 500 | YYY |
| 6 | 600 | TTT |

After being obscured (as specified above), this data would look as shown in TABLE 2 below:

TABLE 2

| Day | Customer ID | Product ID |
| --- | --- | --- |
| 1 | 0 | 0 |
| 2 | 1 | 1 |
| 3 | 1 | 2 |
| 4 | 0 | 0 |
| 5 | 1 | 1 |
| 6 | 2 | 1 |

To understand this, you read down each column, and think in groups of three days (the first time block of DDIDs covers, for each obscured field, days 1-3, and the second covers 4-6).

For the first three days, customer ID is: 500, 600, 600. The resulting encoding is: 0, 1, 1 (note that 600 is repeated, so its DDID, 1, is also repeated.)

For the second three days, customer ID is: 700, 600, 500. And (starting over from 0), the result is: 0, 1, 2 (note that 500 was 0 before, now it's 2).

Product ID uses a separate context, and thus stream of DDIDs, so it also starts from zero:

For the first time block (XXX, YYY, TTT) becomes (0, 1, 2). For the second time block (TTT, YYY, TTT) becomes (0, 1, 0).

Another "Context" could be employed to obscure the indication of a disassociated (obscured) data element's type (iii above), where the column names are examples of Attribute Keys (A_K)). This could be done using one DDID-to-value mapping for the whole set (effectively substituting DDID for the column names), or in time blocks (as with the other fields in this example) such that (if an appropriately random DDID generation strategy were employed) the affected records could not be analyzed without the assistance of the Circle of Trust.

Notes on Locality and Time

The example APIs defined above presume that when data is encoded, the encoding time is passed with each datum or record. This is only necessary when DDIDs are being "reused" within the same context (and thus time is needed to discriminate between the two potential meanings of that DDID). When a DDID is only assigned to one value per context, that DDID is sufficient to discover the (single) original value.

Time could also become an issue where "reused" DDIDs are being employed across different systems, which might have slightly different notions of time. If it is not possible to pass the time associated with a DDID encoding, a (chronological) "buffer" could be employed to prevent a DDID from being re-used too close to its original assignment. And when it is possible to pass the time associated with the data to be encoded, the time could be "sanity-checked" against the local system clock: skew within a small window (smaller than the DDID reuse buffer) could be tolerated, whereas larger differences would trigger an error report.

Finally, note that there is also flexibility regarding where data is being encoded: data could be streamed to a machine residing within the CoT, and then sent along to its destination after encoding. But, alternatively, the encoding portions of the above algorithms could be run outside the Circle of Trust, provided that the resulting DDID-to-value associations were (a) not stored on the local host, and (b) safely (e.g. using encryption, and with appropriate safeguards against data loss) streamed to a CoT host for persistence, lowering latency in critical applications.

Dynamic Anonymity: De-Identification without De-Valuation

"De-identification" techniques traditionally used in certain circumstances (e.g., HIPAA or health related circumstances) to protect data privacy/anonymity may be largely defensive in nature—e.g., a series of masking steps is applied to direct identifiers (e.g., name, address) and masking and/or statistically-based manipulations are applied to quasi-identifiers (e.g., age, sex, profession) in order to reduce the likelihood of re-identification by unauthorized third parties. This approach may result in a trade-offs between protecting against re-identification and retaining access to usable information.

Dynamic Anonymity may have significant offensive value in that the value of information can be retained and leveraged/exploited for authorized purposes, all with a statistically insignificant risk of re-identification of any datum. Dynamic Anonymity may reject the proposition and traditional dichotomy that, in order to minimize risk, one must sacrifice the value of information content. Instead, Dynamic Anonymity may minimize both risk and the amount of information lost, enabling most—if not all—of it to be recovered, but only upon authorization by the Data Subject/Trusted Party, not by unauthorized adversaries/"black hat" hackers.

Dynamic Anonymity may uniquely enable information to be used in different ways by multiple parties in a controlled environment that facilitates unlocking and maximizing the value of data. Dynamic Anonymity may maximize the value of potential business intelligence, research, analysis and other processes while simultaneously significantly improving the quality and performance of data privacy/anonymity processes.

When collected or stored, sensitive data may be "disassociated" from its subject using one or more of the following strategies, none of which incurs any loss in value:

1. Segmentation: Sensitive data may be split into several pieces, by data type, and transmitted and/or stored separately (either in separate Circles of Trust, or using different DDID mapping sets maintained by the same Trusted Party) so that each piece, alone, yields no Personal Data.
2. ID replacement: Static identifiers can be replaced with dynamically changing and re-assignable DDIDs obscuring the relationship between data and the Data Subject to which that data refers.
3. Obscuring: data values and data type indicators may also be replaced with DDIDs.

The DDIDs associated with these operations are stored within a Circle of Trust (CoT) as shown in FIG. 1C-1; the original data may thus be reconstituted by reversing these transformations, but only with the cooperation of the CoT itself, and thus only when granted such permissions by, and/or on behalf of, the Data Subject.

FIG. 1 illustrates an example of an embodiment of the invention, including a system having a privacy server 50 or privacy server module which securely manages various data attributes and data attribute combinations (which may include but are not limited to behavioral data, transaction histories, credit ratings, identity information, social network data, personal history information, medical and employment information, and education history) relating to a Data Subject for use in different applications 56. These applications 56 may include, but are not limited to:

Healthcare Applications
    Medical Records
    Mobile Applications
    Real-time Critical Care Applications
    Regulatory Compliance (e.g., HIPAA)
    Research
    Education Applications
    Student Records
    Research
    Mobile Applications
    Geolocation (Beacons, GPS, Wi-Fi Fingerprinting)
    Mobile Payment and Loyalty
    Financial Service Applications
    Banking, Brokerage, etc.
    Payment Processing
    Payment Card Industry (PCI) Security
    Authorization
    Verification of card holder status
    Regulatory Compliance
    Research
    Credit assessment
    Fraud detection
    Web Applications
    Ad serving
    Content review
    E-commerce
    Social networks
    'Internet of Things' Applications
    Telematics
    Smart Grid
    Smart Cities
        Traffic Monitoring
        Utility Monitoring
            Power
            Fuel
            Water/Sewage
        Waste Management
    Smart Offices
    Smart Factories
    Smart Homes
        Connected Entertainment
            TV
            Streaming Devices
        Automation
            HVAC
            Lighting
        Security
            Window/Door Locks
            Fire/Smoke/Carbon Monoxide Detectors
        Appliances
    Smart Vehicles
    Agriculture-Field Sensors
    Wearable Devices
        Healthcare Monitoring
        Fitness devices
        Eyewear
        Clothing
    Drones
    Private Wireless/Wired Networks
    Crop Sensors
    Tagged Animal Tracking
    Troop Movements
    Private Security Applications
    E-Commerce Applications
    Offline Retail Applications
    Human Resources/Hiring Applications
    Governmental Applications
    National Security Applications
        Analysis of call detail records
        Analysis of web browsing behavior
        Analysis of online and offline purchasing behavior
        Analysis of travel behavior
        Analysis of social media activity
        Analysis of circles of friends, acquaintances and other relationships
    Attorney/Law Firm Applications
    Maintaining of confidentiality/attorney-client privilege
    E-Discovery
    Consumer Contest Entry Applications
    Dating Applications
    Gambling and e-Wagering Applications FIG. 1A illustrates an example of an embodiment of the invention, including a system having a privacy server 50 or privacy server module which receives electronic data from one or more external databases 82 and securely converts various data attributes and data attribute combinations from such one or more external data bases (which may include but are not limited to behavioral data, transaction histories, credit ratings, identity information, social network data, personal history information, employment information, medical and education history) relating to a Data Subject into TDRs for use in different applications. Alternatively, applications store only Data Subject-to-DDID association information within the privacy server 50 and use Dynamic Anonymity-defined procedures to obscure, encrypt, and/or segment data stored in external databases 82. In this manner, Data Subject-to-DDID association information stored within the privacy server 50 could provide greater context and/or business value to information generated, collected and/or stored in external databases 82.

In one example, embodiments of the invention may form a secure and comprehensive aggregated data profile 58 of a Data Subject for use in one or more applications 56. A Data Subject or related party thereto, e.g., user 59, may anonymously communicate or selectively disclose the Data Subject's identity and/or data attributes from the Data Subject's aggregated data profile 58 (comprised of data attributes, attribute combinations or portions thereof, potentially from unrelated data sources) to vendors, service providers, advertisers or other entities with whom the Data Subject or related party is interested in communicating 57 via a network 72 (for instance, to possibly receive services or enter into a purchase transaction) based on one or more of the Data Subject's characteristics as expressed in the Data Subject's aggregated data profile 58 (comprised of data attributes, data attribute combinations or portions thereof, potentially from unrelated data sources). In this manner, embodiments of the invention provide for digital rights management for individuals ("DRMI") referring to a Data Subject, a related party or a third party managing data attributes and data attribute combinations pertaining to a Data Subject or digital rights management for de-identification ("DRMD") comprised of a third party managing data attributes and data attribute combinations associated with one or more Data Subjects. In one example, the extent to which information regarding the data attributes, data attribute combinations, Data Subjects and/or related parties may be made available to other parties may be controlled by embodiments of the present invention.

In the examples of FIG. 1 and FIG. 1A, a plurality of users 59, for example Data Subjects or service providers, utilize devices such as smart devices 70 (e.g., wearable, mobile or immobile smart devices), smartphones, tablets, notebooks, desktop computers, wired or wireless devices, or other computing devices running a privacy client application 60 to access a network 72 such as the Internet. As shown in FIG. 1 and FIG. 1A, a system 80 is illustrated which is coupled with and in communication with the Internet or other public or private network, and the system may include a privacy server 50 securely coupled with one or more databases 82. In one example, the privacy server 50 may be implemented using computer program modules, code products, or modules running on a server or other computing device. The one or more databases 82 may be implemented using any conventional database technology, including technology that securely stores data (such as through encryption) in redundant locations such as but not limited to RAID storage devices, network attached storage, or any other conventional databases.

In one example, the privacy server 50 implements one or more of the operations, processes, functions or process steps described herein, and the privacy server 50 may include or be configured to include other operations, functions or process steps as desired depending upon the particular implementation of the invention, including but not limited to the following processes, operations or functions performed by the indicated modules:

An authentication module 51 that may provide for both internal and external authentication including the following processes:

a. Internal authentication of privacy client 60 requests for TDRs, and privacy server 50 generation of TDRs.

b. External authentication before allowing participation in desired actions, activities, or processes and use of TDRs to authenticate recipients as approved to receive Time Keys (TKs), Association Keys (AKs) and/or Replacement Keys (RKs) as may be necessary to unlock contents of TDRs.

c. One example implementation of the authorization module may include allowing delegation of the ability to request generation of DDIDs and associated TDRs to other parties authorized by the controlling entity.

An abstraction module 52 that may provide internal and external abstraction that may include one or more of the following processes:

a. Selecting DDIDs by means of generating unique DDIDs or accepting or modifying temporally unique, dynamically changing values to serve as DDIDs.

b. Associating DDIDs with data attributes or attribute combinations to form TDRs for given Data Subjects, actions, activities, processes or traits.

c. Including only a portion of relevant data attributes in TDRs thereby disassociating the data attributes pertaining to a Data Subject and/or relevant for a given action, activity, process or trait.

d. Replacing one or more of data attributes contained in one or more TDRs with DDIDs.

e. Replacing with DDIDs one or more references to external networks, internets, intranets, and/or computing devices that may be integrated, or communicate, with one or more embodiments of the present invention.

A maintenance module 53 that may store:

a. TDR information pertaining to Data Subjects, actions, activities, processes or traits, "Pertinent Data" (defined as data initially associated with a DDID and/or data aggregated with a DDID during and/or following the time period of association) and/or DDIDs; and b. Key information pertaining to (a) Time Keys (TKs) reflecting information regarding the time periods during which each DDID was associated with a particular Data Subject, attribute, attribute combination, action, activity, process or trait, (b) Association Keys (AKs) and/or (c) Replacement Keys (RKs);

Thereby allowing the TDRs to be later re-associated with a particular attribute, attribute combination, action, activity, process, trait and/or associated Data Subject. In addition, the maintenance module may perform further analysis and processing of attributes, or attribute combinations in a secure environment.

An access log module 54 that may include collecting and storing information to enable post-incident forensic analysis in the event of system error and/or misuse.

A verification module 55 that may include validating and verifying the integrity of aggregated data profiles including data attributes, attribute combinations, DDIDs, and TDRs at any point in time.

As described herein, embodiments of the present invention are directed to promoting privacy, anonymity, security, and accuracy in relation to electronic data and network communication, analysis and/or research. In one example, data elements pertaining to Data Subjects, actions, activities, processes or traits may be abstracted by linking data elements pertaining to the Data Subject, action, activity, process or trait to independent attributes or dependent attributes and/or separating data elements pertaining to the Data Subject, action, activity, process or trait into independent attributes or dependent attributes. For purposes of this disclosure, a data attribute may refer to any data element that can be used, independently or in combination with other data elements, to identify a Data Subject, such as a person, place or thing, and/or associated actions, activities, processes or traits.

As mentioned above, in addition to abstracting data that may be used to identify Data Subjects such as a person, place or thing, the abstraction module 52 of FIG. 1 or FIG. 1A may also be used to abstract data related to Data Subjects such as things which may include, but are not limited to: physical or virtual things and entities; hardware or virtual devices; software applications; legal entities; objects; images; audio or video information; sensory information; multimedia information; geo-location information; privacy/anonymity information; security information; electronic messaging information including senders and receivers, message content, hyperlinks in messages, embedded content in messages, and information relating to the devices and servers involved in sending and receiving the messages; social media and electronic forums; online websites and blogs; RFID (radio frequency identification); tracking information; tax information; educational information; identifiers related to military, national defense, or other government entity programs; virtual reality information; massively multiplayer online role-playing games (i.e., MMORPGs); medical information; biometric data; behavior metric information; genetic information; data referring to the physical or virtual location of other data; and instantiations or representations of data or information.

The systems, methods and devices described herein may be used in one example to provide digital rights management for an individual (DRMI) and/or digital rights management for de-identification (DRMD). Digital rights management for an individual may comprise individual directed privacy/anonymity wherein a related party manages data attributes pertaining to one or more related parties. In this situation, the related party would serve as the controlling entity. Alternatively, a third party may manage data attributes pertaining to one or more related parties thereby comprising entity directed privacy/anonymity. In this situation, the third party would serve as the controlling entity. Digital rights management for de-identification also comprises entity directed privacy/anonymity, wherein a third party manages data attributes associated with data attributes associated with related parties, and controls the extent to which information regarding the data attributes and/or related parties is made available to other parties.

The systems, methods and devices disclosed herein may be used to provide DRMI such that one or more related parties, directly or indirectly, may manage their online digital fingerprint of data. The related parties may also control the extent to which information pertaining to data attributes, Data Subjects or one or more related parties is made available to third parties, such that the information and data may be made available in an anonymous, non-re-identifiable manner. The systems, methods and devices provide a dynamically changing environment in which related parties may want to share data at one moment but not at the next moment. This is done with the understanding that the time intervals, specific receiving entities, physical or virtual whereabouts, or other mechanisms that trigger changes in the data to be shared may be dynamic in nature. Implementing DRMI enables non re-identifiable anonymity, and may allow for different information pertaining to data attributes, Data Subjects and related parties to be shared for different purposes on a dynamically changing, time and/or place sensitive, case-by-case basis. Particular needs with respect to information pertaining to data attributes, Data Subjects or related parties at specific times and places may be accommodated without revealing additional, unnecessary information, unless such revealing is authorized by the controlling entity. Additional, unnecessary information may be, for example, the true identity of the Data Subject or related party, mailing addresses, email addresses, previous online actions, or any other information not necessary for an unrelated party with respect to a specific action, activity, process or trait with respect to a Data Subject or related party.

The systems, methods and devices disclosed herein may be used to provide DRMD such that entities may centrally manage the online digital fingerprint of information pertaining to data attributes, Data Subjects and related parties for which they are responsible; and such entities may control the extent to which information is made available to other parties in a non-re-identifiable versus identifiable manner. This allows the entity to satisfy de-identification objectives and/or obligations to comply with desires of Data Subjects, related parties and regulatory protections and prohibitions.

Example implementations of some embodiments of the invention can be configured to provide DRMI and/or DRMD capabilities with regard to data attributes comprised of images or video files revealing identifying facial characteristics are discussed below. A Data Subject or related party may benefit from others being able to make inferences about identity based on unique facial characteristics of the Data Subject in an electronic image. However, the rapidly expanding commercial availability and use of facial recognition technologies combined with the growing availability of electronic images pose issues with regard to privacy/anonymity and security of Data Subjects and related parties. In one example, privacy/anonymity and security can be safeguarded using one or more aspects of the present disclosures, with respect to Data Subjects and related parties, in the context of data attributes that are photos including facial images and characteristics of Data Subjects.

In some embodiments, the systems, methods and devices disclosed herein can be configured to distinguish between the status of parties as registered/authorized versus nonregistered/unauthorized visitors to a website or other electronic image-sharing application containing a data attribute. A distinction may also be made between registered/authorized visitors to a website or other photo sharing application containing data attributes pertaining to contacts/friends of a Data Subject or related party versus not contacts/friends of a Data Subject or related party depending on the status of a party. In one example, a system of the present invention may control whether any image data attribute is presented containing facial features. If an image data attribute is presented containing facial features, the system may further control and limit unauthorized use and copying of photos that can lead to unintended secondary uses through additional protection techniques. In addition, some embodiments of the present invention may provide Data Subjects, related parties and controlling entities with the ability to designate which additional parties and for which specific purposes the image data attribute may be presented at all. If the data attribute is presented, the Data Subjects, related parties or controlling entities may designate whether the image makes use of known protection techniques aimed at limiting unauthorized use and copying of photos, thereby preventing or reducing the risk of unintended secondary uses of the image.

DRMI may enable Data Subjects and related parties, directly or indirectly, to manage photos containing facial images and control the extent to which photos pertaining to the related parties are made available to third parties in an identifiable, non-identifiable, reproducible or non-reproducible manner.

An example of a potential implementation of the present invention may involve use of DRMI by a provider of wearable, implantable, embeddable, or otherwise connectable computing technology/devices to mitigate potential public concern over information obtained and/or processed using the technology/device. For example, GOOGLE® could adopt DRMI to facilitate wider adoption of GOOGLE GLASS® by establishing a do-not-digitally-display-list (analogous to the do-not-call-list maintained by the FTC to limit undesired solicitation calls to individuals) that enables Data Subjects or related parties to register to prohibit the digital display of unauthorized photos taken using or displayed by GOOGLE GLASS®. (GOOGLE® and GOOGLE GLASS® are trademarks of Google, Inc.)

DRMI provided by one example of the present invention may further provide a Data Subject or related party who is a member of the professional networking site LinkedIn.com with a feature to manage the extent to which photos are made available to third parties in an identifiable, non-identifiable, reproducible or non-reproducible manner. Access to, use of, and copying of photos containing facial images of a Data Subject or related party may be controlled using, in one example, a three-tiered categorization schema:

Category A treatment or status may apply to visitors to the LinkedIn.com website who are not registered/authorized members of LinkedIn.com. These visitors may be provided no means to view or copy photos containing facial images of registered/authorized LinkedIn® (LinkedIn® is a trademark of LinkedIn Corporation.) members. Instead, they may be served via their web browser, mobile application or other application a graphic, image, indicator or avatar that indicates photos are available only to registered/authorized users of the LinkedIn.com website.

Category B treatment or status may apply to registered/authorized members of LinkedIn.com who are not authenticated contacts of a registered/authorized member of LinkedIn.com. By using additional protection techniques aimed at limiting unauthorized use and copying of photos that can lead to unintended secondary uses, these registered/authorized members may be provided with limited means to view or copy photos containing facial images of LinkedIn® member with regard to whom they are not an authenticated contact. These additional protection techniques may include but are not limited to:
 1. Tiling to divide an image into smaller image tiles that will appear as a continuous image but are limited to only one tile piece at a time with respect to any entity endeavoring to copy the image;
 2. Employing image watermarking techniques;
 3. Hiding layers to place an image containing facial characteristics behind a transparent foreground image;
 4. Providing images without a color profile or palette;
 5. Preventing downloads through table instructions that disable 'right click' copying or use of images;
 6. Preventing downloads through JavaScript technology that disables 'right click" copying or use capabilities images;
 7. Preventing downloads through Flash technology that disables 'right click" copying or use capabilities images;
 8. Hiding images by URL encoding techniques images;
 9. Using META tags to prevent images containing facial features from being indexed by search engine spiders, robots or bots images; and
 10. Using Robot.txt files to prevent images containing facial features from being indexed by search engine spiders, robots or bots images.

Category C treatment or status may apply to registered/authorized members of LinkedIn.com who are also authenticated contacts of another registered/authorized member of LinkedIn.com. These registered/authorized members may be provided with full means to view or copy photos containing facial images of the other LinkedIn® member.

DRMD may be provided by some example of the present invention such that entities can centrally manage photo data attributes containing facial images for which they are responsible and can control the extent to which the photo data attributes are made available to other parties in an identifiable, non-identifiable, reproducible or non-reproducible manner.

One example of a potential implementation of the present invention may involve use of a system providing DRMD by a controlling entity that leverages known facial image recognition capabilities to limit disclosure of elements by parties who are not authorized by a Data Subject or related party of a photo data attribute which contains recognizable facial elements of said registered/authorized Data Subject or related party to view the facial elements. Rather, a party who tries to upload, use or view a photo that includes facial elements of a registered/authorized Data Subject or related party whose facial characteristics are registered with the DRMD system, but which party has not been authorized by the registered/authorized Data Subject or related party, may see and be able to use only a modified version of the photo altered by the DRMD system to block out or 'de-tag' the recognizable facial elements of the registered/authorized Data Subject or related party. For example, a picture taken at a public bar that includes the face of a Data Subject or related party registered with a system providing DRMD may be modified to block out or 'de-tag' the face of the related party on all versions of the photo except those as explicitly authorized by the Data Subject or related party.

In one example of the present invention, the authentication module can be configured so that decisions as to who sees what information are determined by a controlling entity on a configurable basis. In one example, the configurable control may include automatic and/or manual decisions and updates made on a timely, case-by-case manner by providing each controlling entity with the ability to dynamically change the composition of information comprised of data attributes at any time. The enhanced customization achieved by dynamically changing the composition of data attributes leads to greater relevancy and accuracy of information offered pertaining to a data attribute and/or related party. As disclosed herein, use of DDIDs as a component of privacy, anonymity and security enables each recipient entity receiving information to receive different information as appropriate for each particular purpose, thereby fostering the distribution of fresh, timely and highly relevant and accurate information, as opposed to stale, time burdened, less accurate accretive data such as provided via conventional persistent or static identifiers or other mechanisms.

FIG. 1 and FIG. 1A also illustrate various examples of privacy clients 60 operating on user devices 70 such as computers, smartphones or other wired or wireless devices, wherein the user devices may communicate with the privacy server 50 over a network 72 such as the Internet or other public or private network.

In one example, a privacy client component of the present disclosure may be resident on a mobile device. The privacy client may be provided as part of a mobile application or operating system running on the mobile device, or may be configured as a hardware device, integrated circuit or chip of a mobile device. Mobile devices implementing one or more aspects of the present disclosure may possess real-time knowledge of location, activity and/or behavior with respect to Data Subjects and/or related parties pertaining to the device. The mobile device may also transmit, receive and process information with other devices and information sources. Mobile applications interacting with the privacy client may provide the controlling entity with control over both the timing and level of participation in location and time sensitive applications, and the degree to which information is shared with third parties in an anonymous—rather than personally identifiable—manner. Mobile devices implementing one or more aspects of the present disclosure may also leverage the unique capabilities of mobile devices to aggregate a user's personal preference information gathered from across a variety of unrelated and disparate sources (whether they be mobile devices, more traditional computer systems or a combination of both) and—only with the users' approval—share a user's information (on an anonymous or personalized basis) with vendors to facilitate time- and/or location-sensitive personalized commercial opportunities. As may now be understood more clearly, users may determine whether the benefits of such time- and/or location-sensitive personalized commercial opportunities justify identifying themselves in connection with the transactions.

For example, without embodiment of the invention, static identifiers conventionally associated with a mobile device may enable mobile application providers and other third parties to aggregate information pertaining to use of the mobile device; and by aggregating the data on use of the mobile device, application providers and other third parties may obtain information which may include but not be limited to information related to the device user's frequent physical locations, calling habits, content preferences, and online transactions that they could not obtain through data from any one time interaction with the device user. Through the use of some embodiments of the present invention, application providers and other third parties would be prevented from aggregating information pertaining to use of a mobile device by Data Subjects and related parties; and some embodiments of the present invention may be configured to provide a mobile device with use mobile applications requiring access to geolocation information (e.g., direction or map applications), without revealing the identity of the mobile device, Data Subject or related party by means of dynamically created, changeable and re-assignable DDIDs described herein; rather than conventional static identifiers.

In one example, embodiments of the present invention may be configured to provide enhanced privacy, anonymity, security and accuracy over persistent and/or static identifiers, and by leveraging DDIDs rather than aggregate on a static identifier; thereby, embodiments of the present invention can provide a solution to online digital fingerprints being left across networks and internets. As a result, embodiments of the present invention may provide a controlling entity with the ability to decide who sees what data, prevent data aggregators from understanding data connections pertaining to a Data Subject or related party without the controlling entity's permission, and provide control to the controlling entity over upstream and/or downstream dissemination of information.

In one example of the present invention, continued access may be provided for the benefits of big data analytics by using DDIDs to provide multiple protective levels of abstraction. Systems, methods and devices embodying some aspects of the present invention also do not suffer from the fundamental flaws of Do-Not-Track and other initiatives that eliminate access to the data required for effective big data analytics and that are inconsistent with economic models offering free or discounted products or services in return for information. Do-Not-Track is a technology and policy proposal that enables Data Subjects or related parties to opt out of certain tracking by websites and third party data collecting entities as they are online, including analytics services, advertising networks, and social platforms. Although Do-Not-Track provides Data Subjects and related parties with enhanced privacy, anonymity and security, it denies them the benefits of receiving customized, personally relevant offerings while online through big data analytics. This impacts the economic benefits that big data analytics provides to merchants, service providers, and Data Subjects or related parties themselves.

In contrast, some embodiments of the present invention may have a net neutral to positive revenue impact (versus the net negative revenue impact of Do-Not-Track initiatives), because with some embodiments of the present invention, a controlling entity may include data attributes in TDRs that enable recipient entities to use existing tracking technology to track TDRs for the duration of their existence. The controlling entity may also include information that is more accurate than available via tracking alone to facilitate personalization and customization. For example, a controlling entity may elect to include certain data with regard to past browsing sessions on a website in the attribute combinations pertaining to a Data Subject or related party that are sent via a privacy client to that website, augmented with other specific more up-to-date information beneficial to both the website and the Data Subject or related party.

Referring to FIG. 1 and FIG. 1A, one embodiment of the present invention may comprise a computer network 72 in which one or more remote privacy clients 60 comprised of computer hardware, firmware or software resident on one or more computing devices 70 or resident on and accessible via a network device send requests/queries to, and receive services/responses from, one or more computing devices that act as privacy servers 50. Privacy client computing devices 70 may comprise smart devices (i.e., wearable, movable or immovable smart devices), smartphones, tablets, notebook computers, desktop computers, or other computing devices with programs that (i) enable requests for services from, and/or submission of queries to, privacy servers, (ii) provide user interface capabilities, (iii) provide application processing capabilities, and/or (iv) offer localized storage and memory. Privacy server 50 computing devices may comprise large personal computers, minicomputers, mainframe computers or other computing devices with programs that (i) respond to requests for services/queries from privacy clients, (ii) provide centralized or decentralized administration of the system, (iii) provide high-volume application processing capabilities, and/or (iv) offer high-volume storage and memory capabilities integrated with one or more databases. Privacy servers 50 may also be configured to perform one or more of the operations or features described herein. Communications capabilities between and among privacy servers and privacy clients may be comprised of computer networks, internets, intranets, public and private networks or communication channels, and supporting technologies.

Referring to FIG. 1 and FIG. 1A, another potential embodiment of the present invention may comprise a computer network in which one or more remote privacy clients 60 comprised of computer hardware, firmware or software resident on one or more computing devices 70 or resident on and accessible via a network device-send requests/queries to and receive services/responses from, one or more computing devices that act as privacy servers 50 wherein said privacy servers 50 may transmit via the Internet, internets, intranets or other networks electronic information to cards, mobile, wearable and/or other portable devices that may include means of electronically receiving and storing information, wherein said cards, mobile, wearable and/or other portable devices contain information pertaining to data attributes and/or DDIDs until such time, if any, as said information pertaining to data attributes and/or DDIDs is modified by said privacy servers.

The privacy servers and privacy clients may implement modules including program code that carry out one or more steps or operations of the processes and/or features described herein. The program code may be stored on a computer readable medium, accessible by a processor of the privacy server or privacy client. The computer readable medium may be volatile or non-volatile, and may be removable or non-removable. The computer readable medium may be, but is not limited to, RAM, ROM, solid state memory technology, Erasable Programmable ROM ("EPROM"), Electrically Erasable Programmable ROM ("EEPROM"), CD-ROM, DVD, magnetic cassettes, magnetic tape, magnetic disk storage, other magnetic or optical storage devices, or any other conventional storage technique or storage device.

Privacy servers and associated databases may store information pertaining to TDRs, time periods/stamps, DDIDs, attributes, attribute combinations, Data Subjects, related parties, associated profiles and other related information. Privacy servers and associated databases may be managed by and accessible to the controlling entity, but, in one example, not by other parties unless authorized by the controlling entity. In one example, an authentication module of one or more privacy servers controls access to data through the TDRs. Privacy clients may request information from privacy servers necessary to perform desired actions, activities, processes or traits and/or query privacy servers whether TDRs are authorized to participate with respect to a requested action, activity, process or trait at a particular time and/or place. Privacy clients may also aggregate data with respect to actions, activities, processes or traits in which TDRs associated with the privacy client engage, such as tracking data, obviating the need to return to the database for data extrapolation. Insights gleaned by other parties may become part of a TDR for its duration, in one example.

In one example implementation of the invention, the abstraction module 52 is configured such that a controlling entity (which may be the Data Subject or a related party) links data pertaining to a Data Subject to attributes and/or separates data pertaining to a Data Subject into attributes that can be divided, combined, rearranged, or added into various attribute combinations. These combinations may contain any combination of attributes or previously created attribute combinations associated with the Data Subject.

In this example with regard to each intended action, activity, process or trait involving the privacy server, the abstraction module in one example enables the controlling entity to limit the degree of identifying information transmitted or stored by selecting from among the attributes only those that are necessary with respect to a desired action, activity, process or trait and linking those data attributes to one or more attribute combinations and/or separating those data attributes into one or more attribute combinations. The controlling entity may then use the abstraction module to dynamically create and/or assign a DDID to form a TDR for each attribute combination. The DDID may be configured to expire after preset delays or cues, and may be re-used for data associated with another action, activity, process or trait and/or other Data Subjects or related parties, thereby leaving no precise trail of association outside of the privacy server. In one example, before assigning or accepting a DDID to form a TDR, the abstraction module may verify that the DDID is not actively being used in another TDR. In order to make this verification, an additional buffer timeout period may be included to address potential outages and system down time. The greater the number of data attributes and associated TDRs generated with respect to a desired action, activity, process, or trait, the greater the privacy, anonymity, and security achieved. In this situation, an unauthorized party gaining access to one of the TDRs would gain access to only that information contained in the TDR. In one example, the information in a single TDR may be only a fraction of the attributes necessary with respect to the desired action, activity, process, or trait, and further does not provide the information necessary to determine other TDRs containing necessary attributes, or to determine any Data Subjects and/or related parties that may be associated with the TDRs.

In one example, the creation of TDRs by means of the abstraction module may be based on one or more processes that match prescribed steps necessary to describe or perform different actions, activities or processes with specified categories of attributes associated with the steps, and selecting or combining those attributes necessary with respect to the particular action, activity, process or trait. The process of creating TDRs by means of the abstraction module may be performed directly by the controlling entity or indirectly by one or more parties authorized by the controlling entity.

For example, a first database containing credit card purchasing information may include information necessary for a credit card issuer to conduct big data analytics on the purchasing information. However, the database need not include identifying information for the users of the credit cards. Identifying information for the users of the credit cards could be represented in this first database by DDIDs, and the Replacement Keys (RKs) necessary to associate the DDIDs with the users could be stored in a separate secure database accessible to a privacy server and/or system modules. In this manner, the system may help protect the identity of credit card users and limit potential financial loss in the event of unauthorized entry into the first database containing credit card purchasing information because the DDIDs and related information would not be decipherable to unauthorized parties.

In addition, in one example of the present invention, real-time or batch analysis of data from mobile/wearable/portable devices can be performed in a manner that would be beneficial to receiving entities, such as merchants or service providers, without sacrificing the privacy/anonymity of the users of the mobile/wearable/portable devices. Each user may be considered a related party to the mobile/wearable/portable device in question as well as the Data Subject associated with the device itself or use of the device. In return for special offers or other concessions proffered by receiving entities, users of the mobile/wearable/portable devices could elect to have non-identifying TDRs shared in an anonymous fashion based on the users' real-time location, real-time activities, or during a particular temporal period, e.g., with receiving entities that are located within a prescribed distance of a particular geographic location (e.g., 1 mile, 1000 feet, 20 feet, or other distance depending upon the implementation) or within a prescribed category (e.g., jewelry, clothes, restaurant, bookstore, or other establishment) with respect to the location of the mobile/wearable/portable device. In this manner, receiving entities could have an accurate aggregated view of the demographics of their potential customer base—in terms of age, gender, income, and other features. These demographics may be revealed by TDRs shared by the mobile/wearable/portable device users at different locations, times of the day and days of the week that may help receiving parties more effectively determine what services, desired inventory and other sales, supply chain, or inventory-related activities to offer with regard to related parties. In one example, Data Subjects and related parties, which may be the users of the mobile/wearable/portable devices, would benefit from special arrangements or offers without ever having to reveal their personal information to the receiving entities (who would simply know that a Data Subject or related party was registered, but would not know what specific information to associate with any particular Data Subject or related party) unless and only to the extent desired by the Data Subject or related party.

In one example implementation of the invention, the authorization module can provide the controlling entity with control over which other entities may be provided access to, or use of, TDR information. The controlling entity may further use the abstraction module to control the degree to which the other entities have access to specific elements of information contained in the system. For example, a mobile/wearable/portable platform provider serving as the controlling entity may provide performance data to a mobile/wearable/portable device manufacturer without having to reveal the identity of the device, Data Subject or related party user or location of the device, Data Subject or related party user. The mobile/wearable/portable platform provider may also provide a mobile/wearable/portable application provider with geolocation data necessary for a mobile/wearable/portable device to use a mapping or other application without having to reveal the identity of the device, Data Subject or related party user. Conversely, the mobile/wearable/portable platform provider may use the system to provide an emergency 911 system with location and identity data pertaining to the device as well as the Data Subject or related party user of the device. One example implementation of the authorization module may include allowing delegation of the ability to request generation of DDIDs and associated TDRs to other parties authorized by the controlling entity.

According to one example implementation of the present invention, receiving entities could use information regarding mobile/wearable/portable device related parties to customize user experiences or opportunities at locations where related parties gather, without requiring that personal identifying information be revealed. For example, a band that plays both country-western and gospel music could, in real-time or near real-time, determine that the majority of related parties attending the concert preferred gospel music and adjust their song selection for the concert accordingly by receiving TDRs related to the Data Subjects or related parties that are concert attendees. Similarly, in stores using video screens to display merchandise or special offers, store management could know in real time when they have a large presence of customers of a particular demographic in the store by receiving and analyzing TDRs associated with Data Subjects or related parties that are customers from clients in mobile/wearable/portable devices. The store could then play videos targeted to that particular demographic, and change the videos throughout the day in response to changes in the demographics of Data Subjects or related parties as communicated to the store system via clients in mobile/wearable/portable devices. The demographics obtained from information in the TDRs may include, but are not limited to, age, gender, or level income of Data Subjects or related parties. Similarly, in retail stores using real-time geolocation to identify a given customer's specific location in the store, special discounts or offers could be made to a customer that is a Data Subject or related party via their mobile phone, tablet or wearable device by receiving and analyzing TDRs associated with the Data Subject or related party's personal tastes, brand preferences and product buying preferences, where such TDRs would also include exogenous information added in real-time based on the products available to that Data Subject or related party at the location in the store at which they are present.

In one example implementation of the invention, the abstraction module of the privacy server assigns DDIDs to attribute combinations necessary to fulfill requests by and/or queries from privacy clients that may reside in numerous locations including but not limited to on Data Subject devices, on service provider devices, accessible via and reside in a cloud network, or reside on the same computing device as the privacy server thereby creating TDRs for the period of the association between the DDID and the desired attribute combinations. The TDR in a privacy client may interact freely with a recipient entity for the configured time, action, activity, process or trait. Once a period of interaction with a designated recipient entity is completed, the privacy client may in one example return the TDR augmented by attribute combinations pertinent to activity of the privacy client to the privacy servers and associated databases. The privacy server may then associate various attribute combinations back with particular Data Subjects, as well as update and store the attribute combinations in the aggregated data profile for the Data Subject in the secure database(s). At this time, the DDID assigned to the attribute combinations may be reassigned with respect to other actions, activities, processes or traits, or Data Subjects to continue obfuscation of data relationships, in one example.

Other implementations of the invention are contemplated herein, including various systems and devices. In one embodiment, disclosed herein is a system for improving electronic data security. In one example, the system may include an abstraction module configured to dynamically associate at least one attribute with at least one Data Subject; an abstraction module configured to generate DDIDs or accept or modify temporally unique, dynamically changing values to serve as DDIDs, and further configured to associate DDID with the at least one Data Subject; a maintenance module configured to track activity related to the DDIDs, and configured to associate any additional DDIDs, tracked activity, and time periods during which a DDID is used for conducting the tracked activity by means of time keys (TKs) or otherwise. In one example, the abstraction module is configured to add or delete attributes associated with the at least one Data Subject, and the abstraction module may be configured to modify attributes already associated with the at least one Data Subject.

In another implementation, disclosed herein is a device for conducting secure, private, anonymous activity over a network. In one example, the device may include a processor configured to execute program modules, wherein the program modules include at least a privacy client module; a memory connected to the processor; and a communication interface for receiving data over a network; wherein the privacy client that may reside on a Data Subject device, on a service provider device, accessible via and reside in a cloud network, or reside on the same computing device as the privacy server is configured to receive TDRs including DDIDs and associated data attributes necessary for conducting the activity over the network from a privacy server. In one example, the privacy client may be further configured to capture activity conducted using the device, and to relate the conducted activity to the TDRs. In another example, the privacy client may be configured to transmit the captured activity and TDRs to the privacy server. The privacy client may reside on a mobile device as a mobile application, in one example. The privacy client may reside in, and be accessible via, a network as a cloud based application, in another example. The privacy client may reside on the same computing device(s) on which the privacy server(s) resides as a local application, in another example.

In another example, the device may also include a geolocation module, wherein the TDRs are modified with information from the geolocation module, and wherein the TDRs restrict access to information regarding the identity of the device. The device may also include a user interface configured to allow a user to modify the TDRs, including options to change the DDID or data attributes associated with a particular TDR. The user interface may include selectable options for sharing the TDRs only with other network devices with a predetermined physical, virtual or logical proximity to the mobile device.

In another example, the device may receive, in response to TDRs, targeted advertising or marketing information based on the physical, virtual, or logical location of the device; wherein the TDRs include demographic information related to a user of the device, and further comprising receiving targeted advertising or marketing information based on demographic information. In another example, the TDRs may include information related to purchase transactions made or desired to be made using the device, and further comprising receiving targeted advertising or marketing information based on previous or desired purchase transactions.

In another implementation of the invention, disclosed herein is a system for providing electronic data privacy and anonymity. In one example, the system may include at least one user device having a first privacy client operating on the user device; at least one service provider device having a second privacy client operating on the service provider device; and at least one privacy server coupled to the network, the privacy server communicating with the first and second privacy clients; wherein the privacy server includes an abstraction module that electronically links Data Subjects to data attributes and attribute combinations and separates data into data attributes and attribute combinations, and the abstraction module associates a DDID with the data attributes and attribute combinations. In one example, the privacy server may include an authentication module that generates one or more of said DDIDs. In another example, the privacy server may include a maintenance module that stores a combination of the DDIDs with their associated data attributes and attribute combinations. In another example, the privacy server may include a verification module that verifies the integrity of data attributes, attribute combinations, and DDIDs. In another example, the privacy server may include an access log module that collects and stores information relating to the DDIDs and the data attributes for use in one or more post-incident forensic analysis in the event of an error. In one example, the DDID expires after a predetermined time, and after expiration of the DDID, the abstraction module assigns the DDID to another data attribute or Data Subject.

FIG. 1B highlights some examples of how assignment, application, expiration and recycling of DDIDs may occur. It should be noted that, in the context of potential implementations of embodiments of the present invention, DDIDs may exist forever but be reused for multiple Data Subjects, data attributes, attribute combinations, actions, activities, processes and/or traits. While a DDID may be reused, two of the same DDIDs may not be used simultaneously unless so desired and authorized by the controlling entity. Reassignment of DDIDs may be accomplished by utilizing existing capabilities of data collection and analysis to reassign DDIDs to similar attribute combinations or Data Subjects, or to distinctly different attribute combinations or Data Subjects. This reassignment enhances the privacy/anonymity and security viability of the dynamically created and changeable digital DDIDs.

As indicated in FIG. 1B, the system may be configured such that the assignment, expiration and/or recycling of any given DDID may occur based on any one or more of the following factors: (1) change in the purpose for which a DDID (and associated TDR) was created, e.g., association with a specific browsing sessions, Data Subject, transaction, or other purpose; (2) change in the physical location associated with a DDID (and associated TDR), e.g., upon exiting a physical location, upon arrival at a general physical location, upon arrival at a specific physical location, upon entering a physical location, or some other indicia of physical location; (3) change in the virtual location associated with a DDID (and associated TDR), e.g., upon entering a virtual location, upon changing a virtual location, upon exiting a virtual location, upon arrival at a specific page on a website, upon arrival at a specific website, or some other indicia of virtual location; and/or (4) based on temporal changes, e.g., at randomized times, at predetermined times, at designated intervals, or some other temporally based criteria. As may be appreciated, DDIDs separate data from context because, external to the system, there is no discernable relationship between Pertinent Data, the identity of a Data Subject or related party or Context Data associated with different DDIDs and/or TDRs. Internal to the system, relationship information is maintained for use as authorized by Data Subjects and trusted parties/proxies.

FIG. 1C-1 represents the concept of a Circle of Trust (CoT) from the perspective of a trusted party or trusted proxy (indicated in FIG. 1C-1 as "Trusted Proxy" and referred to herein as "Trusted Proxy" and/or "Trusted Party.") Note first that the Data Subject is included on the diagram at the bottom left. Diagrams of most current data use systems do not include Data Subjects since participation by Data Subjects generally takes the form of a binary decision whether to agree to "take-it-or-leave-it" online terms and conditions using the traditional "notice and consent" model. After that initial point, the Data Subject typically loses all power to affect what happens to their data since "they are the product, not the customer." It is well acknowledged that this is a broken model for the digital age and provides few effective limitations on current or future use of data.

Figures 1, 1C, 2:
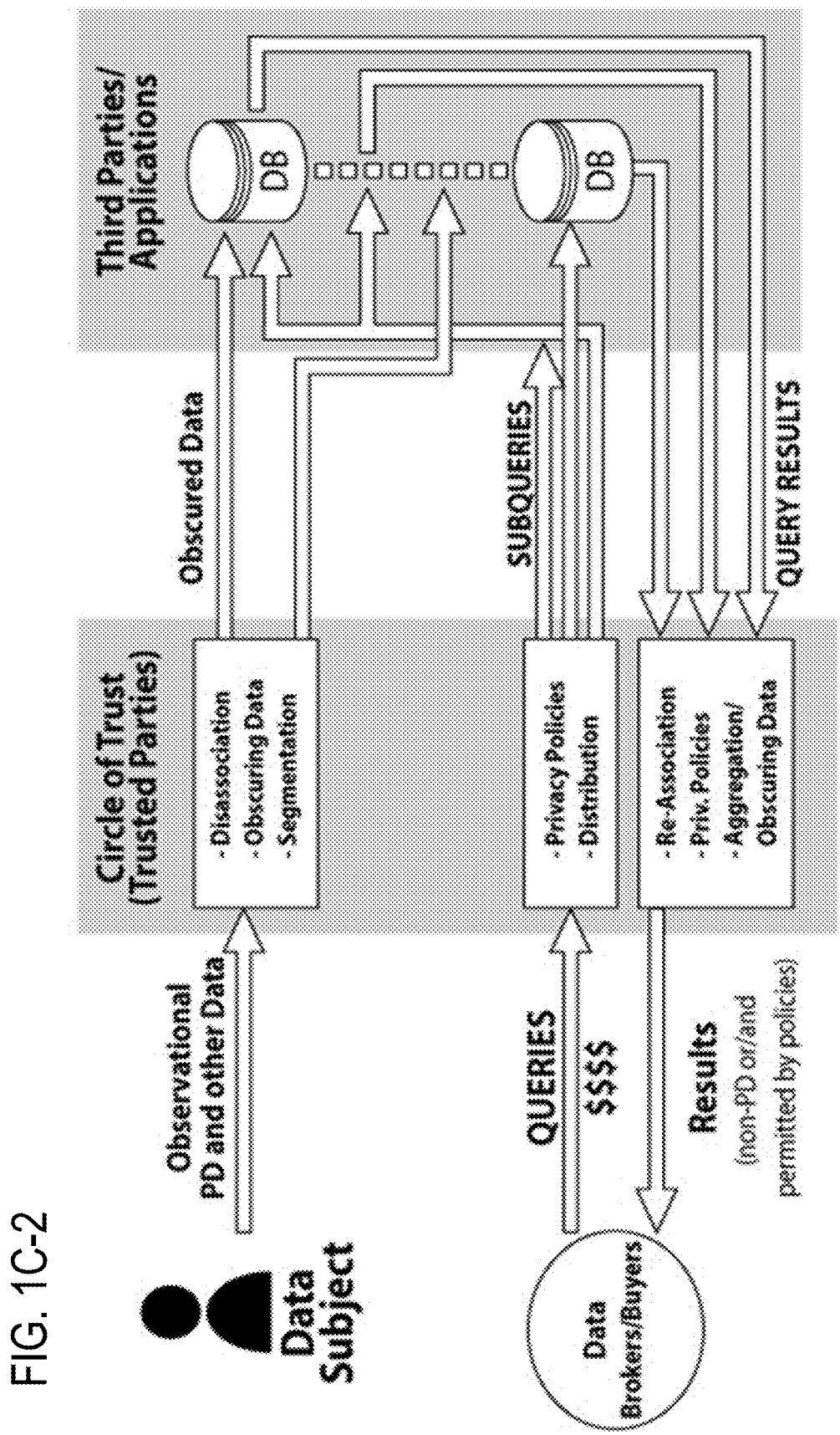

It should be noted that there may be more than one Trusted Party working cooperatively in connection with a single Circle of Trust and that Data Subjects may be participants in any number of Circles of Trust. Circles of Trust can be implemented by means of a centralized or federated model for increased security. Arrows in FIG. 2 represent data movement; data inputs and outputs will contain different information.

FIG. 1C-1 shows a data process flow for two potential embodiments of the invention. In a first example embodiment of the invention, a user (1) may indicate that they are interested in using the system to create data inputs regarding a specific Data Subject, (in this example, the user is the Data Subject) by forming one or more TDRs (each TDR may initially be comprised of a DDID intended to collect and retain data attributes associated with activity involving the TDR or comprised of a DDID together with data attributes or attribute combinations retrieved from the Data Subject's aggregated data profile) to participate, in this example embodiment, in the desired action of web browsing. Data associated with web browsing engaged in by the one or more TDR may be tracked and collected by the system and transmitted to a controlling entity serving as a trusted party or trusted proxy (3). The TDRs reflecting the tracked data collected in connection with the web browsing would represent output from web browsing which the controlling entity serving as a trusted party may select to augment the aggregated data profile of the user/Data Subject. In a second example embodiment of the invention, a user (2) may indicate that they are interested in using the system to create a privatized/anonymized version of a data set that the user has which contains personal information about Data Subjects (1). In this example, the data set of the user containing personal information about Data Subjects may serve as input to the system. The system may identify and track the data values contained in the data set reflecting personal information and the processing performed by the controlling entity serving as a trusted party or trusted proxy (3) may select said personal information to be replaced with DDIDs that require access to one or more Replacement Keys (RKs) to re-identify the personal information about Data Subjects. In this example, the resulting modified data set would represent output from the system containing dynamically changing DDIDs in lieu of personal information about Data Subjects. In this manner, the RKs could be altered in the future so that access to personal information about any one or more Data Subject may no longer be re-identified so the applicable Data Subject(s) have the "right to be forgotten," i.e., they can remove their digital traces from the Internet.

As shown in the boxes labeled "Privacy Policy" and "Authorization Request" in FIG. 1C-1, data use may be managed by "Users" in accordance with permissions ("PERMs") managed by trusted parties and/or proxies. "Users" may be the Data Subjects themselves who are the subject of the data in question (e.g., users, consumers, patients, etc. with respect to their own data—for purposes hereof, "Subject Users"); and/or third parties who are not the subject of the data in question (e.g., vendors, merchants, healthcare providers, lawfully permitted governmental entities, etc.—for purposes hereof, "Non Subject Users").

PERMs relate to allowable operations such as what data can be used by whom, for what purpose, what time period, etc. PERMS may also specify desired anonymization levels such as when/where/how to use DDIDs in the context of providing anonymity for the identity and/or activities of a Data Subject, when to use other privacy-enhancing techniques in connection with, or in lieu of, DDIDs, when to provide identifying information to facilitate transactions, etc.

In a Data Subject implementation of the present invention (e.g., DRMI), Subject Users may establish customized PERMS for use of their data by means of pre-set policies (e.g., Gold/Silver/Bronze—note that this is only an example, and that mathematically, this could be a discrete set of k choices or it could be represented by a value on a continuum between a lower- and an upper-bound) that translate into fine-grained dynamic permissions or alternatively could select a "Custom" option to specify more detailed dynamic parameters.

In a "stewardship" implementation of Dynamic Anonymity (DRMD), Non Subject Users may establish PERMs that enable data use/access in compliance with applicable corporate, legislative and/or regulatory data use/privacy/anonymity requirements.

Within the CoT reflected in FIG. 1C-1 based on PERMS, business intelligence, data analysis and other processes may be performed by means of any combination or interpolation of I, D, T and/or X with regard to one or more Data Subjects, as shown in TABLE 3 below:

TABLE 3

| "I" | "D" | "T" | "X" |
|---|---|---|---|
| Identifier for Data Subject | Value of Assigned Dynamic De-Identifier | Time period of association between I and D | Pertinent Data during T |

FIG. 1C-2 shows a Circle of Trust (CoT) from a Data Subject perspective.

Figure 1D:
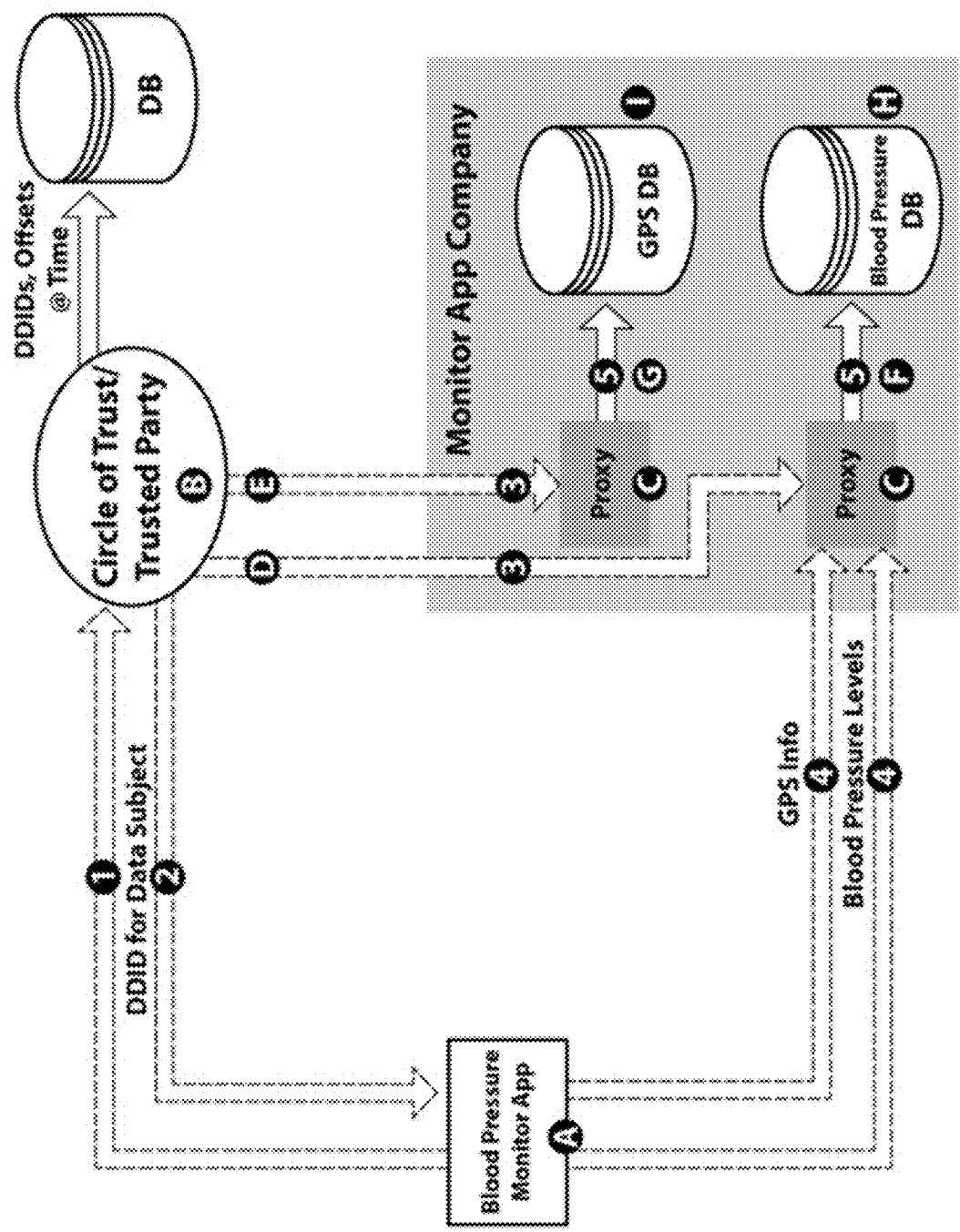
FIG. 1D illustrates an example of the use of DDIDs in connection with a networked blood pressure monitor, in accordance with one embodiment of the invention.

FIG. 1D illustrates a smartphone application that can track both geolocation and blood pressure levels. Using Dynamic Anonymity, such a device could split data into two streams, each obscured such that either stream, if intercepted and/or compromised (or even examined once stored), would not reveal Personal Data (PD) without the addition of critical information protected within the CoT.

More particularly, FIG. 1D illustrates:
1. The blood pressure monitoring application (A) contacts a Trusted Party within a Circle of Trust (B) requesting a DDID for the Data Subject patient.
2. The CoT Trusted Party provides a DDID for the Data Subject.
3. An application operated by the Trusted Party sends back two sets of periodically-changing information (one for GPS data, one for blood pressure levels), each consisting of DDIDs, offsets (to obscure blood pressure level data and geographic position), and encryption keys; refreshed for each new time period. (These are also stored to a database for later use.)
4. The monitor application transmits two encrypted and obscured streams of data to a Dynamic Anonymity-controlled "proxy" application or network appliance (C) within its corporate network. (Here, both location and levels have a periodically changing offset applied to them.)
5. The "proxy" (C) uses the streams of data (D & E) from the Trusted Party (containing only decryption keys) to convert the transmitted data into "plaintext." The proxy also hides the incoming IP address and provides stream(s) (containing multiple Data Subjects' information) of DDIDs and obscured blood pressure level data (F) or GPS locations (G) to the corresponding databases (H) and (I).

At each point in FIG. 1D outside of the Circle of Trust (and outside the smartphone itself) the patient's data is protected; no Personal Data (PD) is made available or ever produced.

Transmissions to and from the Trusted Party (1, 2) have no privacy/anonymity-harming Personal Data, nor is any stored in the Trusted Party's database.

Location and blood pressure levels (4) are transmitted separately (intercepting any one stream reveals nothing), keyed by DDIDs, and obscured so that even the data itself neither reveals nor contains anything, directly or indirectly, about the patient's true location or blood pressure levels.

The Dynamic Anonymity proxies (C) must be connected to the Trusted Party in order to decrypt the data (preventing a man-in-the-middle attack). Each merges multiple streams of data together, after decryption, so that the originating IP address cannot be associated with its decrypted data.

Once at rest, when residing in two separate databases (H and I), the blood pressure levels and location data each have different sets of DDIDs, so that even the hosting company cannot draw any association between the two, much less link each set of data to the Data Subject who produced it.

Figure 1E:
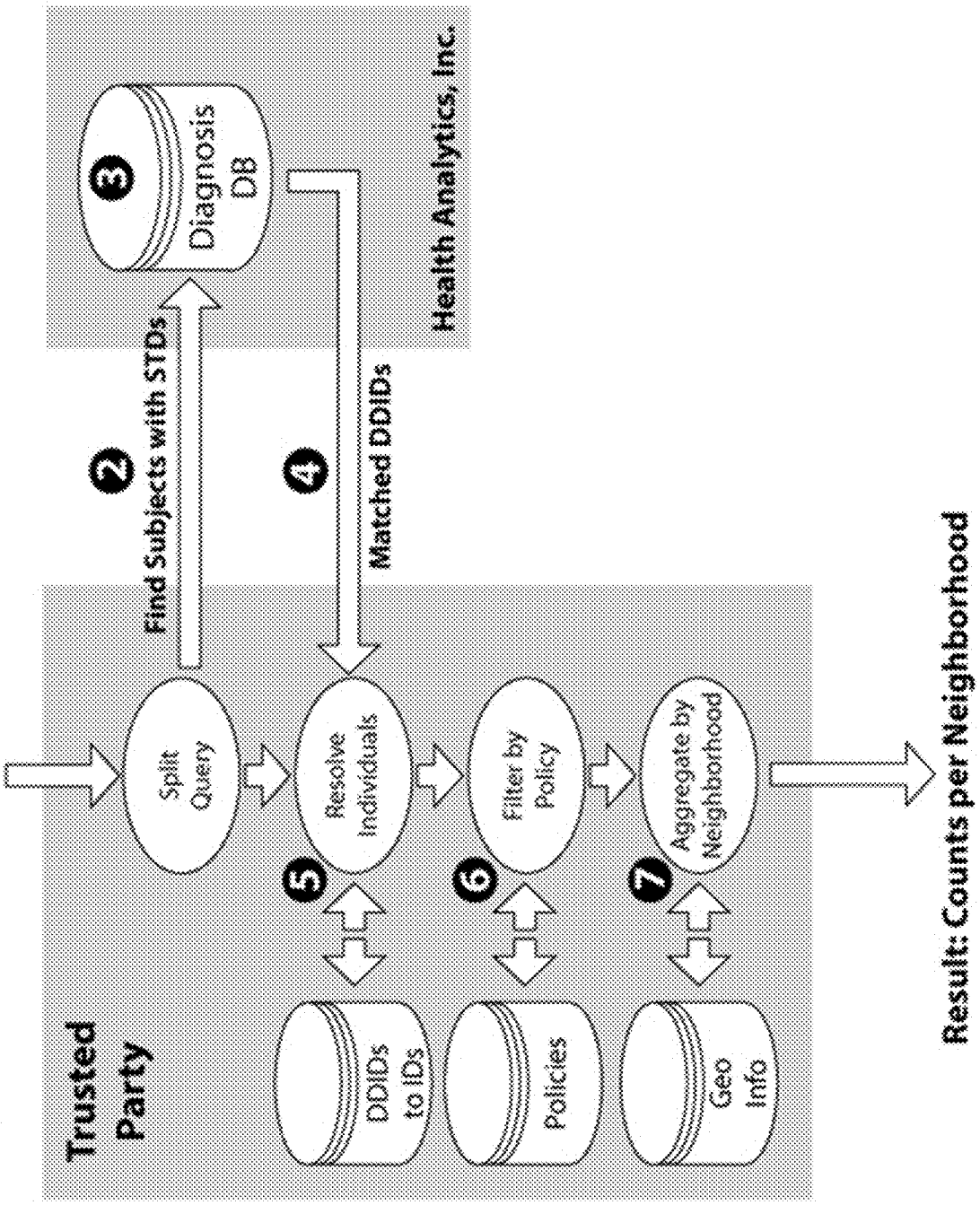
FIG. 1E illustrates an example of the use of DDIDs in connection with serving patients with sexually transmitted diseases (STDs), in accordance with one embodiment of the invention.

FIG. 1E illustrates use of one embodiment of the invention to assist in the task of choosing a location for a new clinic to serve patients who are 20 to 30 years old with sexually transmitted diseases (STDs). One "cleansed" data set may show the incidence of STDs, aggregated by neighborhood to protect privacy/anonymity. Another data set may show how many patients reside in each neighborhood. But, even when these are aggregated, one cannot know exactly how many identified cases of STDs fall into particular age ranges.

Dynamic Anonymity alleviates this dilemma by supporting two different modes of analysis.

In cases where data must be exposed externally (that is, outside the CoT), Personal Data elements can be obscured or encoded as DDIDs, with the resulting associations stored inside the CoT. Additionally, when required, the data (or field) type identifiers can also be obscured in a similar manner.

Later, after analysis is performed, the results of that analysis can then (when permitted) be associated back with the original Data Subjects, field types, and values.

Another way Dynamic Anonymity enables lossless analysis is through the use of federated, anonymized queries, either among different Trusted Parties within a CoT, different data stores within the same Trusted Party, or between Trusted Parties and application developers whose data stores reside outside the CoT.

Consider again the problem of choosing where to site a clinic to serve patients who are between 20 and 30 years old with STDs. The Dynamic Anonymity system improves upon existing techniques by allowing the target query to span multiple data stores and dividing it up such that each participant does not know what purpose it serves, so there is no risk of divulging PD.

In this scenario, the query for the number of patients who are 20-30 years old with STDs within a set of (sufficiently large) geographic areas is presented to numerous Trusted Parties within the Circle of Trust. This aggregate query is then broken down into several steps, such as:

1. Find patients between 20-30 years of age in some broad geographic area.
2. Select only those with STDs.
3. Select only those whose privacy/anonymity policies allow this level of analysis.
4. "Join" those results to the home addresses of those patients.
5. Aggregate these results by neighborhood, revealing only counts of patients.

The actions needed to satisfy this query could span completely different data stores, in different organizations—nonetheless protected and facilitated by the Circle of Trust.

FIG. 1E shows the following processes:

1. The prospective clinic owners send a query to a Trusted Party, asking to find individuals who are between 20-30 years old with STDs.
2. The Trusted Party contacts healthcare-related data stores to find individuals who are between 20-30 years old with STDs.
3. The healthcare-related data stores (which store diagnoses by DDIDs rather than by identifiable keys) find matching records.
4. Matching DDIDs are then transmitted back to the Trusted Party.
5. The Trusted Party then resolves these DDIDs to unveil identified individuals.
6. The Trusted Party filters that list by those whose privacy/anonymity policies allow this particular kind of query.
7. The CoT then uses a database of their addresses to aggregate counts (or incidence frequency, if the query is incomplete) by neighborhood, producing the desired result.

In this scenario, companies operating healthcare-related databases do not need to know (or divulge) the identity, location, or other potentially identifiable information of the patients whose data they possess. The records they possess are keyed by DDID, and also potentially obscured, so that no Personal Data is generated when performing the specified query, nor when transmitting results.

Note that the party posing the query does not have access to this information. Their only interaction with the CoT consists of posing a question and receiving a high-level, aggregated, non-PD result. Note that not having access to this information in no way affects the quality, accuracy or precision of the end result. Dynamic Anonymity thus eliminates Personal Data that contributes nothing to the end result and that only serves to weaken privacy/anonymity without any attendant benefit to any other party. By filtering out irrelevant data, the analysis of which would otherwise consume time and resources, Dynamic Anonymity actually increases the utility and value of the information received.

Personal Data is only produced temporarily, within the Circle of Trust managed by the Trusted Party (the appropriate place for such information)—such as when the DDIDs are resolved. Such operations are transient and leave no lasting trace other than the intended query result, and could also be confined to certain dedicated servers for increased security. The use of DDIDs in the context of Circles of Trust avoids potential shortcomings of normal data analytics that could generate discriminatory or even identifiable results.

Figure 1F:
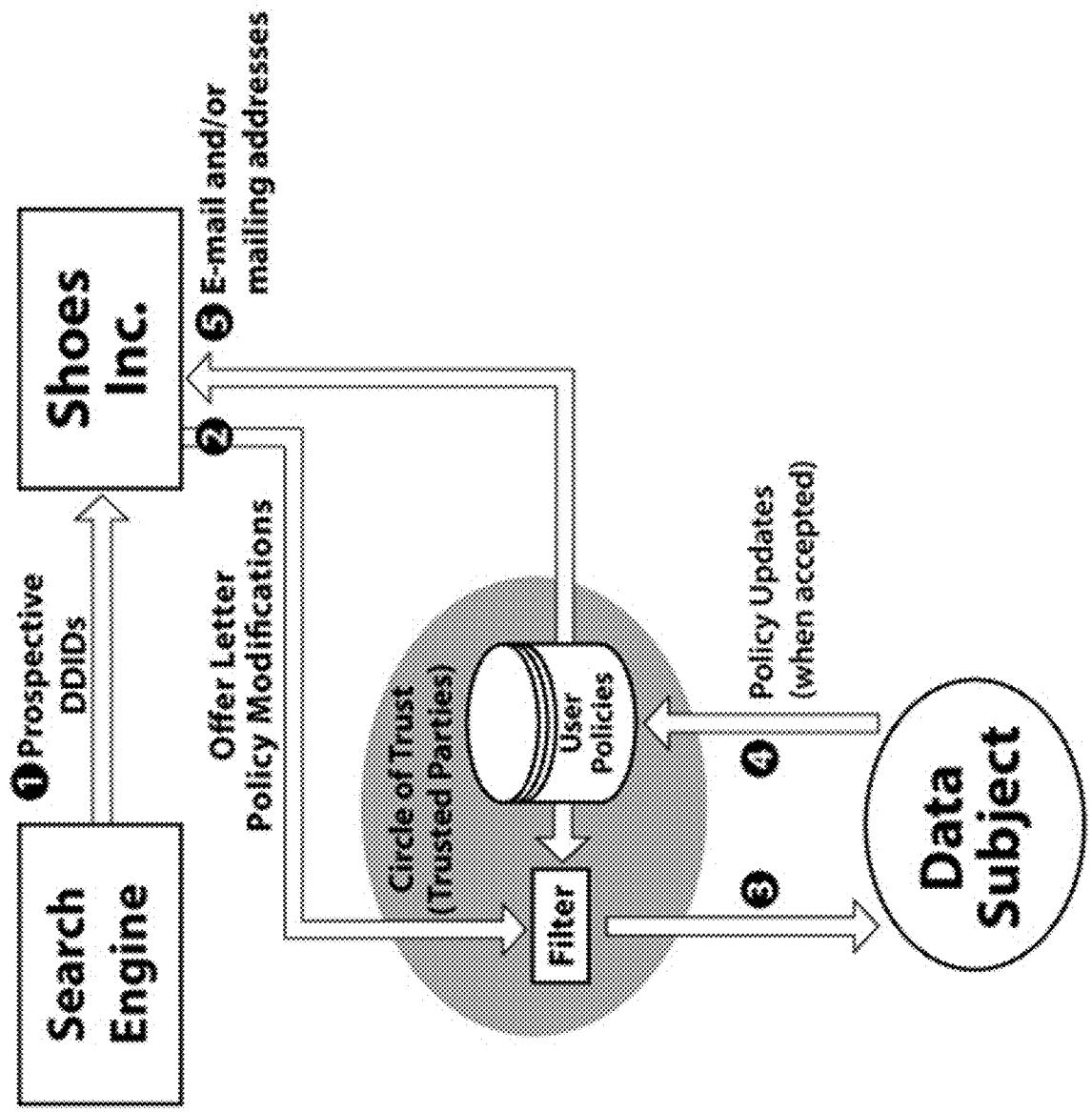
FIG. 1F illustrates an example of the use of DDIDs in connection with offering a coupon, in accordance with one embodiment of the invention.

FIG. 1F illustrates use of one embodiment of the present invention to enable a shoe manufacturer to send a coupon for a new line of shoes to people who have recently performed web searches related to the sport of running within a certain city. In exchange for offering discounts on the shoes, the manufacturer wishes to receive qualified consumers' email and/or home addresses, and to send those who redeem the coupon a survey to assess their satisfaction with the new shoe.

Explanation:

1. The manufacturer, outside the CoT, purchases a list of matching DDIDs from a search engine.

2. The DDIDs are submitted to one or more Trusted Parties, accompanied by an offer letter and a policy modification allowing access (upon acceptance) to Data Subjects' email and/or home addresses.
3. Each Trusted Party then forwards the offer letter to the Data Subjects matching those DDIDs (provided they have opted-in to receiving such an offer).
4. If a Data Subject recipient accepts the offer, the recipient's policy is updated with (perhaps temporally-limited) permission for exposing their home and/or e-mail addresses to the shoe company.
5. The shoe manufacturer, now part of the CoT, but only with respect to this specific offer and only in the most limited sense, then receives a list of e-mail and home addresses of those who wish to receive the coupons. Note that this list is necessarily highly targeted and accurate and therefore of maximum value to the shoe manufacturer. This is precisely how the CoT, by increasing privacy/anonymity, also increases value. The shoe manufacturer may be assured that all mailings done this way will be sent to those with substantial interest in the manufacturers' offer.

Figure 1G:
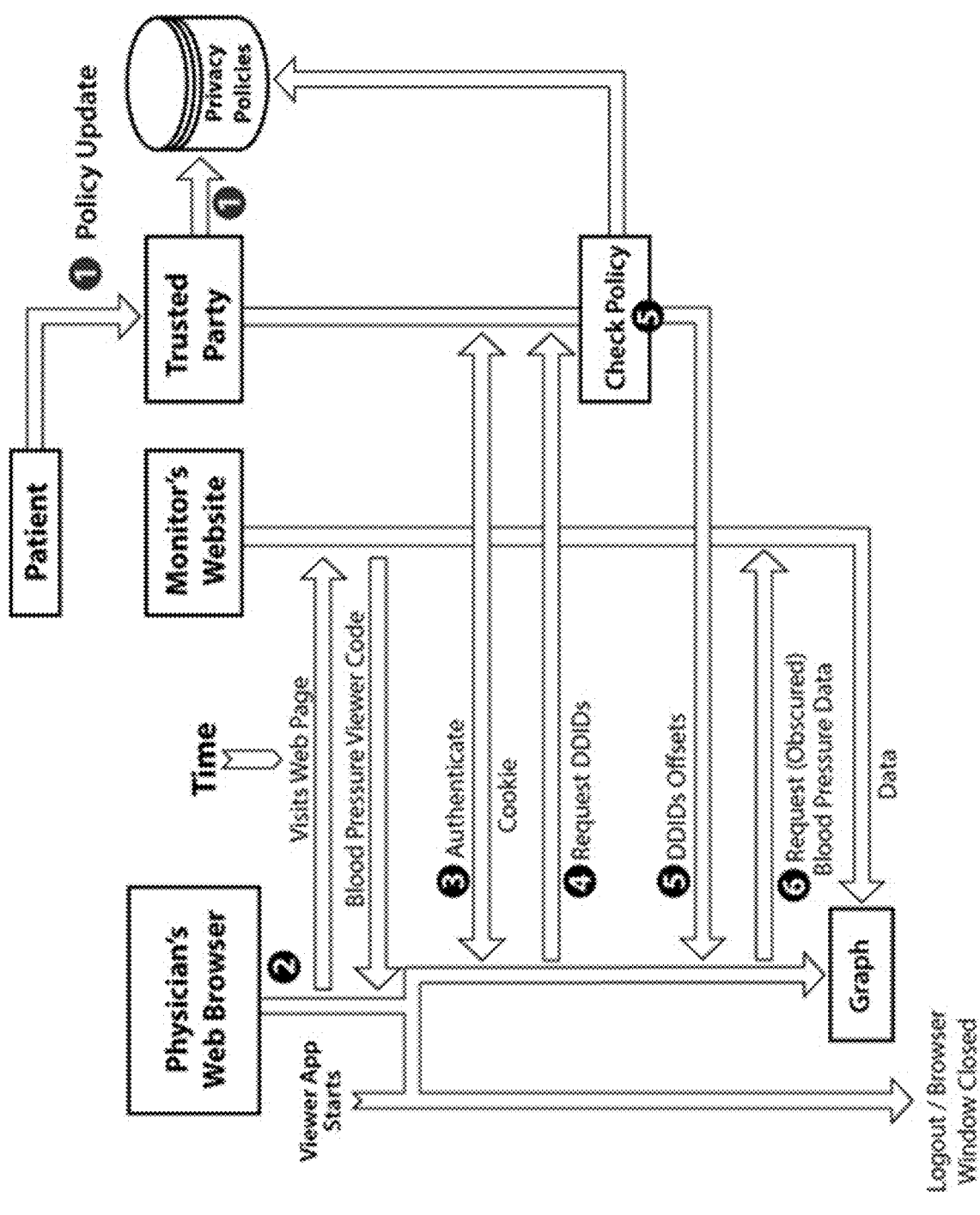
FIG. 1G illustrates an example of the use of DDIDs in connection with a physician viewing blood pressure levels, in accordance with one embodiment of the invention.

FIG. 1G builds upon the prior example in FIG. 1D where a GPS-enabled blood pressure monitor securely stored patients' locations and blood pressure levels via Dynamic Anonymity. Dynamic Anonymity may be leveraged to:
1. Avoid imposition of HIPAA data handling obligations on business associates involved in data processing flows if data in their possession does not constitute Personal Data (PD).
2. Ensure that access to, and use of the data, by the physician satisfies HIPAA obligations.

Note that the following scenario assumes that both a Data Subject patient and his/her physician have accounts inside the Circle of Trust.

Explanation:
1. The monitoring application cooperates with the patient's Trusted Party to allow the patient to update his/her privacy/anonymity policy rules so that his/her physician can now access his/her blood pressure levels (but not his/her GPS location data). Note that this grant can be temporary (analogous to the temporally limited nature of photographs that can be shared with Snapchat—the grant expires after a period of time)—or ongoing.
2. The physician (via his/her web browser) browses to the blood pressure monitor's web site, which launches a JavaScript-based blood pressure level viewer application which thus runs in the physician's browser, and not on the monitor company's servers (i.e., that the stitching together of data necessary to make it personally identifiable is done via the Trusted Party server which is itself trusted—see steps 4 and 5 below).
3. The blood pressure-level viewing application asks the physician to log in via her Trusted Party (similar to the way many applications allow you to authenticate using a FACEBOOK® or GOOGLE® account), and receives a session cookie that continues to identify them to that party. (FACEBOOK® is a trademark of Facebook, Inc.)
4. After the physician selects a range of time to view, the viewer application requests the relevant DDIDs and offsets from the Trusted Party, for that patient.
5. The Trusted Party validates the physician's access to this information (checking the patient's privacy/anonymity policy rules) and then returns the DDIDs and offsets.
6. The viewer application then contacts its own corporate website, requests the blood pressure data corresponding to those DDIDs, receives the result, applies the offsets, and renders the blood pressure levels as a graph.

At this point, the image on the physician's screen is HIPAA-protected PHI data. If the physician prints the data, that paper will be subject to HIPAA. When the physician is done viewing the graph, he/she logs out or closes the browser, the application ends, and the data is erased.

Note that re-identified HIPAA-controlled data only resides in the physician's browser. The original blood pressure level data stored in the application provider's databases remains untouched and obscured. The Trusted Party's data remains unaffected as well.

Also note that the permission to view the blood pressure data is enforced within the Circle of Trust. It is not enforced (as is common practice today) merely by the viewer application—or only by the application's backend servers. This means that an adversary could not gain unauthorized access to the data merely by hacking into the blood pressure level viewer application, because the data would not be there in any usable or identifiable form. The dynamic data obscuring capabilities of Dynamic Anonymity DDIDs combined with the dynamic data privacy/anonymity control capabilities of a "Circle of Trust," maximize both data privacy/anonymity and value to support personalized medicine/medical research.

With respect to FIG. 1H, the different nodes depicted in 1H-A represent data elements related to two different Data Subjects that are capable of being tracked, profiled and/or analyzed by third parties because they can be associated with, and/or re-identified for, each of the Data Subjects. 1H-B represents a simplified visual depiction of the same data elements that can be retained with Dynamic Anonymity without loss of context. The Family Educational Rights and Privacy Act (FERPA) is a federal privacy statute that regulates access to and disclosure of a student's educational records that disclose personally identifiable information (PII). FERPA provides that PII cannot be disclosed, however, if PII is removed from a record, then the student becomes anonymous, privacy is protected, and the resulting de-identified data can be disclosed. In addition to statutorily defined categories (e.g., name, address, social security number, mother's maiden name, etc.), FERPA defines PII to also include " . . . other information that, alone or in combination, is linked or linkable to a specific student that would allow a reasonable person in the school community, who does not have personal knowledge of the relevant circumstances, to identify the student with reasonable certainty." The ability of Dynamic Anonymity to obfuscate connections between each of the Data Subjects and the data elements in a controlled manner by means of an Anonos-enabled Circle of Trust (CoT), as visually depicted in 1H-B, enables educational-related data to be used without disclosing PII.

Figure 1I:
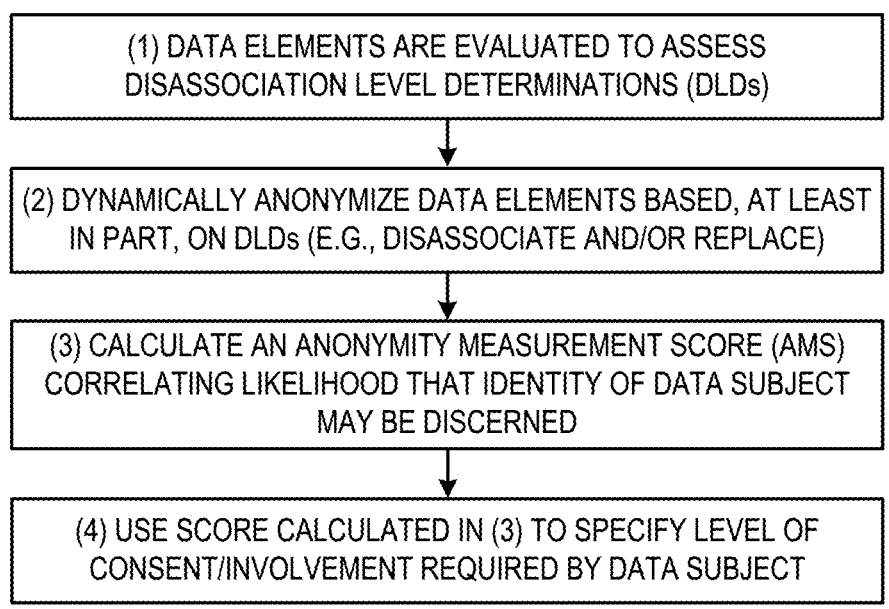
FIG. 1I shows an example of a process to perform Disassociation Level Determination (DLD) and create an Anonymity Measurement Score (AMS), in accordance with one embodiment of the invention.

FIG. 1I shows an example of a process to perform Disassociation Level Determination (DLD) and create an Anonymity Measurement Score (AMS), in accordance with one embodiment of the invention. Determining DLDs may entail undertaking a mathematical and/or empirical analysis of the uniqueness of a data element prior to Disassociation to assess the level of Disassociation required to reduce the probability of identification or re-association by adversaries without proper permission. DLD values may be used as input to determine the relevant level of Disassociation/Replacement appropriate for different types of data elements.

AMS may be used to correlate mathematically derived levels of certainty pertaining to the likelihood that personally sensitive and/or identifying information may be discernible by third parties to tiered levels and/or categories of anonymity. In other words, AMS values may be used to evaluate the output from Disassociation/Replacement activities to determine the level/type of consent required before data can be used.

In Step (1) of FIG. 1I, data attributes may be evaluated to assess DLDs, i.e., data elements are analyzed to determine the potential likelihood of directly or indirectly revealing personal, sensitive, identifying or other information with regard to which anonymity protection is desired. In Step (2), based at least in part on the determined DLDs, the data elements may be dynamically anonymized by means of Disassociation. In addition, data elements may also undergo Replacement. In Step (3), a calculation may be performed, e.g., by means of a mathematical function/algorithm (e.g., the mathematical function/algorithm whose output is reflected in FIG. 1J) to calculate an AMS that correlates to the likelihood that the identity of the Data Subject to which said data attributes pertain may be discernible by third parties after Disassociation/Replacement with DDIDs. Finally, in Step (4), the score/rating calculated in Step (3) above may be used to specify the level of consent/involvement required by the Data Subject to which the anonymized data attributes pertain versus what level of discretion/use a third party may exercise with regard to the anonymized data attributes without requiring consent/involvement by the Data Subject, such as is shown in the example AMS usage reflected in FIG. 1K below.

Different categories of information hold different statistical likelihoods of being re-identifiable. Every data element has associated with it with an inherent level of uniqueness as well as a level of uniqueness when combined with other pieces of data as determined by placement, order and/or frequency of occurrence. For instance, looking at single data points, a social security number is highly unique and therefore more easily re-identifiable than a single data point such as sex, since each person has an approximate 1:1 probability of being male or female. Since gender is less unique as an identifier than a social security number, gender is significantly less likely on an independent basis to re-identify someone than a social security number.

The Anonymity Measurement Score (AMS) measurement schema ties statistical probabilities of re-identification to create multiple ratings depending on the level and degree of disassociation and/or replacement applied to data elements. As a single data point example, a social security number, which has not been disassociated or replaced at all, may merit an AMS rating of 100 meaning the uniqueness classifies it as a very high risk of re-identification. Whereas sex as a single data point identifier without disassociation or replacement may merit an AMS score of 10 since it is classified at a low risk of re-identification even without de-identification measures in place.

In an example implementation with a social security number as a singular data point, a Level 1 implementation could assign DDIDs for purposes of disassociation and/or replacement while retaining the initially assigned value—i.e. permanent assignment (e.g., where data is used as output in hard copy representations of the data). In the case of a social security number, a Level 1 application of DDIDs could reduce the AMS score by 10% and result in a modified AMS score of 90. This is still a high level of risk associated with re-identification but is more secure than non-disassociated and/or replaced elements.

In an example Level 2 implementation, the social security number could have DDIDs assigned for purposes of disassociation and/or replacement while retaining the initially assigned value until the value is changed on a one-directional basis—i.e. ad hoc changeability (e.g., where data values can be changed unilaterally by sending new information to remote cards, mobile, wearable and/or other portable devices that include means of electronically receiving and storing information). The social security number AMS score could thereby be reduced another 10% to achieve an AMS score of AMS.

In this example, continuing to a Level 3 implementation, it could have DDIDs assigned for purposes of disassociation and/or replacement while retaining the initially assigned value but the DDIDs could change on a bi-directional basis, i.e. dynamic changeability (e.g., where data values can be changed bilaterally by sending and/or receiving data dynamically between client/server and/or cloud/enterprise devices with the ability to receive and change specified data dynamically). The social security number would then have an AMS score that is further reduced by 50% resulting in an AMS score of 40.5.

As de-identification measures are applied to a data point through disassociation and/or replacement via use of DDIDs, the risk of re-identification is lowered. AMS score determinations are derived from the function of the likelihood of an identifier or identifiers taken together to be re-identifiable. This, combined with the processes used to obfuscate data elements can then be separated into categorical or other types of classification schemas to determine various functions such as permitted uses and what level of permission entities need to have before using data. This process may also be applied to single or aggregated AMS scores. Aggregated AMS scores are the likelihood of multi data point re-identification expressed through AMS scores as compounded together to express the level of uniqueness of combined data points.

As an example of a possible categorical classification schema, the AMS score could be broken into Categories A, B and C. Where category A is data with a single or aggregated score of 75 or more may be used only with current, express and unambiguous consent of the Data Subject. Category B may represent a single or aggregated AMS score of 40 to 74.9 that would mean the data set could be used with (i) current or (ii) prior express consent of the Data Subject. A Category C could represent a single or aggregated AMS score of 39.9 or lower which could allow for use of the data set without requiring consent of the Data Subject.

In the example disclosed in FIG. 1J, each of the identifiers other than the Social Security Number discussed above (i.e., Credit Card Number, First Name, Last Name, Birthdate, Age and Sex) are similarly assigned a Non-Disassociated/Replaced AMS rating in the first column. In each of the next two subsequent columns (i.e., Level 1 and Level 2) their AMS scores are adjusted by successive 10% reductions, and in the last columns (i.e., Level 3) their AMS scores are adjusted by a 50% reduction, resulting in decreasing AMS scores as DDID-enabled obfuscation increases by means of permanent assignment (Level 1), ad hoc changeability (Level 2) and dynamic changeability (Level 3).

As mentioned above, FIG. 1J illustrates exemplary calculated Anonymity Measurement Scores, in accordance with one embodiment of the invention. These AMSs are for illustration purposes only and demonstrate the fact that certain types of potentially personally-identifying information are more likely to reveal a Data Subject's true identity than other types of information, and that additional levels of Disassociation/Replacement, e.g., ad hoc (i.e., Level 2) and/or variable changeability (i.e., Level 3), may increase the amount of anonymity afforded to the Data Subject by the anonymization systems and scheme.

As mentioned above, FIG. 1K illustrates exemplary categories for the level of consent/involvement required by the Data Subject for certain calculated Anonymity Measurement Scores, in accordance with one embodiment of the invention. These categorizations are given for illustration purposes only and demonstrate the fact that certain aggregated scores may apply different categories of treatment. For example, Category A data may be used only with current, express, and unambiguous consent of the Data Subject; while Category B data may be used with current or prior express consent of the Data Subject; and Category C data may be used without requiring consent of the Data Subject. Other schemes may be employed to meet the needs of a particular implementation.

Figure 1L:
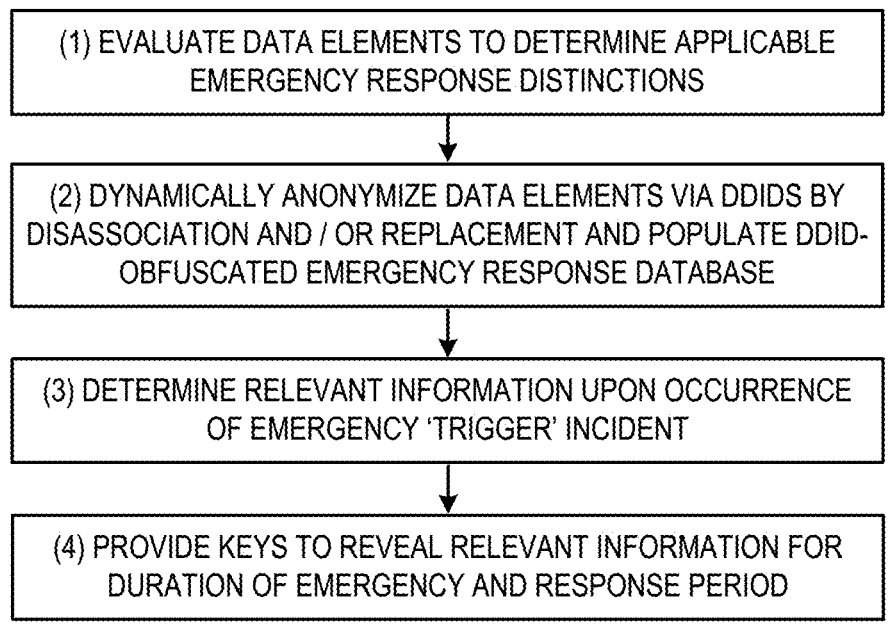
FIG. 1L illustrates an example of the use of DDIDs in the area of emergency response, in accordance with one embodiment of the invention.

FIG. 1L shows an example embodiment of the present invention using DDIDs for emergency response purposes. In Step (1) of FIG. 1L, data attributes are evaluated to determine applicable emergency response distinctions—e.g., whether a house is located in a flood plain, whether an individual is in immobile or in need of particular life-saving equipment or medical care. In Step (2), applicable data elements are dynamically anonymized by a trusted party by means of disassociation and/or replacement using DDIDs to protect the privacy/anonymity of citizens and the obfuscated information is sent to a DDID-obfuscated emergency response database. In Step (3), information is evaluated by the trusted party to determine data elements relevant to respond to a specific emergency. Finally, in Step (4), the trusted party provides to the obfuscated emergency response database association keys (AKs) and/or replacement keys (RKs) necessary to reveal desired information otherwise represented by DDIDs for the duration of the emergency event and associated response.

In the example embodiment reflected in FIG. 1L, data is resident in an emergency response database in a dynamic DDID obfuscated state such that identifying information is not discernable or re-identifiable until such time as necessary association keys (AKs) and/or replacement keys (RKs) are provided when an appropriate triggering incident occurs. A triggering operation carried out by a trusted party would issue time sensitive AKs/RKs with respect to portions of appropriate data at specified levels of obfuscation or transparency depending on the type of incident. Identifying information could be maintained inside the emergency response database but in a dynamic DDID obfuscated state; a data mapping engine controlled by a trusted party would maintain correlative information pertaining to dynamically changing DDIDs and AKs/RKs necessary to discern and/or re-identify data which would only be provided upon the event of an appropriate emergency incident.

Policy external to the system would determine which information may be relevant for different incidents and stages of incidents, as well as what level of obfuscation/transparency is appropriate at different times so not all information would be released at once and so that irrelevant but sensitive information would not be released without cause. These permissions would then be encoded for ease of triggering access in an emergency. This method allows for bidirectional communication with, and verification of the locations of, impacted individuals compare to capabilities of static lists or unidirectional communication.

AKs/RKs would be changed and reintroduced to the emergency response database after each incident so that information would be maintained on an ongoing electronic basis in a DDID obfuscated state, i.e., a new trigger would be required to make portions of data readable via new AKs/RKs following a prior release of AKs/RKs in response to an earlier incident (i.e., following resolution of an emergency response incident, AKs/RKs previously provided would no longer reveal the underlying identifying information associated with dynamically changing DDIDs. This would protect the privacy/anonymity of individual citizens while protecting their safety in major incidents by allowing appropriate access to data for a limited period of time. On the emergency management side, this could reduce the need for resource intensive information intake and handling procedures employed during large incidents.

Additionally, new data pertaining to individuals could be added during incidents, such as 'accounted for' or 'missing' status designation during evacuation. This new input could become part of an individual's personal profile held in stasis by an embodiment of the present invention and maintained for future authorized use if helpful in the same, or subsequent emergency.

In a local opt-in example, citizens could register to have information that would be relevant in an emergency stored in a DDID obfuscated emergency database. The emergency database could be stored locally or elsewhere but could be interoperable in case of cross-jurisdictional incidents. Once the citizen data is input into the DDID obfuscated system, no one could see or access the data in a discernable or re-identifiable manner until a trigger mechanism controlled by a trusted party results in release of dynamic, situational based AKs/RKs as necessary to discern/re-identify appropriate components of the stored data.

Two examples of emergency management views of potential embodiments of the present invention could include:
  1. Interactive screen(s) could present overlays that allow Geographic Information System (GIS) and other data to be imposed or correlated to location specific data—i.e. clicking on a house may show information that has been submitted by a citizen as well as information that a jurisdictional authority has on the subject property as well as associated disaster risks. For instance, flood alerts are a great example of a notification that could provide different amounts of information on different people depending on their specific location. A general flood warning may go out to an entire area but a specifically targeted warning may be sent to those directly in the flood plain who are at greater risk for flooding.
  2. More traditional formats, such as electronic tables, etc. could be augmented to provide non-geographic data.

The above two variations in format could be interoperable as well with the data from each being represented in the other either interactively or linked.

In the case of watches and warnings, the locality of the weather phenomenon (as determined via weather radars, GIS mapping, etc.) will determine the subset of information released, which may be further revealed inside the database.

In another example case, there may be a criminal who is profiling a particular demographic as targets. In this situation, DDIDs such as contact and demographic information would be relevant—in addition to partially obfuscated location data—in order to create general perimeters on the message send out. The relevant data fields and their DDIDs would be activated to point to individuals matching the demographic, who may then be put on notice of the criminal activity.

In an emergency situation that requires evacuation, this information could be triggered to assist emergency personnel in more effective resource deployment in addition to assisting in evacuation or identifying those who may need additional assistance in emergency situations. In another example, such as a blizzard, the system could be triggered to let emergency personnel know exactly where kidney dialysis patients are located in their city for emergency transportation via snowplow by means of GPS location information associated with mobile devices associated with the patients—which information would be represented by indiscernible/non re-identifiable DDIDs until such time as a trigger event results in the release applicable AKs/RKs reflecting appropriate correlative information.

Just-In-Time-Identity (JITI)-Enabled Contextualized Security and Privacy

The terms "Just-In-Time Identity" and/or "JITI" are used herein to refer to the dynamic anonymity methods and systems described herein. The term "JITI keys" or the term "keys" are used herein to refer to the terms "Association Keys," "Replacement Keys," "Time Keys," "AKs," "RKs," "TKs," and/or "keys" as used herein.

The methods and systems for general-purpose granular, contextual, programmatic protection of data disclosed in this section shift the focus away from who has access to data (since, without Anonos Just-In-Time-Identity (JITI) keys, the data is unintelligible), and refocus that attention toward who has access to the JITI keys and the scope of use enabled by each JITI key.

By technologically and programmatically enforcing data privacy and security policies in a contextually flexible, selective manner all the way down to lower data element levels or even to the individual data element level, JITI maximizes authorized use of data while minimizing unauthorized use of data. JITI facilitates compliance with and auditability against established privacy policies by enabling the mathematical, statistical and/or actuarial measurement and monitoring of data use. JITI enables the same data store(s) to simultaneously programmatically support privacy policies applicable to multiple companies, states, regions, countries, industries, etc. and to adjust in real-time to changing requirements of said policies by dynamically modifying the intelligible form of data into which DDIDs are transformed.

With JITI, data down to the smallest desired data element level (e.g., down to the individual datum level) is dynamically obscured by replacing the data with Dynamic De-Identifiers (DDIDs) as more fully described herein. For example, rather than storing a person's actual name, that person's name can be replaced by a DDID. Importantly, JITI replaces data elements at the data layer rather than masking data at the presentation layer. By dynamically obscuring data down to the element level at the data layer by replacing data elements with DDIDs and further, by dissociating relationships between data elements, it becomes extremely hard to track, profile, infer, deduce, analyze or otherwise to directly or indirectly understand—or correlate—data without access to JITI key(s) necessary to "transform" DDIDs into an intelligible form. For purposes of this application, "transform" means, without limitation, correct, shorten, compress, encode, replace, render, compute, translate, encrypt, decrypt, substitute, exchange or otherwise perform mathematically functional or cognizable operations upon the DDIDs, whether by mechanical, physical, electronic, quantum or other means.

Turning back to FIG. 1H, the spheres on the left side of FIG. 1H represent data elements with respect to which metadata (i.e., data that provides information about other data) reveals interrelationships between and among the top three spheres representing data elements and between and among the bottom four spheres representing data elements, thereby enabling tracking, profiling, inferences, deduction, analysis, understanding and correlations represented by the dotted lines between and among the spheres on the left side of FIG. 1H. On the right side of FIG. 1H, the different design on each of the spheres represents a unique dynamic de-identifier (DDID) used to replace the data element represented by the sphere. As a result of using different DDIDs, no metadata can exist or relate to any of the spheres on the right side of FIG. 1H to indicate any interrelationship between or among any of the spheres representing data elements. Without access to JITI key(s) necessary to transform DDIDs into an intelligible form, the replacement of data elements with DDIDs significantly increases the difficulty of successful attempts at tracking, profiling, inference, deduction, analysis, understanding or establishing correlations between or among any of the spheres representing data elements.

Granular, contextual, programmatic enforcement on the front-end makes it easier to audit compliance with data protection (e.g., security, privacy, and/or anonymity) policies on the back-end, thereby increasing the accountability and trust necessary for the wide-scale, domestic and international acceptance of data analysis and use that maximizes the value of data, while improving protection for that same data. The same data may be subject to different jurisdictional requirements based on the source and/or use of the data. For example, data representing a heart rate reading (e.g., 55 beats per minute) may be subject to different privacy policies, depending on how the data is captured.

For example, if the data is captured by means of a personal health device in the U.S., use of the data may be subject only to terms and conditions of the device and/or application used to capture the information. If the data is captured in connection with providing healthcare services in the U.S., use of the data may be subject to the federal Health Insurance Portability and Accountability Act (HIPAA) and applicable state laws. If the data is captured in connection with federally funded research in the U.S., use of the data may be subject to the "Common Rule," as codified, e.g., in: 7 U.S. Code of Federal Regulations (CFR) Part 1c by the Department of Agriculture; 10 CFR Part 745 by the Department of Energy; 14 CFR Part 1230 by the National Aeronautics and Space Administration; 15 CFR Part 27 by the Department of Commerce—National Institute of Standards and Technology; 16 CFR Part 1028 by the Consumer Product Safety Commission; 22 CFR Part 225 by the Agency for International Development (USAID); 24 CFR Part 60 by the Department of Housing and Urban Development; 28 CFR Part 46 by the Department of Justice—National Institute of Justice; 32 CFR Part 219 by the Department of Defense; 34 CFR Part 97 by the Department of Education; 38 CFR Part 16 by the Department of Veterans Affairs—Office of Research Oversight—Office of Research and Development; 40 CFR Part 26 by the Environmental Protection Agency—Research and Development; 45 CFR Part 46 by Department of Health and Human Services (also applicable to the Central Intelligence Agency, the Department of Homeland Security, and the Social Security Administration); 45 CFR Part 690—by the National Science Foundation; and 49 CFR Part 11 by the Department of Transportation. As a result, scalable programmatic, general-purpose data protection and compliance technology solutions, such as JITI, may be needed for, among other reasons, accommodating jurisdiction of disparate privacy policies of different business, industry, government, regulator and/or other stakeholder group(s).

Possible implementations of methods and systems for granular, contextual, programmatic enforcement of privacy polices disclosed herein include, in one preferred embodiment, real-time de-identification and anonymity solutions and/or services that help to address concerns over unintended access to, and use of, data in violation of privacy policies, thereby overcoming the limitations of other approaches to protecting data. In contrast, other approaches for protecting data (e.g., improving security, privacy and/or anonymity of data) are generally binary: either data protection is facilitated at the sacrifice of data value or data value is facilitated at the sacrifice of data protection. For example, efforts to improve data security by encrypting data result in data being protected but unusable in its protected form or, conversely, in the data's becoming vulnerable when it is decrypted for the very purpose of enabling use.

FIG. 1M compares the impact of other approaches to data protection (security and privacy) on the preservation of data value versus the preservation (or expansion) of data value in the present invention, i.e., JITI, and on other inventions contained herein. Column 1 of FIG. 1M represents the effect of binary alternatives (e.g., encryption) wherein the top black sphere shows the value of original data (in unprotected form) and the dotted sphere represents the loss of data value when that data is in a protected form, rendering it unusable. Column 2 of FIG. 1M represents the reduction in data value due to removing data from the ecosystem in response to concerns over use of data for purposes other than the primary intended purpose ("Data Minimization") and from using traditional static approaches to obfuscating data in order to achieve de-identification, which reduce data value. Column 3 of FIG. 1M shows that 100% of data value is retained with JITI. Last, Column 4 of FIG. 1M represents the possibility of positive data fusion due to using JITI.

It should also be mentioned that JITI-based techniques do not have to be used in lieu of other known techniques for data protection (i.e., security and privacy). In fact, JITI can be used in conjunction with such other techniques. A primary benefit of using JITI to render data into DDIDs is that if and when other approaches fail, then the exposed data will have neither value nor meaning without access to JITI key(s) necessary to render DDIDs into intelligible form.

Figure 1N:
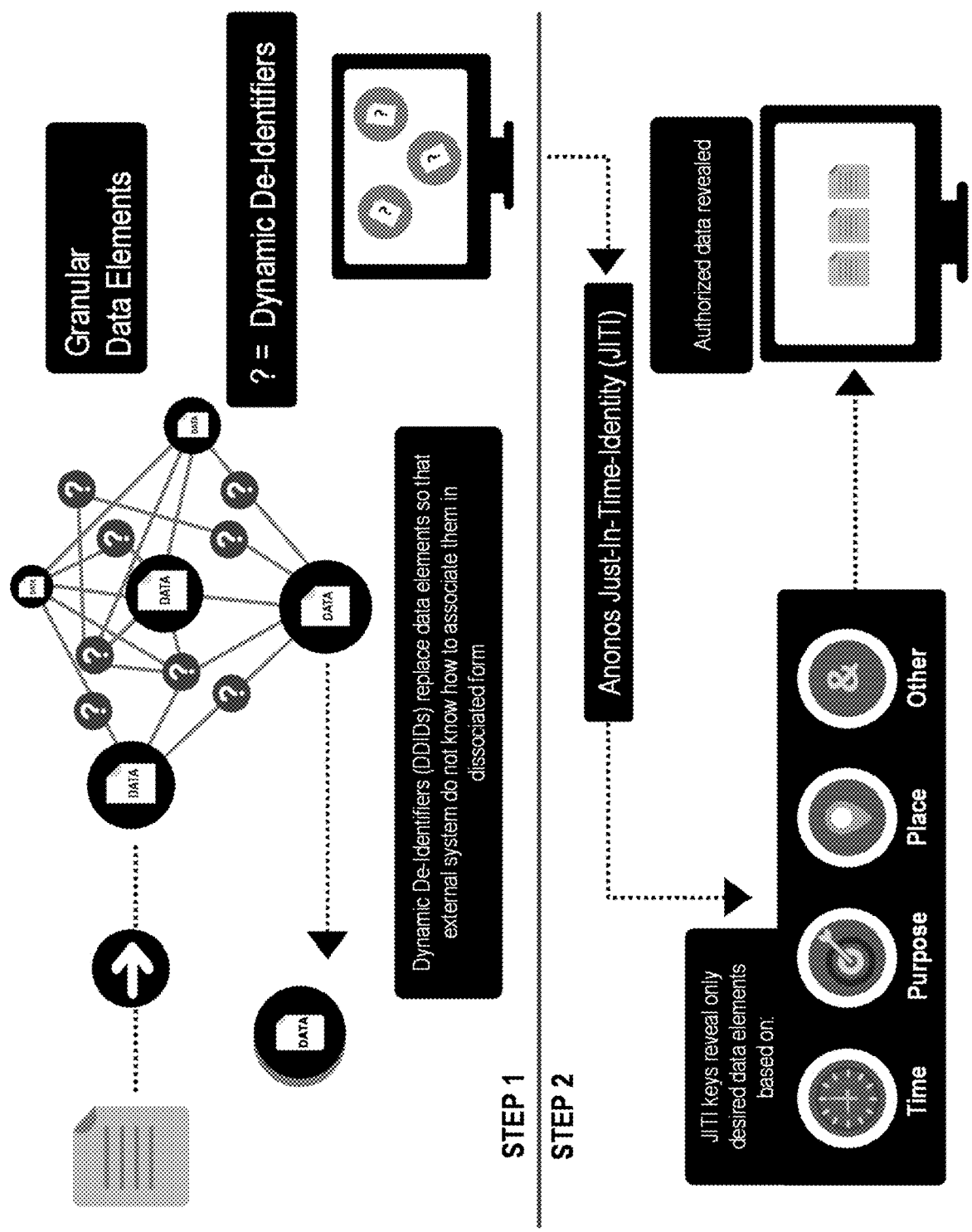
FIG. 1N illustrates an example of the use of Just-In-Time-Identity (JITI)-enabled security and privacy, in accordance with one embodiment of the invention.

FIG. 1N represents two important steps in one potential embodiment of the present JITI invention. Step 1, i.e., above the horizontal dividing line in FIG. 1N, highlights eliminating visible links between data elements so a party cannot infer or deduce relationships between data elements. Rendering data elements as DDIDs dynamically obscures cleartext source data. Data that is rendered with DDIDs is still present but from an information theory perspective the knowledge or context necessary to understand the data is dissociated from the data by means of JITI keys: ergo, the DDIDs contain no information about the underlying data element(s). Step 2, i.e., below the horizontal dividing line in FIG. 1N, involves assignment of JITI keys to allow selective disclosure of data based on JITI key-enabled policy controls (e.g., purpose, place, time and/or other designated trigger factors); in selectively revealing data, the level of detail/clarity provided to each key holder—e.g., original cleartext, perturbed value, summary information, etc.—can also be dynamically controlled. Notably, there is no limit to the number of different selective disclosures that can be made serially or in parallel; no limit to the number of different authorized users to which any one or more of the disclosures can be made; and no limit to the constraints or policies (such as time, purpose, place, other (association, relationship, quantitative), etc.) governing such disclosures.

Granular, contextual, programmatic enforcement of data protection (e.g., data security, privacy and/or anonymity) policies with JITI supports the statistical assessment of the probability that a data breach and/or data re-identification will occur or of the rank ordering of such incidents (i.e., non-parametric methods). JITI is more efficient from an information theory perspective than other approaches to protecting data because the value of the data is still accessible but the identifying information is not. In other words, the identifying information has no leakage, meaning zero information is leaked, while the value of the data is safely and intentionally "leaked," in a positive way (which may itself be subjected to standard information theoretic optimizations), meaning the value is made available to those who are authorized users.

The granular, contextual, programmatic structure of JITI supports a mathematical proof of the significantly reduced probability of a data breach or re-identification. An example of a mathematical proof of JITI's effectiveness is an analysis by a data scientist concluding that data which has been replaced with DDIDs down to the data element level (a process referred to herein as "Anonosizing" the data) results in no greater probability of re-identification than guessing the identity of highly encrypted data. However, unlike encrypted and other non-"Anonosized" data, Anonosized data can be used in its protected form to generate value from the data. In addition: (a) different DDIDs can be assigned to the same data element(s) at different times and/or different places and/or different purposes and/or according to other criteria, thus making it extremely difficult for parties not in possession of JITI keys to track, profile, infer, deduce, analyze or otherwise understand protected data; and (b) the same DDID(s), if expired for any reason, can be (but are never required to be) assigned to different data elements, also at different times and/or different places and/or different purposes and/or according to other criteria, thus making it extremely difficult for interloping parties or other "bad actors" ever to establish any meaningful continuity or audit trail, since these reassigned DDIDs would refer to data elements that bore no meaningful relationship, correlative or otherwise, to any and all data elements to which they had been assigned. Refer back to FIG. 1B for criteria that may trigger assignment, application, expiration and recycling of DDIDs and/or JITI keys.

JITI's granular, contextual, programmatic enforcement of privacy policies severely depreciates the "Mosaic Effect"—defined to mean that even if data is not identifiable by itself, the data poses a privacy or security risk when combined with other data. For example, Harvard University Professor in Residence of Government and Technology Latanya Sweeney is credited with disclosing that knowledge of only three discrete identifiers—(1) zip code, (2) gender and (3) date of birth—can result in 87% (i.e., 216 million of 248 million then-U.S.-citizens) of the U.S. population being personally re-identified. However, for this to be true, a zip code, gender and date of birth must be known to apply to the same person. Using JITI, the owner of these data elements can be obscured by associating each data element with a different (or dynamically changing) DDID rather than associating all three with the same static identifier. With JITI, it would be extremely difficult to know whether a zip code, gender or birth date applied to one person or to multiple people—thereby severely depreciating the "Mosaic Effect."

One potential implementation of the methods and systems for granular, contextual, programmatic protection of data disclosed herein would involve the development of mathematical/statistical/actuarial models to reduce insurance risks. Granular, contextually driven, programmatic protection of data as disclosed herein enables mathematical measurement of compliance as required to develop algorithms that better assess price and insure against risk. By ensuring protection of data security, privacy and/or anonymity at the individual consumer level, it becomes more acceptable to aggregate larger amounts of data on a broad, more population-representative basis, one which can improve the accuracy and value of risk-related data.

A further potential embodiment of the methods and systems for granular, contextual, programmatic protection of data disclosed herein is, prior to rendering the DDIDs, requiring use of multiple JITI keys to ensure the consent of multiple relevant parties. Requiring multiple JITI keys (i.e., an "n of m" model, in which all available key fragments or a specified percentage of available key fragments is required) to unlock data values from DDIDs can ensure that interests of various stakeholders in a multi-stakeholder or highly sensitive data access/disclosure situation are respected by requiring that the JITI keys held by each of the interested stakeholders be used to trigger the simultaneous renderings of DDIDs into intelligible forms.

An additional potential embodiment of the methods and systems for granular, contextual, programmatic protection of data disclosed herein is to encapsulate highly granular (to a ratio as low as 1:1 for JITI key triggers to data elements, although this should not be construed to limit many-to-one, one-to-many or many-to-many mappings between JITI key triggers and data elements, as such embodiments are also envisioned) access rules setting forth, without limitation and among multiple potential parameters, any, some or all of the degree, context, specificity, abstraction, language, and accuracy into which DDIDs are authorized to be transformed. In this embodiment, access rules may be encoded into one or more JITI keys that are programmatically enforced to ensure that DDIDs are unlocked and their original contents revealed, but only when all the explicit access rules are observed and enforced. JITI provides support for multiple and/or cascading policies embodied in assigned JITI keys by enabling an "override," such that when more than one policy applies, only the most restrictive applicable policy will be enforced; or alternatively, the union of the most restrictive policies could be combined to create a new "maximum" restricted policy, statically or dynamically, and in any of batch, near-time and real-time scenarios.

Figures 1, 1P:
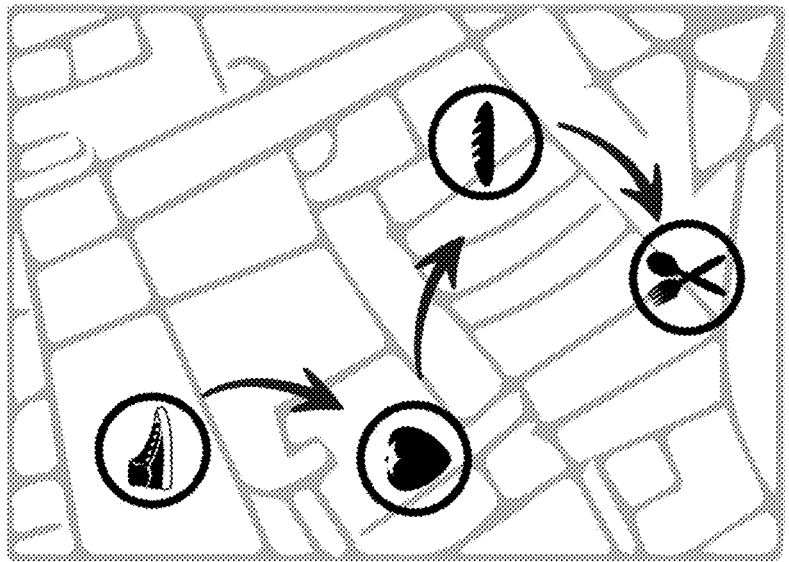

FIG. 1P-1 highlights how metadata captured in financial transactions entered into by a hypothetical consumer, "Scott," (represented in 4 different purchasing transactions by the static anonymous identifier 7abc1a23) is used to re-identify him. Using JITI, each of the occurrences of the static anonymous identifier—7abc1a23—that represented "Scott" in FIG. 1P-1 is replaced with a DDID after the first time 7abc1a23 is assigned.

FIG. 1P-2, on the other hand, shows that the DDID 7abc1a23 appears only once, and that, in the three other transaction records where 7abc1a23 previously appeared, the DDIDs: 54ಐ, DeTym321 and HHyargLM appear instead. Changing DDIDs that refer to Scott using JITI effectively de-identify Scott for each transaction—providing him with a JITI for each transaction. As a result, Scott cannot be re-identified by correlating these dynamic anonymous identifiers.

Different JITI keys can "unlock" different views of the same DDID or its underlying value, thereby providing granular control over the level of detail or obfuscation visible to each user based on the context of said user's authorized use of data (e.g., authorized purpose(s), place(s), time(s) or other attributes of use). For purposes of this application, "unlock" means decode, translate, unveil, make visible permanently or ephemerally, or provide a unique "slice" consisting of a subset of a larger set of data, where such slice can contain no data elements, a single data element, or any combination of any number of data elements. The rendering of DDIDs into intelligible form by JITI keys is triggered by the existence of prescribed JITI key trigger factors (e.g., purpose, place, time and/or other designated trigger factors) that are used alone or in combination with other trigger factors so that DDIDs, including obfuscated ones, are rendered in different ways for different users and/or different times and/or in different places and/or on other attributes of use, all based on satisfying JITI key trigger factors. As mentioned above, FIG. 1B describes various exemplary events that may trigger the assignment, application, expiration and recycling of DDIDs with respect to data elements (e.g., data attributes and/or attribute combinations) and/or JITI keys to occur.

Another example embodiment of the present invention relates to medical services. In this example embodiment, the cleartext value of 55 heartbeats per minute (BPM) is replaced with a DDID having the value of "ABCD." Note that, solely for the purposes of simplifying exposition, the example DDIDs provided in this application are often presented as being a few characters in length, but in an actual embodiment, these DDIDs may be of any finite length. The DDID used in this potential example, ABCD, is programmed to be rendered as its unaltered original value of "55 BPM" only by those JITI keys for which the said key holders satisfy all of the following applicable requirements (by "applicable," it is meant that JITI key access may be based on one, some or all of the attributes set forth below):

1.) Purpose Based: In this example, either with respect to:
   a. Authentication of the identity of the key holder (e.g., by means of a password, multi-factor authentication or any other authentication process); and/or
   b. Authorization for the individual key holder to view the JITI key-authorized data (e.g., by comparing the authenticated identity of the key holder to the identities of medical personnel assigned to care for the patient) or indirect authorization for said key holder by means of inheritance of attributes (e.g., from a set, collection, group, class or other structure of any size to which the individual belongs) enabling JITI-enabled access to the source data.

2.) Physical Location Based: In this example, either with respect to:
   a.) A physical location relevant to providing care to or for the patient (e.g., within a specified distance from the patient's room and/or from a medical station on the same floor as the patient's room); and/or
   b.) A physical location pertaining to authenticated, authorized persons (e.g., within a specified distance from a mobile phone, device and/or sensor that is intended to be kept on the person of each authenticated and authorized nurse).

3.) Temporally (Time) Based: Verification of permissible time periods (e.g., by comparing then-current time to the times when the key holder is scheduled to be providing care to the patient).

Figure 1Q:
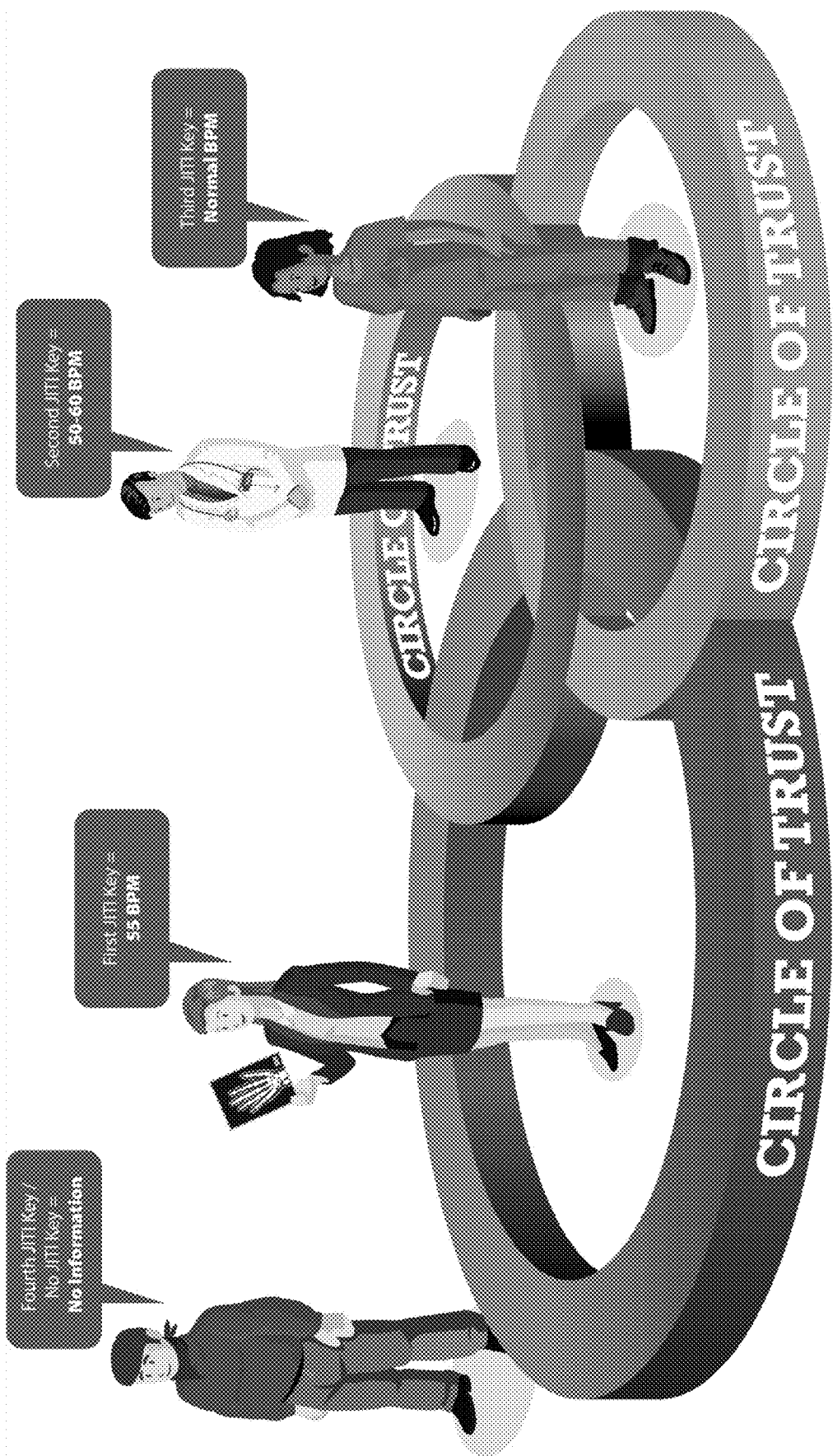
FIG. 1Q illustrates an example of the use of Just-In-Time-Identity (JITI)-enabled security and privacy in the medical services context, in accordance with one embodiment of the invention.

FIG. 1Q illustrates the medical services embodiment described above. For example, a first JITI key used by an authorized medical provider during the provider's shift within a specified distance of the patient's room or associated medical station may be configured to unlock the full original value of the DDID "ABCD", so the provider would be shown "55 BPM." A second JITI key used by an authorized medical provider during the provider's shift but beyond the specified distance from the patient's room or associated medical station would be configured to unlock a perturbed (e.g., changed) version of the original value of the DDID "ABCD," so the provider would be shown a range of "50-60 BPM." A third JITI key used by an authorized medical provider both outside the provider's shift hours and beyond the specified distance from the patient's room or associated medical station would be configured to unlock a descriptive statement about the original value of the DDID "ABCD," so the provider would be shown a description of "Normal Heart Rate" but which lacked any timely information about the patient's heart rate. A fourth scenario in which an authorized medical provider (following a successful authentication action) possesses a fourth JITI key that is not authorized to reveal information specific to the patient's heart rate data, thereby preventing the provider from seeing any information other than the DDID itself. Similarly, if no JITI key is presented or if a person who is not authenticated and authorized attempts to use a JITI key, that person will not see any information other than the DDID itself.

Figure 1R:
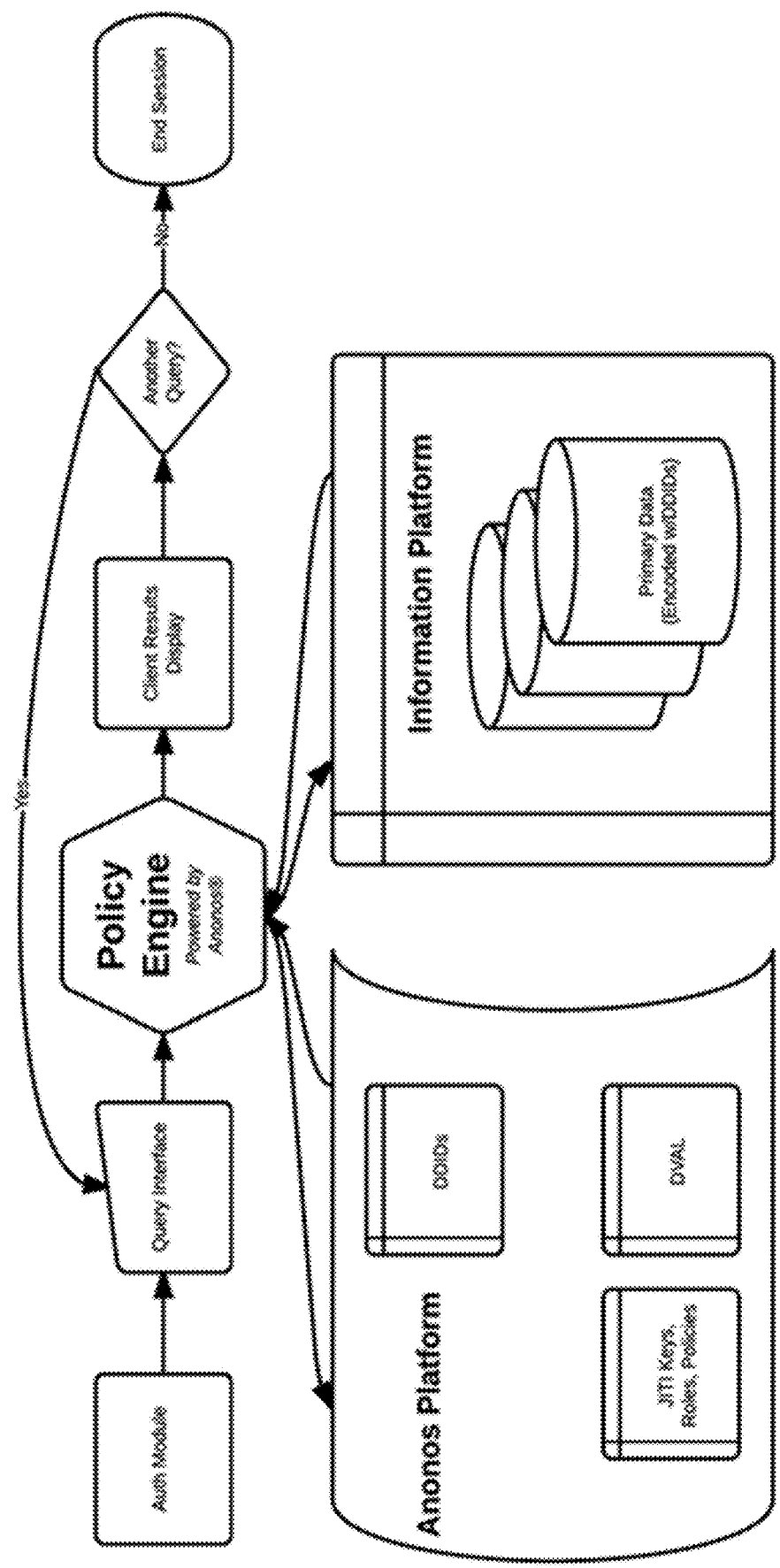
FIG. 1R illustrates an example of a system for implementing Just-In-Time-Identity (JITI)-enabled security and privacy, in accordance with one embodiment of the invention.

FIG. 1R illustrates one potential architectural embodiment for supporting the above exemplary medical services embodiment of JITI. In this potential embodiment, an "Auth Module" is used to verify authorization of a user to retrieve DDIDs, e.g., by using what is referred to below as the "Anonos JITI Policy Engine," but the subsequent order and application of the various JITI key scenarios would dictate to what extent the source value was revealed and returned to the medical provider. A user, using the "Query Interface" interacts with the Policy Engine which in turn accesses data in the "Anonos Platform" (e.g., DDIDs, JITI keys, Roles and policies—which determine when DDIDs will be transformed, and DVALs—which provide yet another level of abstraction for DDIDs) and data in the "Information Platform" (e.g., primary data that has been replaced at the data element level with DDIDs). This potential embodiment illustrates that possession of a DDID on its own, even if the active user is trusted and correctly authenticated, may be insufficient to unlock any original data element. Every action against the stored data must work in concert with both the DDIDs and an allowable set of one or more valid JITI keys. In all other cases, the "End Session" step results in a "fail close" (i.e., reject the access and stop, shut down, terminate the application, etc.—as appropriate to the particular scenario) and the system will not return any data with value.

The following description is neither inclusive of all possible considerations nor intended to define a minimum or maximum scope. For example, while the following description uses traditional tabular database structures, it is only a single example and a single embodiment of an implementation. JITI could be implemented using NoSQL and/or other approaches, including without limitation emerging technologies such as quantum databases, quantum relational databases, graph databases, triple stores (RDF) or S3DB (as a means to represent data on the Semantic Web without the rigidness of relational/XML schema).

Further, any of such approaches and/or databases may be used to support, implement and/or be integral to the creation, implementation and/or deployment of a Privacy Client and/or a Privacy Server, which are themselves used to support an implementation of JITI or any other aspect of the inventions set forth herein or in letters patent or patent applications in the same family. Either or both of the Privacy Client and Privacy Server may be integrated with, controlled by and/or populated with data by a client-side application, where such application may, in certain embodiments, (i) run on siloed computer equipment not connected to the Internet; (ii) run on mobile devices connected directly or indirectly to the Internet, including devices on the Internet of Things; (iii) run directly as an application or through an application that itself runs on any standard Internet browser (e.g., Chrome, Internet Explorer, Microsoft Edge, Firefox, Opera, Safari, native Android browsers, etc.); and/or (iv) utilize components and services commonly associated with or that are part of the Semantic Web. Similarly, the various queries and record create/modify events described below are not intended in any way to limit embodiments to Relational Database Management System (RDBMS) type designs; such language is used only to simplify the characterizations of the types of actions performed.

An embodiment of the present invention involving DDIDs and JITI keys as described herein might include at a minimum, an implementation whereby a Privacy Client (and, at a maximum, both the Privacy Client and the Privacy Server, including as many instances of such Clients and Servers, equal in number, respectively to one or greater) would reside on the client side (e.g., as part of an application running in the browser, on virtual, physical or logical computing devices of any kind described herein on which a Privacy Client can run and where such devices or applications running thereon interact directly or indirectly with such a browser). One such potential implementation using DDIDs and JITI keys could harness capabilities of the Semantic Web (the extension of the Web through standards established by the World Wide Web Consortium (W3C) like the Resource Description Framework or RDF) as a unifying computational environment.

FIG. 1S illustrates one potential JITI-enabled embodiment of a JITI-enabled system to support the OpenHealth Platform (OH) using native, W3C standardized, data management resources, such as NoSQL IndexedDB, wherein one or both of the Privacy Client and/or Privacy Server could reside on or logically "behind" the OH Platform. Note that, as contrasted with Example A of FIG. 1S, in Example B of FIG. 1S, all data and computation, including but not limited to Privacy Client and/or Privacy Server functionalities, could be performed by either data providers or by domain consumers, such that dedicated computational infrastructure would no longer be required to support JITI-enabled or other operations. By implementing OH as a JITI-enabled deployment via the Semantic Web, OH could manage and orchestrate health-related digital assets to simultaneously maximize data value and data protection (both security and privacy) free from restrictions on server side resources, since, optimally, from a resource perspective, neither any Privacy Client nor any Privacy Server would consume any such resources, thereby enabling and delivering greater scalability.

Unlike a traditional DB, no raw data may be stored in the Main DB of a JITI-enabled system (i.e., only DDID data may be stored). There may instead be two databases: a "Main DB" (with DDID data) and a "JITI DB" which contains keys that decrypt the Main DB on a cell-by-cell basis. Each new value in the "Main DB" is in this example assigned a unique DDID value 8 characters long, wherein each character is a member of the character class a-z, A-Z, 0-9. (Such syntax and structural constraints are arbitrary and could be reconfigured to suit any particular deployment or policy goal, including defining a DDID syntax to comply with the original syntax requirement of the source data field type, while still inserting random values with no greater chance of re-identification than would be possible via guessing.) In total, there are 62 possible values per character (26 lower case alpha+26 upper case alpha+10 numeric). There are thus 62^8 (approximately 2.1834*10^14) possible values (and this range can increase significantly by adding additional characters to achieve higher entropy). This could easily be changed to BASE64 (or some other encoding) in the future—this choice is just for aesthetic value in this example embodiment.

In one embodiment, the underlying value of every DDID in the Main DB may also be assigned a new, unique 8-char DDID. For convenience's sake, to distinguish the underlying value of a DDID from the DDID itself, we will call the underlying value of the DDID the "DVAL." For simplicity, a random 8-char DVAL is sufficient, provided it is subjected to a uniqueness check. For future use, random generation might not be adequate for very large data sets (trillions of records). Sequential values (such as aaaaaaaa, aaaaaaab) are not used because sequential unique ID's can be used to launch an inference attack if the ordering of the original raw table is known (such as during a database import).

In one embodiment, each raw value will be encrypted using AES, which produces a unique ciphertext even for the same plaintext due to different initialization vectors. For example, TABLE 4 below give a set of exemplary "original" values.

TABLE 4

| Name | DOB | Location |
|---|---|---|
| John | Oct. 9, 1940 | Purgatory |
| Paul | Jun. 18, 1942 | St John's Wood |
| George | Feb. 25, 1943 | Heaven |
| Ringo | Jul. 7, 1940 | Los Angeles |

The DVAL's for the values shown in TABLE 4 might (with random generation) be the values shown in TABLE 5 below.

TABLE 5

| Name | DOB | Location |
|---|---|---|
| 93ziqklq | 75goAaoa | ukyg8tbd |
| 8sydz6q4 | B5hnpkiE | 7y6E21lg |
| Ct1tsBA0 | Fp950mby | fbwui9ja |
| 3mtxke9c | btoml49f | eFinqw1q |

In order to re-associate each DVAL with its original value, each DVAL may be written to the DVAL Table with its encrypted ciphertext and an Initialization Vector (IV), as is shown in TABLE 6 below (which was AES encrypted using a secret key of "for-demo-purposes-only".

In another embodiment, a one-way hash function may be used to generate a DDID that obscures each raw value. In yet another embodiment, the DDID may be generated using various stochastic processes unrelated and not correlated in any way to the DDID, its underlying value or any other related data (e.g., a list of worldwide zip codes divided into 8 character strings and randomly resorted every 15 minutes).

Return to the AES example, the Initialization Vector (IV) may be passed along with ciphertext because the secret key is what keeps the data secret. One benefit of the IV is that the same plaintext value can have different ciphertexts. For example, if there are 10 records with the same last name or zip code, while the plaintext values for those 10 names or 10 zip codes are identical, the DVAL, ciphertext and IV will all be unique.

To query the Anonosized database, a user needs to have permission by way of JITI Keys. These are broadly intended to apply policy controls specific to intended purpose, place, time of use, and other relevant attributes. In addition, JITI Keys may enforce expiration-based constraints, resulting in, with respect to one preferred embodiment, a triumvirate of measures: Query Constraints; Display Constraints; and Time Constraints. JITI Keys may be stored in the JITI Key DB and provide granular access control; they also may determine how the raw data is displayed (e.g., in DDID form, transformed via one of the transformation rules, or raw).

Methods of "Anonosizing" Data

As mentioned above, the terms "anonosize" and/or "anonosizing" refer to replacing data with DDIDs down to the data element level. More particularly, anonosizing, as used herein, may refer to the encoding and decoding data under controlled conditions to support specific uses of such data, e.g., within designated contexts as authorized by a data subject or by an authorized third party.

Implementations of anonosizing data may allow a data management system to retain the capability to reproduce data with its original value (e.g., economic, intelligence-wise, or other) and utility intact, but enable the level of identifying information that is revealed to be authorized, e.g., by a data subject and/or an authorized third party. In some embodiments, data may be revealed only to the extent necessary to support each designated data use. By anonosizing data controls, e.g., via "identifying" and "associating" data elements within a population and/or cohort of individuals, data uses may be restricted to those uses that are permissioned by a particular data subject or authorized third party. If new authorized data uses arise, all original data value and utility may be retained to support the new uses of the data to the extent authorized by the data subject or

TABLE 6

| DDID | CipherText | Init Vector |
|---|---|---|
| 93ziqklq | acK1Z8Orw7BUwro9wrDCmMOGwqHDgsOawq/Cpw== | fCeCe66AA6EE4A44 |
| 8sydz6q4 | ETLCmcO3UAgBYcK5wp0wwr5qKMO3w6E= | 87DaDeF8eFaad2c1 |
| Ct1tsBA0 | wprCrcKbDSHDpCt2JCTCoMOEw4HCrUTDvw== | 9bFbB6AcbCd3A5cF |
| 3mtxke9c | wpbDuXR4w6ZKHSkiw6DCqGHDmyxHPA== | bdA0a691b2c6DBCC |
| 75goAaoa | w4TDmMOgDcKYw6rCvhvCmcK7ZMOtXzBuw5k= | 2fDDE99Da1A17f9f |
| B5hnpkiE | HUTCp31tw4Mrw55bS0/DsgTCssOCwq0= | 20546c0DDBaf5dec |
| Fp950mby | wqYIAcOvw6jCmiYQLMOYwrJRPcKgLSk= | CBC0846fFFF78Bf0 |
| btoml49f | VTE5IMO8PBUHw6vCp07DqXHCpFZZ | aDCCF6b94B175385 |
| ukyg8tbd | w6zDu8KCRBfDt8OIwq1FwrltLWQ4PcOk | 72e0BeCb691BC710 |
| 7y6E21lg | w6PDpMOIwo4AWMO8SU9rCcKFLsOfRMKY | 3D2B4DDf512FF7FD |
| fbwui9ja | EXZeWT3Ctk3DnUHDl8KdRR/Cg8O9LQ== | E3Cf320aC66272Ab |
| eFinqw1q | wrDCucKZXcO2w5Q9woXCg8Kjw6nDpsKTBMO2wqY= | 18673fc70ebEE00b | authorized third party, but inappropriate, i.e., non-permissioned, uses of identifying information may be prevented.

Anonosizing data by dynamically changing DDIDs minimizes the ability to re-identify individuals from seemingly non-identifying data due to the Mosaic Effect. Harvard University Professor Latanya Sweeney's research is cited to above as evidence that knowledge of a birthdate, gender and zip code can be enough to identify as many as 87% of the people in the United States. However, in order to combine a birthdate, gender, and zip code to achieve this 87% rate of re-identification, these three pieces of information must be known to relate to the same individual. As an example of dynamism achieved using DDIDs, by associating a different DDID with each of birthdate, gender, and zip code, it would not be known if a given birthdate, gender, or zip code relates to the same person or to some combination of different people. This lack of knowledge thereby defeats re-identification via the so-called "Mosaic Effect."

Thus, embodiments of anonosizing herein may comprise: 1.) providing a method to designate data fields that contain primary and/or secondary "quasi-identifying" data elements, i.e., those data elements that reveal some information about a person—but do not themselves explicitly reveal the person's true identity, to be replaced with a R-DDID and/or A-DDID; and 2.) providing a method to establish de-referencing policy rules for replacing primary and secondary "quasi-identifying" data elements with R-DDIDs and/or A-DDIDs and/or to specify format requirements for said R-DDIDs and/or A-DDIDs, e.g., field length and character type (e.g., alpha, numeric, alphanumeric, etc.), dynamism requirements for changing said R-DDIDs and/or A-DDIDs (e.g., triggers to cause change, frequency of change, etc.).

Data Anonosizing Policy Management and Access Controls

Although some privacy policies (e.g., those that implement fuzzy logic, non-deterministic, or other similar approaches) are intentionally ambiguous with regard to what views of the true underlying data are allowed and not allowed to recipients of such data, described herein are certain policies that are capable of enforcing unambiguous "bright-line" distinctions between which views of the given data are allowed and not allowed (for example, an original heart rate value of 65 beats per minute may be converted into NADEVs obscured through the use of A-DDIDs). Specifically, NADEVs, whether or not obscured by A-DDIDs, may include, but not be limited to: (i) synthetic data, i.e., data applicable to a given situation that are not obtained by direct measurement and are persistently stored and used to conduct business processes (as further defined below); (ii) derived values, i.e., data based on logical extensions or modifications of the original data; (iii) generalized data, i.e., generalized versions of data obtained by inference or selective extraction from the original data such as classes or cohorts; or (iv) aggregation, i.e., the result of applying one or more algorithms on multiple data elements in the same record or across multiple records). In one example, a first NADEV may comprise a range of 61-70 beats per minute, and a second NADEV may simply comprise the textual description "normal," (each of which may be suppressed or revealed individually). Additionally, the people or entities that are authorized to create or use such views (and for what purpose(s)) may also be individually specified. Such policies may also provide for the setting of temporal parameters governing when creation or use is authorized or not, as well as location parameters, which may govern where, e.g., via place name, GPS coordinates, or other identification methods, the creation or use of such data is authorized.

One particular form of generalized data occurs with respect to unstructured data. According to Wikipedia, "Unstructured Data (or Unstructured Information) refers to information that either does not have a pre-defined data model or is not organized in a pre-defined manner. Unstructured information is typically text-heavy, but may contain data such as dates, numbers, and facts, as well. This results in irregularities and ambiguities that make it difficult to understand using traditional programs as compared to data stored in fielded form in databases or annotated (semantically tagged) in documents." Unstructured data may also include multimedia data, such as pictures, audio, videos, and the like. Importantly, data may be anonosized whether such data are structured, unstructured or any combination thereof.

In 2016, IBM stated "Today, 80 percent of data comes from previously untapped, unstructured information from the web such as imagery, social media channels, news feeds, emails, journals, blogs, images, sounds and videos. Sometimes called 'dark data,' unstructured data holds the important insights needed for faster, more informed decisions. So, what's the other 20 percent? It's traditional, structured data living in data warehouses, and it's important, too. You can't live without structure." Ginni Rometty, IBM Chairman, President, and CEO said, "First, the phenomenon of data. Data that was invisible will now be visible to you, especially the more-than-80 percent that is 'unstructured'—natural language as found in books, literature and social media . . . video, audio, images. More and more of it comes from the Internet of Things. Computers can process unstructured data, store it, secure it, move it around, but traditional programmable computers cannot understand it. Dark data is data which is acquired through various computer network operations but not used in any manner to derive insights or for decision making. The ability of an organization to collect data can exceed the throughput at which it can analyze the data. In some cases, the organization may not even be aware that the data is being collected. IBM estimates that roughly 90 percent of data generated by sensors and analog-to-digital conversions never get used. In an industrial context, dark data can include information gathered by sensors and telematics. The first use and defining of the term appears to be by the consulting company Gartner. Organizations retain dark data for a multitude of reasons, and it is estimated that most companies are only analyzing 1% of their data. Often it is stored for regulatory compliance and record keeping. Some organizations believe that dark data could be useful to them in the future, once they have acquired better analytic and business intelligence technology to process the information. Because storage is inexpensive, storing data is easy. However, storing and securing the data usually entails greater expenses (or even risk) than the potential return profit." Anonosization may also be applied to such "dark data."

Research firm IDC and storage leader EMC (now owned by Dell Computer) project that data will grow to 40 zettabytes by 2020, resulting in a 50-fold growth from the beginning of 2010. Computerworld states that unstructured information might account for more than 70%—80% of all data in organizations. Therefore, in any given organization, is it highly likely, if not close to certain, that any means of protecting data privacy while enhancing data value must, among other requirements, process unstructured information in order to be practically useful.

Consider, for example, but without limitation, an Electronic Medical Record (EMR). EMRs contain not only specific data, such as red blood cell count, blood pressure, ICD-disease codes and the like, but also "notes" fields, which are primarily, if not exclusively, composed of text. Anonosization of such a notes field results, as the default (i.e., as an automatic opt-in, which can be modified to opt-out), in the de-identifying transformation of that field into an R-DDID. However, contained with that notes field may also be important medical characteristics about a data subject, of which the disclosure of just a few or potentially just one such characteristic could result in the data subject's being re-identified. For example, while "strep throat" is such a common condition that it is unlikely to result in re-identification, "pancreatic islet cell cancer" or the disclosure of a disease for which there are very few cases per year worldwide (or even the use of an orphan drug) is a rare enough condition such that, by itself or perhaps in combination with another datum, the data subject could be easily re-identified.

A first attempt at a solution to this could, as described, simply anonosize the notes field by replacing it with an R-DDID that by itself would not reveal any information in the notes field but would provide the means of retrieving the entirety of the notes field under controlled conditions, e.g., wherein an authorizing JITI key is used. The use of A-DDIDs provides an additional approach. A-DDIDs enable cohorts (e.g., those with pancreatic islet cell cancer, those with strep throat, those with schizophrenia and irritable bowel disorder—the last, perhaps for those studying the gut microbiome, which is now believed to be correlated with mental health) to be identified (inter alia, manually; by the application of machine learning; by the application of artificial intelligence; by the use of quantum computers) and, once identified, to be represented by such A-DDIDs. In this way, while an A-DDID may be associated with a range (e.g., systolic blood pressure>140 and <160), an A-DDID can also be associated with a particular condition that exists within a notes field in an EMR. The production of A-DDIDs, however, may be defaulted to opt-out, so it would require an override to actually produce them. Moreover, any value that could be derived from any analysis of a notes field, including but not limited to Bayesian, Markovian, or heuristic analyses, could also be used to define the existence of a cohort; and membership in that cohort could be enabled by an A-DDID assigned to all records belonging to said cohort. Beyond these applications, consider multimedia forms of unstructured data, such as the outputs of MRI, CT, Positron Emission Tomography, and ultrasound scans and the like, whether represented as snapshots (as might be the case with X-rays) or as videos (as might be the case with Positron Emission Tomography and ultrasound scans). The information extractable from such multimedia data is virtually limitless and organizable into an unlimited or near-unlimited number of cohorts. A-DDIDs, therefore, may be used to de-identify any of the cohorts obtainable from this extractable information to present information in a manner that is not re-identifiable back to a Data Subject, because the cohort and the data values associated therewith may be used independently from the identity of the Data Subject. In all of the foregoing cases, those with a need to use the information extracted could be authorized, e.g., via JITI keys, to re-identify the relevant A-DDIDs, which themselves could be associated with other A-DDIDs, but which would not be associated with R-DDIDs or, if associated, to which R-DDID access would be unnecessary—and therefore unauthorized. Since the R-DDIDs would refer only to the Data Subjects, the researchers would only need the medical information obtainable by re-identifying the A-DDIDs, where such A-DDIDs de-identify not only structured data, but also unstructured data (or structured representations of data inferred or deduced from unstructured data), so that data subject privacy is increased or maximized—while data value to researchers is similarly increased or maximized.

According to some embodiments, after one or more transformations have been performed on the relevant data sets to produce a NADEV or a set of NADEVs, each member of the resulting set of data (or any combination of members thereof) may be obscured via the use of A-DDIDs or otherwise obscured to the extent desired by the policy maker, in order to meet or exceed the requirements of Privacy Enhancing Techniques (PETs) e.g., public key encryption, k-anonymity, l-diversity, introduction of "noise," differential privacy, homomorphic encryption, digital rights management, identity management, suppression and/or generalization. At the same time, the value of the data, e.g., as measured by one or more of a number of factors, such as mean, joint mean, marginal mean, variance, correlation, accuracy, precision, and the like, may be maintained at maximum or optimal levels (i.e., as compared against the value of the original non-transformed data or the input data to a further transformation). These techniques provide an advantage over existing methods of obscuring data, at least because existing methods are generally: (i) policy-based only (with no means of technical enforcement); or (ii) if technically enforced, reduce the data's value, often significantly, thereby preventing desired analytics, correlations, discoveries or breakthroughs from occurring.

The application of data anonosizing policies, as described in the various embodiments disclosed herein, provide a way to programmatically enforce these policies against any simple or complex set of data, as described earlier. The nature of such enforcement consists, but is not limited to, generating further limitations or exclusions on the data by using any combination of time, purpose and place JITI keys or values (or other types of access control-based keys or values).

Part of the utility of using such data anonosizing policies derives from the ability of the policies to transform data "atomically" or "cellularly," i.e., down to the level of a single unit of data, whatever that may be for a given implementation. An atomic unit of data may be a single datum or a group of data that is treated as a single entity for the purpose of analysis, association, computation, anonymization, and the like. As discussed below with reference to FIG. 1U, while previous data protection methods may, for example, be able to protect or encrypt data 'by row' or generalize 'by column' in a 2-dimensional data set, the techniques described herein may protect or encrypt data by row, by column, by a vector in a 3rd, 4th or even nth dimension, or by any combination thereof. Moreover, the techniques described herein may be applied in the opposite direction, i.e., down to the level of a single cell in a multivariate data set, or to any collection or permutation of continuous, discontinuous or discrete cells. The capabilities of these "Cellular Operations," i.e., inter alia, suppression, generalization, public key encryption, k-anonymity, l-diversity, introduction of "noise," differential privacy, homomorphic encryption, digital rights management, identity management, and other PETs, may be enabled by the anonosizing system's ability to tokenize each datum or any group of data de novo.

The tokenization (i.e., anonosizing) of data at the cellular level may also be built into a hierarchy of NADEVs or other values and of references to another datum or groups of data. The tokens produced, along with information about access controls and authorizations, may themselves be stored in relationship and lookup databases, and they may also be obscured through the use of A-DDIDs. Implementation of a given policy may comprise: (i) protecting the data at an elemental or cellular level; (ii) controlling what information is revealed, when and/or for how long it is revealed, to whom it is revealed and for what purpose it is revealed; and/or (iii) controlling the 'clarity' with which the data is revealed, e.g., one authorized party may be given access to the cleartext value of the data at a given authorized time and place, whereas only a NADEV representation of the true value of the data may be revealed to another party that does not need to have access to that level of data specificity. The controlled reveal of data may involve the usage of certain random, stochastic, parametric or non-parametric aspects, but also the ability to control over when (i.e., at what time or times), where (i.e., at what physical or virtual place or places) and why (i.e., for what purpose or purposes) the reveal itself occurs.

Figure 1T:
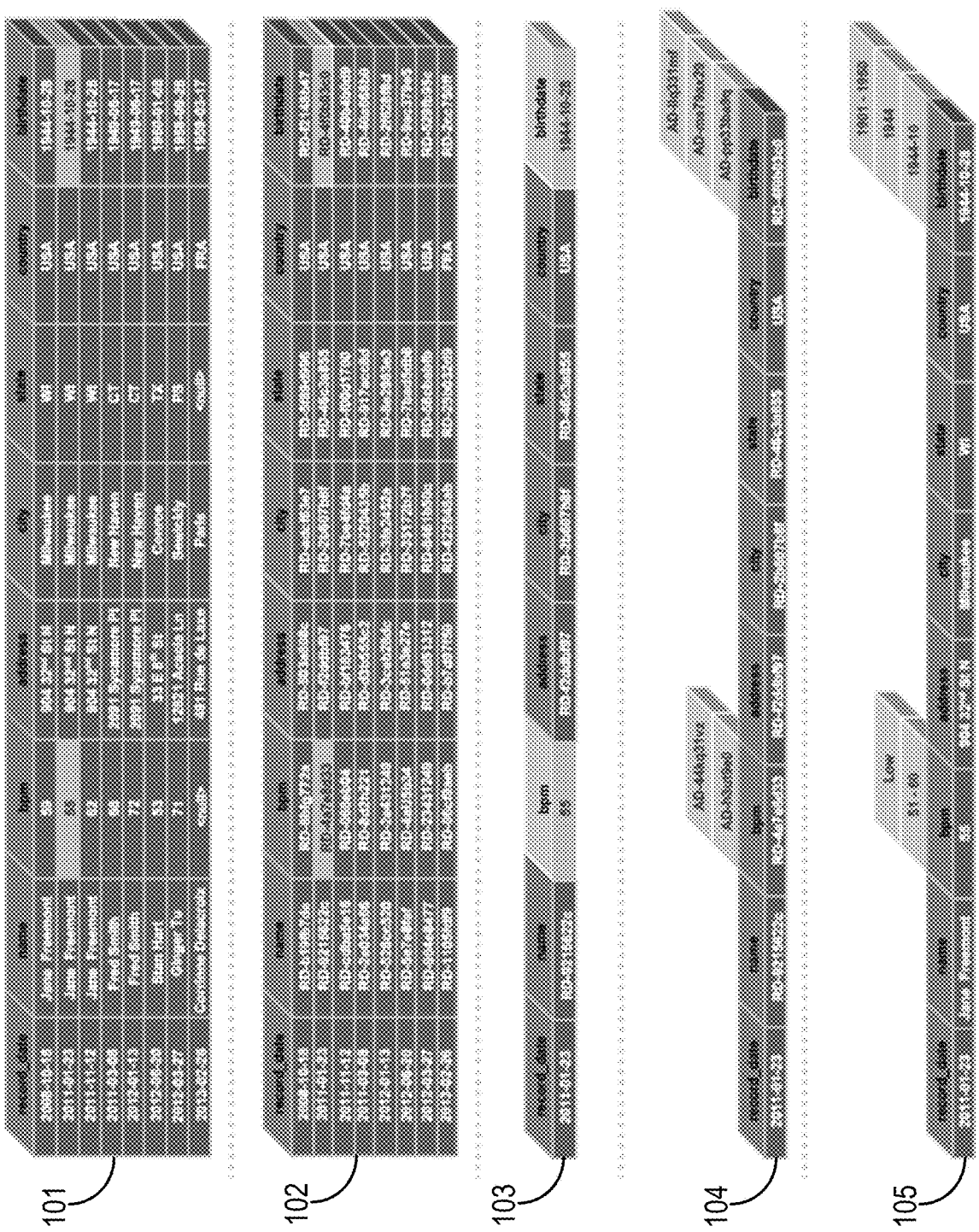
FIG. 1T illustrates an example of a system for implementing data de-risking policy management and access control, in accordance with one embodiment of the invention.

FIG. 1T illustrates an example of a system for implementing data de-risking policy management and access control, in accordance with one embodiment of the invention. First, table 101 represents an original, cleartext representation of a source data table. As is illustrated, table 101 stores unobscured values for each of the fields in the table, i.e., record_date, name, bpm, address, city, state, country, and birthdate. Table 102 represents a data table wherein the data has been transformed by replacing the data with tokens (i.e., pseudonyms) at the data element level. For example, the beats per minute (bpm) value of 55 in the second row of table 102 has been replaced by the token value, "RD-4a7e8d33," and the birthdate of 1944 Oct. 28 in the second row of table 102 has been replaced by the token value, "RD-4f0b03c0." Table 103 represents an exemplary data reveal of the second row of the original source data table 101, wherein selective data from the table (e.g., the bpm field and the birthdate field) have been revealed down to the data element level, while the rest of the data remains anonosized/pseudonymized. Table 104 represents an example of NADEVs, i.e., digitally obscured, partially obscured, granularized, filtered and/or transformed versions of the underlying data that have been inserted into the data table based on one or more policies. For example, as shown in table 104, two NADEVs have been inserted corresponding to the bpm value of 55 from the second row of the original data table 101, and three NADEVs have been inserted corresponding to the birthdate value of 1944-10-28 from the original data table 101. Finally, table 105 represents an example of the underlying values that were obscured, partially obscured, granularized, filtered and/or transformed into NADEVs inserted into the table shown in 104. As explained above, only the necessary level of identifying data may be revealed to a given recipient, based on the one or more policies in place. For example, one authorized recipient may receive a value of "55" for the bpm, whereas another may receive the "51-60" NADEV, and yet another recipient may receive the "Low" NADEV. Likewise, one authorized recipient may receive a value of "1944-10-28" for the birthdate, whereas another may receive the "1944-10" NADEV, another may receive the "1944" NADEV, and yet another recipient may receive the "1901-1950" NADEV. As may now be more fully appreciated, each of the NADEV is accurate for the underlying data, although, separately or together, they just may reveal the true underlying value of the data with greater or lesser degrees of granularity, depending on the implementation and design of the relevant policies.

FIG. 1U illustrates an example of various data de-risking schemes, in accordance with one embodiment of the invention. For example, a traditional means for protecting data (e.g., encryption) is shown in scheme 106. Scheme 106 represents a 'binary' protection scheme, in other words, such a scheme either revels every single data element (i.e., the white squares) or no data elements at all (i.e., the darkened squares). Newer methods of protecting data may enable data to be revealed or obscured on a '2-dimensional' basis, as is shown in scheme 107. In other words, the revealing of data may be done on a row-basis or columnar-basis. Finally, scheme 108 reflects the multi-dimensional or 'n-dimensional' protections schemes described herein, wherein data may be revealed (or obscured) at the individual data level (including any combinations of cells) on a 2-, 3-, or n-dimensional basis.

Virtual Marketplace for Data Anonosizing Policies

FIG. 1V illustrates an example of a marketplace as shown in scheme 110 for various data de-risking policies made available for purchase, in accordance with one embodiment of the invention. The electronic marketplace described herein may sell or otherwise make available for consumption any number of different policies available from in-house or third party privacy policy vendors. The policies may be ranked using non-parametric measures (i.e., rank orderings) and/or parametric measures of, analysis of, and performance attributes of a given policy against quantitative or qualitative metrics (e.g., an "Accuracy Rating" or a "Privacy Rating", as shown in table 110), as well as "user ratings" of a particular policy. Further, the rankings and analyses may be based on the application of that policy to a particular type of privacy or data value challenge (i.e., the "Subject Area" in the table of 110), for example, HIPAA, GLBA or FERPA (in the US) or the European Union's (EU) General Data Protection Regulation (GDPR). No known marketplace provides an objective measure of the quality and relevance of a particular privacy policy i.e., based on its contextual use and the applicable laws and regulations where the policy will be technologically enforced on the underlying data.

Application of Artificial Intelligence to Data Anonosization

As discussed above, certain embodiments of the present inventions may use Digital Rights Management (DRM)-like techniques—analogous to those employed by companies to limit copies that individuals can make of music, movies, and other digital content, and by anonosizing the data, shift the power from the corporate owner of the data to the data subject by enabling a data subject, or an entity that a data subject trusts, to authorize uses of the data subject's personal data. This scheme of data protection is also referred to herein as "Privacy Rights Management" (PRM) or "BigPrivacy." Even in situations where data subjects are not directly involved, PRM technology manages risk to enable responsible use of data that respects the rights of data subjects.

PRM or BigPrivacy may be used to replace static, ostensibly anonymous identifiers with DDIDs. As discussed above, these dynamic identifiers encapsulate data and provide control over re-identification, throughout the full lifecycle of data, down to the data element level. Thus, the same data can mean different things to different people based on technologically-enforced policy controls. BigPrivacy technology may separate sensitive or identifying data into segments and dereference these segments, e.g., using DDID pointers that obscure identities of, and relationships between and among, segmented data elements.

PRM or BigPrivacy technology can also impose common data schemata on data collected from different applications and/or platforms, thereby enabling functional interoperability among heterogeneous data sets to support data fusion, big data analytics, machine learning and artificial intelligence (AI). Anonosized data may then be decoded under controlled conditions to support certain uses within designated contexts, as authorized by a data subject or by an authorized third party (i.e., a "Trusted Party").

The various so-called "Intelligent Policy Compliance" systems and methods described herein may be comprised of artificial intelligence algorithms that may analyze data schemata, metadata, structure, and optionally sample records, of a data set to determine algorithmic actions that may be used to obscure, generalize, or otherwise transform the data set to comply with pre-determined policies using R-DDIDs and/or A-DDIDs, as described above.

According to some embodiments, Intelligent Policy Compliance systems and methods may categorize data by analyzing the data's metadata. For example, field names such as "patient_id" or "prescriber_id" may indicate a healthcare-related data set. Advanced categorization techniques, including those involving remote data look-up, statistical methods, and other algorithms, may be used to enhance the accuracy of the categorization. Sample records of the data set, when available, may improve the accuracy of the categorization even further. According to some embodiments, the categories produced by Intelligent Policy Compliance systems and methods may be aligned to industry verticals (e.g., healthcare) or to specific products and services (e.g., mobile phone call records). Neural network algorithms may also be used to generate conceptual models of disparate domains and industry verticals, enabling cross-industry and cross-vertical categorization. For example, although a jet engine in an aircraft is different from a hydroelectric turbine, both have a capability to direct the flow of a liquid or gas. As such, it would be possible to generate a conceptual model that may be applied to suggest policies for flow measurements.

According to some embodiments, Intelligent Policy Compliance systems and methods may analyze the data provided to it in the context of previous actions configured for data in the determined categories, e.g., by using R-DDIDs and/or A-DDIDs, as indicated above. This analysis may be used to generate a set of actions that may be applied to the data set to modify it in specific ways, e.g., by using R-DDIDs and/or A-DDIDs, as indicated above. For example, a set of actions designed to comply with a particular privacy-related policy may obscure a person's name entirely with an R-DDID, while generalizing that person's phone number to only the area code, by means of an A-DDID. Many combinations of actions such as these may be analyzed by Intelligent Policy Compliance systems and methods to produce one or more combinations of actions appropriate for the data set. The combinations may embody a single "best" combination, multiple combinations selectable by a user, or any other set of combinations.

Through a user interface, a user may modify the actions generated by Intelligent Policy Compliance systems and methods, or apply them to the data as-is. When the user makes such a decision, it may be stored for future use as part of a feedback loop, effectively employing machine learning to allow the Intelligent Policy Compliance systems and methods to learn from successes and mistakes.

Figures 1, 1W:
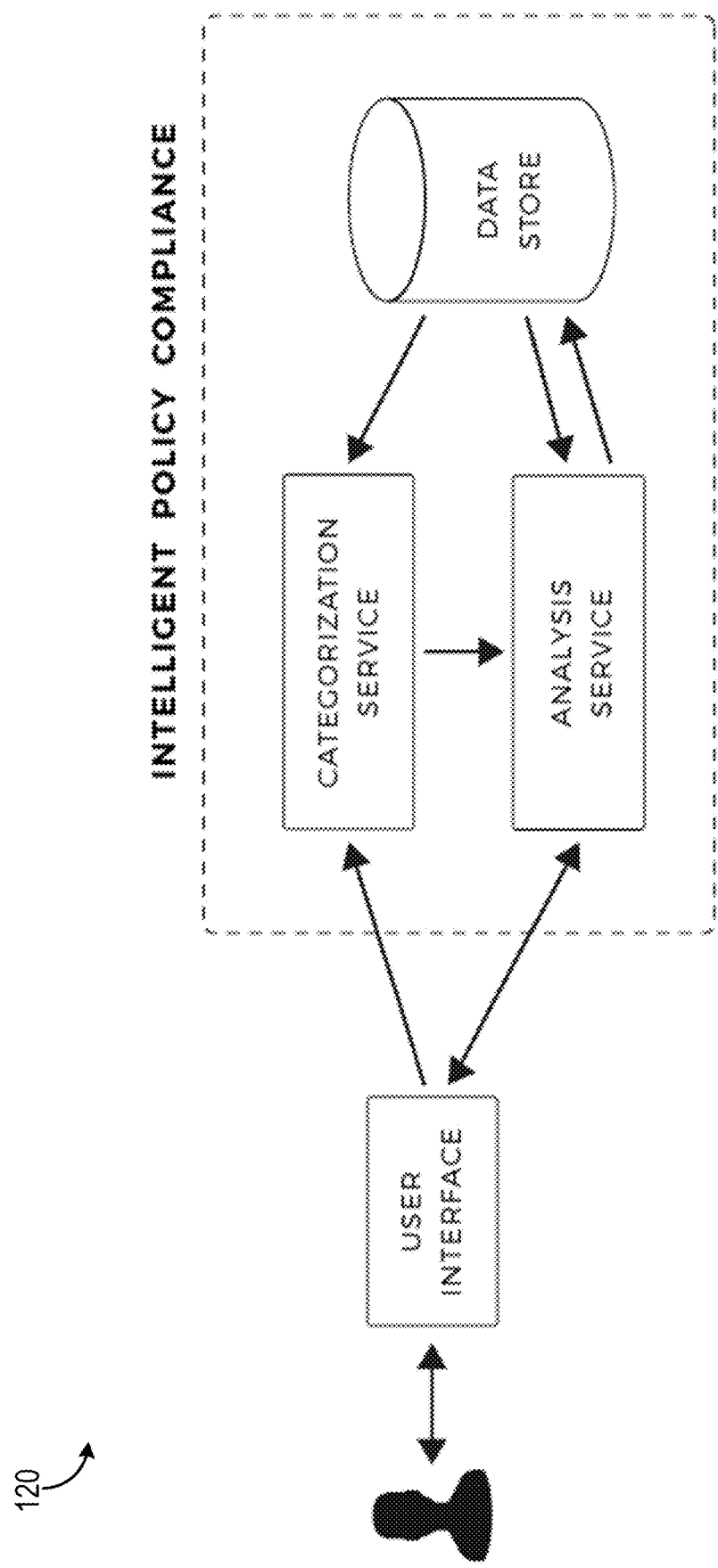
Figures 1, 1W, 2:
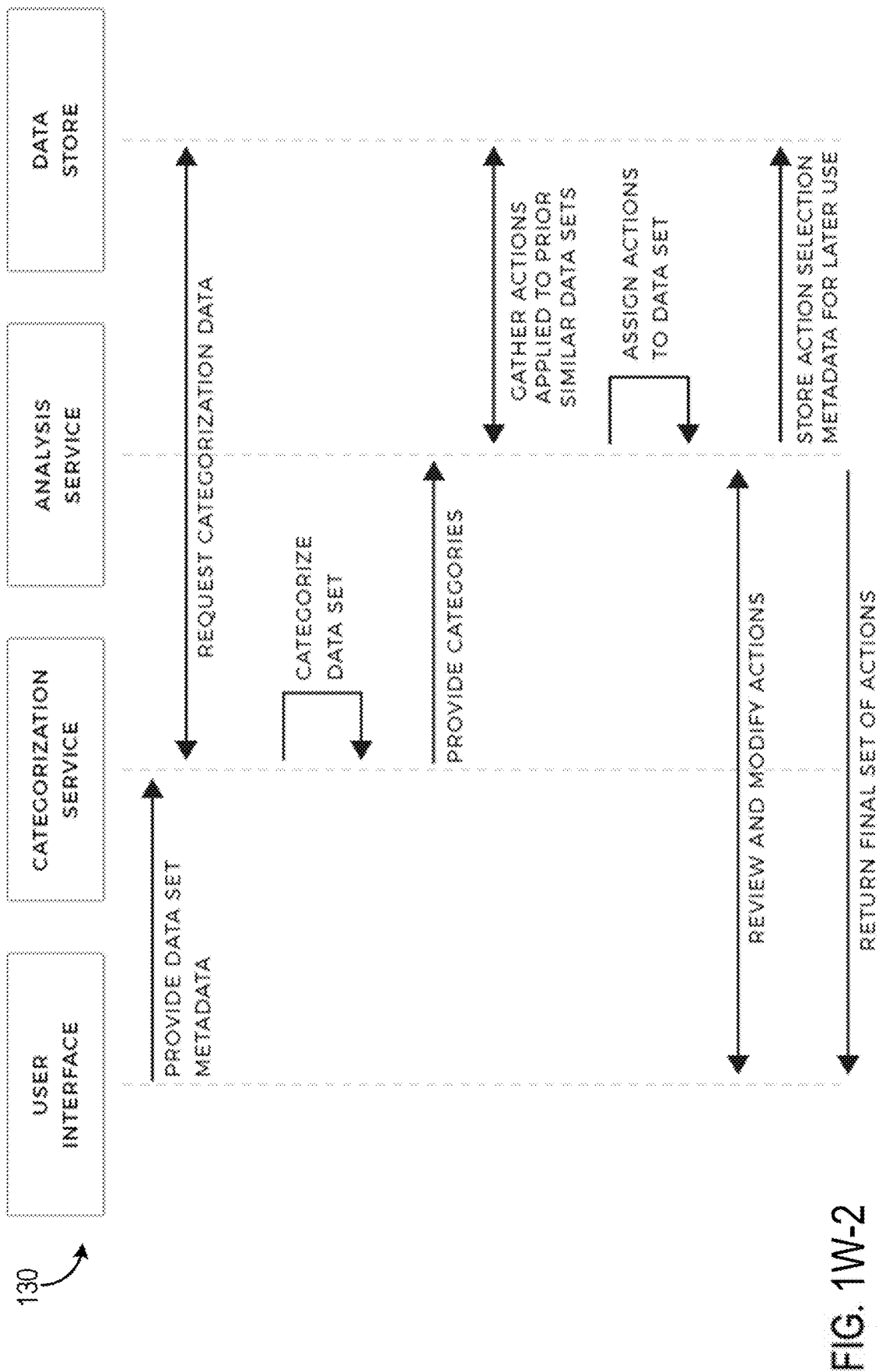

FIG. 1W-1 illustrates an example of an Intelligent Policy Compliance engine, in accordance with one embodiment of the invention. As illustrated, a user may use a user interface to interact with the Intelligent Policy Compliance engine. The policy compliance engine may comprise software that runs one or more categorization services and one or more analysis services. As described above, the categorization service may use AI-related techniques, including machine learning, to determine which category(ies) of data are being stored in the data set of interest. Likewise, the analysis service may analyze the determined categories and suggest one or more privacy policies that may be appropriate for the type of data being managed. The data store may be used over time to both store and update potential data categories and policies related thereto as the Intelligent Policy Compliance system uses machine learning or other methods to "learn" over time which data privacy and anonosization policies are most effective (or preferred, e.g., by users) for a given type of data set.

FIG. 1W-2 illustrates an exemplary flow diagram 130 for the use of an Intelligent Policy Compliance engine, in accordance with one embodiment of the invention. Beginning on the left hand side of the flow diagram 130, a user may provide a data set (including any relevant metadata) via a user interface to a data privacy system's categorization service. The categorization service may request information from a data store that holds intelligence regarding commonly-used data field names and types of data and their associations to particular categories of data that are stored by users. With the benefit of this stored historical information, the categorization service may then apply AI techniques to categorize the incoming data set that has been provided by the user. The determined data category(ies) may then be provided to an analysis service of the data privacy system. The analysis service may likewise request information from the data store that holds intelligence regarding data anonosization actions that have been applied to prior similar data sets. Based on an analysis of the returned information, the analysis service may make various policy decisions and assign various actions to the data set to enforce the data anonosization. The assigned actions and policies may then be reviewed and modified (if desired) by the user via the user interface before the anonosization policies are placed into effect on the data set. Any desired modifications are then stored in the data store so that the policy may be updated, and a final set of policy actions may be returned to the user for approval and to use on the data set at the desired time.

Application of Synthetic Data to Data Anonosization and of Data Anonosization to Synthetic Data According to Wikipedia, and as noted hereinabove, synthetic data are "any production data applicable to a given situation that are not obtained by direct measurement" according to the McGraw-Hill Dictionary of Scientific and Technical Terms; where Craig S. Mullins, an expert in data management, defines production data as "information that is persistently stored and used by professionals to conduct business processes." In other words, synthetic data is created using various modeling, statistical, Bayesian, Markovian and other methods, but it does not represent any real-world data that has actually been measured. Instead, synthetic data is a model of the real-world data. Note that real-world data ultimately refers to actual data subjects, and that de-identified real-world data, if re-identified, would reveal the identities of those data subjects and of any quasi-identifiers associated with those data subjects. In contrast, synthetic data, whether in plaintext or in re-identified form, does not refer to real-world data, but, rather, to a model of it. Thus, while synthetic data may retain certain abstract statistical properties of real-world data, the synthetic data can never be dereferenced to produce real-world data, unless the application(s) producing the synthetic data remain connected to or able to continue to access the real-world data, in which case the real-world data would be accessible by any authorized (or potentially unauthorized) user of said application(s).

The suggested "privacy policies" referenced above may include, but not be limited to, the use of synthetic data. This is because synthetic data does not refer to actual data subjects present in real-world data, and data without a connection to actual data subjects should, in principle, protect the data subject's data privacy. However, as explained elsewhere herein, this is not necessarily true in practice.

A privacy policy can therefore: (i) singularly specify the use of synthetic data; (ii) specify the anonosization of synthetic data, because in principle, one could reverse engineer synthetic data to produce a model for the real-world data, and then this model could be used to identify high correlations between actual real-world data sets associated with data subjects and the model, which is the Mosaic Effect as applied to synthetic data and its models; and the anonosization of synthetic data would make it unavailable to all but authorized parties, thereby reducing the ability of interlopers and bad actors to exploit this potential flaw; (iii) recognize that for a limited period of time, a synthetic data generator must have access to the underlying real-world data for the purpose of modeling the synthetic data, but that after the synthetic data has been produced, the need for such access to the underlying real-world data ceases to exist and can therefore by terminated via the use of JITI keys that constrain access based on time, place and/or purpose; (iv) combine both the foregoing (ii) and (iii) such that not only were synthetic data anonosized but also that synthetic data-generating applications were cut-off from access to the real-world data and its associated data subjects once the synthetic data had been generated and/or depending on where or for what reason (i.e., purpose) said data had been generated; (v) support any of the foregoing in which some of the underlying data are real-world and some are synthetic.

In one embodiment, BigPrivacy may support a privacy policy that specifies the use of some, mostly, or only synthetic data.

In another embodiment, BigPrivacy may support the anonosization of some, mostly, or only synthetic data, so that access even to the synthetic data is available only to authorized parties for limited times, in limited places and/or for limited purposes.

In another embodiment, BigPrivacy may support limiting access to real-world data and associated data subjects only for the time necessary or in prescribed places or for prescribed purposes necessary or related to producing the synthetic data, whether that synthetic data ultimately comprises some, most or all of the total data set to be used.

In another embodiment, BigPrivacy may support the cases of some, most or all of the total data set's being comprised of synthetic data with respect to any combination or combinations set forth above.

BigPrivacy techniques, as described herein, may be employed to facilitate compliance with regulatory and contractual restrictions in a way that helps unlock the full value of data, e.g., by enabling greater data use, while simultaneously enhancing data security and privacy.

One exemplary implementation of BigPrivacy may be used to help an organization to comply with new data protection regimes such as, by way of illustration and not limitation, the GDPR, which contains new protections for EU data subjects and threatens significant fines and penalties for non-compliant data controllers and processors starting in spring 2018. The GDPR applies to all companies processing personal data for one or more EU citizens, regardless of where the company is located or has operations, and, as of the date hereof, provides fines of up to 4% of global gross revenues, class action lawsuits, direct liability for both data controllers and processors, data breach notification obligations, etc.

Under the GDPR, a company cannot rely on prior approaches to and/or legal bases for data analytics, artificial intelligence, or machine learning. While consent remains a lawful basis under the GDPR, the definition of consent is significantly restricted under the GDPR. Consent must now be "freely given, specific, informed and unambiguous indication of the data subject's agreement to the processing of personal data relating to him or her." These requirements for GDPR compliant consent are not satisfied if there is ambiguity and uncertainty of data processing, as is often the case with data analytics, artificial intelligence, or machine learning (e.g., big data analytics). These heightened requirements for consent under the GDPR shift the risk from individual data subjects to data controllers and processors. Prior to the GDPR, risks associated with not fully comprehending broad grants of consent were borne by individual data subjects. Under the GDPR, broad consent no longer provides sufficient legal basis for Big Data. Thus, data controllers and processors managing the information of EU data subjects must now satisfy an alternate legal basis for Big Data processing. A company may be able to establish an alternate legal basis for the right to perform Big Data processing by meeting GDPR requirements for "legitimate interest," which requires that two new technical requirements are satisfied: "Pseudonymisation" and "Data Protection by Default," which will each be discussed in greater detail below.

GDPR Article 4(5) defines "Pseudonymisation" as requiring separation of the information value of data from the means of linking the data to individuals. The GDPR requires technical and organizational separation between data and the means of linking (or attributing) the data to individuals. Traditional approaches, e.g., persistent identifiers and data masking, do not satisfy this requirement, since correlations between data elements are possible without requiring access to separately protected means of linking data to individuals. The ability to re-link data to individuals is also referred to as the "correlative effect," "re-identification via linkage attacks," or the "Mosaic Effect," because the same party who has access to data can link the data to specific individuals.

GDPR Article 25 also imposes a new mandate for "Data Protection by Default," which requires that data must be protected by default, and that steps are required to use it (in contrast to the pre-GDPR default, where data is available for use by default and steps are required to protect it) and requires that those steps enforce use of only that data necessary at any given time, for any given user, and only as required to support an authorized use, after which time the data is re-protected.

BigPrivacy may support Pseudonymisation by separating the information value of data from the ability to attribute the data back to individuals and may also satisfy the Data Protection by Default requirement of the GDPR by revealing only the data that is necessary at a given time, for a given purpose, for a given user, and then re-protecting the data. BigPrivacy may be used to satisfy these requirements by replacing "restricted data elements" (e.g., "personal data" under the GDPR, "protected health information" under HIPAA, contractually restricted elements, etc.) with dynamically changing pseudonymous tokens which are associated with original data values in a lookup table (these dynamically changing pseudonymous are referred to herein as R-DDIDs because the pseudonymous token identifiers serve to de-identify and, in this scenario, the de-identifiers are used to replace data elements). Using R-DDIDs, a data set may be granularly pseudonymised using tokens that do not enable correlations or "linkage attacks" back to the identity of individuals without access to keys. In addition, BigPrivacy may provide access to more accurate data because alternative technologies tend to apply PETs on a generalized basis, i.e., without knowing what data will be used for what purpose, which degrades the value of the data.

As described above, an initial step in BigPrivacy may involve using R-DDIDs to replace common occurrences of the same data element with different pseudonymous tokens. A second step may involve inserting NADEVs that may reflect or contain, among other things, "cohorts," "ranges," or "classes" to which data elements belong, without providing the means of linking the data back to individuals (i.e., without providing identifying elements). An example of a NADEV may be the replacement of a person's age with a digital representation of an age range. In such an example, any data subject having an age within the particular age range would be assigned the same digital representation (i.e., NADEV) to reflect that they fall within that "class" of ages. A-DDIDs may also be used to insert alternate data models (related or derived data values) into protected data fields for uncommon NADEVs. Common A-DDIDs protecting or obscuring NADE values may be assigned to all identical data values (i.e., NADEVs) in the same cohort or class, as those NADEVs do not need to be converted to do processing. In this manner, cohort tokenization is accomplished, wherein either (i) the value of the cohort, i.e., the NADEV itself, becomes the primary identifier for data, that is, the NADEV essentially functions here as an A-DDID, because the additional level of protection or obfuscation of the NADEV is not necessary, relevant or chosen; or (ii) if additional data protection is desired, the A-DDID obscuring the NADEV becomes the primary identifier for data. Under current schemes, such anonosization is not possible because an individual's identity serves as the primary identifier for data.

Figures 1, 1X:
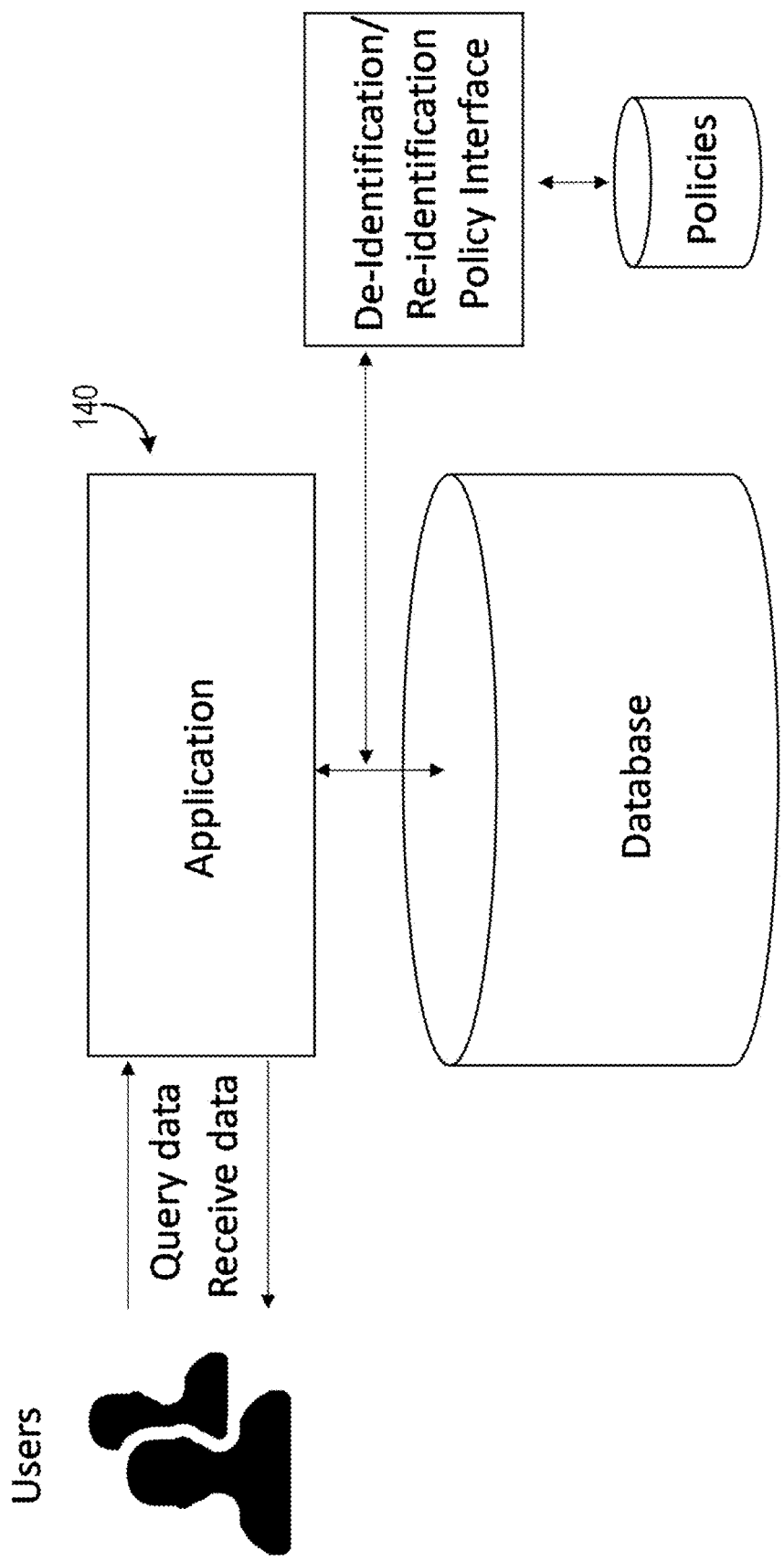
Figures 1, 1X, 2:
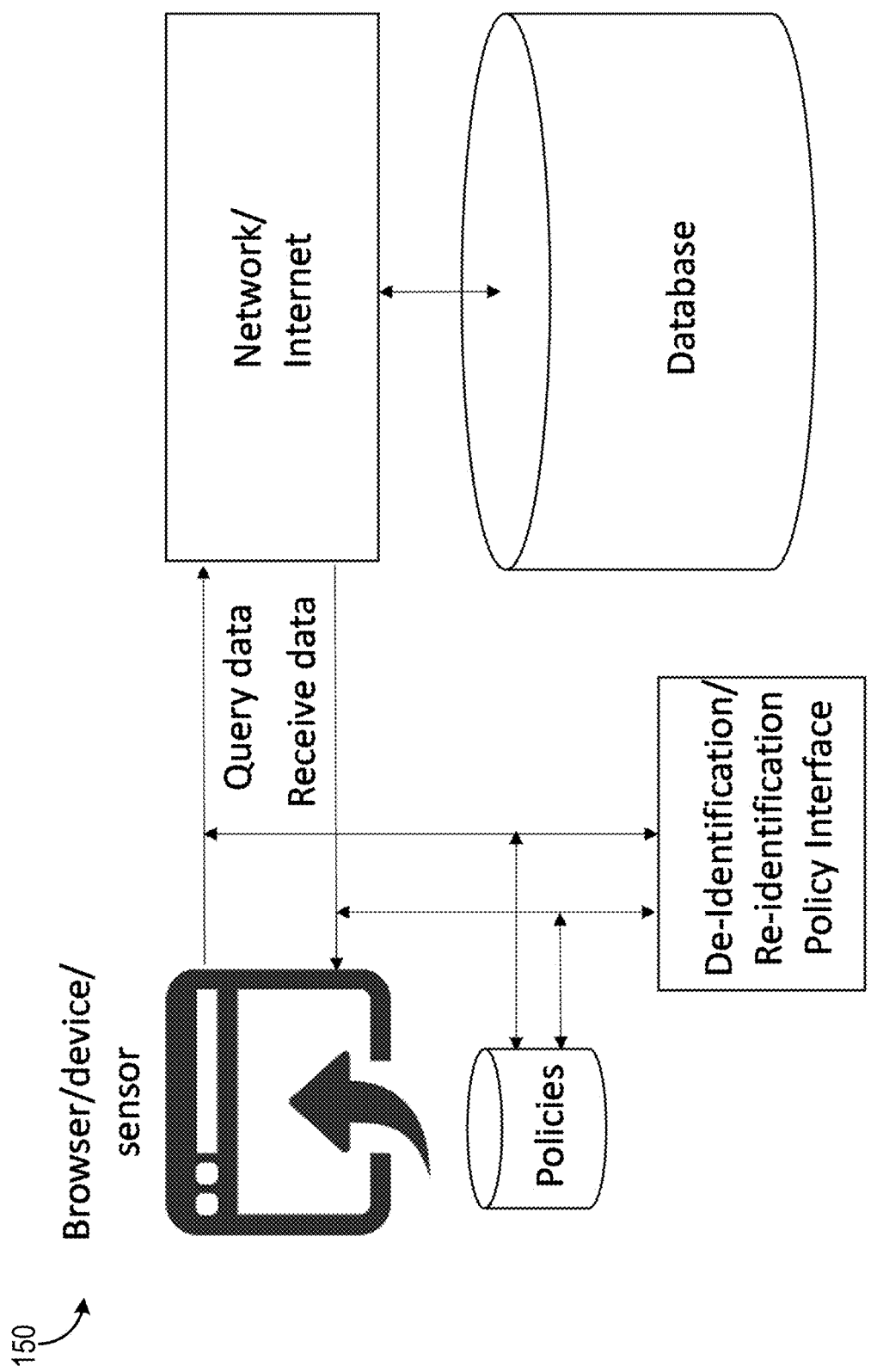

FIG. 1X-1 shows a generalized approach for an application that offers BigPrivacy (140). In particular, the incoming data may be sent to the system through a "shim" application (e.g., a small library that transparently intercepts API calls and changes the arguments passed, handles the operation itself, or redirects the operation elsewhere) each time the privacy system is accessed. Shims may also be used for running programs on software platforms different from those for which they were originally developed. Because implementations of BigPrivacy may leverage randomized look-up tables whereby correlations between R-DDIDs and/or A-DDIDs and underlying data values are not mathematically derived but rather randomly correlated, a third party would have no ability to re-identify the underlying data without access to the proper keys.

As shown in FIG. 1X-2, anonosizing can also be accomplished "in line" by using a system (150) that leverages data communications to and/or from browsers, devices and sensors over a network by enforcing de-identification and/or re-identification policies at the point of data ingress or egress to the system.

Figures 1, 1Y:
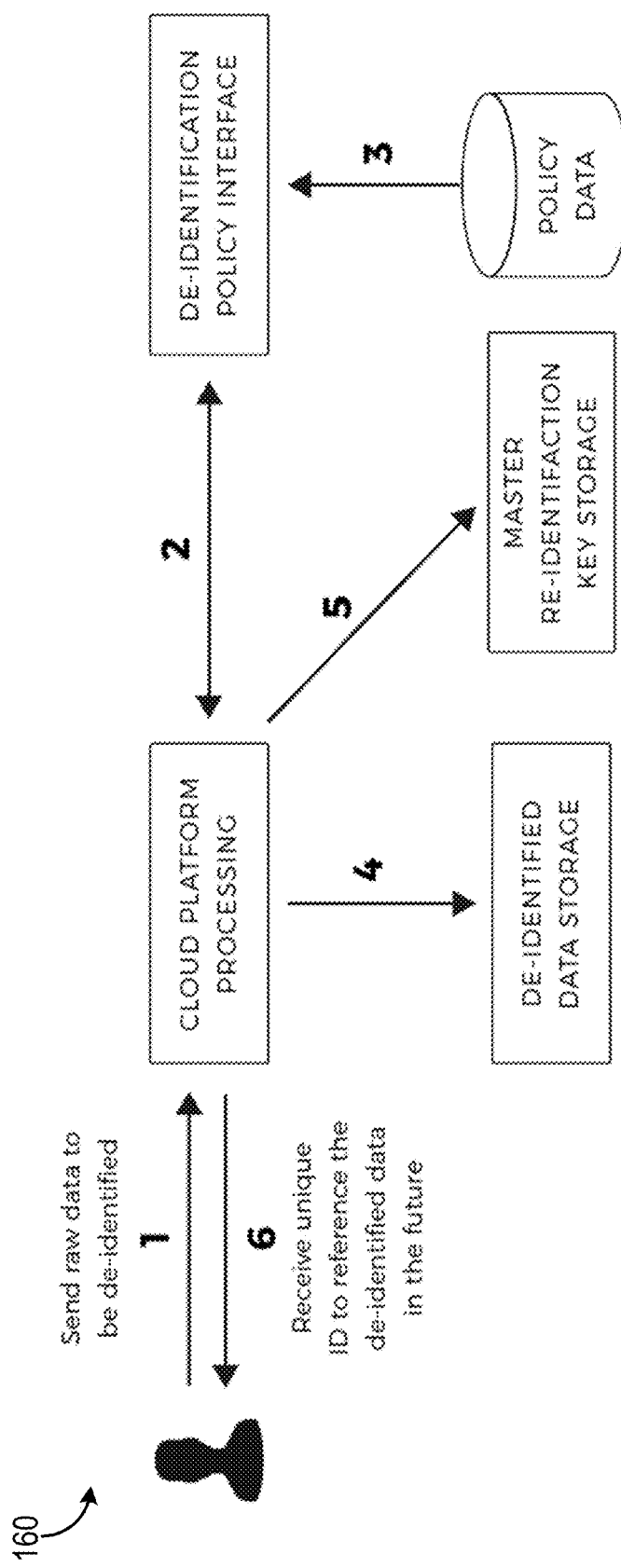
Figures 1, 1Y, 2:
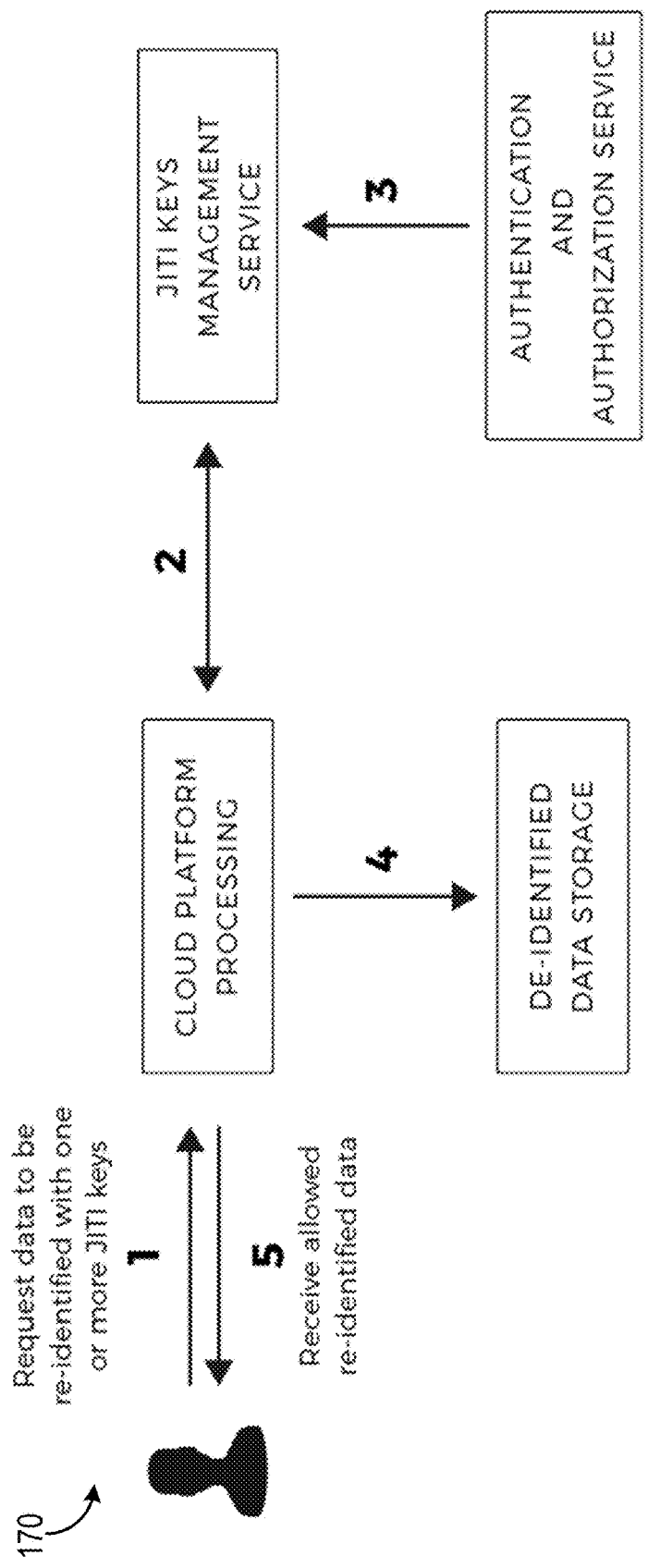

FIG. 1Y-1 illustrates a cloud-based platform and application for offering BigPrivacy services to de-identify data (160). A user, automated process, Internet-connected device, or other entity (the "user") may send "raw" data (i.e. data as it exists before de-identification), along with metadata that may specify properties of the data, to the BigPrivacy cloud platform processor (Step 1). The data may be specified as individual data elements, records, entire data sets, or any combination thereof. The system may determine how to process that data by analyzing the provided metadata and looking-up a de-identification policy via a separate interface (Step 2). Policies undergirding the de-identification policy interface may be stored in an Intelligent Policy Compliance engine residing in a relational database, as files on a server's filesystem, or by other means (Step 3). Having determined the policy to apply to the user-provided data, the system may de-identify that data, per the policy. Should the user configure the system to store the de-identified data in a data store, message bus, map reduce system, or other endpoint, the system may then send the de-identified data to that destination (Step 4). Nonexclusively from the previous option regarding de-identified data storage, should the user configure the system to retain a mapping between "raw" data elements and their de-identified values ("R-DDIDs") and NADEVs, which themselves may function as A-DDIDs or be identified by de-identifying the associated A-DDIDs, then the system may establish a persistent mapping in a data store for future use (Step 5). An identifier may be returned to the user so that the user may reference the de-identified data set or the mapping between R-DDIDs and any of NADEVs, A-DDIDs, or both in the future (Step 6).

The persistent mapping described in Step 5 of FIG. 1Y-1 above may be used at a future time, manually, by an automated key generation service, or by other means, to create a re-identification key (e.g., JITI key) that may restore some or all of the persistent R-DDIDs and either NADEVs or A-DDIDs (or both) in the de-identified data set generated by the system.

FIG. 1Y-2 illustrates a cloud-based platform and application for offering BigPrivacy to re-identify data that has been de-identified (170), e.g., by the BigPrivacy de-identification phase described above with reference to FIG. 1Y-1. A user, automated process, Internet-connected device, or other entity (e.g., the "user") may request the re-identification of one or more data elements. The user provides a reference to the data to re-identify, by referring to a unique identifier returned to the user during the de-identification phase, by specifying the data to re-identify explicitly, or by other means. The user also provides a reference to a JITI key containing the mapping between the specified de-identified data and its re-identified counterpart, e.g., by specifying the unique identifier returned to the user during the de-identification phase, etc. (Step 1). To ensure only appropriate entities may access the re-identified data, the system may utilize a JITI Key Management Service (Step 2) to authenticate the user and authorize the user's request before processing that request (Step 3). As discussed above with reference to FIG. 1Y-1, the system may also establish a persistent mapping in a data store for future use (Step 4). The system then accesses the user-specified de-identified data and JITI key, reverses the de-identification mappings per the data contained in the JITI key, and finally may return the requested re-identified data to the user or another authorized destination configured by the user (Step 5).

Multiple users may be permitted to re-identify different sets of R-DDIDs and A-DDIDs based on the access rights they have to the underlying data elements. Access rights validation may be performed via identity (i.e. if the user has a JITI key, the user may reveal all data in that key), via an access request to an authentication and authorization service (e.g. LDAP), via geographic, temporal or other parameters, or via any combination of these and/or other methods. In this way, different people, services, and/or other entities, may see different "views" of the underlying raw data based on the permissions they have to access that data.

BigPrivacy may generate NADEVs (which may also have been obscured by A-DDIDs) during the de-identification phase, thereby precomputing derived, related and/or synthetic data required for the re-identification of the data set ("cohort tokenization") before the re-identified data needs to be used in an analytics or other application. This represents an improvement in re-identification speed, server power usage, multi-tenancy ability, and other factors over systems that must perform such operations during the re-identification phase.

FIG. 1Y-3 illustrates an application of BigPrivacy that integrates with Extract, Transform, and Load (ETL) applications (180). A user may use an ETL application to harmonize, transform, and otherwise manipulate data, as well as to perform de-identification tasks with BigPrivacy plugins (also known as "add-ons," i.e. functionality that may be added or removed from software in a modular fashion) (Step 1). Using an ETL application, the user may store de-identified data and/or master re-identification data on their local computer, in a corporate data center, on the BigPrivacy platform, and/or at other authorized location(s) (Step 2). Connectivity between the user's ETL application and the BigPrivacy platform may be achieved with industry-standard security by using protocols and services like Transport Layer Security (TLS), Virtual Private Networking (VPN), and other methods. The system receives the user-provided de-identified data and/or re-identification key data and stores the data (Step 3). In the future, another user with access rights to the re-identified versions of the de-identified data may interact with BigPrivacy and request the re-identification of one or more data elements originally de-identified with an ETL application (Step 4).

As described above, the process of anonosizing data may reduce the data breach notification obligations and liability in various jurisdictions, e.g.: (i) in the EU under GDPR Articles 33 and 34; (ii) in the US under (a) federal statutes like the HIPAA Breach Notification Rule, 45 CFR §§ 164.400-414, and (b) under laws of forty-seven states, the District of Columbia, Guam, Puerto Rico and the Virgin Islands that have enacted legislation requiring private or governmental entities to notify individuals of security breaches of information involving personally identifiable information; and/or (iii) under other similar notification obligations imposed by other regulatory schemes. In other words, if a table of anonosized data is breached, the data custodian would not necessarily have to notify data subjects of the breach, because the data would remain protected from a re-identification standpoint. Also, established capabilities of key management systems may be leveraged to make it even more difficult to use stolen keys to access the master table, e.g., one or more of "heartbeat" authorization certification, multi-key requirements, GPS requirements, etc. may be employed to manage the keys for a given system. Further, the level of informational value to which access is provided with a combination of such controls may be restricted on an individual basis.

All types of BigPrivacy can support NADEVs via anonosizing to enable full performance analysis and processing using those NADEVs, without requiring transformation of data or reference to de-identification/re-identification policy engines, API calls, or "shims." Specifically, A-DDIDs may be processed directly, and only when desired results at that de-identified level of abstraction are achieved is a "call" issued to retrieve the NADEV. In such instances, then, NADEV may be retrieved for only the small number of users (say, 50 users from a data table) whose A-DDID represents the cohort or class relevant to the query, while the vast majority of users (say, the remaining 500,000 users from the data table) whose A-DDID does not match the cohort or class relevant to the query do not have to have their data be retrieved. Notwithstanding the foregoing, BigPrivacy does not require that a NADEV be obscured by an A-DDID; it simply provides the methods and apparatuses to do so and, in the event a NADEV is not obscured by an A-DDID, then the NADEV effectively functions as the A-DDID.

BigPrivacy may also support different levels of abstraction, wherein, rather than just supporting a primary and secondary level or table, additional levels or tables, including but not limited to NADEVs, may represent R-DDIDs and/or A-DDIDs that associate data with a fictitious person, company, and/or attribute that is not the "true" value of the person, company, and/or attribute revealed by referencing the primary table. This prevents disclosure of the identity of the "true" person, company, and/or attribute with respect to which NADEVs, R-DDIDs and/or A-DDIDs relate, but indicates when NADEVs, R-DDIDs and/or A-DDIDs relate to a common (but unidentified) person, company, and/or attribute. Since different types of data controllers may need different levels of identifying data, they can be provided with access to different tables, levels and/or JITI keys only as necessary to satisfy their specific authorized requirements—without revealing any greater level of identifying information than is authorized.

BigPrivacy also enables data processors the ability to implement a data subject's individual "Right to be forgotten" (e.g., as required under GDPR Article 17), e.g., by removing links to an individual by "deleting" the keys necessary to create the linkage within the de-identification policy engine—without requiring deletion of the data itself. Rather, just the links between the data and the true identity of the data subject need to be deleted from the look-up table or database.

Applications of Anonosization to Quantum Computers, Quantum Computing, Quantum Cryptography and Quantum Privacy We distinguish between Classical Computers (CCs) and Quantum Computers (QCs) as follows: CCs, as used herein, refer to binary machines, in which the smallest piece of representable information is a binary digit (or bit, i.e., 0 or 1); QCs, as used herein, refer to quantum machines, in which the smallest piece of representable information is a quantum bit (or qubit). Qubits can be 0 or 1—or both—at the same time. Qubits are typically atoms or photons, although they can, in principle, be any particle sufficiently small, i.e., any particle to which quantum mechanical principles apply. This quantum mechanical property is called superposition. Further, a QC's qubits are entangled. This means that when one qubit changes, it affects the other qubits, too. (In contrast, in CCs, bits are independent, i.e., a change in one bit does not necessarily mean that any other bit will change.)

Because of these two properties (superposition and entanglement), QCs can perform extremely large numbers of computations simultaneously in parallel (CC's perform large numbers of computations serially; or they require additional processors to achieve parallelism, rather than simply additional bits). For example, there are computations, generally solutions to otherwise intractable problems, that could be achieved in principle by a QC within seconds, if not less, while these same solutions could take a CC almost as long as or longer than the age of the universe to solve (i.e., hence, intractable).

Current cryptographic methods typically involve, inter alia, public-key encryption and elliptic curve encryption, the first of which can be decrypted only by determining the prime factors (p1 and p2) of a very large composite number (i.e., p1*p2). Even the fastest, most powerful computers on Earth cannot break public-key encryption involving large numbers of bits (e.g., 512-bit, 1024-bit, 2048-bit ciphers). In contrast, a QC could potentially break such encryption in a matter of seconds by evaluating all potential solutions simultaneously and "solving" for the one solution that breaks the encryption.

De-identification, outside of BigPrivacy, often involves so-called 1-way hash functions, because in principle, the initial value cannot be determined by "going the other way," i.e., from the hash to the re-identified original string. Again, while QCs would be able to quickly determine an original string from its 1-way hash, CCs must perform brute-force operations (if no exploit of the underlying hashing algorithm is known) to decode the hash, which may require days, months, years or significantly longer to finish. The same flaw generally exists with respect to other forms of de-identification, including other Privacy Enhancing Techniques (PETs) discussed elsewhere herein.

A fundamental problem with all cryptographic methods is that they in some way encode the original information. Theoretically, at least, with QCs, even with methods that are not as easily breakable by QCs, a data subject and all its quasi-identifiers are, at some deep level, recoverable, i.e., re-identifiable from the encoded form. While BigPrivacy does not require that an implementation prevent encoding, BigPrivacy does not depend on encoding, but on the dynamic substitution of uncorrelated strings for the original data, whether for generating R-DDIDs or A-DDIDs. If a string is fundamentally random, a property for which QCs are ideally suited, but for which other methods exist, then there cannot be any means of re-identifying any type of DDID, because the DDID is an arbitrary string, not an encoding of the original data. Further, since the same datum is represented by different DDIDs, there is not even any relationship among the DDIDs. Put another way, DDIDs are maximally entropic, containing no useful a priori information about the data subject or any original data, from an information theoretic point of view. Because of this, QCs would not be able to determine original content based on DDIDs that contain zero information about that content. For this reason, among others, DDIDs provide a technique of preserving individual privacy and preventing the re-identification of de-identified data—even in a quantum computing world.

Thus, BigPrivacy further addresses not only the goal of maximally increasing privacy but also of maximally increasing data value at the same time. Other PETs, in contrast, increase privacy at the cost of decreasing or eliminating data value; or, conversely, decreasing or eliminating privacy as the result of increasing or maximizing data value. Therefore, even if, arguendo, QCs could maintain or enhance privacy, they would still decrease or eliminate data value. This is because massive parallelism and speed, even simultaneously, does nothing to increase or enable data value. Instead, even if QCs were to become the standard for all computing, only BigPrivacy (in conjunction with QCs) can maximize data privacy and data value.

BigPrivacy may also be applied to encrypted forms, even QC-encrypted forms. In other words, BigPrivacy is computationally independent of the fundamental nature of a computer, as it severs any link between original data (which can be encrypted or not) and the data after de-identification by BigPrivacy.

BigPrivacy can also take advantage of fundamental quantum mechanical properties. For example, QCs are themselves ideal for producing truly random numbers. However, using a truly random number as input to a computable function defeats the purpose of de-identification because a correlation still exists between the randomization of the original data and that data. In BigPrivacy, however, a truly random number is, as described before, used only as a DDID—the random number stands alone and bears no correlation to (or relationship with) the underlying data. In this way, BigPrivacy can actually exploit a property of QCs to, in one embodiment, ensure there exists zero correlation (or, alternatively, near-zero correlation) between the DDID (whether an R-DDID or A-DDID) and the underlying data.

Enforcing Centralized BigPrivacy Controls in De-Centralized Systems

The aforementioned BigPrivacy technologies may also enable the establishment, enforcement, validation, and modification by a controlling entity of centralized privacy and security controls on and/or across decentralized networks or platforms (including permissionless systems or distributed ledger technologies), including networks or platforms (including permissionless systems or distributed ledger technologies) linked on a peer-to-peer basis or other non-centralized basis.

One embodiment of the present invention applies to a decentralized network built on blockchain-based technology. Blockchain is the underlying technology behind many of today's popular cryptocurrency platforms. While blockchains are best known for their use in enabling cryptocurrencies and cryptocurrency transactions, they have a broad range of other applications, such as in storing medical data, supply chain management, financial transaction management and verification, enabling and implementing so-called "smart contracts," and social networking.

The term "blockchain" has no single definition, but it is generally used in one of two ways: (i) to refer to a particular method or process for recording, in a digitized, distributed ledger, verifiable, unique, theoretically incorruptible transactions across a decentralized peer-to-peer network of computers; and (ii) to describe the underlying data structures (i.e., blocks) used to represent the transactions themselves, i.e., a chain of blocks of data, where each such block is linked (or "chained") to the previous block according to a particular algorithmic/programming method. As used herein, blockchain may contextually have either meaning or both meanings. In the event the term "blockchain" is used in a different sense, which will be elaborated in the context of its use. A transaction from any client or node participating in a blockchain network is recorded on the network in the form of a "block" of data, which is time stamped and linked to the previous block in the blockchain, no matter which client or node initiated that transaction. Linking each block to the previous block confirms the integrity of the chain of transactions—all the way back to the first block in the blockchain. Failure to be able to link each block to the previous block confirms a failure of that integrity, which may indicate tampering (i.e., alterations of any kind in the data stored in one or more of the blocks in the blockchain), fraud, etc. Information in the block is encrypted and protected through cryptographic methods.

The blockchain is stored across a decentralized network; in other words, no centralized or "official copy" of the data stored in the blocks exists. Instead, multiple identical copies of the blockchain can and do exist. Every instantiation of the blockchain at a particular node in the network is identical (or, if a node does not have the latest version of the blockchain, this node will be considered to have left the network with regard to the validation of later transactions until that node has 'caught up' or rejoined the cryptocurrency network. This is an important aspect of the decentralized nature of the storage that is integral to blockchain itself. The process of adding transactions to the blockchain is performed by mining "nodes." Mining is essentially an algorithmic process that can be used to produce (i.e., increase the supply of) a given virtual currency (e.g., in the case of cryptocurrencies), as well as to verify transactions in the blockchain.

As discussed above, the EU's GDPR imposes certain obligations on data "controllers" (i.e., the natural or legal person, public authority, agency or other body which, alone or jointly with others, determines the purposes and means of the processing of personal data) and data "processors" (i.e., a natural or legal person, public authority, agency or other body which processes personal data on behalf of the controller). In addition to introducing penalties for data processors, the GDPR imposes even more stringent obligations on the controller of personal data and drastically increases the potential penalties for non-compliance.

Article 17 of the GDPR codifies the "right to erasure/right to be forgotten," i.e., the ability to provide individual data subjects with the right to request the deletion or removal of personal data where there is no compelling reason for its continued processing.

A key feature of blockchains is their integrity (i.e., the ability for users of network to trust the accuracy of the data stored in the blocks of the chain), which is guaranteed by their immutability. Once a block has been verified and added to the chain, it generally may not be removed, edited, or updated. In fact, blockchains are designed such that, modifying the data stored in any one block would 'break' (i.e., invalidate) all the downstream blocks in the chain. While, in the vast majority of cases, blockchain data is protected by encryption or static tokenization, it is possible to envision a case where an individual may want to exercise their "right to erasure/right to be forgotten" pursuant to the GDPR (or other similar regulation providing such a right) by requesting that their data be removed from the blockchain. With public blockchain platforms, such a request would not be possible to fulfill without destroying the integrity of the entire chain.

The Financial Conduct Authority financial regulatory body in the United Kingdom (FCA) has warned firms developing blockchain technology to beware of the incompatibility between immutability and the GDPR. Some solutions to this issue have been proposed, such as allowing administrators to edit the blockchain where necessary. As noted above, however, editing the blockchain destroys the very concept of the blockchain, because it makes the blockchain mutable, thereby removing a guarantor on the blockchain's integrity.

The GDPR was designed using the assumptions that custodians of data would continue to be centralized entities. The GDPR did not consider decentralized systems, such as blockchain. The BigPrivacy techniques described herein add significantly more to the underlying blockchain technology for several reasons. For example, BigPrivacy can be used to enable the blockchain to remain immutable with respect to data—while at the same time enabling data compliance with the "right to erasure/right to be forgotten" criterion of the GDPR. The BigPrivacy techniques described herein (e.g., the use of DDIDs) may also be applied in the novel context of decentralized storage systems (the novelty of which is evidenced, e.g., by the fact that the GDPR itself did not contemplate the problems that the use of immutable decentralized ledgers to store user data would pose on the implementation of its requirements). BigPrivacy further enables the use of blockchains to handle/process other obligations of data controllers and processors under the GDPR in numerous ways including, which will be discussed in further detail below.

Right to Erasure/Right to be Forgotten

Figures 1, 1Y, 2, 3:
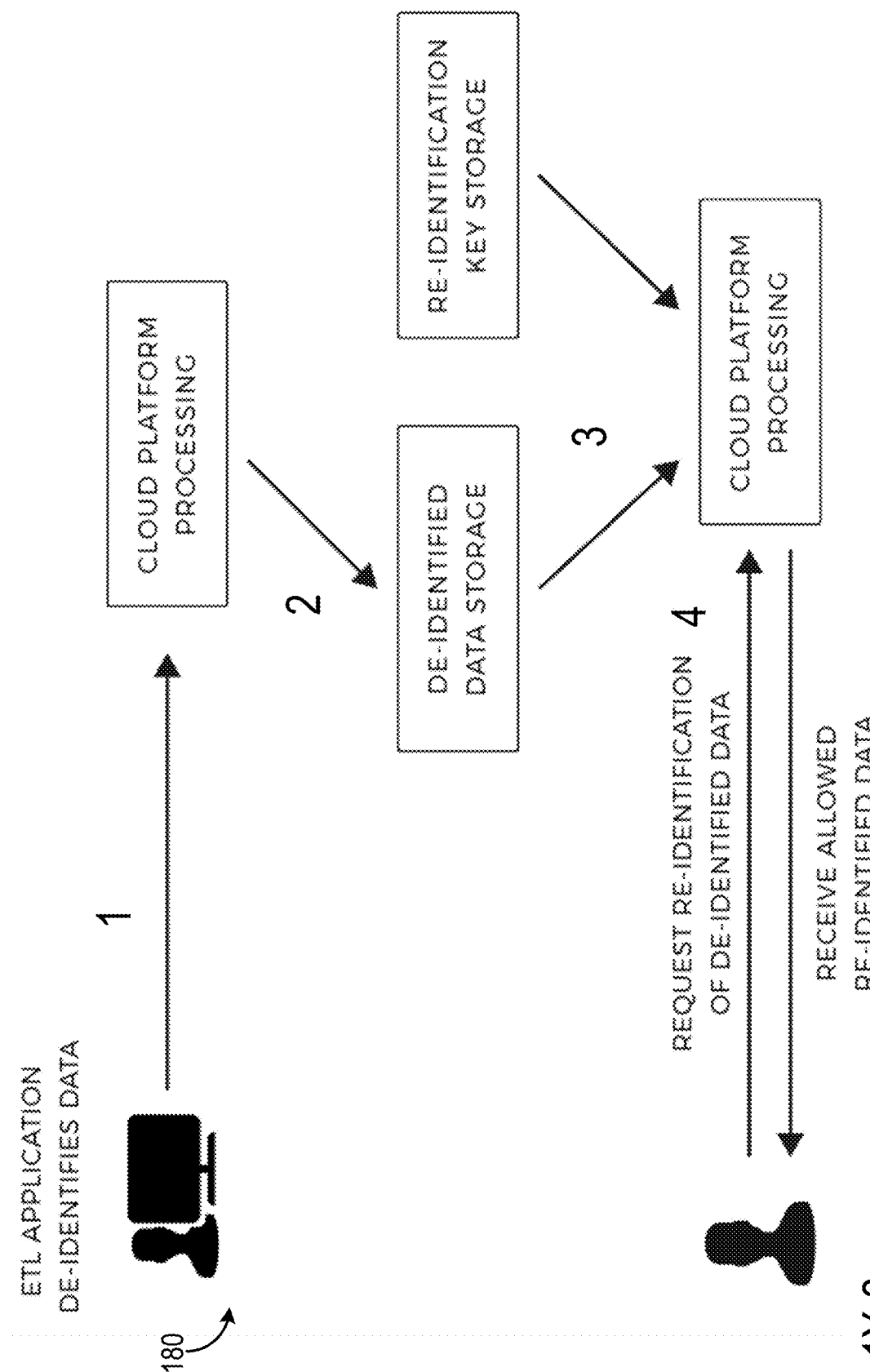
Figures 1, 1Z:
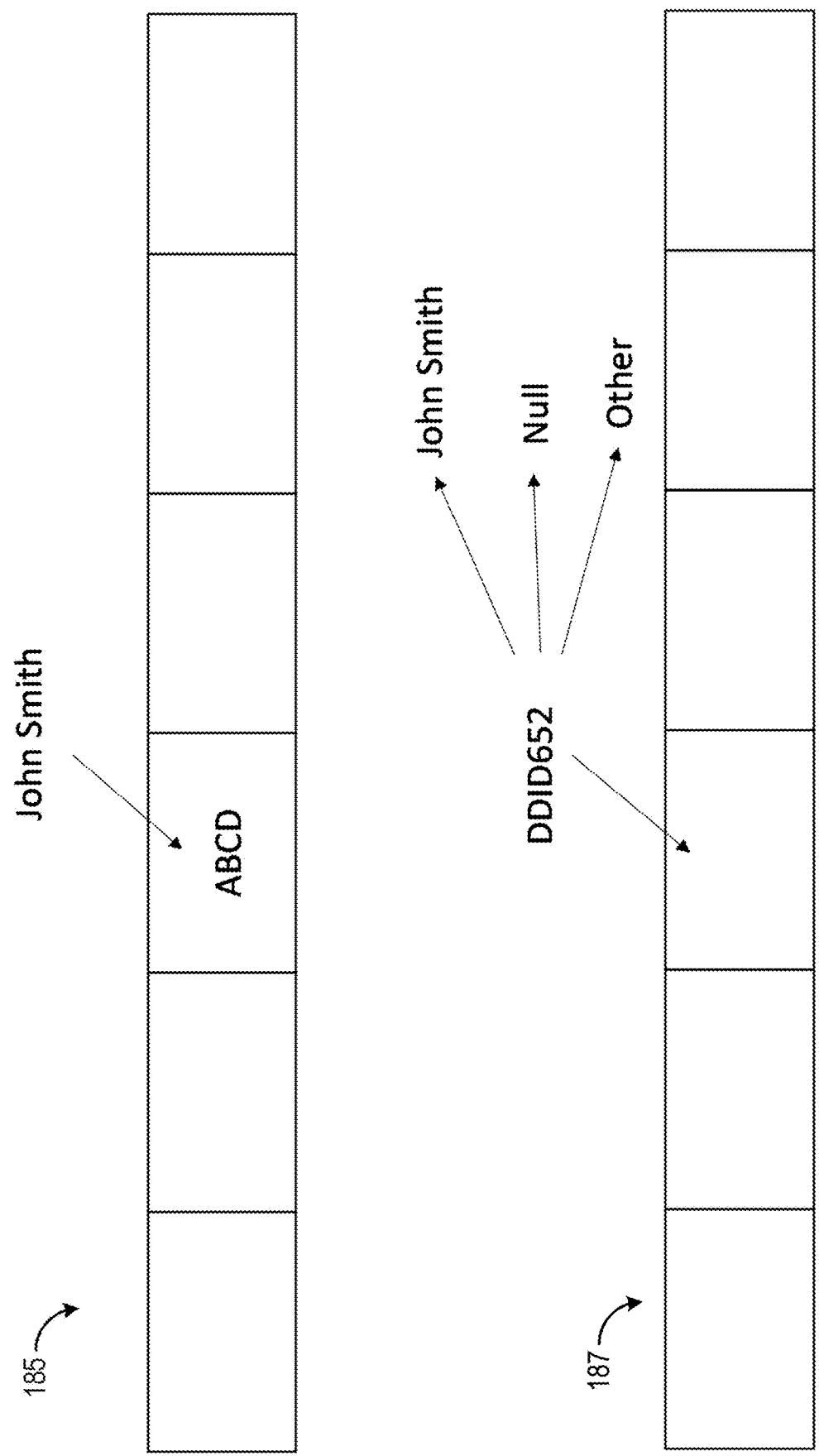
Figures 1, 1Z, 2, 3:
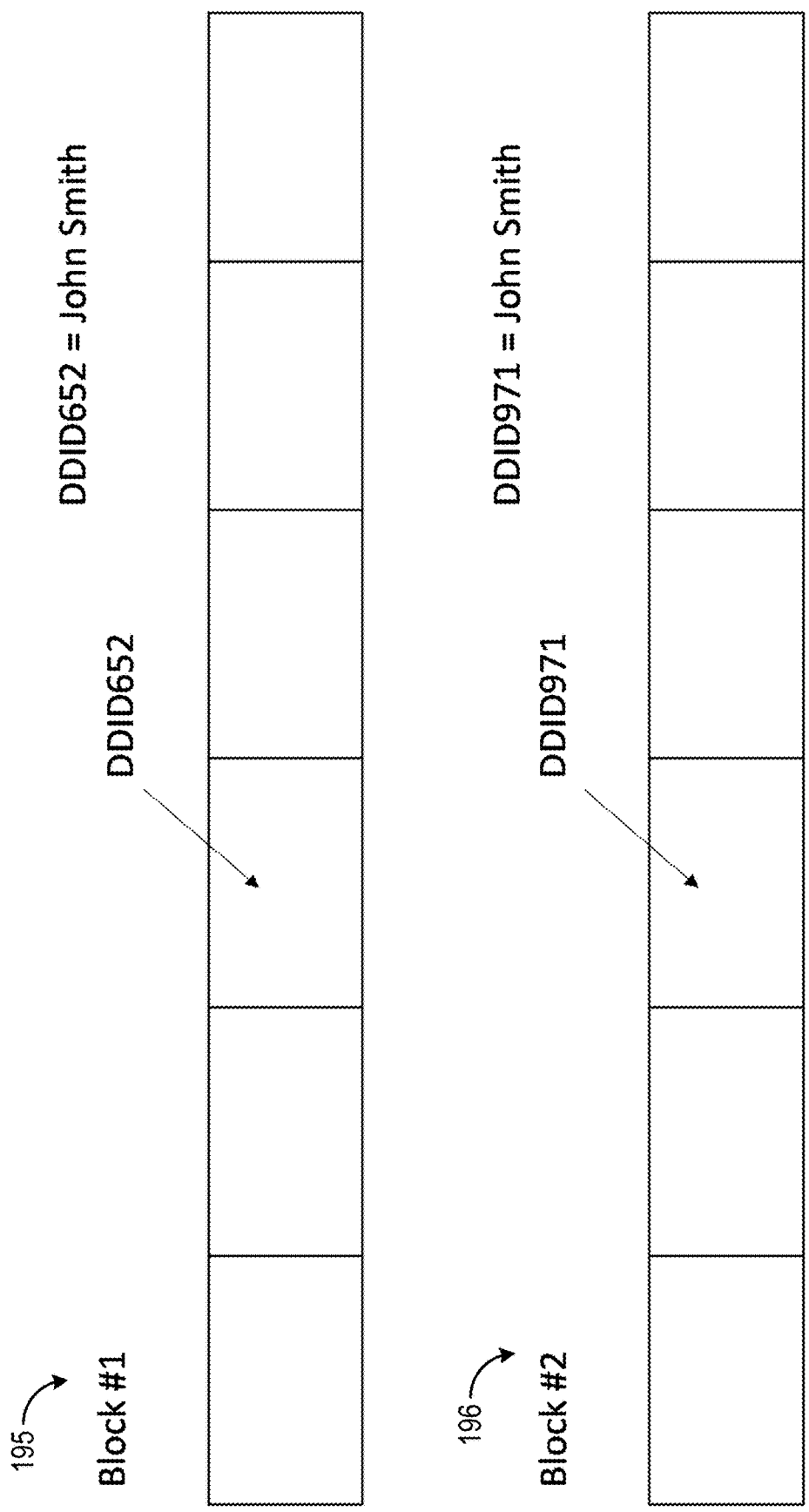
Figure 2:
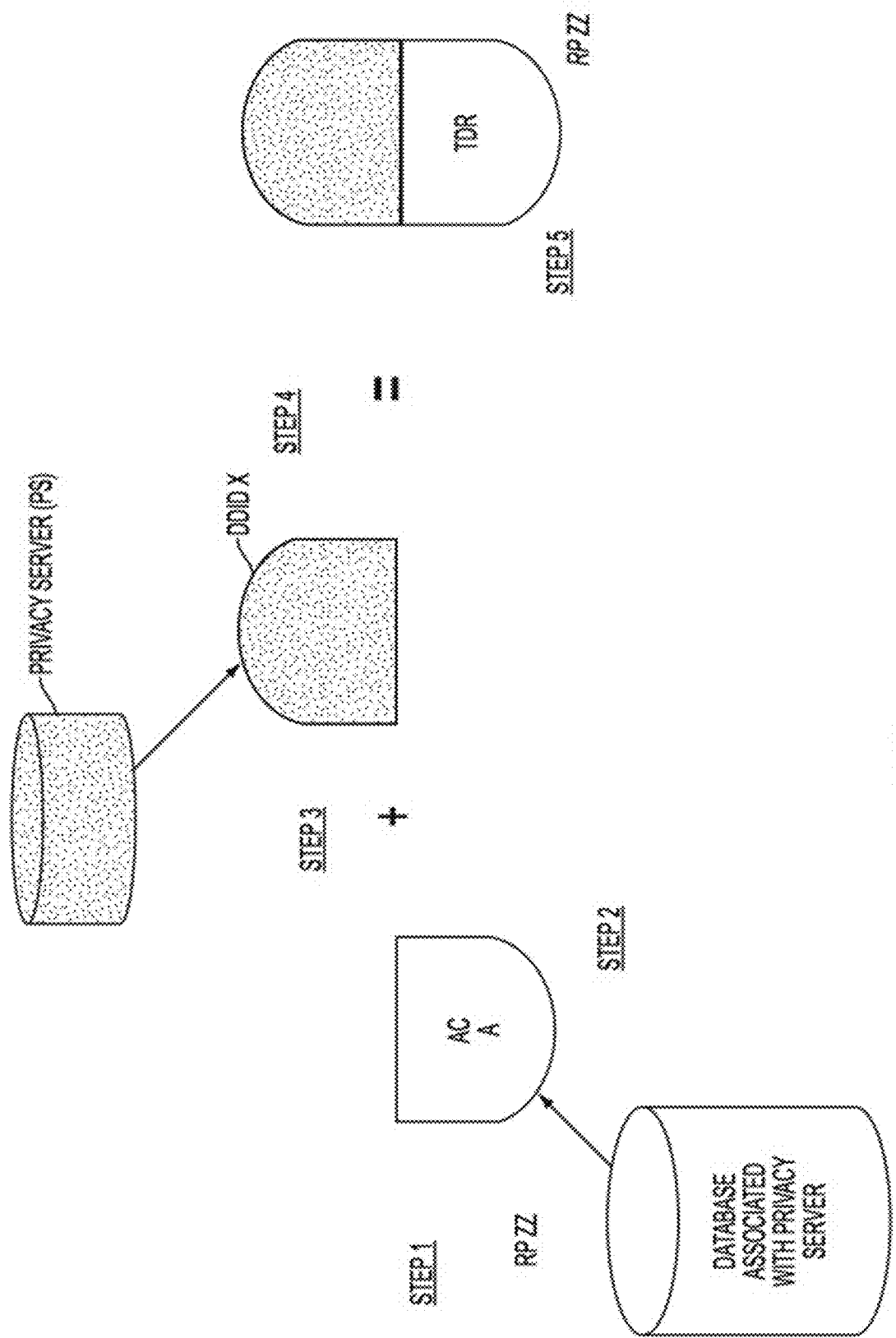
Figure 3:
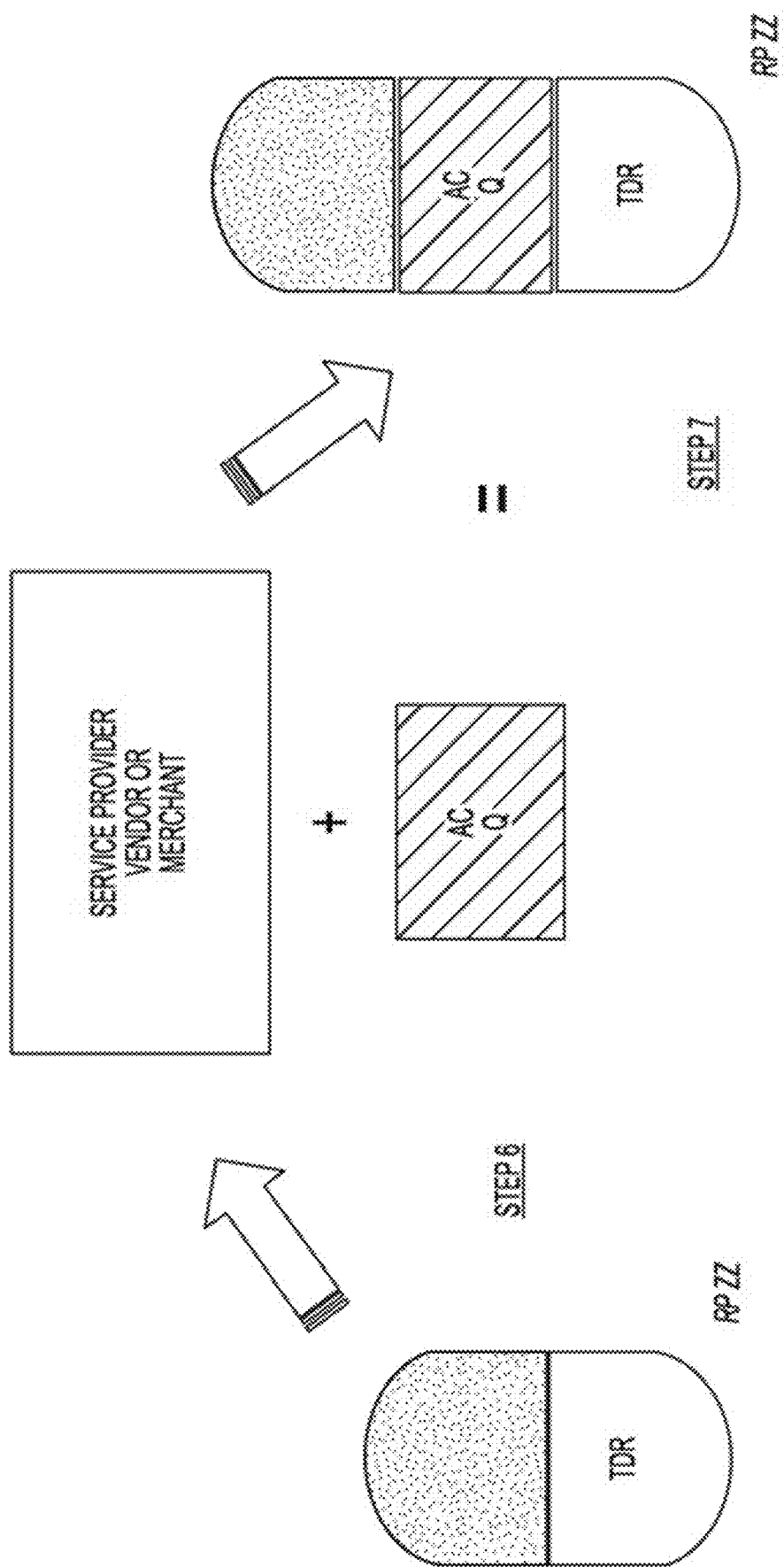

Turning now to FIG. 1Z-1, an exemplary decentralized network built on blockchain-based technology, wherein anonymizing privacy controls may be employed, is illustrated, according to one or more embodiments. The top part of FIG. 1Z-1 (185) shows the current situation, in which a data subject's name may be encrypted (e.g., using a desired encryption algorithm) or replaced with a static token before being stored in the blockchain. For this example, the acronym "ABCD" is used as an illustrative representation of the result of such encryption or tokenization process. With access to the appropriate key, it can be determined that the encrypted/tokenized value of "ABCD" is "John Smith." This knowledge is immutable and is in conflict with the GDPR's requirement to provide users with the "right to erasure/right to be forgotten," as noted above. This is the case because "John Smith," albeit stored in encrypted form, is contained within the blockchain 185 itself.

The bottom part of FIG. 1Z-1 (187) shows that a Dynamic De-Identifier (DDID), in this example, "DDID652," could be used in the blockchain, i.e., in lieu of the encrypted/tokenized value of "ABCD." As described elsewhere herein, the DDID ("DDID652") could serve as a "pointer" to the underlying name of the Data Subject, "John Smith," unless and until such time as when the data subject exercised their "right to erasure/right to be forgotten," at which time the DDID could then point to a "null" entry. In this manner, the immutable nature and referential integrity of the blockchain could be maintained, while still providing the flexibility to enable a Data Subject to exercise their "right to erasure/right to be forgotten." It is also important to note that the DDID can point to anything else, i.e., not just to "John Smith" or to "null" or to the value of 0, but also to any other location containing any other value that is desired. In the Big Privacy-enabled example (187), as compared to the traditional blockchain example (185), the value of "John Smith" is not actually contained within the blockchain itself; rather, a DDID ("DDID652") that temporarily points to a location containing the value "John Smith" is contained within the blockchain. The DDID value remains immutable within the blockchain 187, but that which the DDID points to can have its value change without changing the blockchain itself.

In another embodiment, BigPrivacy could implement the same "right to erasure/right to be forgotten" in the context of a "smart contract" that has been fulfilled by both parties (or where at least one independent provision out of a number of provisions has been fulfilled by both parties). The reason BigPrivacy is able to provide this level of privacy/anonymity is that, once each counterparty has fulfilled the contract, the record of the counterparties is no longer necessary (i.e., since each has already met its obligation to the other party). In one example, this desire to erase or forget the identities of one or more of the parties involved in a smart contract may arise in the context of the trading or exchange of financial instruments.

Mike Bursell, Chief Security Architect of RedHat, has stated that confidentiality, integrity, and availability are major issues with regard to the performance of smart contracts, as follows:

"Once a transaction—or 'smart contract'—has completed and made its way onto the blockchain or distributed ledger, it is immutable, pretty much by definition. But what about before it's completed? Well, simple transactions of the type described at the beginning of this post are atomic—they happen or they don't, they are 'indivisible and irreducible,' to use the jargon. They are, for most purposes, instantaneous.

The same is not true for 'smart contracts.' They require processing, and therefore must exist over time. This means that, while they are being processed, they are subject to all sorts of attacks to which any system may be vulnerable. [Two relevant components of] the standard list [include]:

Confidentiality: The state of a 'smart contract' may be subject to snooping, which may lead to asymmetric knowledge or leakage to non-approved parties.

Integrity: This is the nightmare case for many 'smart contracts.' If an entity—whether a party to the underlying contract or not—can (intentionally or unintentionally) change the internal state of the code executing the 'smart contract,' then the outcomes of that 'smart contract' will not be as they're expected to be, and any of the parties involved may have good cause to dispute the outcome. What's more, such a dispute may not even depend on proof of loss of integrity, but just on suspicion. Proving run-time integrity—let alone mitigating when it is shown to have been lost—is extremely difficult within an execution context."

The BigPrivacy techniques disclosed herein can also make such snooping issues irrelevant, e.g., by protecting the identities of the counterparties, as well as the information regarding the transactional terms and conditions of the elements of the smart contract. In other words, BigPrivacy takes as a given that snooping may occur through whatever means, but it ensures that any data obtained through such snooping has no value to the snooper, because the data is simply a DDID, not the underlying "true" value of data that the snooper wants. With regard to integrity, BigPrivacy, by making the terms themselves (including the identities of parties to the smart contract) unavailable to snoopers, ensures that parties will not intentionally or unintentionally change the code, because, without knowledge of what the code was implementing, any changes to the code would produce entirely random outcomes.

Data Protection by Design and by Default

GDPR Article 25 requires data controllers to implement appropriate safeguards "both at the time of the determination of the means for processing and at the time of the processing itself." Article 25 goes on to say that one way to do this is by "pseudonymizing personal data."

Data Protection by Design and by Default has to be applied at the earliest opportunity, so that, by default, data use is limited to the minimum extent and time necessary to support specific uses authorized by data subjects. The default today is that data is available for use, and steps and efforts must be taken to protect it. The GDPR mandates that this default must be changed. Whether if it's by pseudonymisation, one item specifically mentioned in GDPR Article 25, or by some other means, the GDPR requires showing protection at the earliest point in time—and that the use is limited both in extent and time to what was specifically authorized by Data Subjects.

GDPR Recital 78 reads as follows: "The protection of the rights and freedoms of natural persons with regard to the processing of personal data require that appropriate technical and organizational measures be taken to ensure that the requirements of this regulation are met. In order to be able to demonstrate compliance with this regulation, the controller should adopt internal policies and implement measures which meet in particular the principles of data protection by design and data protection by default. Such measures could consist of pseudonymizing personal data as soon as possible."

GDPR Article 4(5) defines "Pseudonymisation" as requiring separation of the information value of data from the risk of re-identification. To benefit from GDPR statutory/regulatory incentives and rewards for pseudonymisation, this separation is necessary. Replacing multiple occurrences of the same personal data elements (e.g., name of a Data Subject) with "static" (or persistent) tokens fails to separate the information value of data from the risk of re-identification because re-identifying correlations and linkage attacks (aka the "Mosaic Effect") are possible due to "static" (or persistent) identifiers being used instead of dynamic de-identifiers.

As mentioned above, "static" tokenization approaches to protecting data use persistent identifiers. By searching for a particular, tokenized string that repeats itself within or across databases, a malicious actor or interloper can gain enough information to unmask the identity of a data subject. This is an increasing scope problem for analytics and other processes that combine and blend internal and external data sources. By contrast, if a data element is replaced each time it is stored with a different pseudonymized DDID, where each different DDID bears no algorithmic relationship to the others, the same malicious actor or interloper can no longer determine that the DDIDs belong or relate to the same data subject—let alone uncover a data subject's name or other identifying information.

Turning now to FIG. 1Z-2, another exemplary decentralized network built on blockchain-based technology is illustrated, according to one or more embodiments. FIG. 1Z-2 shows the situation in which a data subject's name is encrypted (e.g., using an encryption algorithm) or replaced with a static token. For these purposes, the acronym "ABCD" is again used as an exemplary representation of the result of such encryption or tokenization process. The same encrypted/tokenized value of "ABCD" is used in multiple blockchains to refer to "John Smith." This is represented in FIG. 1Z-2 by Block #1 (190) and #2 (192) each storing the data "ABCD" in one of their respective blocks. As noted above, this persistent (or static) use of the same encrypted/tokenized value (in this example, "ABCD") can eventually lead to re-identification of John Smith—without requiring access to any key or mapping showing that "ABCD"="John Smith." This inability to protect the identity of John Smith is a likely violation of a data controller's obligations under Article 25 and Recital 78 of the GDPR, noted above.

Turning now to FIG. 1Z-3, yet another exemplary decentralized network built on blockchain-based technology, wherein anonymizing privacy controls may be employed, is illustrated, according to one or more embodiments. FIG. 1Z-3 shows how different DDIDs could be used in different blockchains (in this example, "DDID652" is used in Block #1 (195), and "DDID971" is used in Block #2 (196)), each of which DDIDs could serve as a "pointer" to the name value of "John Smith." In this manner, the immutable nature and referential integrity of the blockchains could be maintained while still providing the dynamism necessary to satisfy the requirements for pseudonymisation under GDPR Article 4(5) and Data Protection by Design and by Default under Article 25 of the GDPR.

BigPrivacy, therefore, does not present a need to change the underlying blockchain algorithm for verification. Rather, Anonos BigPrivacy starts with the fact that blockchain as implemented today is not capable of: (i) complying with key elements of the GDPR (which imposes technical requirements for protecting the privacy of individual data subjects); while also (ii) remaining immutable. These technical requirements imposed by the GDPR (such as the aforementioned right to be forgotten and data protection by design and by default) and the blockchain's requirement for immutability cannot be met unless the inventions disclosed herein are applied to blockchain implementations. Further, BigPrivacy may be used to shield the identities of the original counterparties to "smart contracts" before, during, and after the performance of such "smart contacts."

Other embodiments of the techniques disclosed herein, as applied in the context of distributed ledger technologies, such as blockchain, may include, without limitation: authenticating copyright registrations; tracking digital use and payments to content creators of copyrighted content, such as wireless users, musicians, artists, photographers, and authors; tracking high-value parts moving through a supply chain; securing spectrum sharing for wireless networks; enabling online voting; enabling "governed entitlements"; implementing information systems for medical records; identifying and verifying the ownership of digital art; taking ownership of game assets (digital assets); enabling new distribution methods for the insurance industry such as peer-to-peer insurance, parametric insurance and micro-insurance; and enabling collaborating peers in areas including the sharing economy and the Internet of Things (IoT).

FIG. 2 shows an example of process operations or steps that may be taken by the abstraction module of the privacy server, e.g., abstraction module 52 shown in FIGS. 1 and 1A, in accordance with one embodiment of the present invention. In one example, at step 1 a related party ZZ (shown as "RP ZZ") sends a request via a privacy client that may reside on a Data Subject device, on a service provider device, accessible via and reside in a cloud network, or reside on the same computing device as the privacy server to the privacy server with respect to a desired action, activity, process or trait. The request initiation may be configurable so that it is predictable, random, automatically or manually initiated. For instance, related party RP ZZ initiates a request for a desired online action of web browsing.

At step 2, in one example the abstraction module of the privacy server determines the attribute combinations necessary to perform with respect to a desired action, activity, process or trait and retrieves them from the database as attribute combination A ("AC A"). In this example implementation of the system, the abstraction module of the privacy server is configured to add or delete attributes, retrieve attribute combinations, and to modify attributes within any given combination.

In an example involving an ecommerce site selling sports equipment, the abstraction module of the privacy server may determine that attributes pertaining to a Data Subject's height, weight and budget are necessary to perform with respect to a desired action, activity, process or trait and therefore may retrieve the attributes of height, weight and budget for the specified Data Subject from the database to form an attribute combination comprised thereof. In another example involving a physician requesting blood pressure information, the abstraction module of the privacy server may determine that attributes comprised of the most recently recorded systolic and diastolic blood pressure values are necessary to perform with respect to a desired action, activity, process or trait and therefore may retrieve the most recently recorded systolic and diastolic blood pressure values for the specified Data Subject to form an attribute combination comprised thereof. Another example may involve an Internet user that goes to an online retailer of running shoes. The online retailer may not know who the user is or even if the user has visited the site one or more times in the past. The user may want the visited site to know he has been shopping for running shoes and may want the visited site to know what shoes the user has looked at over the last few weeks on other sites. The user may notify the privacy server to release only the recent shopping and other user defined information to the visited site. As a result, in this example, the privacy server may select the following attributes: shoe size=9, shoes recently viewed at other websites=Nike X, Asics Y, New Balance Z, average price of the shoes viewed=$109, zip code of the shopper=80302, gender of the shopper=male, weight of the shopper=185 lbs. The privacy server may collect these attributes, generate a unique DDID or accept or modify a temporally unique, dynamically changing value to serve as the DDID and assign the DDID to the attributes and send the same to the visited website as a TDR. If the user views a Saucony model 123, the website may append this attribute to the information pertaining to the attributes related to shoes viewed and send this information back to the privacy server as part of the augmented TDR.

Yet another example may involve a personal banker at a bank who is working with a client who wants to add a savings account to the accounts she otherwise holds with the bank. The personal banker may not need to know all information about the client, just the information necessary to open up the account. Using the present invention, the banker may query the bank's privacy server via a privacy client to request opening up a new savings account for the customer. The bank's privacy server may determine the data authorization limits for the requester and for the desired action. The bank's privacy server may collect the following attributes on the customer: name=Jane Doe, current account number=12345678, type of current account=checking, address of the customer=123 Main Street, Boulder, Colo. 80302, other signatories on the checking account=Bill Doe, relationship of signatory to customer=husband. After the bank's privacy server collects these attributes, it assigns a DDID for these attributes and sends the information to the personal banker via a privacy client as an augmented TDR.

The controlling entity could elect, in one example, to include data attributes in attribute combination A that enable recipients of the TDR to use existing tracking technology to track related party ZZ anonymously for the duration of existence of the resulting TDR. The controlling entity may also elect to include data that is more accurate than that available via existing tracking technologies to facilitate personalization and customization of offerings for related party ZZ.

At step 3, in one example, a request is made of the privacy server ("PS") for a DDID. This may include a request for specified levels of abstraction, and for the generation of a unique DDID or acceptance or modification of a temporally unique, dynamically changing value to serve as the DDID to be used in the system corresponding with respect to a particular activity, action, process or trait requested. Before assigning the DDID, the PS may verify that the DDID value is not actively being used by another TDR, potentially including a buffer period to address potential outages and system down time.

At step 4, in one example the abstraction module of the PS assigns and stores the DDID in response to requests with respect to actions, activities, processes or traits. Step 4 may also include in one example the operation of assigning a DDID X for the web browsing requested by related party ZZ.

At step 5, in one example the abstraction module of the PS combines the retrieved applicable attribute combination and assigns DDID X to create the TDR. The TDR itself may not include information about the real identify of related party ZZ, but the maintenance module of the privacy server may retain information necessary to re-associate the TDR with related party ZZ. Operation 5 may also include the secure database(s) associating the attribute combination request with the Data Subject associated with the attribute combination, thereby providing an internal record in the aggregated data profile for the Data Subject associating related party ZZ with particular attribute combination A that are deemed necessary to perform with respect to a desired action, activity, process or trait.

FIG. 3 shows examples of additional steps that may be taken by the abstraction module of the privacy server, in accordance with one embodiment of the present invention. At step 6, in one example the TDR created for related party ZZ's web browsing request is transmitted via the privacy client that may reside on a Data Subject device, on a service provider device, accessible via and reside in a cloud network, or reside on the same computing device as the privacy server to the applicable service provider, vendor, or merchant. The privacy client may also capture data associated with the desired browsing activity with the service provider, vendor or merchant.

Once the TDR's purpose is served or a predetermined temporal limitation is reached, in one example the TDR may be sent via the privacy client back to the privacy server, at step 7, the TDR that comes back may be augmented with new attribute combinations with respect to a desired action, activity, process or trait for which the TDR was created. In the example shown in FIG. 3, related party ZZ performs the desired web browsing in connection with the service provider, merchant or vendor, and attribute combination Q ("AC Q") is generated that reflects attribute combinations associated with the desired web browsing performed. When the web browsing is complete, or when the temporal limitations of the TDR expire, the privacy client with the TDR, now augmented with attribute combination Q reflecting data associated with the web browsing, transmits data from the service provider, vendor or merchant to the privacy server. When the data is received back at the privacy server, a time period/stamp is associated with the TDR in one example by means of time keys (TKs) or otherwise, and the relevant attribute combinations returned from the service provider, vendor, or merchant may be updated and stored in the secure database(s) in the aggregated data profile for the Data Subject.

Figure 4:
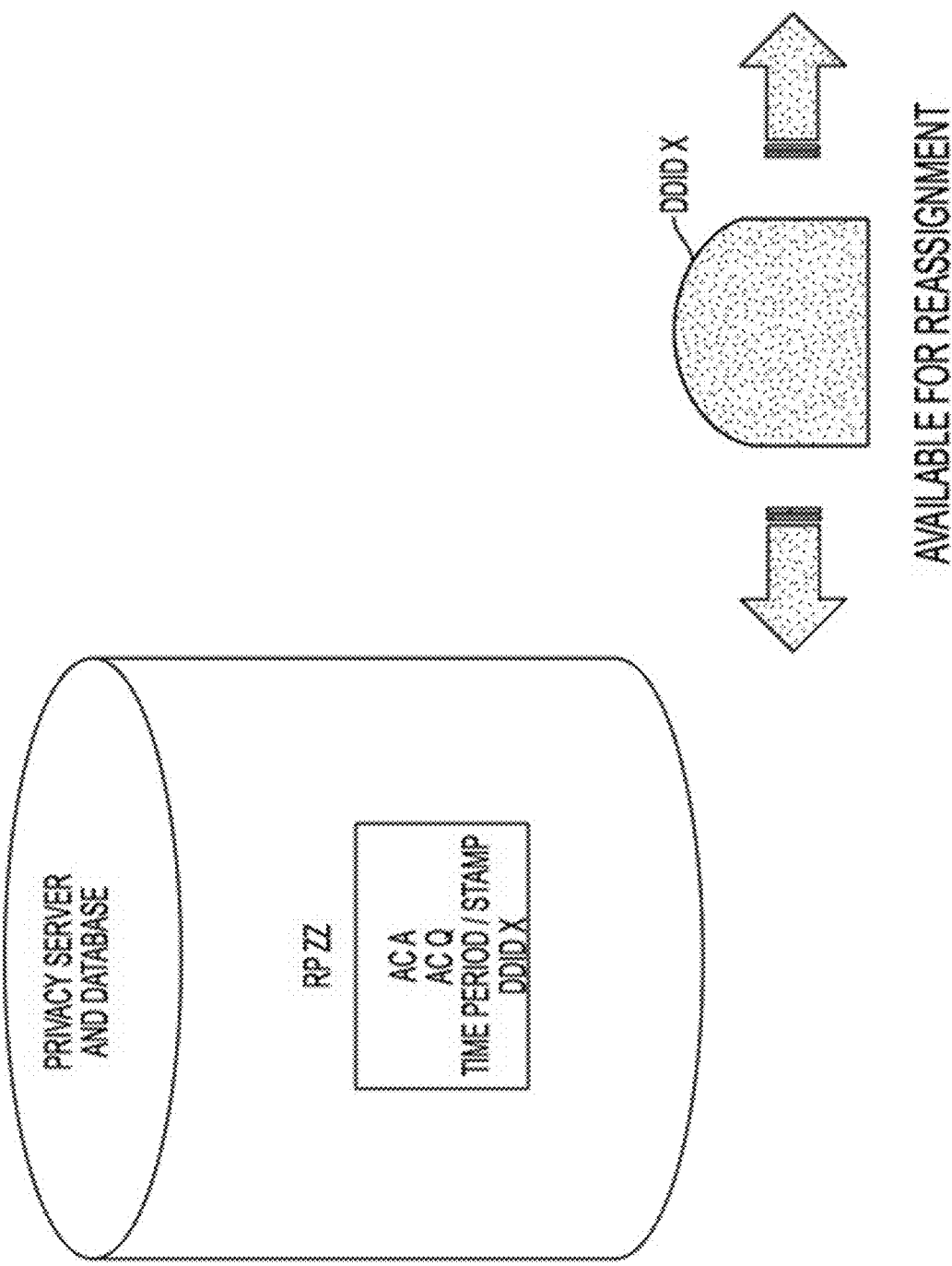

FIG. 4 shows an example of additional steps that may be taken following the operations of FIG. 3, according to one example of an embodiment of the present invention. As each augmented TDR is received back by the privacy server, the maintenance module of the privacy server may update the source data by associating the time period/stamp by means of time keys (TKs) or otherwise, DDID, and attribute combinations with the applicable Data Subject. As shown in the example of FIG. 4, the privacy server may record and associate the time period/stamp by means of time keys (TKs) or otherwise, DDID, attribute combination A, and attribute combination Q with requesting related party ZZ within the secure database. Relationship information between and among time periods/stamps, DDIDs, attribute combinations, Data Subjects and associated profiles may be stored, updated or deleted as applicable in the maintenance module of the privacy server. This may include, in one example, storing or updating all relationship information between all time periods/stamps, DDIDs, attribute combinations, Data Subjects, and profiles within the secure database(s) in the aggregated data profile for the Data Subject. Upon completion of the association of new data with regard to the desired action, activity, process or trait from the attribute combinations, in one example the DDID may then be reassigned for use with new TDRs in the same fashion as described above.

Figure 5:
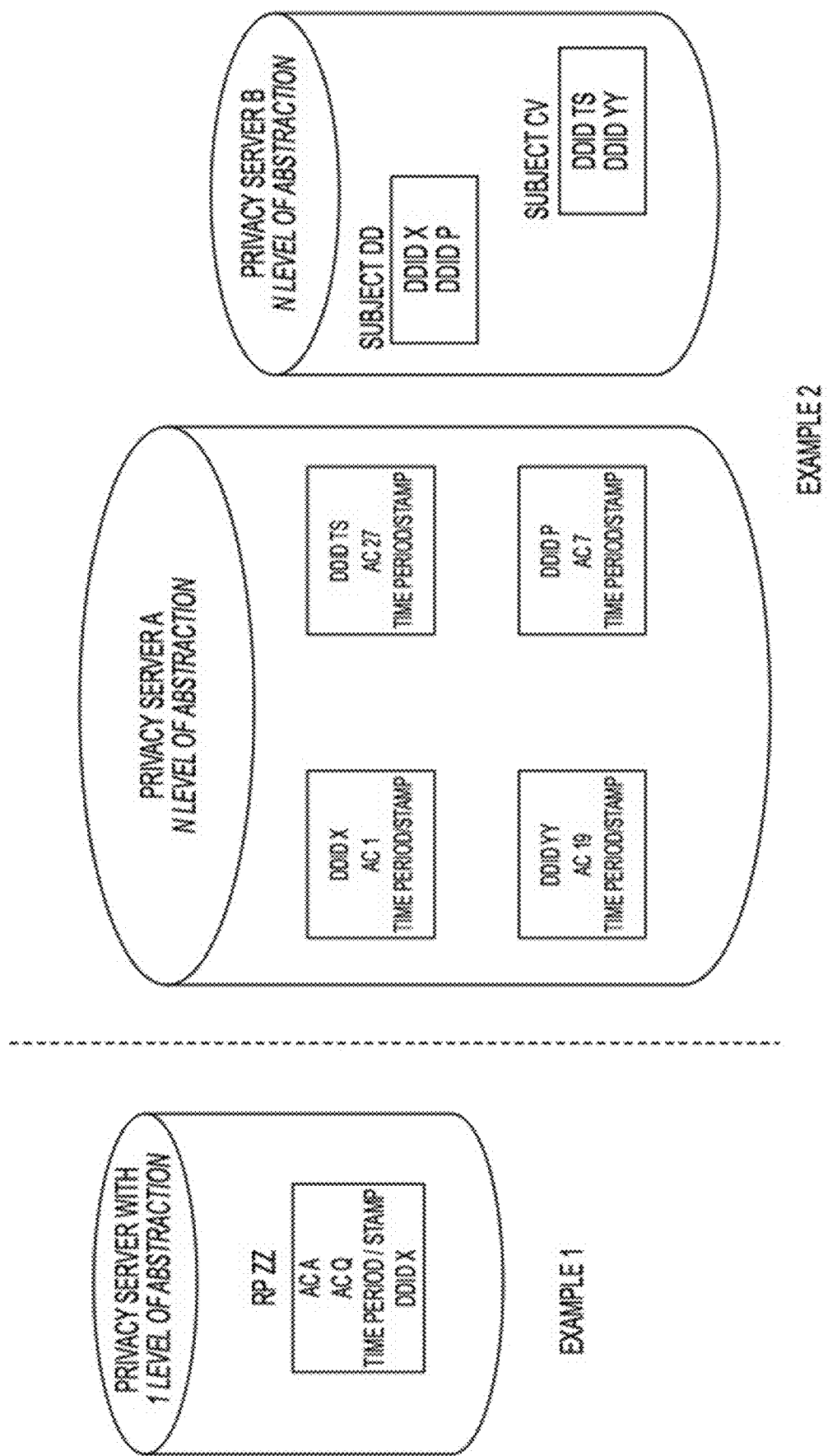
FIG. 5 illustrates two example attribute combinations having different levels of abstraction by means of the association function and the replacement function of the system, in accordance with one embodiment of the invention.

FIG. 5 highlights differences between an example single layer abstraction implementation of a system, as compared to an example multi-layer abstraction implementation of a system, in accordance with one embodiment of the present invention. Example 1 illustrated in FIG. 5 shows an example of a system with a single layer of abstraction, such as described above in the discussion of FIGS. 2-4 with respect to a web browsing activity. Example 1 in FIG. 5 shows an example of a final disposition resulting from the web browsing activity of FIGS. 2-4, where the secure database is updated with a record associating a time period/stamp by means of time keys (TKs) or otherwise, attribute combination A, attribute combination Q, and DDID X associated with requesting related party ZZ. It should be noted that with respect to Example 1, parties outside of the system would not have access to identifying information pertaining to attribute combinations or Data Subjects. However, within the system, though the user of a replacement key (RK) described herein, the identity of related party ZZ would be discernible in one example, as would the relationship between related party ZZ, attribute combination A, attribute combination Q, the time period/stamp and DDID X.

Example 2 in FIG. 5 reflects one potential implementation of a multi-layer abstraction implementation of a system, in accordance with one embodiment of the present invention. The abstraction provided is a function of multiple applications of the system, rather than of wholly different pieces. The dynamic nature of the TDRs allows for the same baseline principles to be used among the levels of abstraction while still providing useable interaction with regard to data as requested. In this example, an entity with authorized access to privacy server A and associated secure database would have access to the associations between DDID X, DDID P, DDID TS and DDID YY, as well as each of the attribute combinations and time periods/stamps associated with the DDIDs. However, the entity would not have access in one example to any information concerning associations between the different DDIDs disclosed. Only upon gaining access to privacy server B and associated secure database would the second level of abstraction be revealed pertaining to the relationship between DDID X and DDID and between DDID TS and DDID YY. As shown in FIG. 5, this second level of abstraction could be the relationship of Subject DD to DDIDs X and P, and the relationship of Subject CV to DDIDs TS and YY.

In the event that Subject CV and Subject DD reflect the identity of Data Subjects in question, Example 2 would reflect one potential implementation of a two-layer abstraction implementation of the system. However, if the values for Subject CV and Subject DD were each assigned dynamically changeable DDIDs, then Example 2 would reflect one potential implementation of a three-layer abstraction implementation of the system. It should be appreciated that any and all of the elements of the system can be abstracted on multiple levels in order to achieve desired levels of security and privacy/anonymity.

In one example implementation of the system, both Example 1 and Example 2 in FIG. 5 may represent an authenticated data structure that permits the verification module of the privacy server to validate and verify attribute combinations and DDIDs embodied in a TDR and/or data profile at any point in time by methodologies such as cyclic redundancy checks ("CRCs"), message authentication codes, digital watermarking and linking-based time-stamping methodologies. These methodologies enable verification of the state and composition of data at various points of time by confirming the composition of each Data Subject, attribute, attribute combination, aggregated data profile and other elements contained in the privacy server at different points in time.

In addition, in one example implementation of an embodiment of the present invention, both Example 1 and Example 2 in FIG. 5 may include data necessary for the access log module to enable post-incident forensic analysis in the event of system related errors or misuse.

Figure 6:
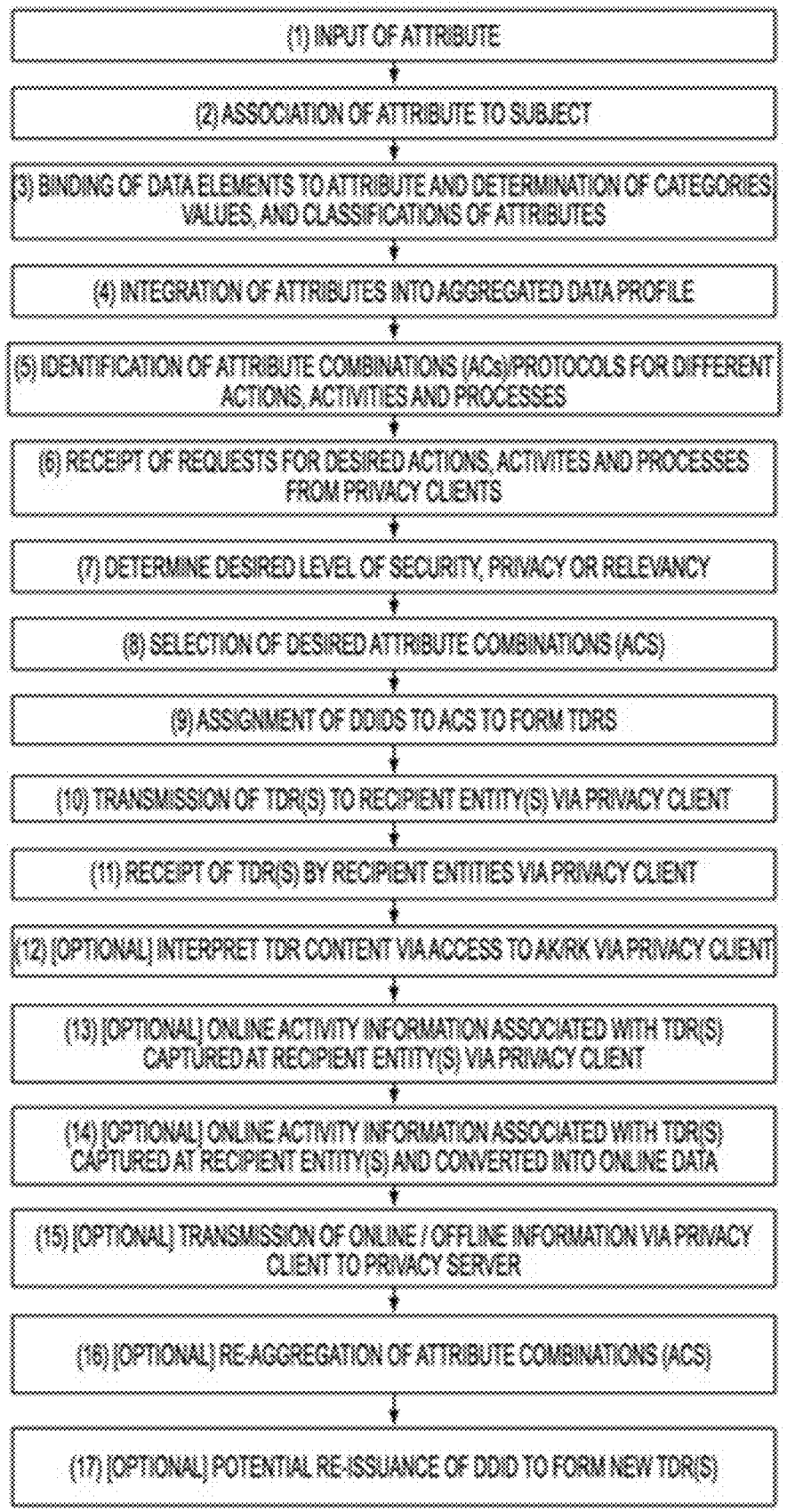
FIG. 6 shows an example of a process (from a sample controlling entity and system perspective) to select attribute combinations, generate TDRs to abstract or anonymize the data, and then re-associate or de-anonymize the data, in accordance with one embodiment of the invention.

FIG. 6 shows one example of a process for providing data security and data privacy/anonymity, in accordance with one embodiment of the present invention. FIG. 6 shows process steps that may be implemented by a controlling party or a system, in one example. The operations outlined in FIGS. 6-10 may be facilitated by means of known programming techniques including but not limited to Simple Object Access Protocol (SOAP), Representational State Transfer (REST) Application Programming Interfaces (APIs) or Service Oriented Architecture (SOA) techniques as well as canonical industry standard data models such as HL7 for healthcare, SID for telecom, ARTS for retail, ACORD for insurance, M3 for multi-commodity models, OAGIS for manufacturing and supply chains; PPDM for oil & gas/ utilities, and the like.

At step 1 in FIG. 6, a data attribute is received or created as input to the system. As noted previously for purposes of this disclosure, a data attribute refers to any data element that can be used, independently or in combination with other data elements, to identify a Data Subject, such as a person, place or thing, or associated actions, activities, processes or traits. One example of a data attribute may be the street address comprised of 1777 6th Street, Boulder, Colo. 80302.

At step 2 of FIG. 6, the data attribute is associated with the applicable subject. In the above example, the data attribute address is associated with the subject Colorado Municipal Court Building.

At step 3 of FIG. 6, the elements associated with each data attribute are linked to or bound with the data attribute and determinations are made comprising applicable category(s); value(s) and classification(s) pertaining to attributes to facilitate use of the attributes with respect to desired actions, activities, processes or traits. For example, elements associated with the above data attribute address may be: (a) categorized as a street address; (b) with values of: 1; 7; 7; 7; 6th; S; t; r; e; e; t; B; o; u; l; d; e; r; C; o; l; o; r; a; d; o; 8; 0; 3; 0; 2; 1777; 6th Street; Boulder; Colorado; 80302 or any combination of the foregoing; and (c) classified as constant in nature since the building is stationary. Another example of a data attribute pertaining to the subject building may be the condition of the building (a) categorized as the condition of the building; (b) with a value of good condition; and (c) classified as variable in nature since the condition of the building may improve of degenerate over time. Another example of a data attribute pertaining to the subject building may be (a) categorized as organizations having offices located in the building; (b) with a value of Boulder Colo. Alternative Sentencing Program (CASP); and (c) classified as variable in nature since CASP may in the future change the location of their office. It should be noted that exogenous information may comprise attributes associated with a Data Subject. For example, in the case of the building identified above, if someone knows that Boulder Colo. Alternative Sentencing Program (CASP) has offices at the Colorado Municipal Court Building and discovers that John Smith works at CASP and that on weekdays John Smith shows up at 1777 6th Street in Boulder, that original person may use this exogenous information to discern the address of the Colorado Municipal Court Building in Boulder. Thus, the fact that John Smith works at CASP may be an attribute of the Data Subject, potentially revealing the Data Subject, i.e., the building at the address.

At step 4 in FIG. 6, each of the data attributes input into the system are added to an aggregated data profile (see, e.g., FIGS. 1 and 1A) for the Data Subject. In the above example, the noted data attributes would be added to the aggregated data profile for the Colorado Municipal Court Building.

At step 5, attribute combinations are identified and formed so as to provide support with respect to a desired activity, action, process or trait. This step may include the creation or loading of templates that specify the one or more attributes necessary with respect to a particular action, activity, process or trait. For example, for an e-commerce action, the template may request information pertaining to the Data Subject's age, sex, size and preferred color(s) as attributes. In another example involving a travel reservation function, the template may request information pertaining to the Data Subject's preferred means of air travel by coach, business class or first class as attributes. The privacy server may be loaded with or have access to a plurality of such templates in order to support a wide variety of differing actions, activities, processes and/or traits. In addition, the privacy server may be configured to facilitate the manual override of established templates if/as desired by the controlling entity and creation of new templates with respect to desired new actions, activities, processes and/or traits. Such manual override may occur for instance by means of a graphical user interface of a privacy client running on a Data Subject's mobile device. For instance, a Data Subject may use the graphical user interface to override the request for information pertaining to the Data Subject's preferred means of air travel by coach, business class or first class because in one example the Data Subject may be traveling by cruise ship and therefore the Data Subject may desire to specify whether he/she wants a suite, balcony stateroom, outside stateroom, or inside stateroom as attributes. In this example, the graphical user interface may permit the Data Subject to elect the minimal attributes for transmission from the Data Subject's aggregated data profile.

At step 6, requests are received by the privacy server from privacy clients that may reside on Data Subject devices, on service provider devices, accessible via and residing in a cloud network, or residing on the same computing device as the privacy server with regard to a specific action, activity, process or trait. The nature and substance of requests that may be received by the privacy server from privacy clients may vary in nature depending on a variety of factors comprising whether the system is implemented as DRMI, DRMD or otherwise, whether a request pertains to healthcare, education, mobile, financial, Web, Internet of Things or other applications, etc.

At step 7, a determination is made regarding the level of abstraction appropriate for the desired level of security, anonymity, privacy and relevancy with respect to a particular action, activity, process or trait. For example, the system may introduce an initial layer of abstraction by linking relevant data attributes, separating relevant data attributes into one or more TDR as determined desirable with respect to a given action, activity, process or trait. Additional layers of abstraction may be introduced beyond separating data attributes into one or more TDR by means of abstracting individual attributes, attribute combinations, or both by replacing them with DDIDs that cannot be understood without access to replacement keys (RKs). The privacy, anonymity and security of attributes contained or referenced within a TDR may be further improved or enhanced by using known protection techniques such as encrypting, tokenizing, pseudonymizing and eliding and further layers of abstraction may be introduced by using additional DDIDs to refer to networks, internets, intranets, and third party computers that may be integrated, or communicate, with one or more embodiments of the present invention.

At step 8, desired attribute combinations are selected by a controlling entity from the privacy server based on the attributes associated with the applicable template as may be necessary with respect to a desired action, activity, process or trait. The abstraction module may determine desired attributes that may be controlled by the controlling entity or delegated to another entity as an authorized party, where the authorized party may choose to use the abstraction module to select attributes based on established templates, select attributes on the fly, or intelligently detect appropriate input, among other methods.

In one example of step 8, with an e-commerce site selling sports equipment, an internet browser provider that is acting as the controlling entity may use the abstraction module of the privacy server to determine that information regarding a Data Subject's height, weight and budget are needed for a receiving website to give options for appropriate sports equipment such as kayaks and paddles.

At step 9, the abstraction module of the privacy server generates unique DDIDs or accepts or modifies temporally unique, dynamically changing values to serve as DDIDs and assigns a DDID to each attribute combination of operation 8, to form TDRs. These DDIDs may serve various functions including, but not limited to, replacement or simple association. For example, if the internet browser provider acting as the controlling entity instructs the abstraction module to create a TDR with a single layer of abstraction it may assign a DDID that is not visibly associated with other TDRs for the same Data Subject without access to association keys (AKs). As another example, if the internet browser provider acting as the controlling entity instructs the abstraction module to create a TDR with two layers of abstraction it may (i) assign DDIDs to be associated with the data attributes for the duration of the TDR and (ii) further abstract the data attributes by assigning a DDID of Ab5 to the Data Subject's weight, a DDID of 67h to the Data Subject's height and a DDID of Gw2 to the Data Subject's budget that cannot be understood without access to replacement keys (RKs). Step 9 may also include obtaining one or more attributes from one or more databases, the attributes relating to the Data Subject. The DDIDs utilized in step 9 may be confirmed as not being currently in use, and may be selected from expired, previously used DDIDs.

At step 10, TDRs comprised of attribute combinations and DDIDs are transmitted, by the privacy server via privacy clients to recipient entities for use by recipient entities in connection with desired actions, activities, processes or traits pertaining to recipient entities. In the above example for instance, the internet browser provider acting as the controlling entity may deliver to the ecommerce site as the recipient entity a TDR comprised of a DDID together with second level abstracted data attributes comprised of Ab5, 67h and Gw2.

At step 11, TDRs (which may be comprised of attribute combinations and DDIDs with respect to desired actions, activities, processes or traits) are received by recipient entities by means of privacy clients. To the extent that the intended use of the system is to enable creation of output for big data analytics, the receipt of the TDRs may be the last step (e.g., see the example of a potential embodiment of the invention discussed in the context of Figure Z to provide privatized/anonymized data for big data analytics so applicable Data Subject(s) have the "right to be forgotten"), however, more interactive use of TDRs may involve optional steps 12 through 17.

At optional step 12, TDRs (which may be comprised of attribute combinations and DDIDs for a desired online action, activity, process or trait) are interpreted by recipient entities by means of privacy clients and provide access to use of AKs and/or RKs as necessary to understand the contents of the TDRs. In the above example for instance, the ecommerce site as the recipient entity would access the RK information to understand the value attributed to Ab5 for the Data Subject's weight, the value attributed to 67h for the Data Subject's height and the value attributed to Gw2 to the Data Subject's budget.

At optional step 13, the privacy client may capture new data attributes associated with the desired online action, activity, process or trait that augment the original TDR data attributes as new information in TDR format.

At optional step 14, the privacy client may capture new data attributes associated with offline activity, if any, associated with the desired online action, activity, process or trait that augment the original TDR data attributes as new information in TDR format.

At optional step 15, privacy clients transmit TDRs comprised of DDIDs and attribute combinations pertaining to online/offline sessions back to the privacy server.

In the context of steps 14 and 15, since TDRs are transmitted via privacy clients to the privacy server without AKs or RKs they are transmitted in a disaggregated and anonymized format, so that, if someone intercepts the TDRs, they will not receive all data applicable to the Data Subject, desired action, activity, process or trait.

At optional step 16, in one example, re-aggregation of attribute combinations is performed through application by the maintenance module of relationship information between and among DDIDs and attribute combinations by means of association keys (AKs) and (DKs) residing at the privacy server. In the example, this would mean that the original or modified TDRs return to the privacy server, which may then modify or add the new information about recommended kayaks and paddles to the aggregated data profile for the Data Subject.

Upon completion of aforementioned re-aggregation of new data regarding the desired action, activity, process or trait from the attribute combinations, in one example the DDID may then be considered expired and reintroduced to the system at optional step 17 for reassignment and use with other attributes, attribute combinations, Data Subjects, actions, activities, processes, traits or data, forming new TDRs in the same fashion as described above.

For instance, the DDIDs Ab5, 67h and Gw2 assigned to the attributes in step 9 above may then be assigned to data attributes pertaining to other Data Subjects for instance in a like case hop or distant case leap manner. For example, a like case hop may include re-association of Ab5 to a second Data Subject of the same or similar weight as the initial Data Subject or re-association of a piece of data on weight or something involving the same number but not associated with the same Data Subject whereas a distant case leap may involve reassigning Ab5 to an unrelated data attribute awaiting an DDID.

In a second example of FIG. 6, a physician may request blood pressure information pertaining to a specified Data Subject who is a patient as collected offline by a nurse and entered online into the Data Subject's aggregated data profile. This request may cause the abstraction module of the privacy server, as part of step 8 above, to extract the attribute combination composed of the most recently recorded systolic and diastolic blood pressure values for the Data Subject. As part of step 9, in lieu of specifying the Data Subject's identity, the privacy server may combine those attribute combinations with a DDID assigned by the privacy server to form a TDR. As part of step 10, the blood pressure attributes may be communicated to the physician together with the assigned DDID via the privacy client that may reside on a Data Subject device, on a service provider device, accessible via and reside in a cloud network, or reside on the same computing device as the privacy server. At this point, the combination of the DDID and attribute combination pertaining to blood pressure would comprise the TDR. As part of step 12, the physician, as the recipient entity, may read the blood pressure values via means of the RKs and as part of steps 13 and 14 may record online and offline observations, recommendations or comments pertaining to the blood pressure reading as new data attributes. As part of step 15, the TDR augmented with online/offline information may be returned to the privacy server via the privacy client. As part of step 16, the privacy server may use the information to update the Data Subject's aggregated data profile. In this manner, an unintended recipient of the TDR would be unable to correlate the identity of the Data Subject and would only see the DDID which may be reassigned to another Data Subject in a like case hop or distant case leap manner after use by the physician.

Figure 6A:
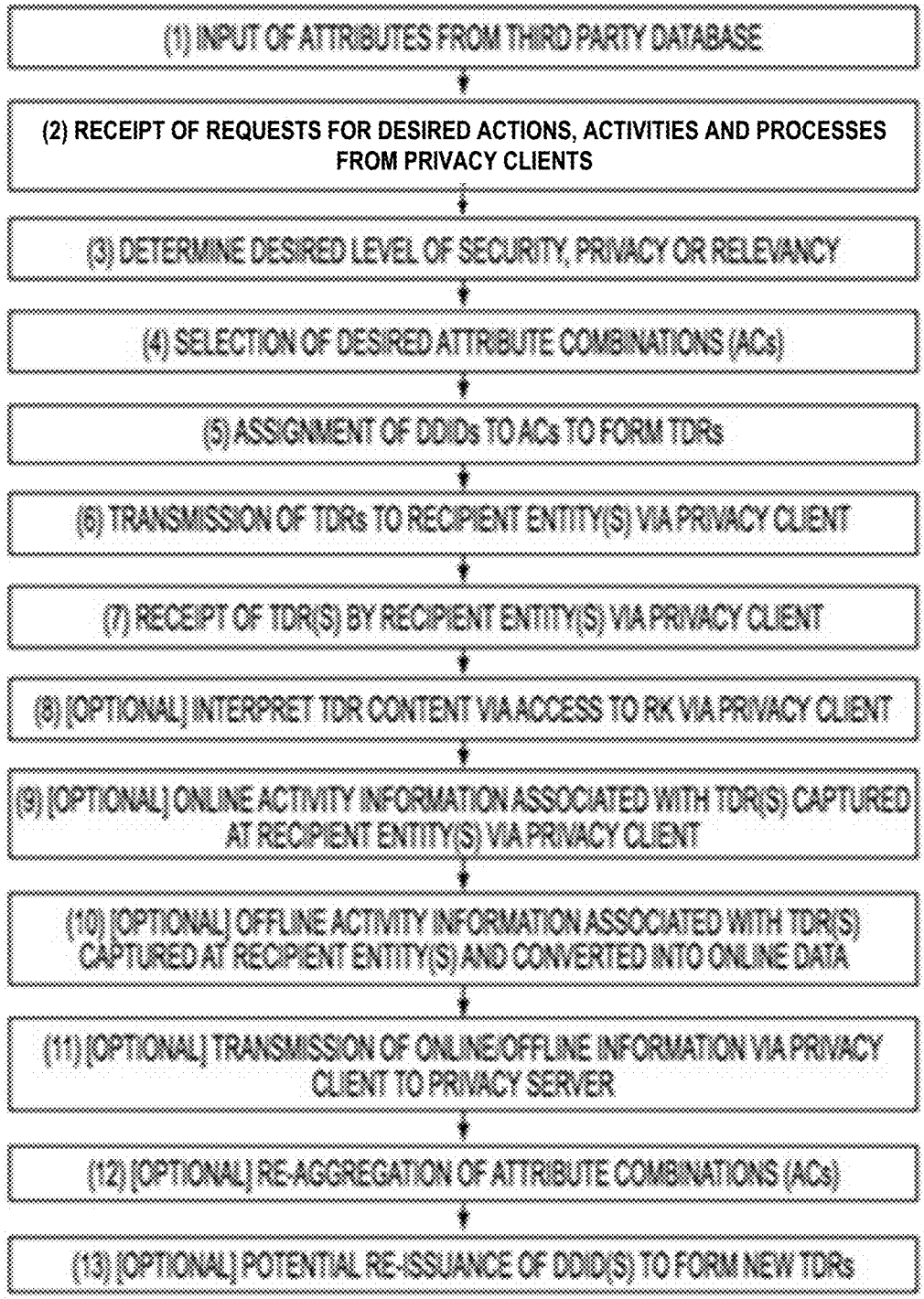
FIG. 6A shows an example of a process (from a sample controlling entity and system perspective) to receive attributes from one or more external database, generate TDRs to abstract or anonymize the data, and then re-associate or de-anonymize the data, in accordance with one embodiment of the invention.

FIG. 6A shows an example of a process for providing data security, data privacy and anonymity, in accordance with one embodiment of the present invention involving interaction with external databases. FIG. 6A shows process steps that may be implemented by a controlling party or a system, in one example.

At step 1 in FIG. 6A, a third-party data source submits data that includes one or more data attributes pertaining to one or more Data Subjects as input to the system. It should be noted that, in the embodiment of the invention represented by FIG. 6A, prior to submitting data that includes one or more data attributes pertaining to one or more Data Subjects input to the system, the third-party data source would have already created an aggregated data profile for each Data Subject (see, e.g., FIG. 1A) which the third-party data source would maintain, directly or indirectly, in one or more databases.

At step 2, requests are received by the privacy server from privacy clients that may reside on Data Subject devices, on service provider devices, accessible via and residing in a cloud network, or residing on the same computing device as the privacy server with regard to a specific action, activity, process or trait. The nature and substance of requests that may be received by the privacy server from privacy clients may vary in nature depending on a variety of factors comprising whether the system is implemented as DRMI, DRMD or otherwise, whether a request pertains to healthcare, education, mobile, financial, Web, Internet of Things or other applications, etc.

The privacy, anonymity and security of attributes contained or referenced within a TDR may be further improved or enhanced by using known protection techniques such as encrypting, tokenizing, pseudonymizing and eliding and further layers of abstraction may be introduced by using additional DDIDs to refer to networks, internets, intranets, and third party computers that may be integrated, or communicate, with one or more embodiments of the present invention.

At step 3, a determination is made regarding the level of abstraction appropriate for the desired level of security, anonymity, privacy and relevancy for a particular action, activity, process or trait. For example, the system may introduce abstraction by means of abstracting individual attributes, attribute combinations, or both by representing them with DDIDs that cannot be understood without access to replacement keys (RKs). The privacy/anonymity and security of attributes contained or referenced within a TDR may be further improved or enhanced by using known protection techniques such as encrypting, tokenizing, pseudonymizing and eliding and further layers of abstraction may be introduced by using additional DDIDs to refer to networks, internets, intranets, and third party computers that may be integrated, or communicate, with one or more embodiments of the present invention.

At step 4, desired attribute combinations are selected by a controlling entity from the privacy server based on the attributes associated with the applicable template as may be necessary with respect to a desired action, activity, process or trait. The abstraction module may determine desired attributes that may be controlled by the controlling entity or delegated to another entity as an authorized party, where the authorized party may choose to use the abstraction module to select attributes based on established templates, select attributes on the fly, or intelligently detect appropriate input, among other methods.

In one example of step 4, in the context of healthcare research, a hospital that is acting as the controlling entity may use the abstraction module of the privacy server to obfuscate information regarding a Data Subject's height, weight and name before sending the information to a research facility.

At step 5, the abstraction module of the privacy server assigns a DDID to each attribute combination of operation 4, to form TDRs. These DDIDs may serve various functions including, but not limited to, replacement or simple association. For example, if hospital acting as the controlling entity instructs the abstraction module to create a TDR with two layers of abstraction it may abstract the data attributes by assigning a DDID of Ab5 to the Data Subject's weight, a DDID of 67h to the Data Subject's height and a DDID of Gw2 to the Data Subject's name that cannot be understood without access to replacement keys (RKs). Step 5 may also include obtaining one or more attributes from one or more databases, the attributes relating to the Data Subject. The DDIDs utilized in step 5 may be confirmed as not being currently in use, and may be selected from expired, previously used DDIDs.

At step 6, TDRs comprised of attribute combinations and DDIDs are transmitted, by the privacy server via privacy clients to recipient entities for use by recipient entities in connection with desired actions, activities, processes or traits pertaining to recipient entities. In the above example for instance, the hospital acting as the controlling entity may deliver to the research facility as the recipient entity a TDR comprised of abstracted data attributes comprised of Ab5, 67h and Gw2.

At step 7, TDRs (which may be comprised of attribute combinations and DDIDs with respect to a desired action, activity, process or trait) are received by recipient entities by means of privacy clients. In the above example for instance, the research facility as the recipient entity would receive the information for analysis but without divulging personally identifying information pertaining to weight, height. Rather, the research facility would receive Ab5, 67h and Gw2 that it could not decipher unless granted access to relevant RK information. To the extent that the intended purpose is big data analysis, the receipt of the TDRs may be the last step, however, more interactive use of TDRs may involve optional steps 8 through 13.

At optional step 8, TDRs (which may be comprised of attribute combinations and DDIDs with respect to a desired action, activity, process or trait) are interpreted by recipient entities by means of privacy clients and provide access to use of AKs and/or RKs as necessary to understand the contents of the TDRs.

At optional step 9, the privacy client may capture new data attributes associated with respect to the desired online action, activity, process or trait that augment the original TDR data attributes as new information in TDR format.

At optional step 10, the privacy client may capture new data attributes associated with offline activity, if any, associated with the desired online action, activity, process or trait that augment the original TDR data attributes as new information in TDR format.

At optional step 11, privacy clients transmit TDRs comprised of attribute combinations and DDIDs pertaining to online/offline sessions back to the privacy server. Since TDRs are transmitted via privacy clients to the privacy server without AKs and/or RKS they are transmitted in a disaggregated and anonymized format so if someone intercepts the TDRs they will not receive all data applicable to the Data Subject, or desired action, activity, process or trait.

At optional step 12, in one example, re-aggregation of attribute combinations is performed through application by the maintenance module of relationship information between and among DDID and attribute combinations by means of association keys (AKs) and/or replacement keys (RKs) residing at the privacy server. In the example, this would mean that the original or modified TDRs return to the privacy server, which may then modify or add the new information about recommended kayaks and paddles to the aggregated data profile for the Data Subject.

Upon completion of aforementioned re-aggregation of new data regarding the desired action, activity, process or trait from the attribute combinations, in one example the DDID may then be considered expired and reintroduced to the system at optional step 13 for reassignment and use with other attributes, attribute combinations, Data Subjects, actions, activities, processes, traits, or data, forming new TDRs in the same fashion as described above.

Figure 6B:
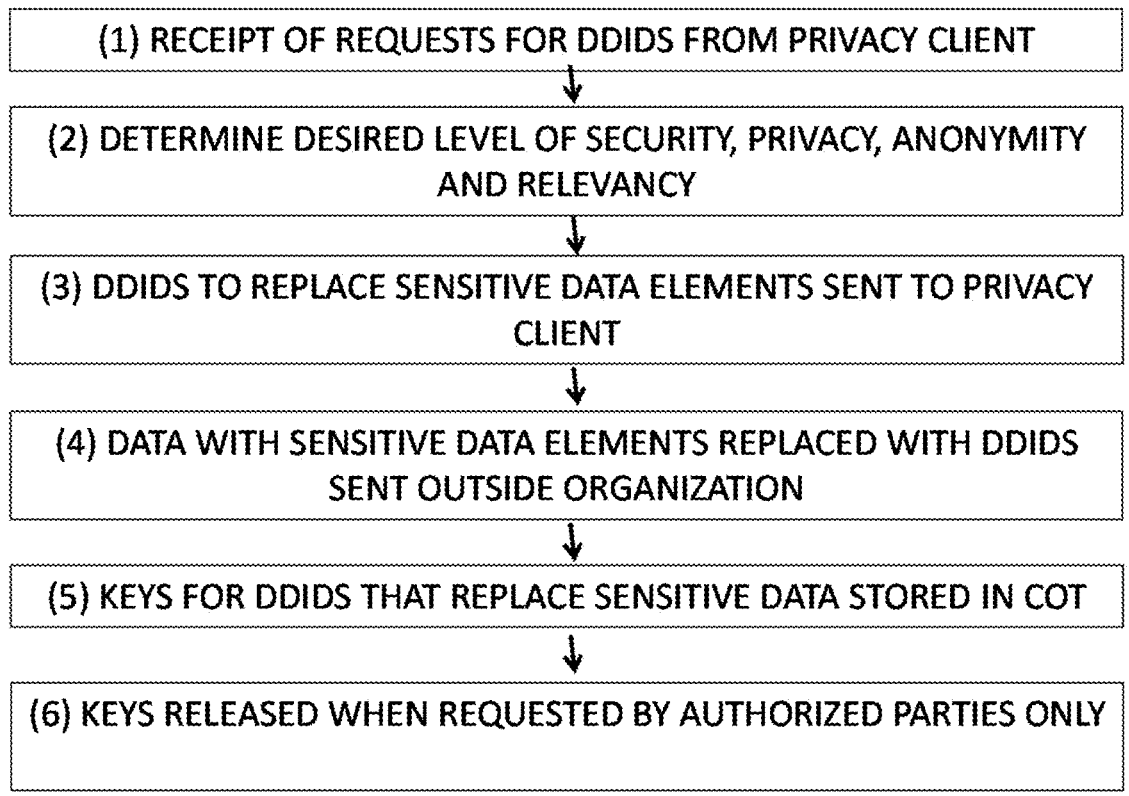
FIG. 6B shows an example of a process (from a sample controlling entity and system perspective) to provide dynamic anonymity for data elements contained in one or more databases considered too sensitive to be revealed in an identifiable manner external to an organization.

FIG. 6B shows how potential embodiments of the present invention may provide dynamic anonymity for data elements contained in one or more databases (whether the one or more databases are internal to the system as illustrated in FIG. 1A and/or external to the system as illustrated in FIG. 1B) that are considered too sensitive to be revealed in an identifiable manner external to an organization—e.g., data which directly identifies a Data Subject or sensitive action, activity, process and/or trait (a direct identifier) or indirectly identifies a Data Subject or sensitive action, activity, process and/or trait when combined with other data (a quasi-identifier). The system may dynamically obscure said sensitive data when exposed externally to the organization by replacing said data with one or more DDIDs. Keys necessary to understand the association between the one or more DDIDs and the obscured sensitive data may then be kept securely in a Circle of Trust (CoT) and only made available to authorized parties. DDIDs may be "designed" (i.e., the data obscuring strategy may be tailored in such a way) to allow varying levels of data use/analysis of DDIDs consistent with PERMS established by a Data Subject or Trusted Party without revealing underlying sensitive data. The sensitive data represented by the one or more DDIDs may not be disclosed until keys are requested by one or more parties that have been authorized by the Data Subject or Trusted Party to receive and/or make use of the underlying sensitive data.

In one potential embodiment of the present invention, the obscuring of sensitive data as described above may occur only with respect to a certain computer application that requests data from the subject one or more databases by intercepting requests for sensitive data from the one or more database(s) at the presentation layer of said computer application and replacing the sensitive data with one or more DDIDs as described above. In another potential embodiment of the present invention, obscuring of sensitive data may occur with respect to one or more computer applications that request data from the subject one or more databases by intercepting requests for sensitive data at the one or more database(s) connection level(s) and replacing the sensitive data with one or more DDIDs as described above.

FIG. 6B shows process steps that may be implemented by a controlling party or a system to obscure sensitive data, in one example.

At step 1 in FIG. 6B, requests are received by the privacy server from privacy clients that may reside on Data Subject devices, on service provider devices, accessible via and residing in a cloud network, or residing on the same computing device as the privacy server with regard to data elements contained in one or more databases (whether the one or more databases are internal to the system as illustrated in FIG. 1A and/or external to the system as illustrated in FIG. 1B) considered too sensitive to be revealed in an identifiable manner external to an organization—e.g., data which directly identifies a Data Subject or sensitive action, activity, process and/or trait (a direct identifier) or indirectly identifies a Data Subject or sensitive action, activity, process and/or trait when combined with other data (a quasi-identifier). The nature and substance of requests that may be received by the privacy server from privacy clients may vary in nature depending on a variety of factors comprising whether the system is implemented as DRMI, DRMD or otherwise, whether a request pertains to healthcare, education, mobile, financial, Web, Internet of Things or other applications, etc.

At step 2, the abstraction module determines the level of abstraction appropriate for the desired level of security, privacy, anonymity and relevancy for the sensitive data elements consistent with PERMS established by a Data Subject or Trusted Party and DDID association strategies are developed for the sensitive data elements consistent with the scope of data use/analysis permitted by said PERMS.

At step 3, the one or more DDIDs determined by the abstraction module to dynamically obscure the sensitive data elements are sent to the privacy client.

At step 4, the one or more sensitive data elements are dynamically obscured by replacing said data elements with one or more DDIDs determined by the abstraction module and resulting DDIDs are used to replace the sensitive data elements in data communicated externally to the organization. In one example of step 3, the obscuring of sensitive data elements occurs only with respect to a certain computer application that requests data from the subject one or more databases by intercepting requests for sensitive data from the one or more database(s) at the presentation layer of said computer application and replacing the sensitive data with one or more DDIDs as determined by the abstraction module. In another example of step 3, the obscuring of sensitive data elements occurs with respect to one or more computer applications that request data from the subject one or more databases by intercepting requests for sensitive data from the one or more database(s) at the one or more database(s) connection level(s) and replacing the sensitive data with one or more DDIDs as determined by the abstraction module.

At step 5, keys necessary to understand the association(s) between the one or more DDIDs and the obscured sensitive data elements are securely stored in a Circle of Trust (CoT).

At step 6, keys necessary to understand the association(s) between the one or more DDIDs and the obscured sensitive data elements that are securely stored in a Circle of Trust (CoT) are made available only to authorized parties. Sensitive data represented by the one or more DDIDs is not be disclosed until keys are requested by one or more parties that have been authorized by the Data Subject or Trusted Party to receive and/or make use of the underlying sensitive data.

Figure 7:
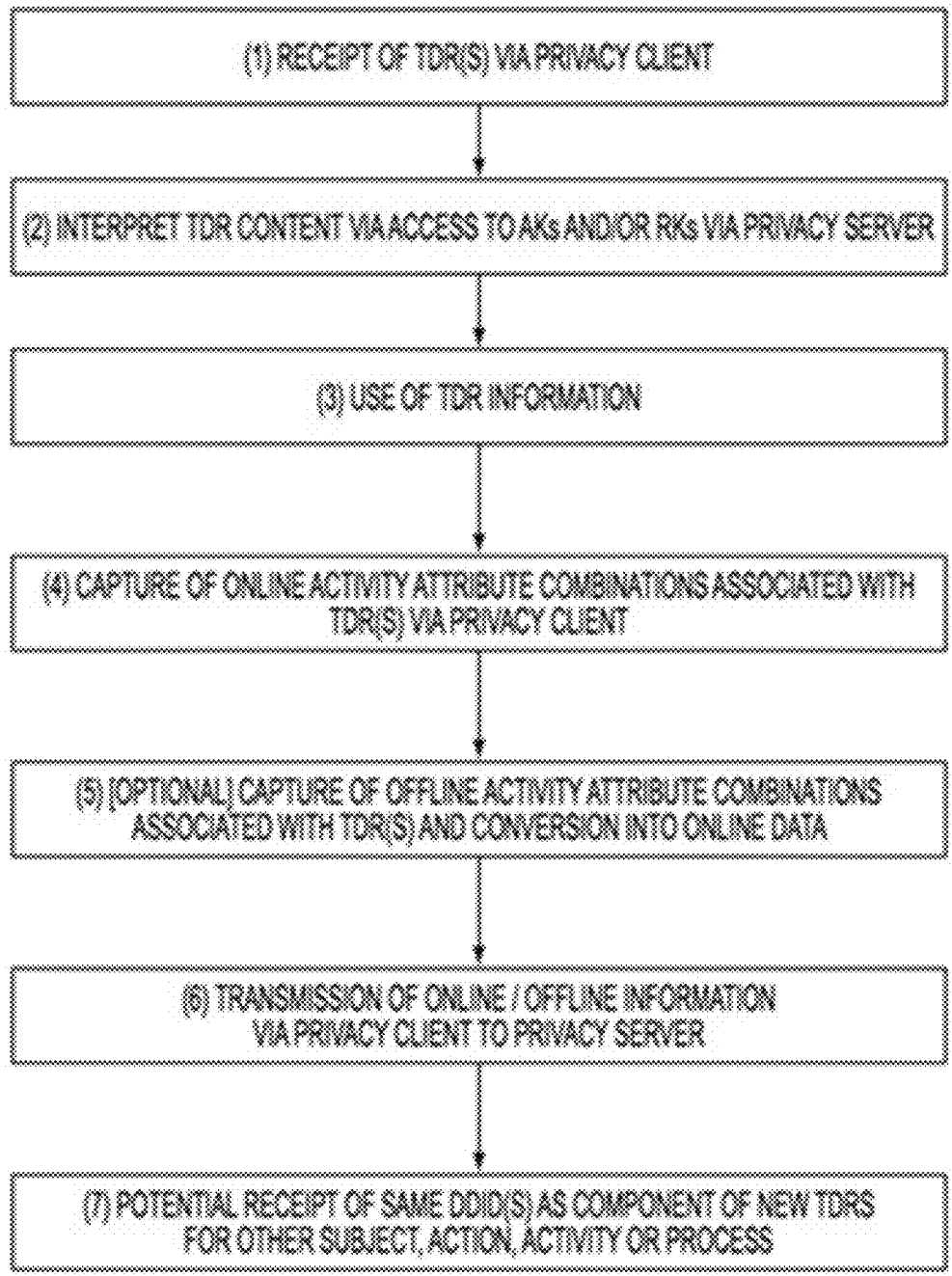
FIG. 7 shows an example of a process (from a recipient entity perspective) of the process of FIG. 6, in accordance with one embodiment of the invention.

FIG. 7 shows an example of process steps that may be implemented by a recipient entity, in one example of the present disclosure.

At step 1, a TDR comprised of attribute combinations selected by the controlling entity combined with a DDID to be associated with the data attributes for the duration of the TDR are received by a recipient client by means of a privacy client residing on a Data Subject device, on a service provider device, accessible via and residing in a cloud network, or residing on the same computing device as the privacy server indicating a request with respect to a desired action, activity, process or trait. For instance, in the kayak example above, the e-commerce site receiving entity may receive the Data Subject's TDR request with respect to a desired action, activity, process or trait.

At step 2, TDRs (which may be comprised of attribute combinations and DDIDs for the desired online action, activity, process or trait) are interpreted by the recipient entity by means of a privacy client that provides access to use of AKs and/or RKs as necessary to understand the contents of the TDRs. In the above example for instance, the ecommerce site would access the RK information residing on Data Subject devices, on service provider devices, accessible via and residing in a cloud network, or residing on the same computing device as the privacy server to understand the value attributed to Ab5 for the Data Subject's weight, the value attributed to 67h for the Data Subject's height and the value attributed to Gw2 to the Data Subject's budget.

At step 3, in one example the receiving entity may use the TDR information it has received to customize a response to the Data Subject's transmitted attributes. In the kayak example, this would allow the ecommerce site to use the information to give the Data Subject suggestions on which kayak and paddle to purchase.

At step 4, in one example the privacy client captures data for online activity performed at the recipient entity that is associated with attribute combinations by means of access to a privacy client that may be residing on a Data Subject device, on a service provider device, accessible via and residing in a cloud network, or residing on the same computing device as the privacy server.

At step 5, in one example, the recipient entity captures data for offline activity, if any, associated with attribute combinations and converts this into online data. In an instance such as the kayak example, if the Data Subject is also a loyalty rewards member at physical store locations also operated by the ecommerce site and has opted to let other preferences be known, the receiving entity may further augment the received data with this online component.

At step 5, in one example, the privacy client then transmits data pertaining to online sessions and offline activity associated with attribute combinations and DDIDs in disaggregated and anonymized format to the privacy server.

At step 6, since the DDID components of TDRs are reintroduced to the system for reassignment and use with other attributes, attribute combinations, Data Subjects, actions, activities, processes, traits, or data, forming new TDRs in the same fashion as described above, the recipient entity may see the same DDID at a later time but the DDID may have no connection to any other TDR associated with the Data Subject or otherwise with regard to which it was previously associated. For example, later that day or week the ecommerce site may see the same DDID again but attached to different information pertaining to an entirely different Data Subject.

In a second example of FIG. 7, the physician requesting the blood pressure information may receive, as part of step 1 via the privacy client, a TDR comprised of the most recently recorded systolic and diastolic blood pressure values and the DDID assigned by the privacy server to the Data Subject. As part of steps 2 and 3, the physician is able to read the blood pressure information. As part of steps 4 and 5, the physician may add observations, recommendations or comments pertaining to the blood pressure that as part of step 6 would then be sent to the privacy server via the privacy client that may be residing on a Data Subject device, on a service provider device, accessible via and residing in a cloud network, or residing on the same computing device as the privacy server.

Figure 8:
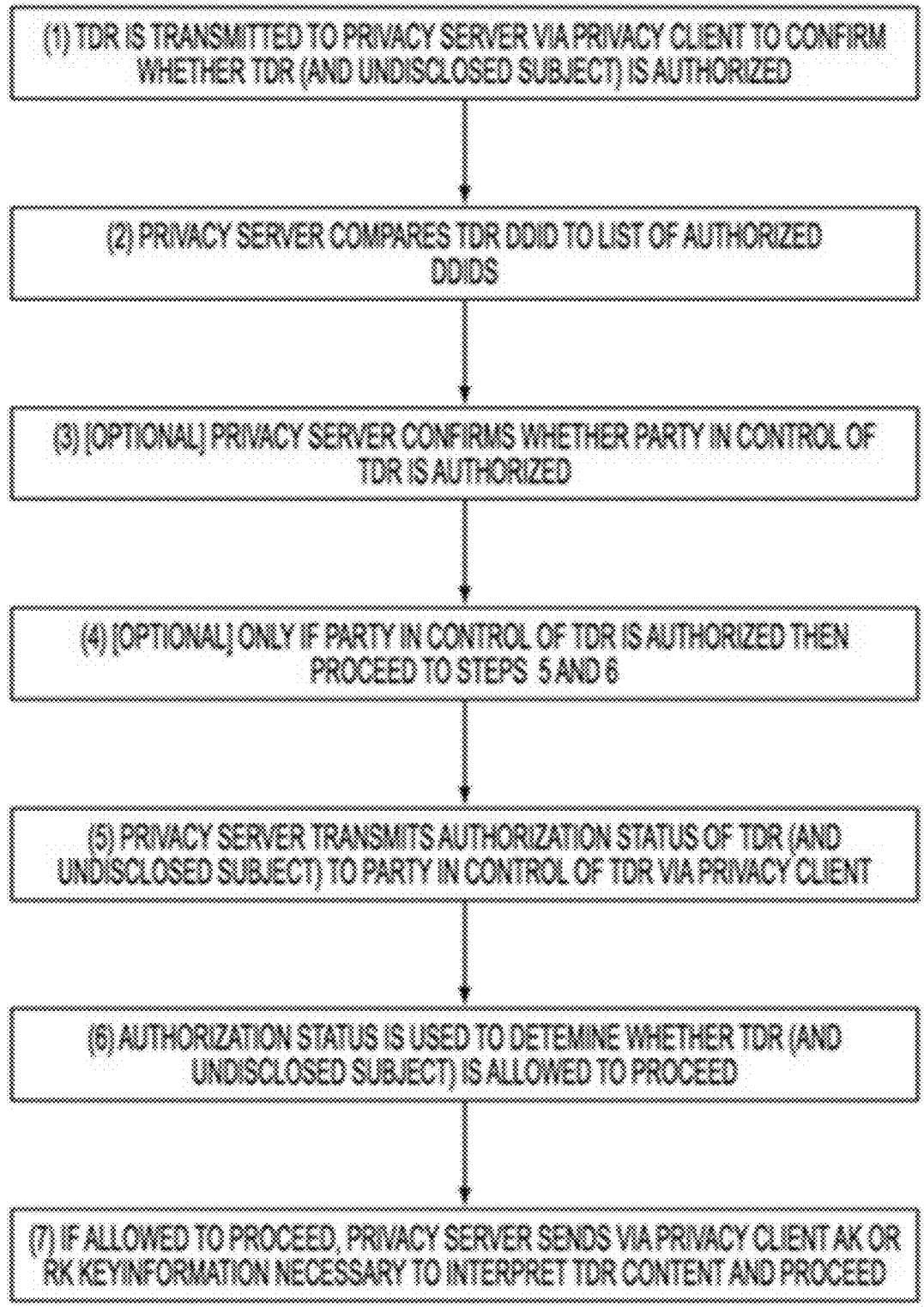
FIG. 8 illustrates an example of a process for verifying authority, in accordance with one embodiment of the invention.

FIG. 8 illustrates an example of a process to verify authority to proceed with respect to an action, activity, process or trait at a particular time and/or place, in accordance with one embodiment of the present invention.

At step 1, in one example a recipient entity transmits a request to the privacy server via a privacy client that may be residing on a Data Subject device, on a service provider device, accessible via and residing in a cloud network, or residing on the same computing device as the privacy server requesting the privacy server to confirm whether an undisclosed Data Subject or related party associated with a TDR is authorized to participate with respect to an action, activity, process or trait at a particular time and/or place. For instance, when after looking through the recommended kayaks and paddles on the e-commerce site, the related party is ready to make a purchase, the e-commerce site may query the authentication module of the privacy server to determine whether the related party is authorized to consummate the requested transaction.

At step 2, in one example the authentication module of the privacy server compares the DDID included in the TDR to a list of authorized DDIDs contained in a database to determine authorization of the Data Subject or related party to participate with respect to a desired action, activity, process or trait at the specified time and/or place. In terms of the kayak example, the authentication module of the privacy server may ensure that the DDIDs being used are still active and authorized, thereby indicating that the Data Subject or related party is authorized to consummate the desired transaction.

Optionally, at step 3, in one example the privacy server may request the party in control of a privacy client that may reside on a Data Subject device, on a service provider device, accessible via and reside in a cloud network, or reside on the same computing device as the privacy server, in this case the e-commerce site, to confirm they are authorized to participate in the desired transaction.

If optional step 3 is invoked, in one example step 4 checks to determine if the party in control of the privacy client is verified as being authorized. For example, in order to avoid deceptive attempts to acquire information such as usernames, passwords, or credit card details by masquerading as a trustworthy entity (also known as "phishing"), step 4 may require verification by the e-commerce site that it is an authorized reseller of the kayak equipment by means of known confirmation techniques.

At step 5, in one example, if verification is obtained, the authentication module of the privacy server transmits the authorization status information to the party in control of the privacy client.

At step 6, in one example the authorization status information is used to allow or deny proceeding with respect to a desired action, activity, process or trait.

At step 7, once the authentication function has been carried out and the optional additional verification steps are completed, the privacy server sends via a privacy client the AK and/or RK information necessary to interpret TDR content so that the related party may purchase the desired products and the transaction may be processed by the receiving entity, which in above example may be the ecommerce site.

In a second example of FIG. 8, a physician may send a TDR to the privacy server via a privacy client to verify whether a Data Subject that is a patient is authorized to participate in an explorative study. This would cause the authentication module of the privacy server, as part of step 2, to compare the Data Subject's DDID in the TDR to a list of authorized DDIDs contained in a database to determine if the Data Subject is authorized to participate in the study. Optionally, at step 3 the authentication module of the privacy server may request the physician submitting the request to confirm they are authorized to request that the Data Subject be a participant in the explorative study. If optional step 3 is invoked, step 4 checks to determine if the physician is authorized by means of known confirmation techniques such as password confirmation or multi-factor authentication. In step 5, if verification is obtained, the authentication module of the privacy server may transmit the authorization status information via the privacy client and in step 6 the authorization status may be used to allow or deny the request for the Data Subject to participate in the explorative study and step 7 would provide access to AK and/or RK key information necessary to interpret TDR content and proceed.

Figure 9:
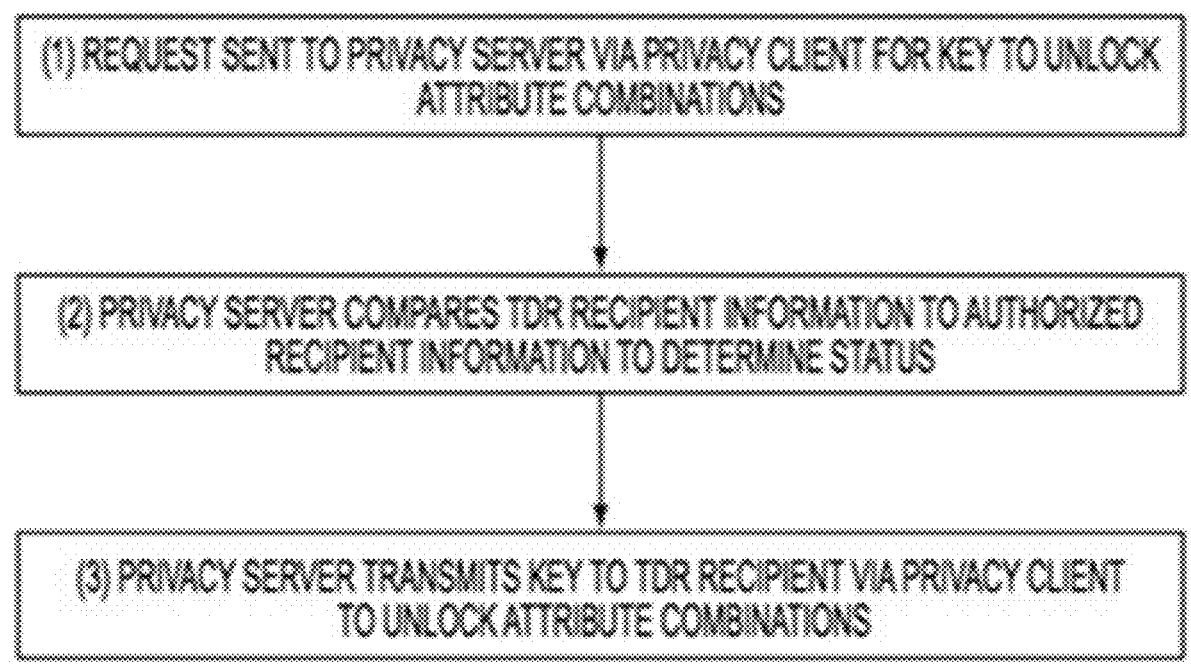
FIG. 9 illustrates an example of a process for withholding key protection information unless verified, in accordance with one embodiment of the invention.

FIG. 9 illustrates an example of a process of withholding replacement key (RK) or association key (AK) information or other protective information unless verified, in accordance with one embodiment of the present invention. As shown at step 1, in one example the party in control of a privacy client including a TDR transmits to the authentication module of the privacy server via a privacy client that may be residing on a Data Subject device, on a service provider device, accessible via and residing in a cloud network, or residing on the same computing device as the privacy server a request for AKs and/or RKs, and/or keys necessary to unlock TDR data attributes protected using other techniques such as encrypting, tokenizing, pseudonymizing or eliding.

In the kayak example, data may be sent using various additional steps to protect it in transit, however, the receiving entity e-commerce site may need the key(s) to unlock and/or associate the three pieces of information regarding height, weight and budget initially sent to it by the privacy client. At step 2, in one example, the authentication module of the privacy server compares TDR recipient attribute combinations to authorized recipient attribute combinations to determine whether the TDR recipient is an authorized recipient. If the authentication module of the privacy server verifies that TDR recipient attribute combinations matches authorized recipient attribute combinations, then the authentication module of the privacy server transmits to the TDR recipient as part of step 3, via a privacy client, in one example, the keys necessary to unlock the TDR.

In a second example of FIG. 8, in step 1 a physician receiving an encrypted, tokenized or elided TDR containing requested blood pressure information may be required to send a TDR to the authentication module of the privacy server via a privacy client to verify that the physician is authorized to view the requested information. At step 2 the authentication module of the privacy server may compare the physician's TDR information to authorized recipient attribute combinations to determine whether the physician is an authorized recipient. If the authentication module of the privacy server verifies that the physician's TDR information matches authorized recipient attribute combinations, then the authentication module of the privacy server may transmit to the physician via a privacy client the keys necessary to unlock applicable protection techniques for the encrypted, tokenized or elided TDR containing requested blood pressure information.

Figure 10:
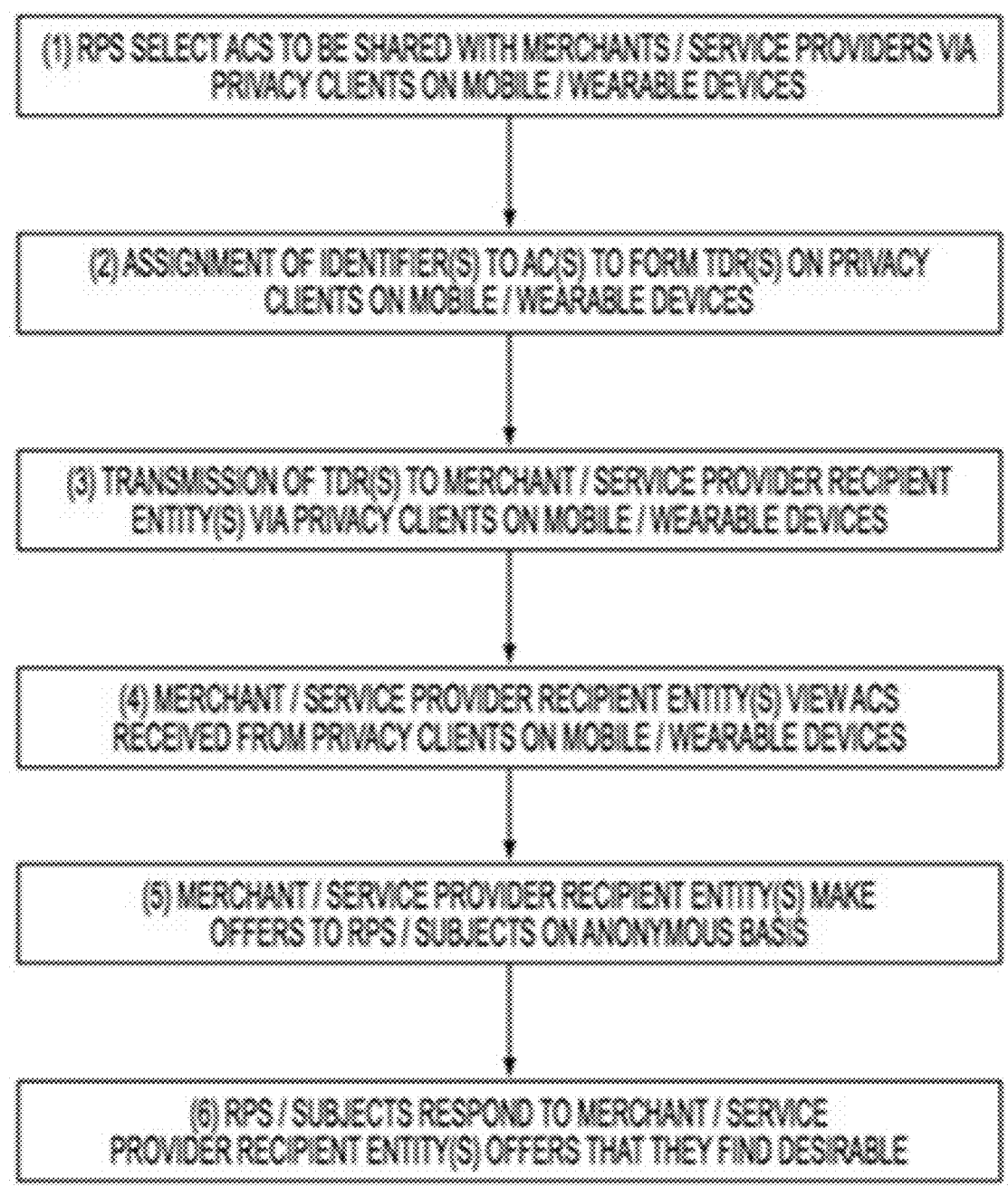
FIG. 10 illustrates an example of a process for analyzing interests of related parties in an anonymous fashion, in accordance with one embodiment of the invention.

FIG. 10 illustrates an example of analyzing interests of related parties in an anonymous fashion in accordance with one embodiment of the present invention. At step 1, in one example, related parties (RPs) select attribute combinations (ACs) to be shared with merchants/service providers via privacy clients on mobile and/or wearable devices. For example, rather than utilizing an ecommerce site, a related party may go to a physical location of an outdoor sporting store and share the same information about height, weight and budget via a mobile or wearable device.

At step 2, in one example, the privacy server may assign DDID(s) to the attribute combinations to form TDR(s) on privacy clients resident on mobile/wearable/portable devices.

At step 3, in one example, the TDR(s) are transmitted to the merchant/service provider recipient entity(s) via privacy clients resident on mobile/wearable/portable devices. As an example, with the kayaks, the store may receive the three separate TDR enabled data attributes via in-store devices, beacons or the like from a mobile/wearable/portable device of a Data Subject.

At step 4, in one example merchant/service provider recipient entity(s) may view attribute combinations authorized by related parties and transmitted to the merchant/service provider recipient entity(s) by privacy clients resident on mobile/wearable/portable devices. For instance, the store may view the height, weight and budget of the related party.

At step 5, in one example, the merchant/service provider recipient entity(s) may make offers to Data Subjects and/or related parties on an anonymous basis without yet knowing the identity of the Data Subjects and/or related parties.

At step 6, in one example, Data Subjects and/or related parties may elect to respond to merchant/service provider recipient entity(s) offers that they find desirable and consummate transactions.

The system and methods described herein may provide related parties with a way to achieve greater anonymity and increased privacy/anonymity and security of data while utilizing one or more communication networks. Without these systems and methods, third parties may be able to obtain the true identity of Data Subjects or related parties based on their activity on the communication networks via network services and/or technology providers that have associated identifying information with the activity of the Data Subjects or related parties on and/or between the networks.

Disclosed herein are other various methods for providing data security and data privacy/anonymity. In one example, a method may include the steps or operations of receiving, at a computing device, an electronic data element; identifying one or more data attributes with the electronic data element; selecting, through the computing device, a DDID; associating the selected DDID with one or more of the data attributes; and creating a TDR from at least the selected unique DDID and the one or more data attributes.

In one example, the step of selecting a data element includes generating the unique DDID or in another example accepting or modifying a temporally unique, dynamically changing value to serve as the DDID. In one example, the method may also include causing the association between the selected DDID and the one or more data attributes to expire. In another example, the method may include storing, in a database accessible to the computing device, information regarding the time periods during which the selected unique DDID was associated with different data attributes or combinations of attributes. In another embodiment, the method may also include re-associating the selected unique DDID with the one or more data attributes following expiration of the association between the DDID and the one or more data attributes. In one example, the expiration of the DDID occurs at a predetermined time, or the expiration may occur following completion of a predetermined event or activity. In another example, the TDR may be authorized for use only during a given time period or at a predetermined location. In another example, the method may include changing the unique DDID assigned to the one or more data attributes, wherein the changing of the unique DDID may occur on a random or a scheduled basis, or may occur following the completion of a predetermined activity or event.

Another method is disclosed herein for facilitating transactions over a network. In one example, the method may include operations of receiving a request, at a privacy server, from a client device to conduct activity over a network; determining which of a plurality of data attributes in a database are necessary to complete the requested activity; creating a DDID; associating the DDID with the determined data attributes to create a combined TDR; making the combined TDR accessible to at least one network device for conducting or initiating the requesting activity; receiving a modified TDR that includes additional information related to the activity performed; and storing the modified TDR in the memory database. In another method implementation, disclosed herein is a method of providing controlled distribution of electronic information. In one example, the method may include receiving a request at a privacy control module to conduct an activity over a network; selecting attributes of Data Subjects located in a database accessible to the privacy control module determined to be necessary to fulfill the request, wherein other attributes of the Data Subject which are not determined to be necessary are not selected; assigning a DDID to the selected attributes and the Data Subject or Data Subjects to which they apply with an abstraction module of the privacy control module, wherein the DDID does not reveal the unselected attributes; recording the time at which the unique DDID is assigned; receiving an indication that the requested activity is complete; receiving the unique DDID and the determined attributes and the Data Subject or Data Subjects to which they apply at the privacy control module, wherein the attributes are modified to include information regarding the conducted activity; and recording the time at which the conducted activity is complete and the unique DDID and the determined attributes and the Data Subject or Data Subjects to which they apply are received at the privacy control module.

In one example, the method may also include assigning an additional DDID to one or more of the selected attributes or Data Subjects. In another example, the method may include re-associating, using the recorded times, the unique DDID and data attributes with the true identity of the Data Subjects. The method may also include reassigning the unique DDID to other data attributes, and recording the time at which the unique DDID is reassigned.

Another method is disclosed herein for improving data security. In one example, the method may include associating the Data Subject with at least one attribute; and associating a DDID with the at least one attribute to create a TDR; wherein the TDR limits access to attributes of the Data Subject to only those necessary to perform a given action. In one example, the method may include assigning an association key (AK) and/or replacement key (RK) to the TDR, wherein access to the AK and/or RK is required for authorized access to TDR. In another example, the method may also include causing the association between the DDID and the at least one attribute to expire, wherein the expiration occurs at a predetermined time and/or the expiration may occur following completion of a predetermined event or activity. In another embodiment, the method may include re-associating the DDID with the at least one different attribute following an expiration of the association between the DDID and the at least one attribute. The method may also include storing, in a database, information regarding one or more time periods during which the DDID was associated with different data attributes or combinations of attributes.

Various approaches may be used to associate DDIDs with different attribute combinations to form TDRs. The DDIDs may have a certain or variable length, and may be made up of various code composition elements such as numbers, characters, cases, and/or special characters. In addition, the DDIDs may be generated in random or consistent intervals. In one example, only authorized parties with access to association keys (AKs) and/or replacement keys (RKs) maintained by the maintenance module necessary to re-aggregate the otherwise disaggregated attribute combinations will have the capability to determine which attribute combinations are properly associated with other attribute combinations, Data Subjects, related parties, or aggregated data profiles. However, sites may still track and utilize the attribute combinations contained within TDRs in real time, with the understanding that they have a temporally limited existence and that associated DDIDs may be reused later for different actions, activities, processes, traits, attribute combinations, Data Subjects and/or related parties.

The attribute combinations transmitted may include single or various combinations of explicit data, personally identifying information (PII), behavioral data, derived data, rich data or other data.

Example A

In a first example, a system may be configured so that a related party is the controlling entity authorized to designate to which other parties attribute combinations will be released. Example A illustrates how the system processes information generated by a related party (related party X or "RP X") that engages in four different online sessions with two different service providers ("SP"s) from various industries over three different Communication Networks ("CN"s). FIGS. 11-20 illustrate this example, and show how information may be managed at various stages and under various circumstances, in one example of an embodiment of the invention. It is understood that FIGS. 11-20 are provided by way of example only, and that embodiments of the present invention may be implemented in ways different than shown in the examples of FIGS. 11-20.

Figure 11:
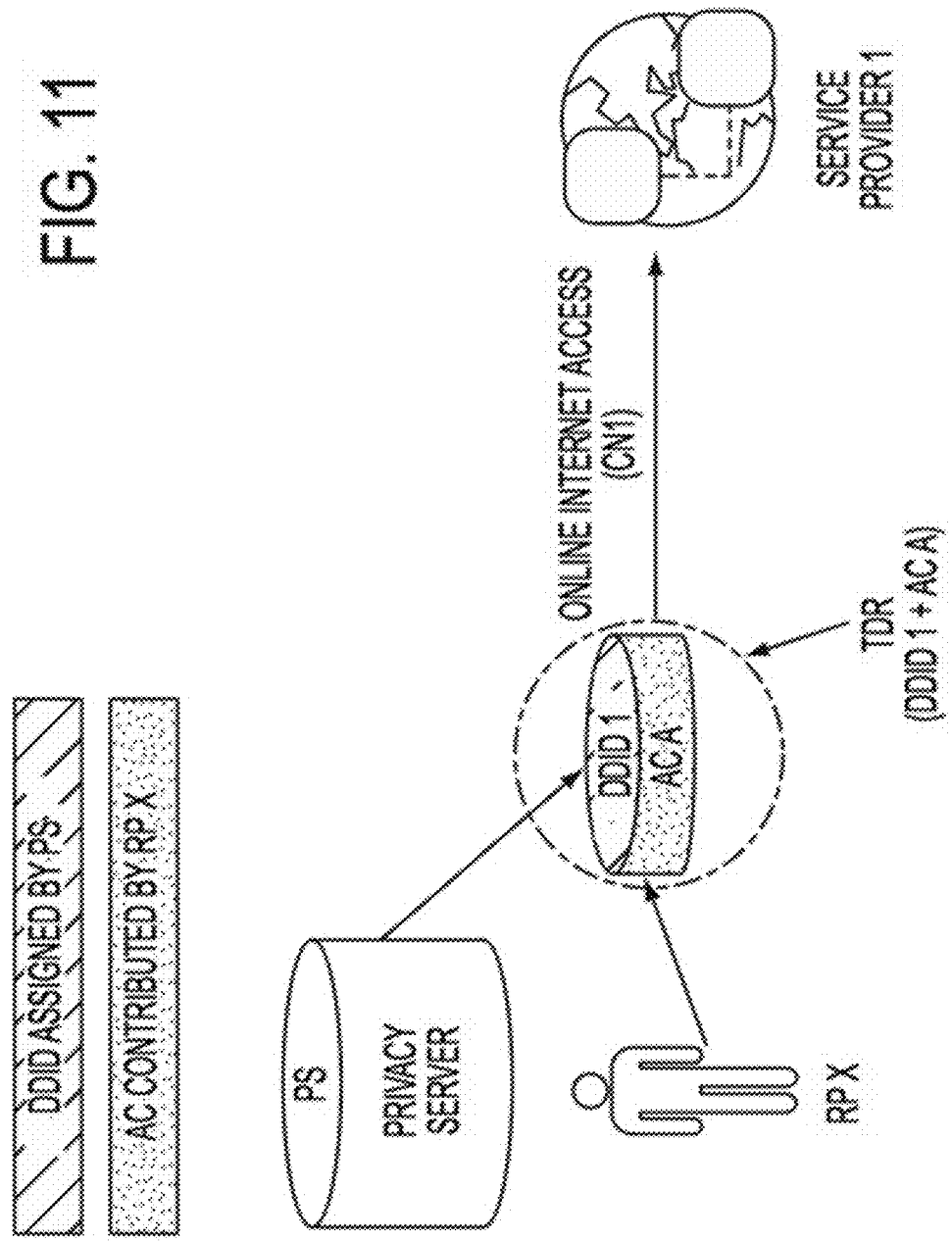
FIGS. 11-18 illustrate various examples of the interactions between a related party, service provider, and privacy server, including DDIDs and attribute combinations generated, sent, and tracked, in accordance with one embodiment of the invention.

FIG. 11 shows an example wherein related party X transmits attribute combination A (Explicit Data) to a website Service Provider such as Pandora Radio ("SP1") via online internet access ("Communication Network 1" or "CN1"). Attribute combination A is assigned an identifier code of DDID 1 (for a limited temporal period) by the abstraction module of the privacy server ("PS"). The identifier code together with attribute combination A is communicated to SP1 via CN1 via a security client. In FIG. 11, the combination of DDID 1 and attribute combination A represent a TDR for related party X for the limited temporal period.

Figure 12:
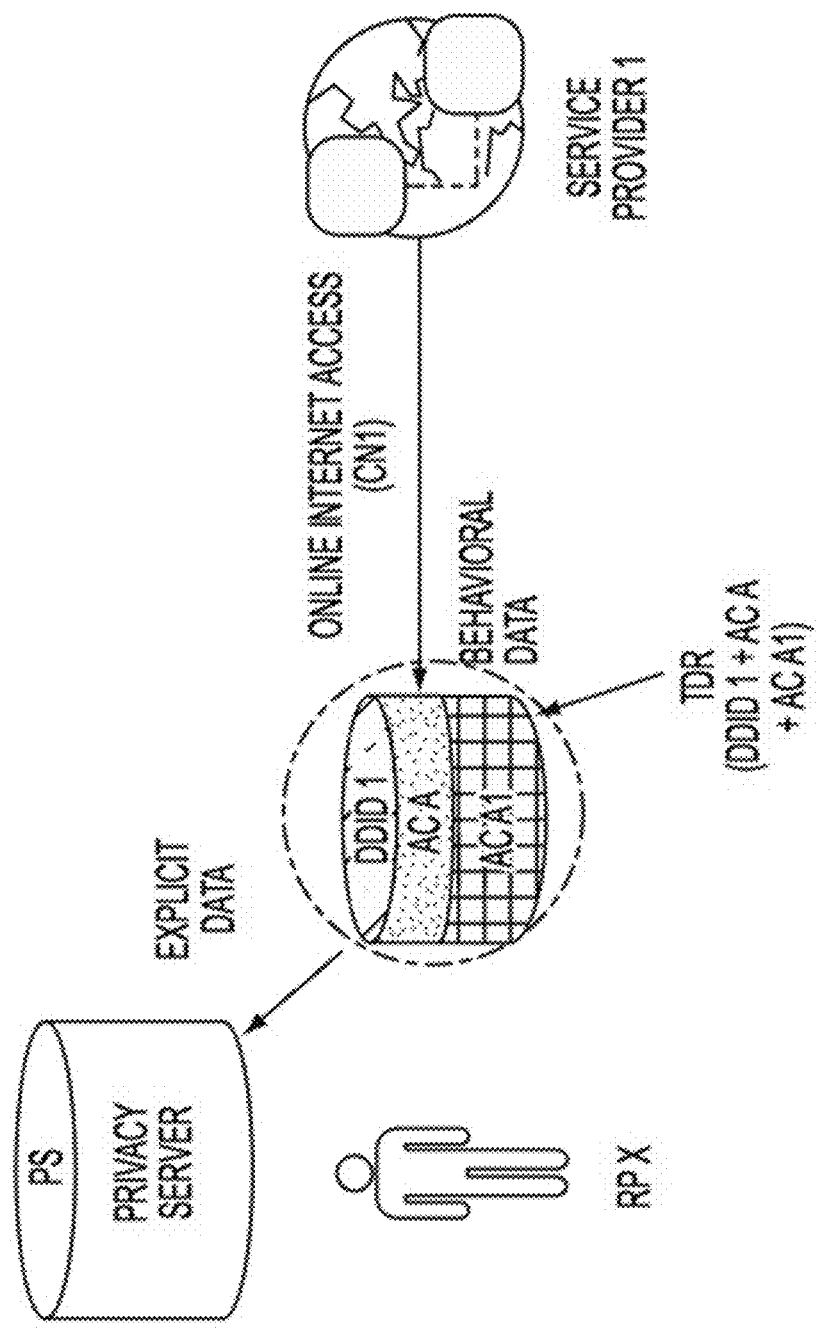

FIG. 12 shows an example wherein when interacting with SP1, related party X generated activity information (Behavioral Data) tracked by SP1 that was transmitted as attribute combination A1 by a privacy client that may reside on a Data Subject device, on a service provider device, accessible via and reside in a cloud network, or reside on the same computing device as the privacy server back to the privacy server. The maintenance module of the privacy server may maintain information regarding attribute combinations and various DDID codes assigned to each attribute combination over time and at different points in time, as well as the CN and SP associated with each attribute combination. In FIG. 12, the combination of DDID 1, attribute combination A, and attribute combination A1 represent a TDR for related party X for the limited temporal period of the association between DDID 1, attribute combination A, and attribute combination A1. Upon completion of the association of the new data regarding the desired action, activity, or process from the attribution combinations, DDID 1 may be reassigned for use in a new TDR. The combination of DDIDs and attribute combinations shown in FIGS. 13 through 20 also represents TDRs for the temporal period of the association between the DDIDs and attribute combinations.

Figure 13:
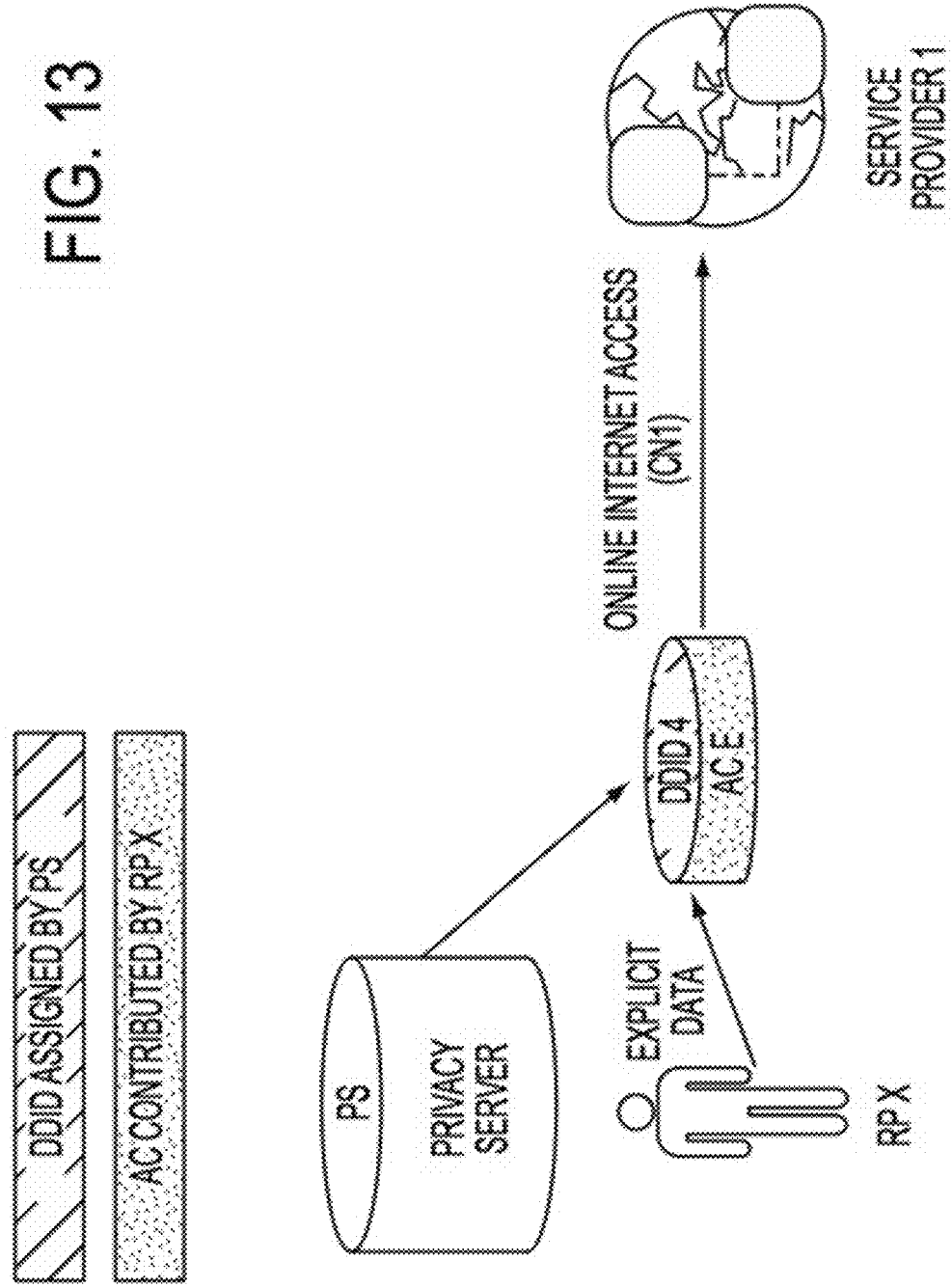

FIG. 13 shows an example where related party X transmits another attribute combination E (Explicit Data) to Pandora Radio ("SP1") via Online Internet Access ("CN1"). Attribute combination E is assigned an identifier code of DDID 4, for a limited temporal period, by the privacy server ("PS") and the identifier code together with attribute combination E is communicated to SP1 via CN1 via a security client.

Figure 14:
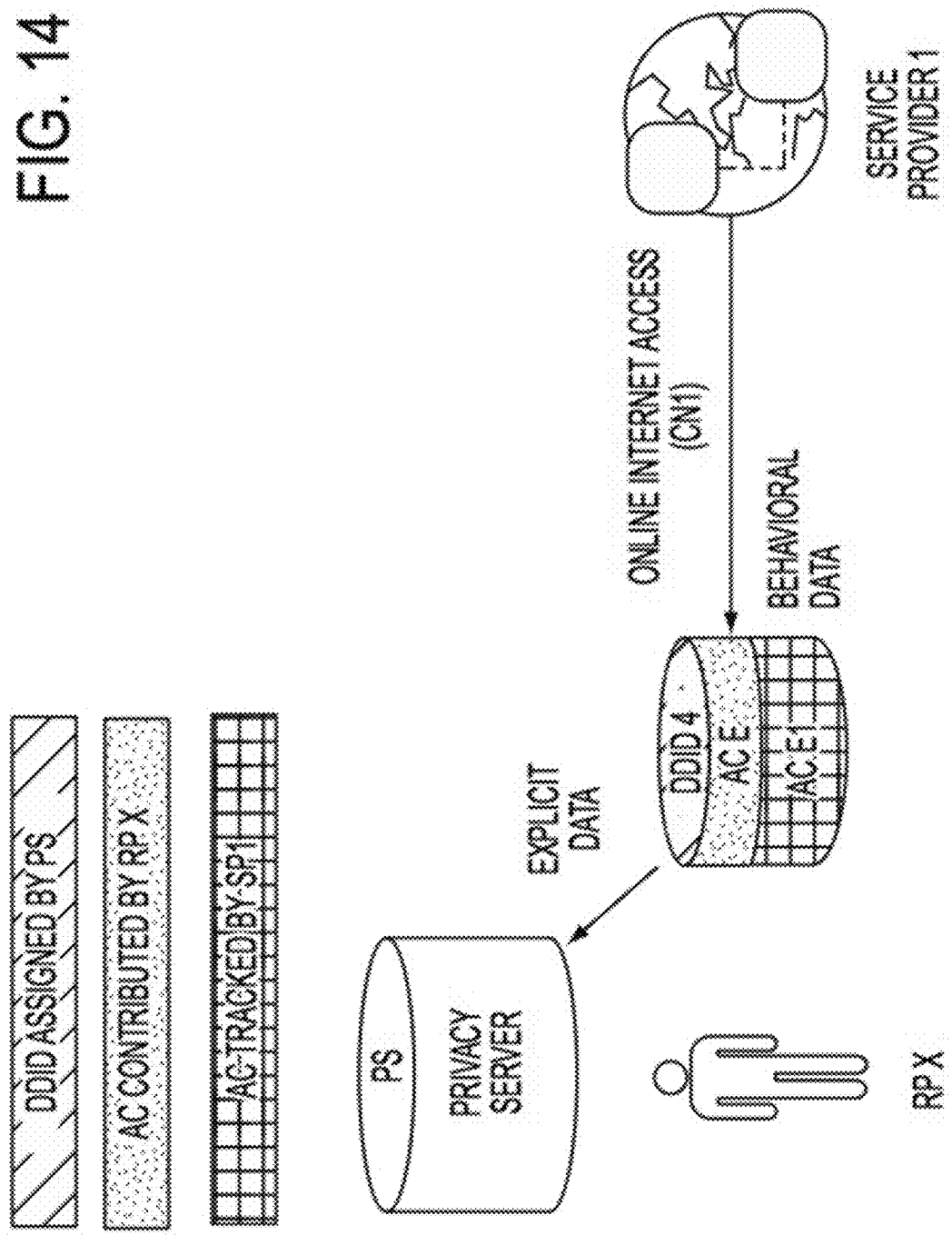

FIG. 14 shows an example wherein when interacting with SP1 in this example, related party X generated activity information (Behavioral Data) tracked by SP1 that was transmitted as attribute combination E1 back to the abstraction module of the privacy server via a privacy client that may reside on a Data Subject device, on a service provider device, accessible via and reside in a cloud network, or reside on the same computing device as the privacy server.

Figure 15:
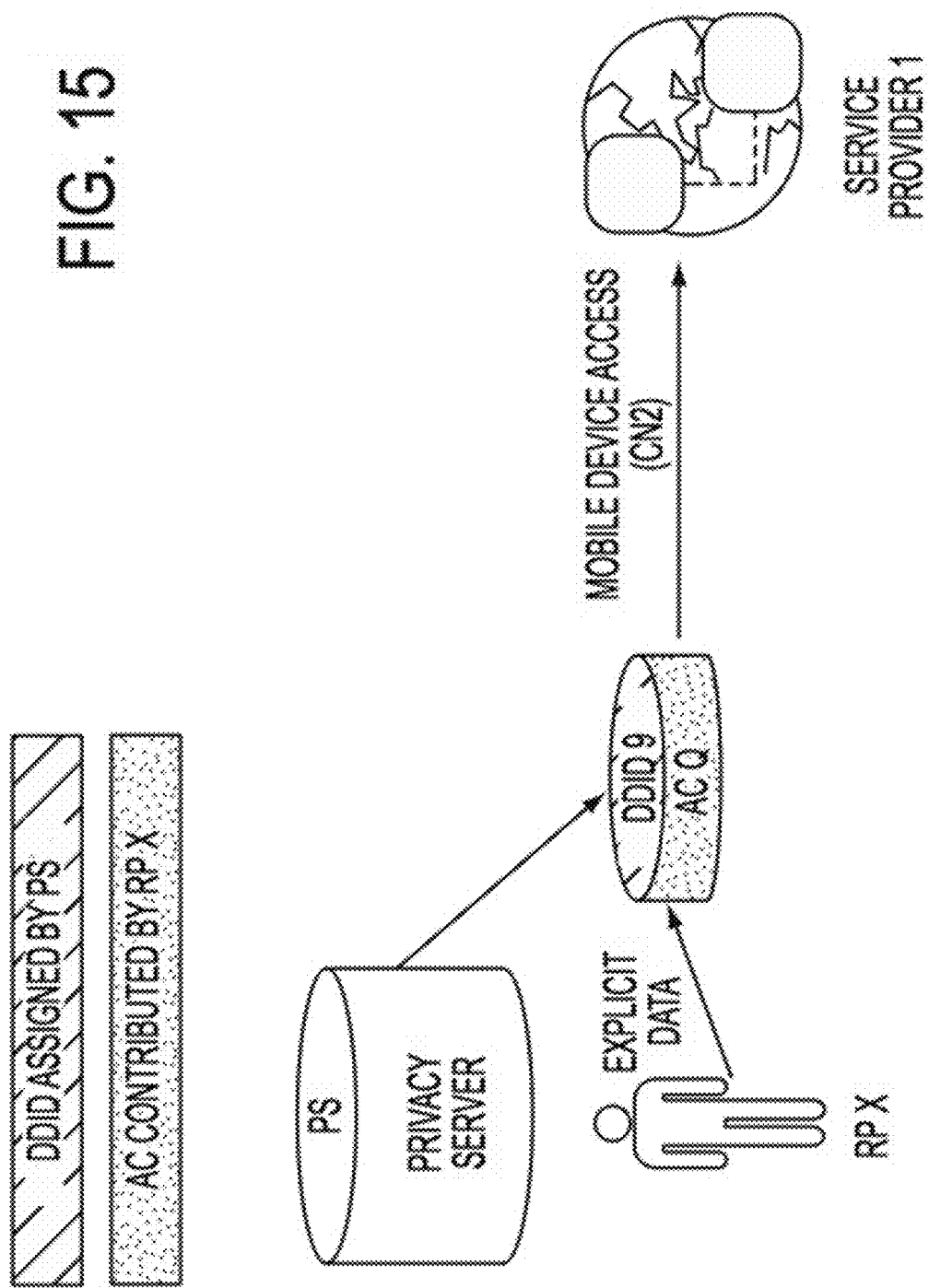

FIG. 15 shows an example wherein related party X transmitted attribute combination Q (Explicit Data) to another version of the SP1 Pandora Radio in mobile application form, accessible via mobile device access communications ("Communication Network 2" or "CN2"). Attribute combination Q is assigned an identifier code of DDID 9, for a limited temporal period, by the privacy server and the identifier code together with attribute combination Q is communicated as a TDR to SP1 via CN2 via a security client.

Figure 16:
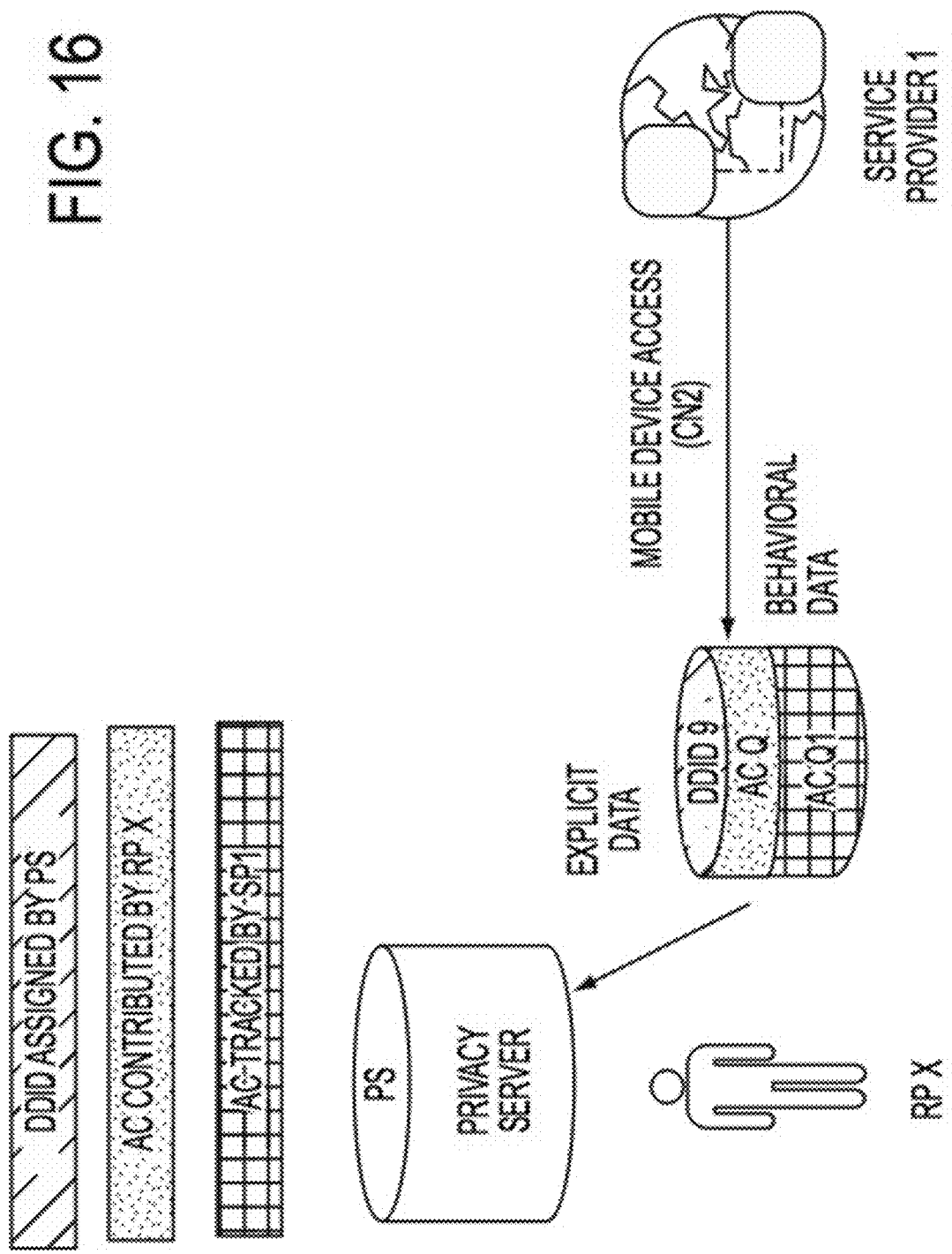

FIG. 16 shows an example wherein when interacting with SP1, related party X generated activity information (Behavior Data) tracked by SP1 that was transmitted as attribute combination Q1 back to the abstraction module of the privacy server via a privacy client that may reside on a Data Subject device, on a service provider device, accessible via and reside in a cloud network, or reside on the same computing device as the privacy server.

Figure 17:
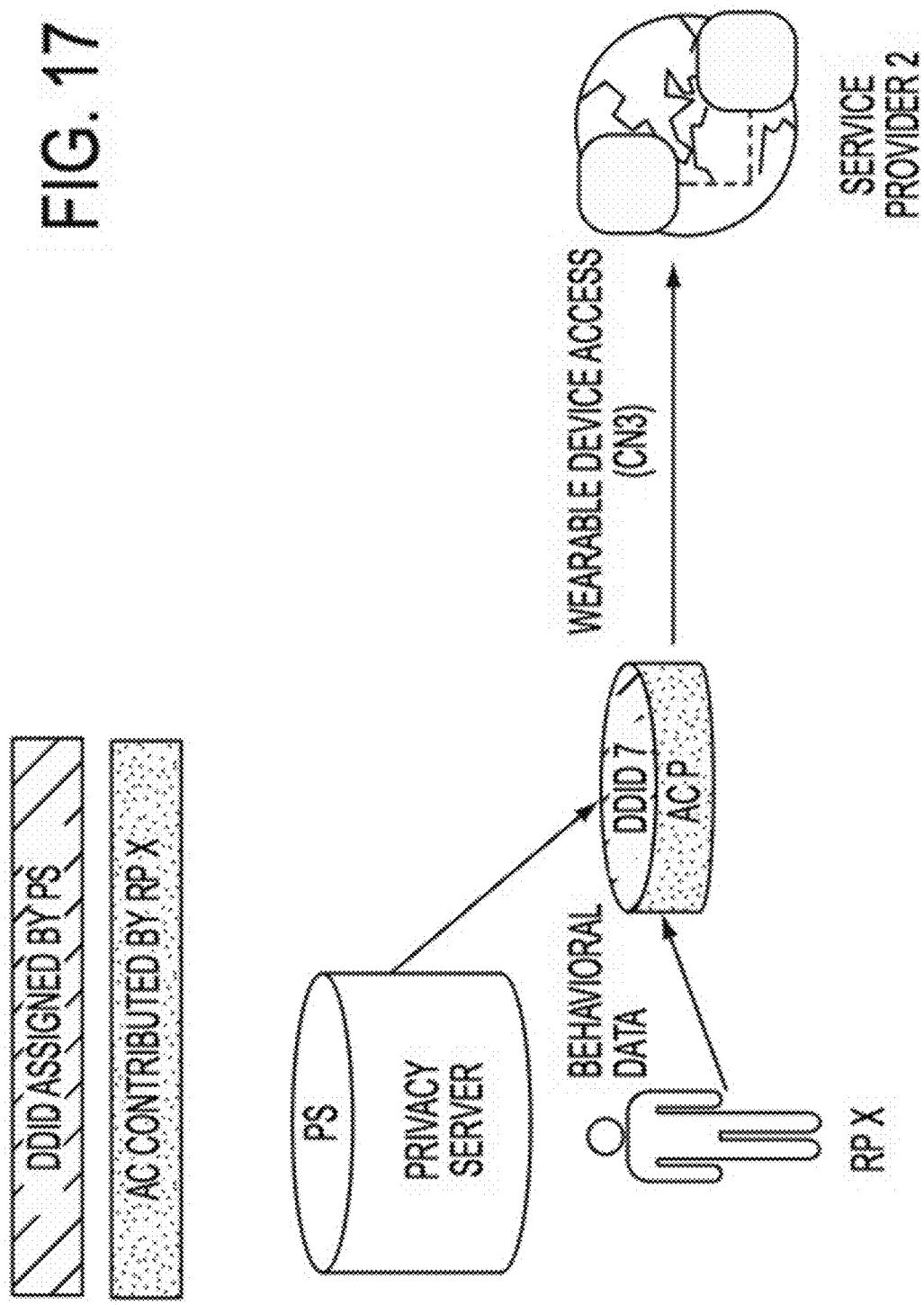

FIG. 17 shows an example wherein party X transmits attribute combination P (Behavioral Data) via a privacy client that may reside on a Data Subject device, on a service provider device, accessible via and reside in a cloud network, or reside on the same computing device as the privacy server to a Service Provider ("SP2") that provides monitoring services related to exercise activity such as FitBit via wearable device access communications ("Communication Network 3" or "CN3"). Attribute combination P is assigned an identifier code of DDID 7, for a limited temporal period, by the PS and the identifier code together with attribute combination P is communicated as a TDR to SP2 via CN3 via a security client.

Figure 18:
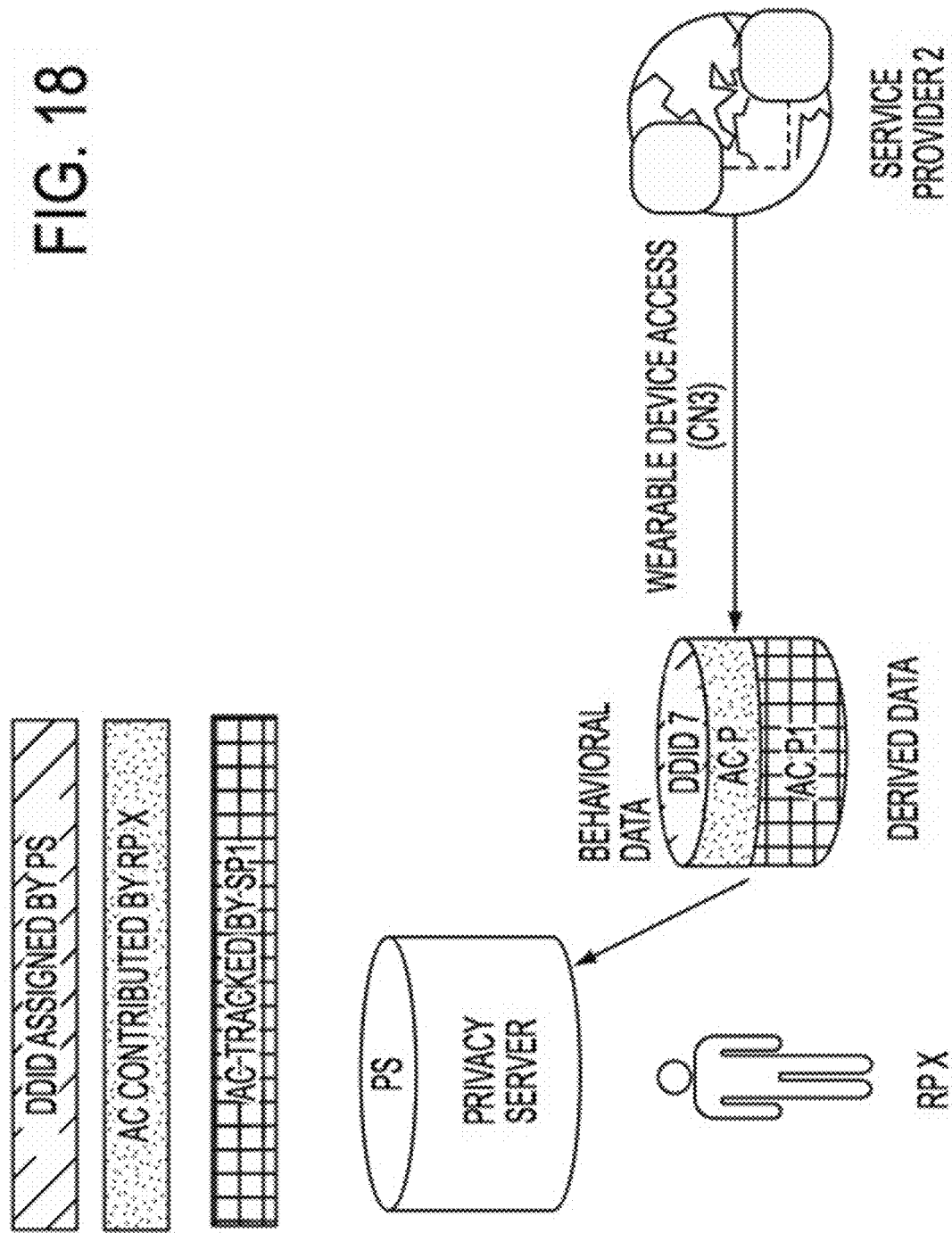

FIG. 18 shows an example wherein when interacting with SP2 in this situation, SP2 calculated the percentage of desired daily calorie burn (Derived Data) accomplished by related party X, and that this information was transmitted via a privacy client that may reside on a Data Subject device, on a service provider device, accessible via and reside in a cloud network, or reside on the same computing device as the privacy server as attribute combination P1 back to the privacy server.

Figure 19:
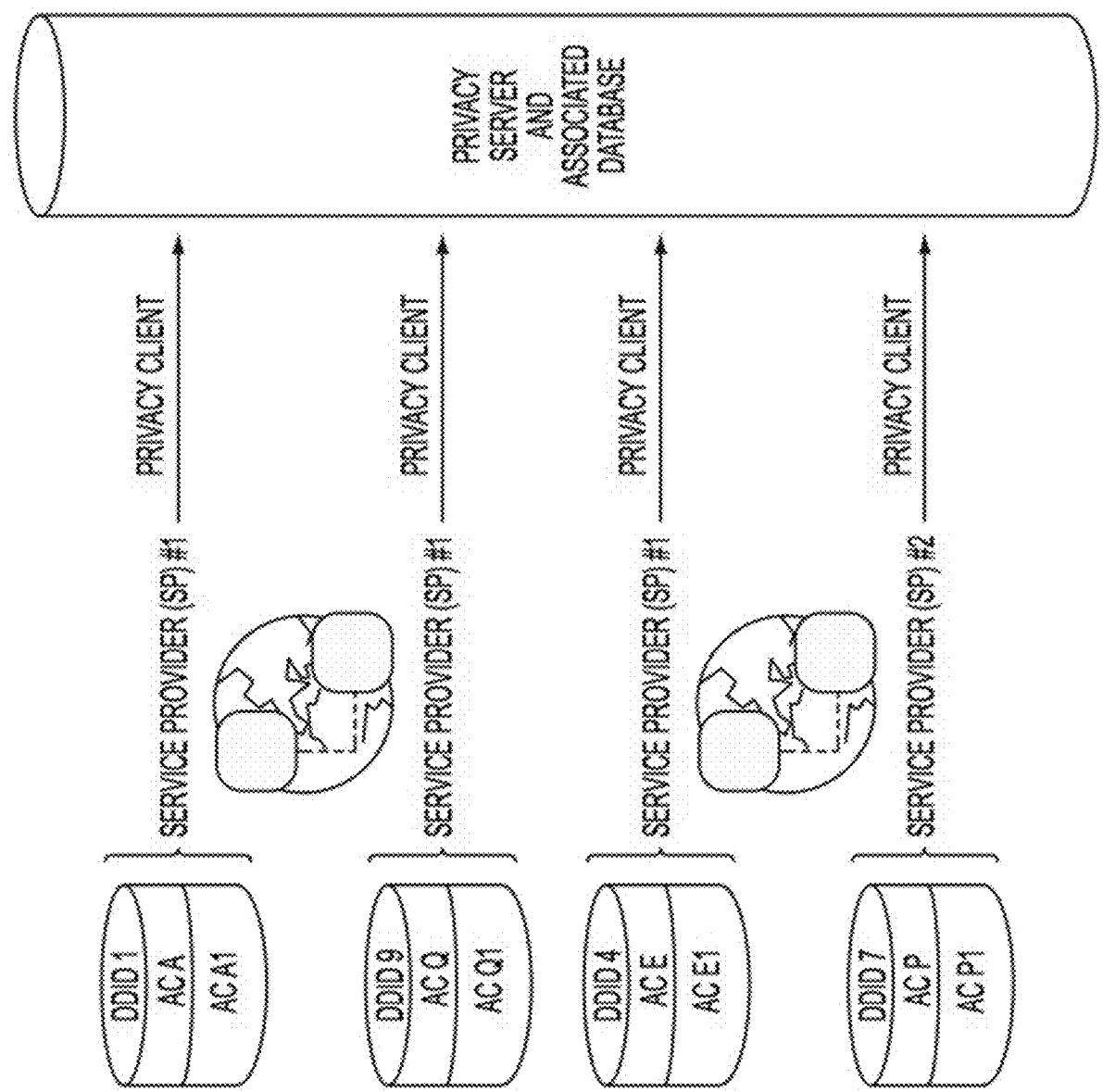
FIG. 19 shows examples of attribute combinations accessible to multiple service providers as well as the attribute combinations re-transmitted by each service provider back to a privacy server, in accordance with one embodiment of the invention.

FIG. 19 shows an example wherein the attribute combinations accessible to each SP as well as the attribute combinations accessible are re-transmitted by privacy clients that may reside on a Data Subject device, on a service provider device, accessible via and reside in a cloud network, or reside on the same computing device as the privacy server back to the privacy server. FIG. 19 highlights that sessions of use within or between SPs may be subset between or within sessions so that without access to the security association keys that may be maintained by the maintenance module, SPs do not have in one example the information necessary to determine associations between the attribute combinations. However, they do have access to the attribute combinations created during each limited temporal period as determined by changing DDIDs, in one example. For example, SP1 does not know that DDID 1 and DDID 9 both pertain to related party X who accessed the two different versions of the website maintained by SP1—one accessed via online internet access and the other accessed via mobile device access.

Figure 20:
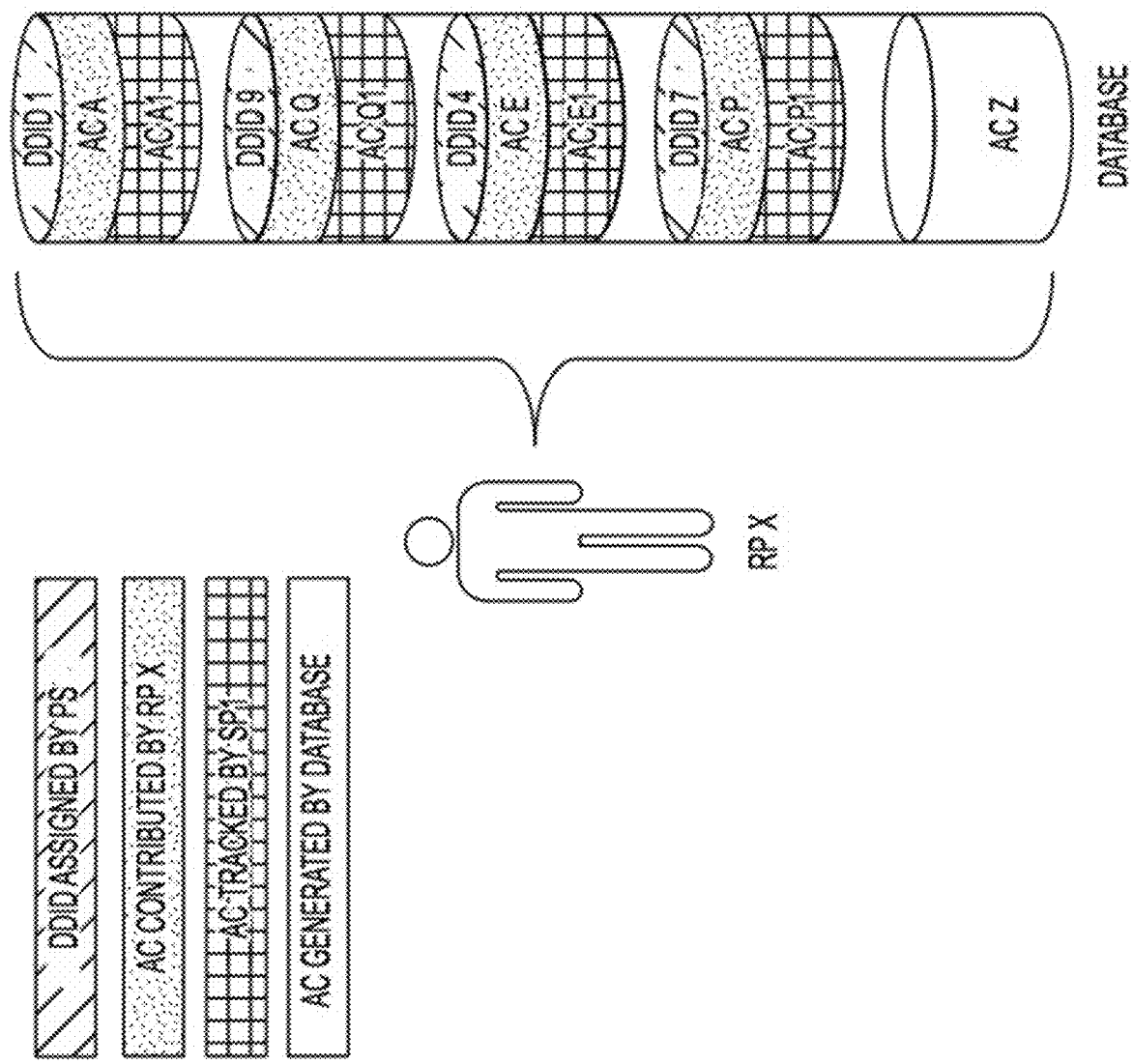
FIG. 20 shows the data accessible to a related party that includes all attribute combinations sent to and retransmitted from service providers, in accordance with one embodiment of the invention.

FIG. 20 shows an example wherein the data accessible to related party X that includes all information sent to and retransmitted from the SPs. FIG. 19 highlights that with access to the security association keys that may be maintained by the maintenance module, related party X, as the controlling entity, may have in one example the information necessary to determine associations between the attribute combinations for aggregation and normalization purposes. In addition, related party X may have the information to use, or have a data facilitator use, the maintenance module to perform further analysis and processing of the data in a secure environment. The new attribute combination Z represents new data ("Rich Data") that was produced by the maintenance module at the request of related party X by comparing all data associated with DDID 1, DDID 9, DDID 4 and DDID 7 to predict what other music choices related party X may enjoy that will assist in helping to attain the desired daily calorie burn. The attribute combination Z may include a list of the other music choices produced from this prediction, as well as data associated with the various other DDIDs. Attribute combination Z will not be communicated to any party (SP1, SP2 or otherwise) until desired by related party X, which is acting as the controlling entity. When related party X desires to share attribute combination Z, in one example it would be assigned a DDID code prior to transmission to the recipient parties designated by related party X. This new attribute combination will be more holistic and current when and if it is distributed to recipient entities as determined by the related party X.

Example B

Figure 21:
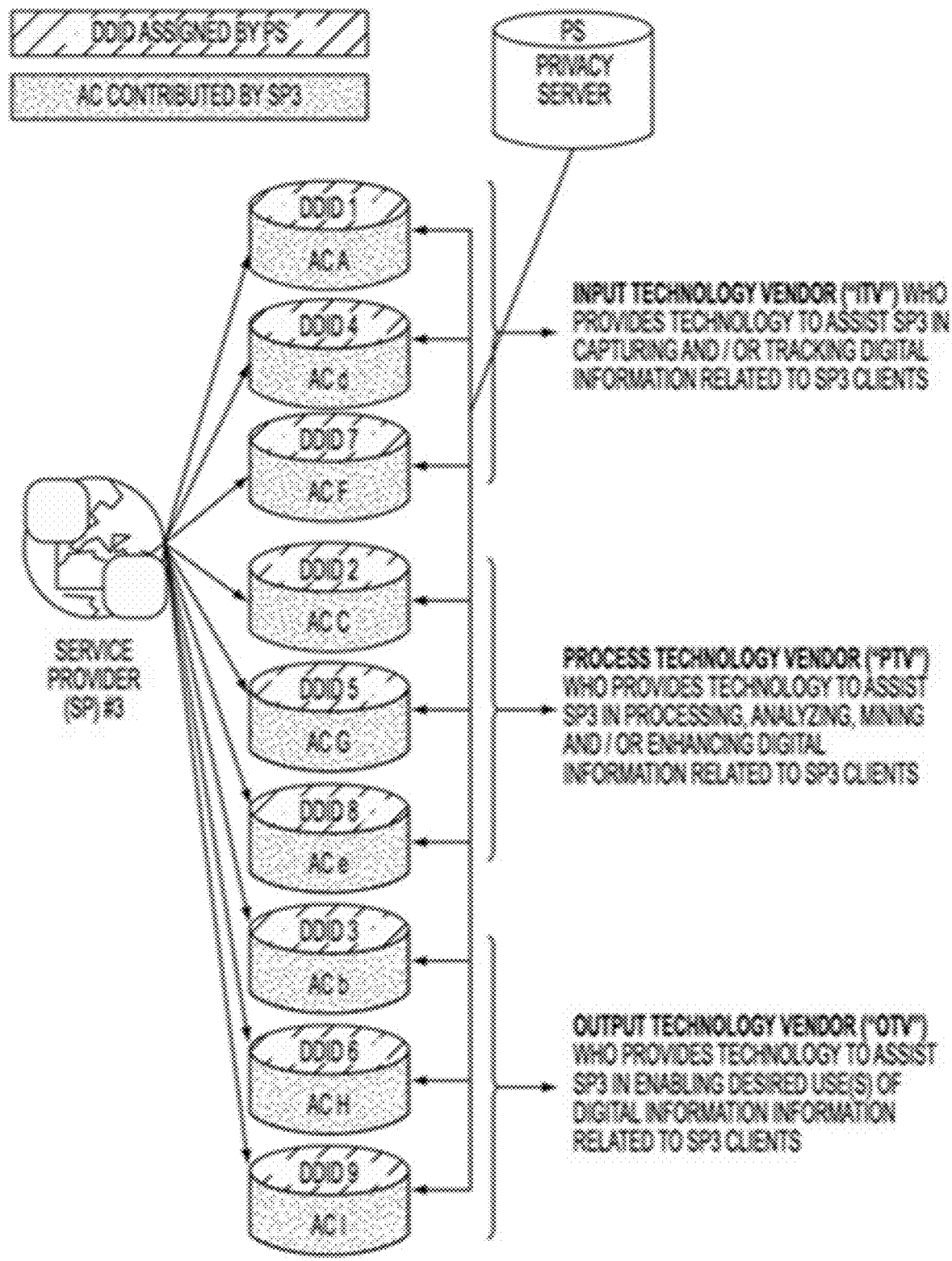

In a second example shown in FIGS. 21-22, a system is configured so that a service provider ("SP3") is the controlling entity authorized to designate parties to whom select attribute combinations related to SP3 clients are released. SP3 may use the system to provide improved protection for its client's identity and privacy/anonymity. This includes reducing the likelihood of consumer or government backlash as a result of potential loss of privacy or anonymity, as well as increasing market penetration, use and acceptance of SP3 offerings. It is understood that FIGS. 21-22 are provided by way of example only, and that embodiments of the present invention may be implemented in ways different than shown in the examples of FIGS. 21-22.

FIGS. 21 and 22 show an example wherein SP3 provides each of an input technology vendor such as a website company that helps to capture order information ("ITV"), a process technology vendor such an online electronic payment processor ("PTV") and an output technology vendor such as a party that delivers selected products electronically to customers ("OTV") with only those attribute combinations necessary to perform the services assigned to each vendor. None of the vendors have access to Personally Identifying Information ("PII") that would reveal the identity of SP3 clients.

Figure 23:
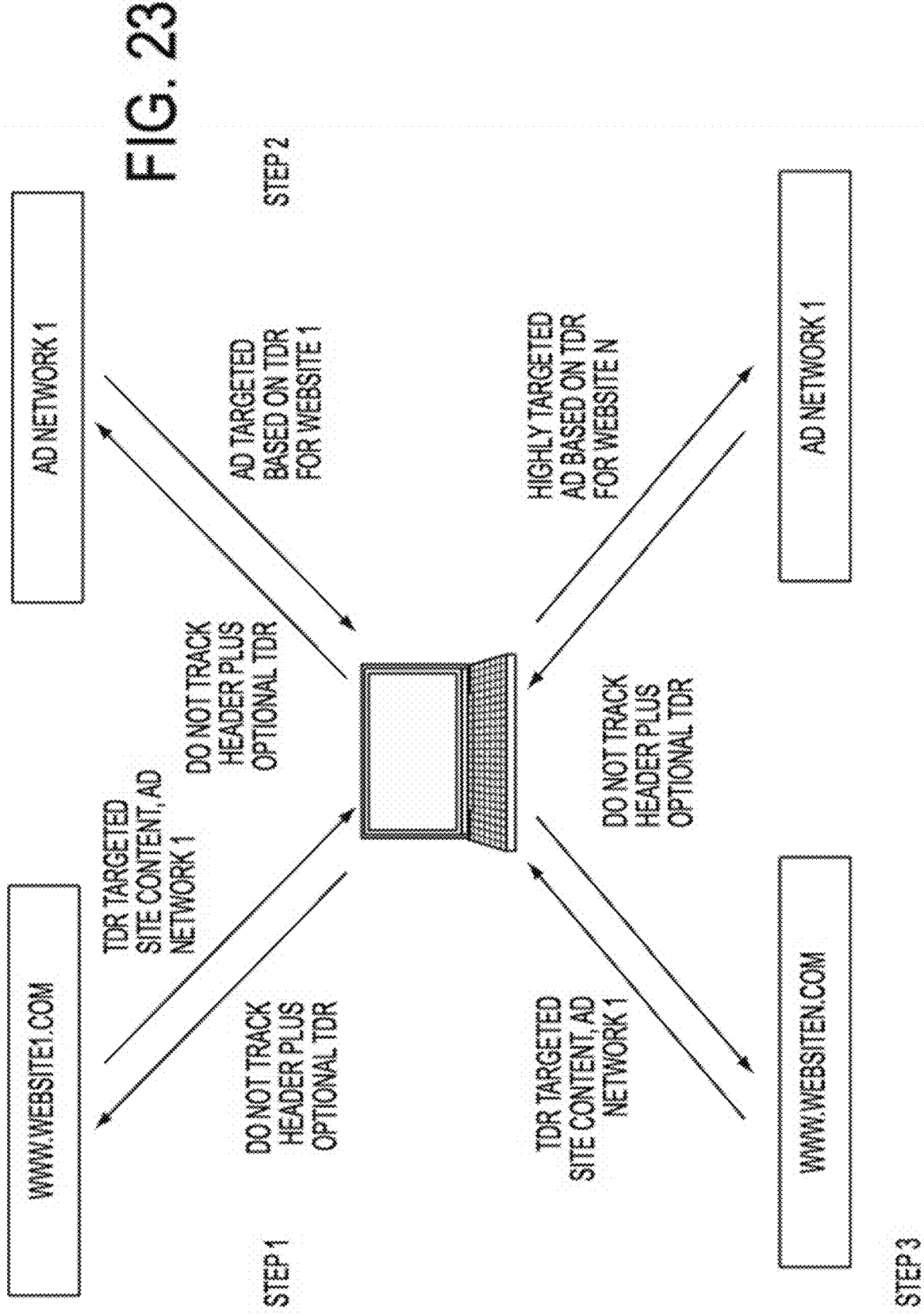
FIG. 23 illustrates an example of an implementation of DDIDs in the area of Internet advertising, in accordance with one embodiment of the invention.

FIG. 23 illustrates an example of implementation of dynamically created, changeable, and re-assignable DDIDs in the area of Internet behavioral ad serving. Without the benefit of some embodiments of the present invention, Internet behavioral ad serving is based primarily on ad networks placing cookies in a user's web browser and building a profile of said user by tracking user-visited websites that carry ads from the same ad network. In this manner, networks build a profile of user-visited websites augmentable with data from other sources, leading to detailed profiles of users for whom they have cookie information.

Typically, when a user visits a website ("Website1") in FIG. 23 for the first time, said website: (i) delivers content from the website to the user's browser; (ii) sends a cookie to the user's browser; and (iii) directs the user's browser to a web address to retrieve ad content to be served on the website from the ad network ("Ad Network 1"). The cookie delivered in (ii) above is referred to as a "First Party Cookie" since it relates to a website selected by the user. First Party Cookies can be beneficial to a user to help keep "state" information such as log-in progress, items in a shopping basket and other relevancies that improve the user's experience. When the user's browser requests ad information from Ad Network 1 as part of (iii) above, Ad Network 1 sends an ad to the user's browser that is displayed as part of Website 1. If this is the first time the user's browser requests ad content from Ad Network 1, Ad Network 1 will also send a cookie to the user's browser. This cookie is referred to as a Third Party Cookie because it is not from a web page intended to be visited by the user. If Ad Network 1 has not previously tracked the user, Ad Network 1 will serve an ad based on traditional ad delivery technology (e.g., the nature of content on Website1 might be delivered). As the user visits more and more websites with ads served by Ad Network 1, Ad Network 1 (via the Third Party Cookie sent by Ad Network 1 to the user's browser) builds a profile of the behavioral data on the user based on the pages visited, time spent on each page and other variables such as information from the user's social network, online or offline buying behavior, psychographics and demographics together with further user information collected either by Ad Network 1's actions or by integrating information available from third party data providers. Based on the profile of the user created and managed by Ad Network 1, Ad Network 1 is able to display an ad targeted to the user based on what Ad Network 1 determined was of highest interest to the user.

This conventional tracking of the user from site to site and page to page by third party Ad Networks has raised privacy/anonymity concerns. In response, the Do-Not-Track (DNT) effort was launched through the World Wide Web Consortium (W3C), an international body in which member organizations, a full-time staff, and the public work together to develop Web standards for adoption by a cross section of regulators, civil society and commercial entities. The major browsers (i.e., IE, Chrome, Firefox, Safari) now offer a DNT option; however, no agreement exists on how recipient websites should respond to a DNT preference.

Despite this, some providers have recognized that DNT applies to third party website tracking—not first party website tracking. Under the draft W3C standard, if a first party receives a DNT:1 signal, the first party may engage in its normal collection and use of data. This includes the ability to customize the content, services, and advertising in the context of the first party experience. Under this recommendation, the first party must not share data about this network interaction with third parties who could not collect the data themselves; however, data about the transaction may be shared with service providers acting on behalf of the first party.

In Do-Not-Track situations, when a user visits a website ("Website1") the user's browser sends a notification to Website1 that the user is not to be tracked; and Website1 sends to the user's browser a First Party Cookie and content, plus the address where the browser should request the ad to be served on Website1 from an ad network ("Ad Network 1"). Ad Network 1 receives the request to not be tracked and sends the ad content to the user's browser, but no Third Party Cookie is placed on the user's browser. The ad is provided to the user based on traditional methods of targeting which may include, without limitation, targeting an ad to the content of the page (i.e., contextual targeting). Depending on how Do-Not-Track is implemented, as stated above, with respect to first parties, the consensus places few limitations on first parties (except that the first party must not share data about a DNT user's network interaction with third parties who could not collect the data themselves).

In contrast, with embodiments of the present invention, Do-Not-Track may be implemented to protect a related party's user's privacy/anonymity while still delivering content and targeted ads to support the primary revenue model of the Internet. FIG. 23 represents one of a number of potential implementations of the present invention for ad serving.

At Step 1 in FIG. 23, in one example a Data Subject or related party visits Website 1 for the first time and the browser sends a Do-Not-Track header to Website 1. If desired by the Data Subject or related party, the browser can also send a TDR to Website 1, thus enabling it to include "state" information for improving the Data Subject or related party's experience there. Website 1 then sends the content to the Data Subject or related party's browser.

At Step 2, in one example the Data Subject or related party's browser requests an ad for Web site 1 from Ad Network 1 (with or without a TDR). When the TDR is not sent, the Data Subject or related party will receive a traditionally targeted ad from Ad Network 1 based on the page's content. When the TDR is sent, Ad Network 1 becomes enable to serve a highly targeted ad to the Data Subject or related party's browser based on the Data Subject or related party's relevant attributes. In this respect, the ad served by Ad Network 1 based on a TDR is likely more relevant to the Data Subject or related party than an ad served traditionally or by aggregated (and therefore more generally inferential) behavioral profile information the Ad Network would otherwise have collected on the Data Subject or related party.

At Step 3, in one example, as the Data Subject or related party visits additional sites ("WebsiteN"), a process similar to that in Steps 1 and 2 will occur. When the TDR is included, the website content and the ad content will be highly targeted; however, at a minimum Ad Network 1 will have no ability to collect information on or track the Data Subject or related party. Further, via the privacy client resident on the browser or through other mechanisms, the TDR may be included in the information sent to the website or to Ad Network 1.

In summary, under existing ad targeting technology, users may be tracked everywhere they go online, yet they are served ads based on aggregated data out of which the ad network makes inferences about the particular user's preferences. This results in no user privacy/anonymity and low-to-moderate ad relevance. By combining aspects of the present invention and Do-Not-Track, users are empowered decide what information gets sent to which websites and ad networks. This not only enhances privacy/anonymity, but also ad relevance (for users) and improves sell-through and return on investment for merchants.

Figure 24:
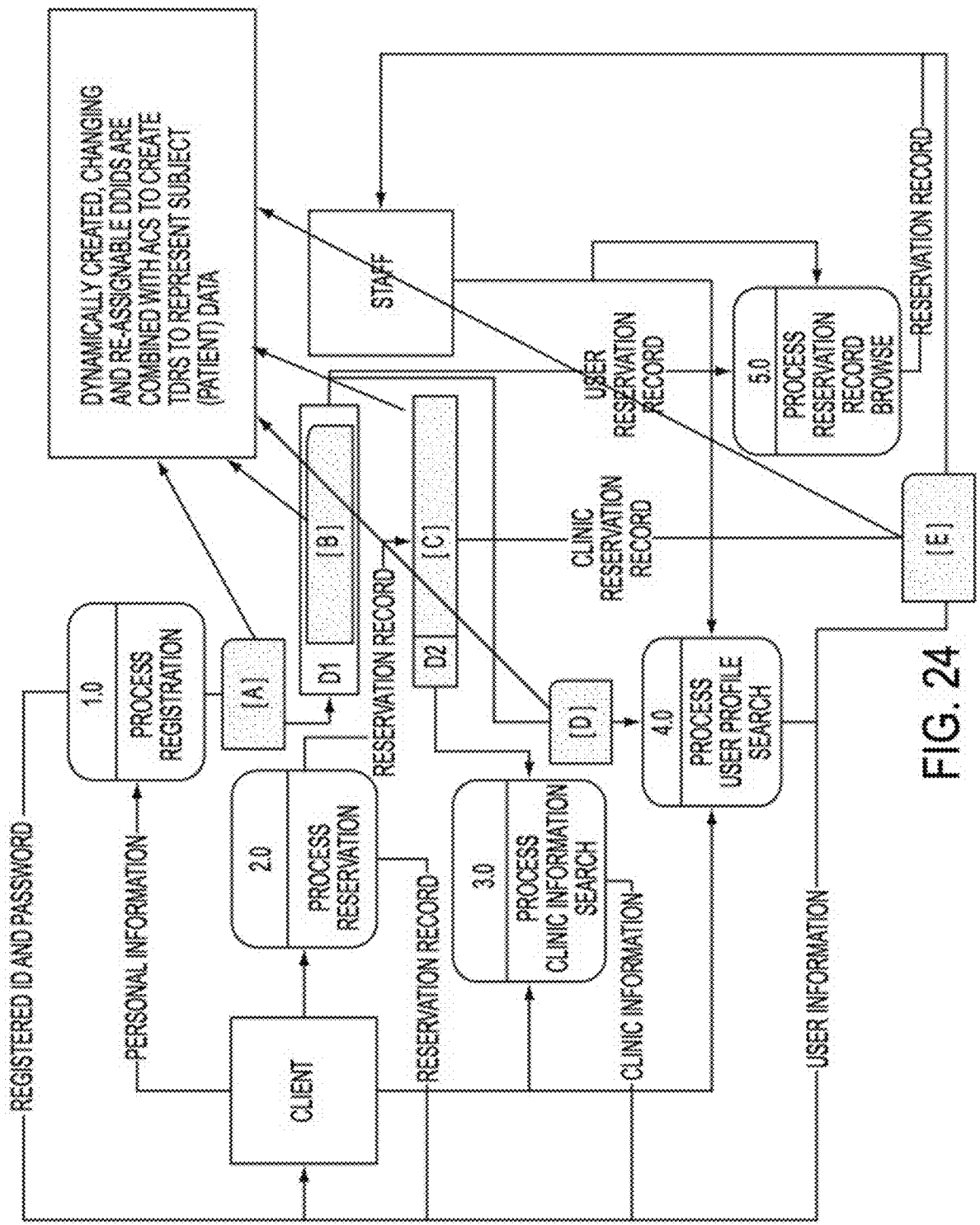
FIGS. 24-25 illustrate examples of an implementation of DDIDs in the area of healthcare, in accordance with one embodiment of the invention.
Figure 25:
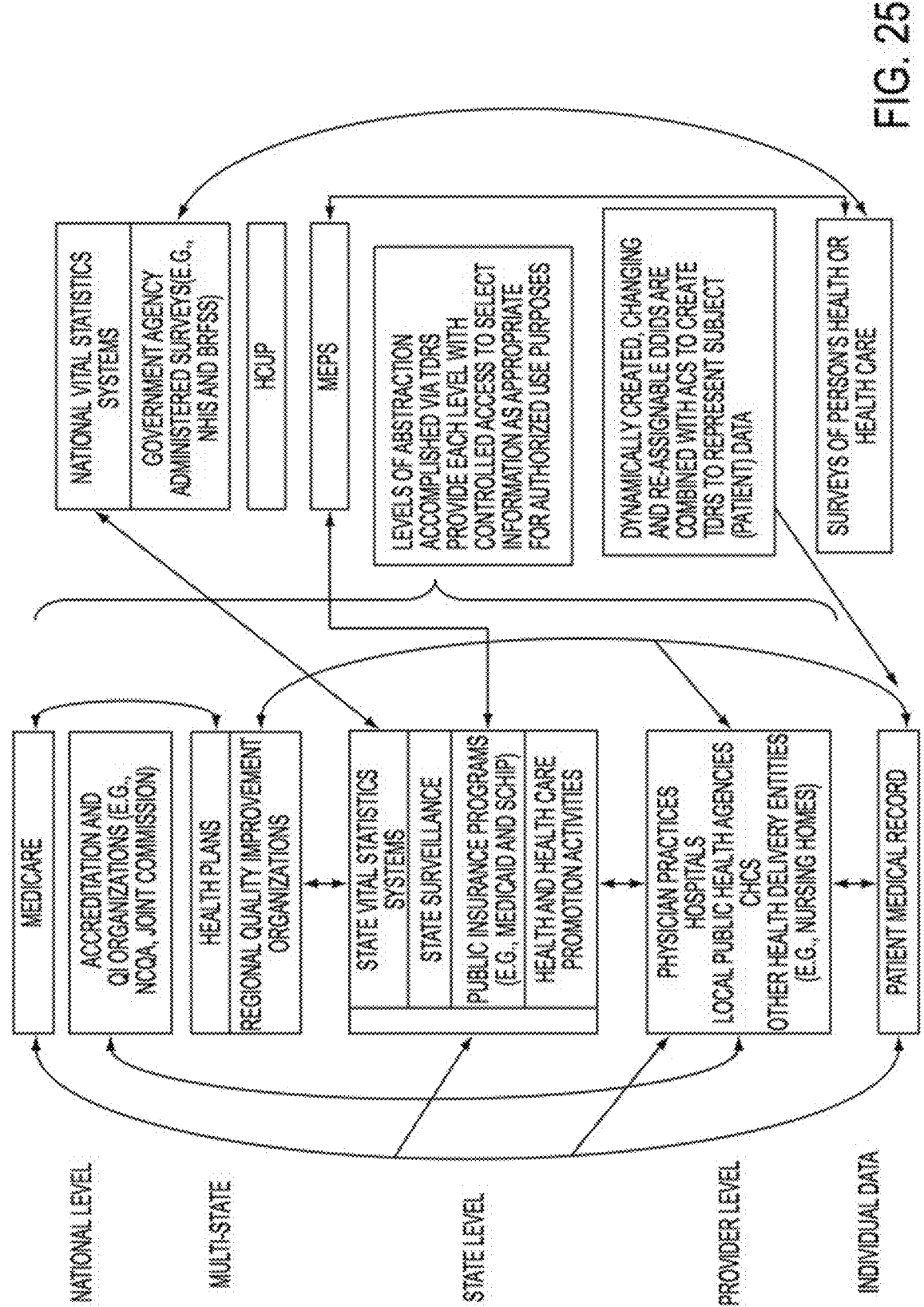

FIGS. 24 and 25 illustrate potential benefits of some embodiments of the present disclosure in the area of healthcare. FIG. 24 highlights how temporally unique and purpose limited data representations (TDRs) may be used in one potential implementation of the invention to protect the confidentiality and privacy/anonymity of user and patient personally identifiable information (PII) and/or personal health information (PHI) in a healthcare information system. With the benefit of one embodiment of the present invention, a healthcare system may generate real-time TDRs that do not reveal sensitive PII/PHI without losing the context of, or access to, such information. In step 1.0, information may be received as input to the system including PII/PHI relevant to the registration process. In order to protect the privacy/anonymity of sensitive PII/PHI information, output from the registration process may replace PII/PHI user information [A] with TDRs (comprised of dynamically changing and re-assignable DDIDs and the PII/PHI information) without revealing the PII/PHI information so sensitive PII/PHI data is not exposed. This user data (including TDRs in lieu of PII/PHI information) would then be used as input to create, augment or alter the user data file at D1 without revealing PII/PHI information [B]. Similarly, PII/PHI information that is output from the step 2.0 reservation process may be replaced with TDRs (comprised of dynamically changing and re-assignable DDIDs and the PII/PHI information) without revealing the PII/PHI information so sensitive PII/PHI data is not exposed. This clinical data (including TDRs in lieu of PII/PHI information) would then be used as input to create, augment or alter the clinical data file at D2 without revealing PII/PHI information [C]. Clinical data from D2 (after undergoing the clinical information search process at step 3.0) may then be combined with User data from D1 as input to the step 4.0 user profile search process without revealing PII/PHI information by means of access to and use of the temporally unique and purpose limited TDRs only. PII/PHI user information components of output resulting from the step 4.0 user profile search process may be replaced with TDRs (comprised of dynamically changing and re-assignable DDIDs and the PII/PHI information) without revealing the PII/PHI information so sensitive PII/PHI data is not exposed. Lastly, user data at D1 (including TDRs in lieu of PII/PHI information) can be used as input to the step 5.0 reservation record browse process without revealing PII/PHI information by means of access to and use of the temporally unique and purpose limited TDRs only. When access to detailed information from the user data file and/or clinical data file is required for authorized healthcare or ancillary service purposes, association keys (AKs) and/or replacement keys (RKs) may be used to discern the relevant sensitive PII/PHI data associated with applicable TDRs and DDIDs.

FIG. 25 illustrates an example wherein dynamically created, changeable and re-assignable TDRs (comprised of dynamically changing and re-assignable DDIDs and the PII/PHI information) could be used to protect the confidentiality and privacy/anonymity of PII/PHI contained in patient medical records. FIG. 25 shows how implementing the present invention with multiple levels of abstraction establishes "rings of privacy" such that only the level of identifying information necessary to perform a desired service or permitted function is provided. In this example, each of the Provider, State, Multi-State and National levels would receive attribute combinations appropriate for their respective permitted purposes. Temporally unique and purpose limited data representations (TDRs) may be used to protect the confidentiality and privacy/anonymity of user and patient personally identifiable information (PII) and/or personal health information (PHI). With the benefit of one embodiment of the present invention, healthcare related information could use TDRs that do not reveal sensitive PII/PHI without losing the context of, or access to, such information. Each successive level (starting with the provider level at the bottom and working up to the national level at the top) could be provided information in which PII/PHI information has been replaced with TDRs (comprised of dynamically changing and re-assignable DDIDs and the PII/PHI information) represented by temporally unique and purpose limited DDIDs only (without revealing the PII/PHI information) so sensitive PII/PHI data is not exposed. When access to PII/PHI information is necessary to perform an appropriate and authorized use at a specific level, association keys (AKs) and/or replacement keys (RKs) may be used to discern the relevant sensitive PII/PHI data associated with applicable TDRs and DDIDs. In addition, DDIDs could help facilitate self-regulation to improve longitudinal studies since DDIDs change over time and information associated with new DDIDs can reflect new and additional information without revealing the identity of a Data Subject/patient. This could be accomplished by using DDIDs to separate "context" or "meta" from the data necessary to perform analysis. The results of the analysis could be shared with a trusted party/proxy who would apply the "context" or "meta" to the data resulting from the analysis. There are a multitude of players in the healthcare industry—many of which use different data structures. Dynamic Anonymity could support collection of disparate data from different sources in different formats, normalize the information into a common structure and separate "context" or "meta" from "content" by means of dynamically assigning, reassigning and tracking DDIDs to enable effective research and analysis without revealing identifying information. This methodology could allow the linking of data together about a single Data Subject/patient from disparate sources without having to worry about getting consent because individuals would not be identifiable as a result of the process. Only within the Circle of Trust ("CoT") identified in FIG. 1C-1 will identifying information be accessible by means of access to the mapping engine that correlates information to individuals. With appropriate oversight and regulation, trusted parties/proxies could offer controls via a Circle of Trust (CoT) to help reconcile tensions between identifiable and functional information. For example, currently in healthcare/life science research, significant "data minimization" efforts are undertaken to ensure that only the minimal amount of identifiable information is used in research because of potential risk to individuals of re-identification. With Dynamic Anonymity, much of the burden placed on regulators regarding enforcement of laws and the burden on companies associated with privacy/anonymity reviews and engineering could be substantially reduced while at the same time, more complete data sets could be made available for healthcare-related research and development. HIPAA sets forth methodologies for de-identifying personal health information (PHI); once PHI is de-identified, it is no longer subject to HIPAA regulations and can be used for any purpose. However, concerns have been raised about the sufficiency of existing HIPAA de-identification methodologies, the lack of legal accountability for unauthorized re-identification of de-identified data, and insufficient public transparency about de-identified data uses. In addition, effective as of Sep. 22, 2014 under the HIPAA/HITECH final rule, in addition to covered entities, business associates are also directly liable for HIPAA compliance. The present invention provides a means of accomplishing the information privacy objectives of HIPAA without diminishing the value of information. By means of application of the present invention, most data may be HIPAA compliant.

Figure 26:
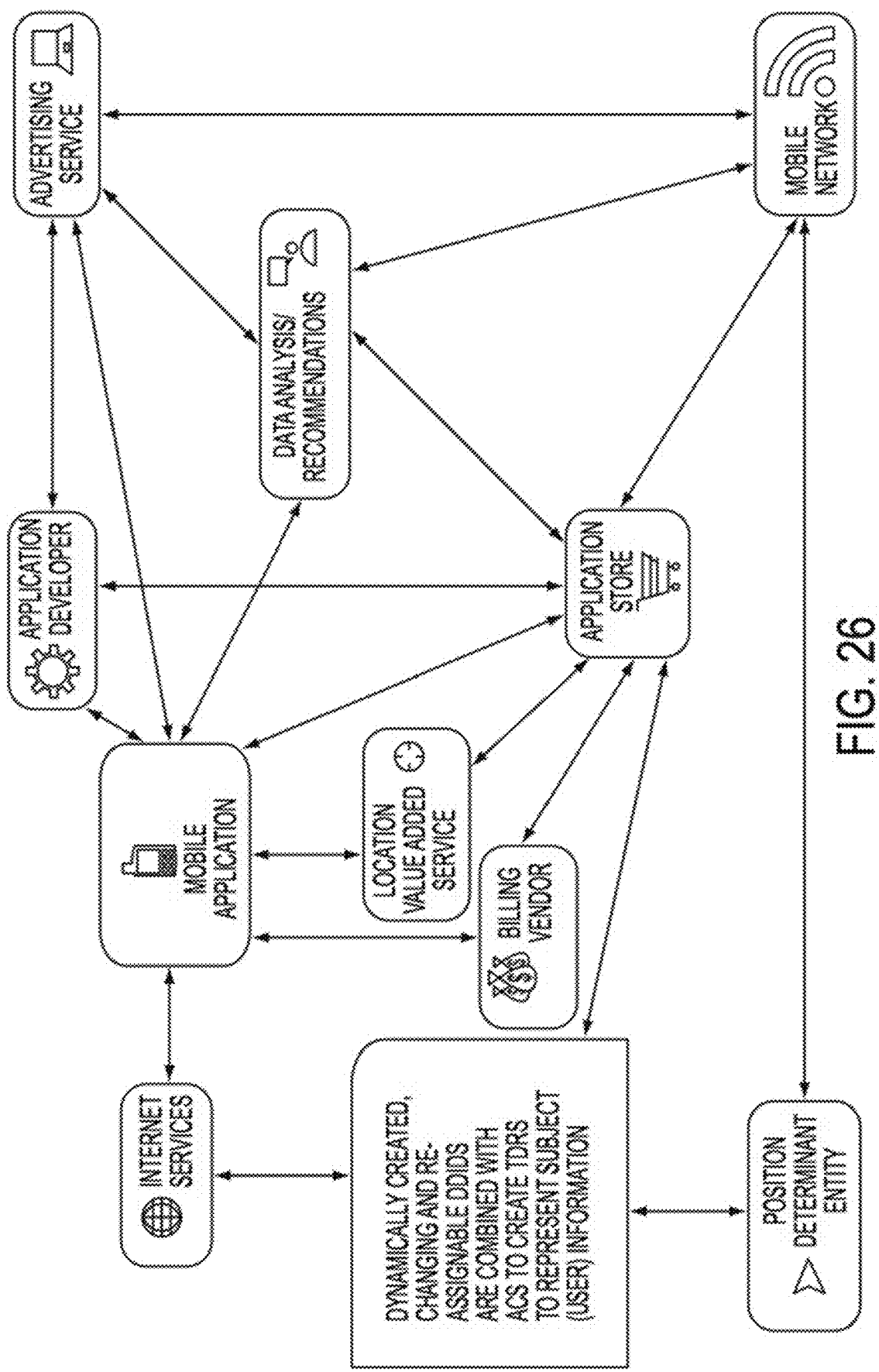
FIG. 26 illustrates an example of an implementation of DDIDs in the area of mobile communications, in accordance with one embodiment of the invention.

FIG. 26 illustrates some potential benefits of an embodiment of the present disclosure in the area of mobile/wearable/portable device communications. Mobile/wearable/portable applications implementing a system or aspects thereof as disclosed herein, may provide the controlling entity control over both the timing and level of participation in location and time sensitive applications. The controlling entity may use the capabilities of the abstraction module of the privacy server to control the degree to which attribute combinations are shared with third parties, doing so in an anonymous versus personally identifiable manner. For example, static identifiers associated with a mobile/wearable/portable device in existing systems may enable mobile/wearable/portable application providers and other third parties to aggregate attribute combination data pertaining to use of the mobile/wearable/portable device. Use of the present invention may prevent application providers and other third parties from aggregating attribute combinations pertaining to use of a mobile/wearable/portable device and may further enable a mobile/wearable/portable device to use mobile applications requiring access to geolocation information (e.g., direction or map applications) without revealing the identity of the mobile/wearable/portable device or user by implementing the use of TDRs and/or DDIDs rather than static identifiers.

Figure 27:
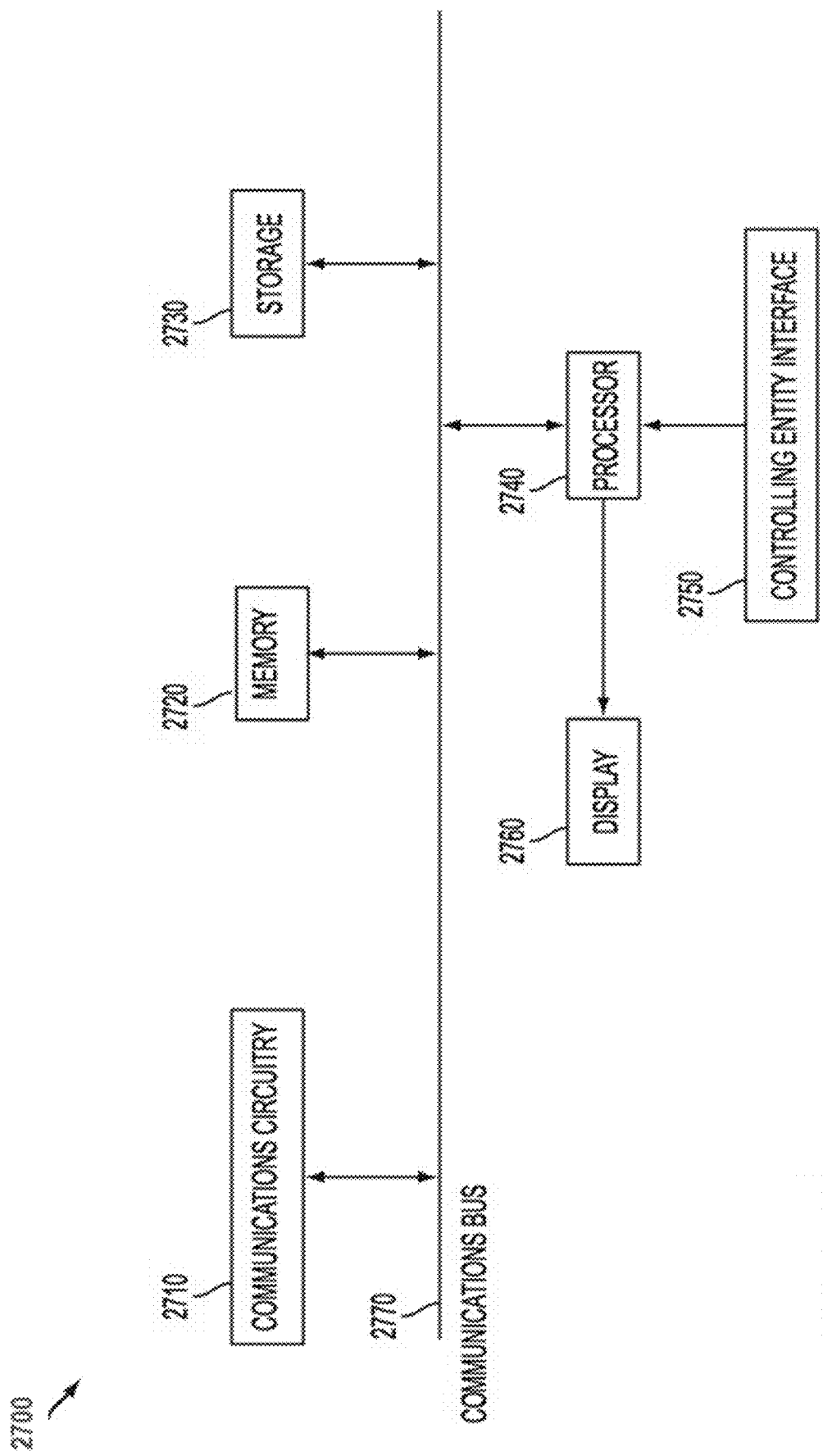
FIG. 27 illustrates a block diagram of an example of a programmable device for implementing techniques for dynamically creating, assigning, changing, reassigning, and using dynamically changeable, temporally unique identifiers (DDIDs) in accordance with one embodiment of the invention.

FIG. 27 is an example of a simplified functional block diagram illustrating a programmable device 2700 according to one embodiment that can implement one or more of the processes, methods, steps, features or aspects described herein. The programmable device 2700 may include one or more communications circuitry 2710, memory 2720, storage device 2730, processor 2740, controlling entity interface 2750, display 2760, and communications bus 2770. Processor 2740 may be any suitable programmable control device or other processing unit, and may control the operation of many functions performed by programmable device 2700. Processor 2740 may drive display 2760 and may receive controlling entity inputs from the controlling entity interface 2750. An embedded processor provides a versatile and robust programmable control device that may be utilized for carrying out the disclosed techniques.

Storage device 2730 may store attribute combinations, software (e.g., for implementing various functions on device 2700), preference information, device profile information, and any other suitable data. Storage device 2730 may include one or more storage mediums for tangibly recording data and program instructions, including for example, a hard-drive or solid state memory, permanent memory such as ROM, semi-permanent memory such as RAM, or cache. Program instructions may comprise a software implementation encoded in any desired computer programming language.

Memory 2720 may include one or more different types of storage modules that may be used for performing device functions. For example, memory 2720 may include cache, ROM, and/or RAM. Communications bus 2770 may provide a data transfer path for transferring data to, from, or between at least memory 2720, storage device 2730, and processor 2740.

Although referred to as a bus, communications bus 2770 is not limited to any specific data transfer technology. Controlling entity interface 2750 may allow a controlling entity to interact with the programmable device 2700. For example, the controlling entity interface 2750 can take a variety of forms, such as a button, keypad, dial, click wheel, mouse, touch or voice command screen, or any other form of input or user interface.

In one embodiment, the programmable device 2700 may be a programmable device capable of processing data. For example, the programmable device 2600 may be a device such as any identifiable device (excluding smart phones, tablets, notebook and desktop computers) that have the ability to communicate and are embedded with sensors, identifying devices or machine-readable identifiers (a "smart device"), smart phone, tablet, notebook or desktop computer, or other suitable personal device.

Figure 28:
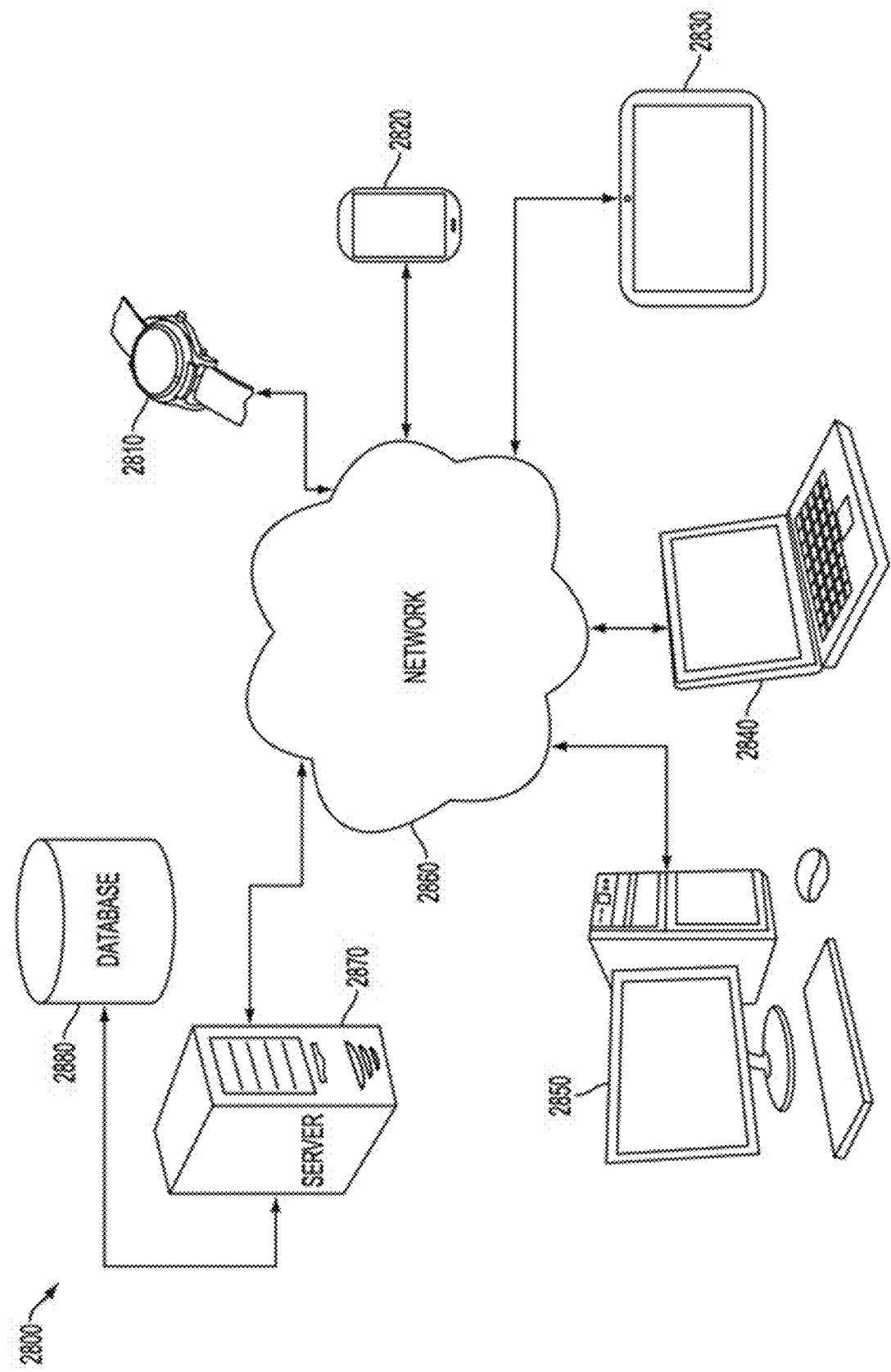
FIG. 28 illustrates a block diagram illustrating a network of privacy clients and a privacy server for implementing techniques for dynamically creating, assigning, changing, reassigning, and using DDIDs in accordance with one embodiment of the invention.

FIG. 28 is an example of a block diagram illustrating a system 2800 of networked devices for implementing one or more of the processes, methods, steps, features or aspects described herein. The privacy client described above may be implemented on any of the smart device (i.e., wearable, movable or immovable smart devices) 2810, smart phone 2820, tablet 2830, notebook 2840, or desktop computer 2850, for example. Each of these devices is connected by one or more networks 2860 to the privacy server 2870, to which is coupled a database 2880 for storing information about attribute combinations, TDRs, Data Subjects, aggregated Data Subject profiles, time periods/stamps by means of time keys (TKs) or otherwise, association keys (AKs), replacement keys (RKs) and their associated information. The database 2880 may be any desired form of data storage, including structured databases and non-structured flat files. The privacy server 2870 may also provide remote storage for attribute combinations, TDRs, Data Subjects, aggregated Data Subject profiles, time periods/stamps by means of time keys (TKs) or otherwise, association keys (AKs), replacement keys (RKs) and their associated information that have been or are to be delivered to the privacy clients on devices 2810, 2820, 2830, 2840, 2850, or other suitable devices either in the database 2880 or in a different database (not shown).

Although a single network 2860 is illustrated in FIG. 28, the network 2860 may be multiple interconnected networks, and the privacy server 2870 may be connected to each of the privacy clients on 2810, 2820, 2830, 2840, 2850, or other suitable devices via different networks 2860. The network 2860 may be any type of network, including local area networks, wide area networks, or the global internet.

Embodiments of the present invention can provide privacy and security applications for various industries, environments, and technologies, including, but not limited to, online transactions, healthcare, education, card payment or processing, information security, shipping, supply chain management, manufacturing resource planning, geolocation, mobile or cellular systems, energy and smart grid technologies, the internet, and the defense and intelligence technologies and programs.

When used in an online transaction environment, embodiments of the present invention can provide consumers with the ability to control collection or use of their data, and may provide data custodians the ability to ensure third parties involved in data communications or dissemination receive only information necessary for them to perform their specific function. The resulting increased consumer confidence may enable continued enjoyment of benefits of the "Internet of Things," as described above, without forsaking subject or related party rights or subjecting the industry to undue regulation.

In the healthcare field, embodiments of the present invention can help retain the efficacy of existing healthcare laws by improving de-identification. In addition, embodiments of the present invention may enable individual consumers and society as a whole to benefit from healthcare big data analytics by improving likelihood of patient consent for research due to increased protection of confidentiality of data.

As another example, when used in educational environments, embodiments of the present invention can provide educators and administrators with secure tools to access and use compartmentalized student-related data to enable students individually, and school systems collectively, to benefit from enhanced data analytics without jeopardizing students' rights to privacy/anonymity.

In the field of national security setting, an example embodiment of the invention may be used for instance by a governmental national security organization to analyze limited telephone records aggregated by individual telecommunications users, without requiring that any personally identifiable information be provided to the security organization. For example, the time of calls, the 'called to' and 'called from" number, the duration of calls and the zip code of the "called to" and "called from" numbers could be disclosed without having to expose telephone numbers making or receiving calls or personal information pertaining to calling or receiving parties. In this example, the security organization may analyze the limited telephone records to determine if any suspicious activity occurred at which point a warrant or other judicial approval may be issued to receive additional, more detailed attributes of the telephone records. In this manner, embodiments of the present invention can be used to further national security interests while at the same time maintaining the privacy/anonymity of telephone users until such time as a judicial review requires the disclosure of additional, more detailed attributes.

EXAMPLES

The following examples pertain to further embodiments. Example 1 is a system, comprising: a communication interface for sending data over a network; a memory having, stored therein, computer program code; and one or more processing units operatively coupled to the memory and configured to execute instructions in the computer program code that cause the one or more processing units to: generate one or more dynamically-changing, temporally unique identifiers; receive, over the network, a first request from a first client for a generated identifier related to a first data subject; associate, in response to the first request, a first generated identifier with the first data subject; generate first time period data, wherein the first time period data comprises information defining a first time period during which the first generated identifier may be used to identify the first data subject; store, in the memory, the first generated identifier and the first time period data; and send the first generated identifier over the network to the first client.

Example 2 includes the subject matter of example 1, wherein the instructions in the computer program code further cause the one or more processing units to: associate one or more data attributes with the first generated identifier.

Example 3 includes the subject matter of example 2, wherein at least one of the one or more data attributes associated with the first generated identifier relates to an action, activity, process, purpose, identity, or trait of the first data subject.

Example 4 includes the subject matter of example 3, wherein the instructions in the computer program code further cause the one or more processing units to: receive, over the network, a second request from a second client for at least one of the one or more data attributes associated with the first generated identifier during the first time period; determine that the second request is authorized; and grant, over the network, the ability of second client to determine the requested one or more data attributes associated with the first generated identifier during the first time period.

Example 5 includes the subject matter of example 1, wherein the instructions in the computer program code further cause the one or more processing units to: associate the first generated identifier with a second data subject during the first time or during a second time period.

Example 6 includes the subject matter of example wherein the instructions in the computer program code further cause the one or more processing units to: associate, in response to the first request, a second generated identifier with the first data subject; generate second time period data, wherein the second time period data comprises information defining a second time period during which the second generated identifier may be used to identify the first data subject; store, in the memory, the second generated identifier, and second time period data; and send the second generated identifier over the network to the first client.

Example 7 includes the subject matter of example 6, wherein the instructions in the computer program code further cause the one or more processing units to: associate one or more data attributes with the second generated identifier, wherein at least one of the one or more data attributes associated with the second generated identifier relates to an action, activity, process, purpose, identity, or trait of the first data subject.

Example 8 includes the subject matter of example 7, wherein at least one of the one or more data attributes associated with the first generated identifier is different from at least one of the one or more data attributes associated with the second generated identifier.

Example 9 includes the subject matter of example 3, wherein the instructions in the computer program code further cause the one or more processing units to: associate the first generated identifier with a second data subject during a second time period, wherein at least one of the one or more data attributes associated with the first generated identifier during the first time period is the same as one of the one or more data attributes associated with the first generated identifier during the second time period.

Example 10 includes the subject matter of example 1, wherein the instructions in the computer program code further cause the one or more processing units to: receive, over the network, from a second client, a second identifier related to a second data subject; associate the second identifier with the second data subject; generate second time period data, wherein the second time period data comprises information defining a second time period during which the second identifier may be used to identify the second data subject; and store, in the memory, the second identifier and second time period data.

Example 11 includes the subject matter of example 4, wherein the instructions in the computer program code further cause the one or more processing units to: revoke, over the network, the ability of the second client to determine the requested one or more data attributes associated with the first generated identifier during the second time period.

Example 12 is a non-transitory computer readable medium comprising computer executable instructions stored thereon to cause one or more processing units to: generate one or more dynamically-changing, temporally unique identifiers; receive, over a network, a first request from a first client for a generated identifier related to a first data subject; associate, in response to the first request, a first generated identifier with the first data subject; generate first time period data, wherein the first time period data comprises information defining a first time period during which the first generated identifier may be used to identify the first data subject; store, in a memory, the first generated identifier and the first time period data; and send the first generated identifier over the network to the first client.

Example 13 includes the subject matter of example 12, wherein the instructions further cause the one or more processing units to: associate one or more data attributes with the first generated identifier.

Example 14 includes the subject matter of example 13, wherein at least one of the one or more data attributes associated with the first generated identifier relates to an action, activity, process, purpose, identity, or trait of the first data subject.

Example 15 includes the subject matter of example 14, wherein the instructions further cause the one or more processing units to: receive, over the network, a second request from a second client for at least one of the one or more data attributes associated with the first generated identifier during the first time period; determine that the second request is authorized; and grant, over the network, the ability of second client to determine the requested one or more data attributes associated with the first generated identifier during the first time period.

Example 16 includes the subject matter of example 12, wherein the instructions further cause the one or more processing units to: associate the first generated identifier with a second data subject during a second time period.

Example 17 includes the subject matter of example 12, wherein the instructions further cause the one or more processing units to: associate the first generated identifier with a second data subject during the first time period.

Example 18 includes the subject matter of example 12, wherein the instructions further cause the one or more processing units to: associate, in response to the first request, a second generated identifier with the first data subject; generate second time period data, wherein the second time period data comprises information defining a second time period during which the second generated identifier may be used to identify the first data subject; store, in the memory, the second generated identifier, and second time period data; and send the second generated identifier over the network to the first client.

Example 19 includes the subject matter of example 18, wherein the first time period and the second time period do not overlap.

Example 20 includes the subject matter of example 18, wherein the first time period and the second time period at least partially overlap.

Example 21 includes the subject matter of example 18, wherein the instructions further cause the one or more processing units to: associate one or more data attributes with the second generated identifier, wherein at least one of the one or more data attributes associated with the second generated identifier relates to an action, activity, process, purpose, identity, or trait of the first data subject.

Example 22 includes the subject matter of example 21, wherein at least one of the one or more data attributes associated with the first generated identifier is different from at least one of the one or more data attributes associated with the second generated identifier.

Example 23 includes the subject matter of example 14, wherein the instructions further cause the one or more processing units to: associate the first generated identifier with a second data subject during a second time period, wherein at least one of the one or more data attributes associated with the first generated identifier during the first time period is the same as one of the one or more data attributes associated with the first generated identifier during the second time period.

Example 24 includes the subject matter of example 12, wherein the instructions further cause the one or more processing units to: receive, over the network, from a second client, a second identifier related to a second data subject;

associate the second identifier with the second data subject; generate second time period data, wherein the second time period data comprises information defining a second time period during which the second identifier may be used to identify the second data subject; and store, in the memory, the second identifier and second time period data.

Example 25 includes the subject matter of example 24, wherein the second identifier comprises an HTTP cookie.

Example 26 includes the subject matter of example 12, wherein the instructions further cause the one or more processing units to: receive, over the network, a second request from a second client for an identity of the first data subject associated with the first generated identifier during the first time period; determine that the second request is authorized; and grant, over the network, the ability of the second client to determine the identity of the first data subject during the first time period.

Example 27 includes the subject matter of example 26, wherein the instructions further cause the one or more processing units to: revoke, over the network, the ability of the second client to determine the identity of the first data subject during the first time period.

Example 28 includes the subject matter of example 15, wherein the instructions further cause the one or more processing units to: revoke, over the network, the ability of the second client to determine the requested one or more data attributes associated with the first generated identifier during the second time period.

Example 29 includes the subject matter of example 13, wherein the first generated identifier is not mathematically derived from any of the one or more data attributes associated with the first generated identifier.

Example 30 includes the subject matter of example 12, wherein the first generated identifier comprises a primary identifier for the first data subject.

Example 31 is a system, comprising: a communication interface for sending data over a network; a memory having, stored therein, computer program code; and one or more processing units operatively coupled to the memory and configured to execute instructions in the computer program code that cause the one or more processing units to: generate a first temporally unique identifier; associate the first temporally unique identifier with a first data subject; associate one or more data attributes with the first temporally unique identifier; generate first time period data, wherein the first time period data comprises information defining a first time period during which the first temporally unique identifier may be used to identify the first data subject and retrieve the associated one or more data attributes; store, in the memory, the first temporally unique identifier, the one or more data attributes, and the first time period data; and send the first temporally unique identifier and the one or more data attributes over the network to a first client.

Example 32 includes the subject matter of example 31, wherein the instructions to generate a first temporally unique identifier are executed based on at least one of the following: time, purpose, and location.

Example 33 includes the subject matter of example 31, wherein the instructions in the computer program code further cause the one or more processing units to: terminate the first temporally unique identifier's ability to identify the first data subject and retrieve the associated one or more data attributes.

Example 34 includes the subject matter of example 33, wherein the instructions to terminate the first temporally unique identifier's ability to identify the first data subject and retrieve the associated one or more data attributes are executed based on at least one of the following: time, purpose, and location.

Example 35 includes the subject matter of example 31, wherein at least one of the one or more data attributes associated with the first temporally unique identifier relates to an action, activity, process, purpose, identity, or trait of the first data subject.

Example 36 includes the subject matter of example 31, wherein the instructions in the computer program code further cause the one or more processing units to: associate the first temporally unique identifier with a second data subject during a second time period.

Example 37 includes the subject matter of example 31, wherein the instructions in the computer program code further cause the one or more processing units to: associate the first temporally unique identifier with a second data subject during the first time period.

Example 38 includes the subject matter of example 31, wherein the instructions in the computer program code further cause the one or more processing units to: receive, over the network, a first request from a second client for an identity of the first data subject associated with the first temporally unique identifier during the first time period; determine that the first request is authorized; and grant, over the network, the ability of the second client to determine the identity of the first data subject during the first time period.

Example 39 includes the subject matter of example 38, wherein the instructions in the computer program code further cause the one or more processing units to: revoke, over the network, the ability of the second client to determine the identity of the first data subject during the first time period.

Example 40 includes the subject matter of example 31, wherein the instructions in the computer program code further cause the one or more processing units to: receive, over the network, a first request from a second client for one or more of the data attributes associated with the first temporally unique identifier during the first time period; determine that the first request is authorized; and grant, over the network, the ability of the second client to determine the requested one or more of the data attributes associated with the first temporally unique identifier during the first time period.

Example 41 includes the subject matter of example 40, wherein the instructions in the computer program code further cause the one or more processing units to: revoke, over the network, the ability of the second client to determine the requested one or more of the data attributes associated with the first temporally unique identifier during the first time period.

Example 42 includes the subject matter of example 31, wherein the first temporally unique identifier is not mathematically derived from any of the one or more data attributes associated with the first temporally unique identifier.

Example 43 includes the subject matter of example 31, wherein the first temporally unique identifier comprises a primary identifier for the first data subject.

Example 44 is a non-transitory computer readable medium comprising computer executable instructions stored thereon to cause one or more processing units to: generate a first temporally unique identifier; associate the first temporally unique identifier with a first data subject; associate one or more data attributes with the first temporally unique identifier; generate first time period data, wherein the first time period data comprises information defining a first time period during which the first temporally unique identifier may be used to identify the first data subject and retrieve the associated one or more data attributes; store, in a memory, the first temporally unique identifier, the one or more data attributes, and the first time period data; and send the first temporally unique identifier and the one or more data attributes over a network to a first client.

Example 45 includes the subject matter of example 44, wherein the instructions to generate a first temporally unique identifier are executed based on at least one of the following: time, purpose, and location.

Example 46 includes the subject matter of example 44, wherein the instructions further cause the one or more processing units to: terminate the first temporally unique identifier's ability to identify the first data subject and retrieve the associated one or more data attributes.

Example 47 includes the subject matter of example 46, wherein the instructions to terminate the first temporally unique identifier's ability to identify the first data subject and retrieve the associated one or more data attributes are executed based on at least one of the following: time, purpose, and location.

Example 48 includes the subject matter of example 44, wherein at least one of the one or more data attributes associated with the first temporally unique identifier relates to an action, activity, process, purpose, identity, or trait of the first data subject.

Example 49 includes the subject matter of example 44, wherein the instructions further cause the one or more processing units to: associate the first temporally unique identifier with a second data subject during a second time period.

Example 50 includes the subject matter of example 44, wherein the instructions further cause the one or more processing units to: associate the first temporally unique identifier with a second data subject during the first time period.

Example 51 includes the subject matter of example 44, wherein the instructions further cause the one or more processing units to: receive, over the network, a first request from a second client for an identity of the first data subject associated with the first temporally unique identifier during the first time period; determine that the first request is authorized; and grant, over the network, the ability of the second client to determine the identity of the first data subject during the first time period.

Example 52 includes the subject matter of example 51, wherein the instructions further cause the one or more processing units to: revoke, over the network, the ability of the second client to determine the identity of the first data subject during the first time period.

Example 53 includes the subject matter of example 44, wherein the instructions further cause the one or more processing units to: receive, over the network, a first request from a second client for one or more of the data attributes associated with the first temporally unique identifier during the first time period; determine that the first request is authorized; and grant, over the network, the ability of the second client to determine the requested one or more of the data attributes associated with the first temporally unique identifier during the first time period.

Example 54 includes the subject matter of example 53, wherein the instructions further cause the one or more processing units to: revoke, over the network, the ability of the second client to determine the requested one or more of the data attributes associated with the first temporally unique identifier during the first time period.

Example 55 includes the subject matter of example 44, wherein the first temporally unique identifier is not mathematically derived from any of the one or more data attributes associated with the first temporally unique identifier.

Example 56 includes the subject matter of example 44, wherein the first temporally unique identifier comprises a primary identifier for the first data subject.

Example 57 is a device, comprising: a user interface; a communication interface for sending data over a network; a memory having, stored therein, computer program code; and one or more processing units operatively coupled to the memory and configured to execute instructions in the computer program code that cause the one or more processing units to: request, over a network, a first temporally unique identifier from a first privacy server; associate the first temporally unique identifier with a first data subject that is a user of the device; associate one or more data attributes with the first temporally unique identifier; generate first time period data, wherein the first time period data comprises information defining a first time period during which the first temporally unique identifier may be used to identify the first data subject and retrieve the associated one or more data attributes; store, in the memory, the first temporally unique identifier, the one or more data attributes, and the first time period data; and send, in response to a determination that a first condition has been met, the first temporally unique identifier, the first time period data, and the one or more data attributes over the network to the first privacy server.

Example 58 includes the subject matter of example 57, wherein the determination that the first condition has been met comprises a determination of at least one of the following: that a predetermined amount of time has passed; that a flexible amount of time has passed; that a purpose for the first temporally unique identifier has expired; or that a location of the first data subject has changed.

Example 59 includes the subject matter of example 57, wherein the instructions in the computer program code further cause the one or more processing units to: modify one or more of the data attributes associated with the first temporally unique identifier.

Example 60 includes the subject matter of example 57, wherein the instructions in the computer program code further cause the one or more processing units to: track the use of the first temporally unique identifier.

Example 61 includes the subject matter of example 57, wherein the instructions in the computer program code further cause the one or more processing units to: revoke the ability of the first temporally unique identifier to identify the first data subject and retrieve the associated one or more data attributes.

Example 62 includes the subject matter of example 57, wherein the device resides on the same computing device as the privacy server.

Example 63 includes the subject matter of example 57, wherein the instructions in the computer program code further cause the one or more processing units to: send, in response to a change in the first temporally unique identifier, the first time period data, or the one or more data attributes, at least one of: the first temporally unique identifier, the first time period data, and the one or more data attributes over the network to one or more client devices that have registered with the first privacy server to be synchronized with the device.

Example 64 includes the subject matter of example 57, wherein the first temporally unique identifier, the first time period data, and the one or more data attributes are sent over the network to the first privacy server in the form of an HTTP cookie.

Example 65 includes the subject matter of example 57, wherein the first temporally unique identifier is not mathematically derived from any of the one or more data attributes associated with the first temporally unique identifier.

Example 66 includes the subject matter of example 57, wherein the first temporally unique identifier comprises a primary identifier for the first data subject.

Example 67 is a non-transitory computer readable medium comprising computer executable instructions stored thereon to cause one or more processing units to: request, over a network, a first temporally unique identifier from a first privacy server; associate the first temporally unique identifier with a first data subject that is a user of a first client device; associate one or more data attributes with the first temporally unique identifier; generate first time period data, wherein the first time period data comprises information defining a first time period during which the first temporally unique identifier may be used to identify the first data subject and retrieve the associated one or more data attributes; store, in a memory of the first client device, the first temporally unique identifier, the one or more data attributes, and the first time period data; and send, in response to a determination that a first condition has been met, the first temporally unique identifier, the first time period data, and the one or more data attributes over the network to the first privacy server.

Example 68 includes the subject matter of example 67, wherein the determination that the first condition has been met comprises a determination of at least one of the following: that a predetermined amount of time has passed; that a flexible amount of time has passed; that a purpose for the first temporally unique identifier has expired; or that a location of the first data subject has changed.

Example 69 includes the subject matter of example 67, wherein the instructions further cause the one or more processing units to: modify one or more of the data attributes associated with the first temporally unique identifier.

Example 70 includes the subject matter of example 67, wherein the instructions further cause the one or more processing units to: track the use of the first temporally unique identifier.

Example 71 includes the subject matter of example 67, wherein the instructions further cause the one or more processing units to: revoke the ability of the first temporally unique identifier to identify the first data subject and retrieve the associated one or more data attributes.

Example 72 includes the subject matter of example 67, wherein the first client device resides on the same computing device as the privacy server.

Example 73 includes the subject matter of example 67, wherein the instructions further cause the one or more processing units to: send, in response to a change in the first temporally unique identifier, the first time period data, or the one or more data attributes, at least one of: the first temporally unique identifier, the first time period data, and the one or more data attributes over the network to one or more client devices that have registered with the first privacy server to be synchronized with the first client device.

Example 74 includes the subject matter of example 67, wherein the first temporally unique identifier, the first time period data, and the one or more data attributes are sent over the network to the first privacy server in the form of an HTTP cookie.

Example 75 includes the subject matter of example 67, wherein the first temporally unique identifier is not mathematically derived from any of the one or more data attributes associated with the first temporally unique identifier.

Example 76 includes the subject matter of example 67, wherein the first temporally unique identifier comprises a primary identifier for the first data subject.

Example 77 is a device, comprising: a user interface; a communication interface for sending data over a network; a memory having, stored therein, computer program code; and one or more processing units operatively coupled to the memory and configured to execute instructions in the computer program code that cause the one or more processing units to: obtain, over a network, a first temporally unique identifier from a first privacy server, wherein the first temporally unique identifier is associated at the first privacy server, during a first time period, with a first data subject that is a user of the device; associate one or more data attributes with the first temporally unique identifier; generate first time period data, wherein the first time period data comprises information defining a first time period during which the first temporally unique identifier may be used to identify the first data subject and retrieve the associated one or more data attributes; store, in the memory, the first temporally unique identifier, the one or more data attributes, and the first time period data; send, the first temporally unique identifier, the first time period data, and the one or more data attributes over the network to the first privacy server; and receive over the network, a second temporally unique identifier from the first privacy server, wherein the second temporally unique identifier is associated at the first privacy server, during a second time period, with the first data subject and the one or more data attributes.

Example 78 includes the subject matter of example 77, wherein the instructions in the computer program code that cause the one or more processing units to receive over the network, the second temporally unique identifier from the first privacy server are executed in response to a determination that a first condition has been met.

Example 79 includes the subject matter of example 78, wherein the determination that the first condition has been met comprises a determination of at least one of the following: that a predetermined amount of time has passed; that a flexible amount of time has passed; that a purpose for the first temporally unique identifier has expired; or that a location of the first data subject has changed.

Example 80 includes the subject matter of example 77, wherein the instructions in the computer program code further cause the one or more processing units to: modify one or more of the data attributes associated with the first temporally unique identifier.

Example 81 includes the subject matter of example 77, wherein the instructions in the computer program code further cause the one or more processing units to: track the use of the first temporally unique identifier.

Example 82 includes the subject matter of example 77, wherein the instructions in the computer program code further cause the one or more processing units to: revoke the ability of the first temporally unique identifier to identify the first data subject and retrieve the associated one or more data attributes.

Example 83 includes the subject matter of example 77, wherein the instructions in the computer program code further cause the one or more processing units to: request, from the first privacy server, confirmation as to whether an identity of the first data subject or the one or more data attributes may be revealed to a first requesting party; and in response to receiving confirmation from the first privacy server that the identity of the first data subject or the one or more data attributes may be revealed to the first requesting party, send the identity of the first data subject or the one or more data attributes to the first requesting party.

Example 84 includes the subject matter of example 83, wherein the requested confirmation further comprises a requested confirmation as to whether the identity of the first data subject or the one or more data attributes may be revealed to a first requesting party for a particular action, activity, process or trait.

Example 85 includes the subject matter of example 83, wherein the requested confirmation further comprises a requested confirmation as to whether the identity of the first data subject or the one or more data attributes may be revealed to a first requesting party for a particular time period or location.

Example 86 includes the subject matter of example 84, wherein the requested confirmation further comprises a requested confirmation as to whether the identity of the first data subject or the one or more data attributes may be revealed to a first requesting party for a particular time period or location.

Example 87 is a system, comprising: a communication interface for sending data over a network; a memory having, stored therein, computer program code; and one or more processing units operatively coupled to the memory and configured to execute instructions in the computer program code that cause the one or more processing units to: generate one or more dynamically-changing, temporally unique identifiers; receive, over the network, a first request from a first data subject for a generated dynamically-changing, temporally unique identifier to be related to an attribute of the first data subject; associate, in response to the first request, a first generated dynamically-changing, temporally unique identifier with the attribute of the first data subject; transform the value of the first generated dynamically-changing, temporally unique identifier into a first unintelligible form, wherein a first key may be used to transform the first unintelligible form back into a first view of the first generated dynamically-changing, temporally unique identifier, wherein a second key may be used to transform the first unintelligible form back into a second view of the first generated dynamically-changing, temporally unique identifier, wherein the first key is different from the second key, and wherein the first view is different from the second view; store, in the memory, the first generated dynamically-changing, temporally unique identifier, the first key, the second key, and the first unintelligible form; and send the first unintelligible form over the network to the first data subject.

Example 88 includes the subject matter of example 87, wherein the first view provides more detail than the second view.

Example 89 includes the subject matter of example 87, wherein the unintelligible form comprises encrypted text.

Example 90 includes the subject matter of example 87, wherein the instructions in the computer program code further comprise instructions that cause the one or more processing units to also associate the first generated dynamically-changing, temporally unique identifier with an attribute of a second data subject.

Example 91 includes the subject matter of example 90, wherein the instructions in the computer program code that cause the one or more processing units to also associate the first generated dynamically-changing, temporally unique identifier with an attribute of a second data subject are executed in at least one of the following situations: at a different time than the first generated dynamically-changing, temporally unique identifier is associated with the attribute of the first data subject; at a different physical or virtual location than the first generated dynamically-changing, temporally unique identifier is associated with the attribute of the first data subject; and for a different purpose than the first generated dynamically-changing, temporally unique identifier is associated with the attribute of the first data subject.

Example 92 includes the subject matter of example 87, wherein the instructions in the computer program code further comprise instructions that cause the one or more processing units to: associate a second generated dynamically-changing, temporally unique identifier with the attribute of the first data subject.

Example 93 includes the subject matter of example 92, wherein the instructions in the computer program code that cause the one or more processing units to associate the second generated dynamically-changing, temporally unique identifier with the attribute of the first data subject are executed in at least one of the following situations: at a different time than the first generated dynamically-changing, temporally unique identifier is associated with the attribute of the first data subject; at a different physical or virtual location than the first generated dynamically-changing, temporally unique identifier is associated with the attribute of the first data subject; and for a different purpose than the first generated dynamically-changing, temporally unique identifier is associated with the attribute of the first data subject.

Example 94 is a non-transitory computer readable medium comprising computer executable instructions stored thereon to cause one or more processing units to: generate one or more dynamically-changing, temporally unique identifiers; receive, over a network, a first request from a first data subject for a generated dynamically-changing, temporally unique identifier to be related to an attribute of the first data subject; associate, in response to the first request, a first generated dynamically-changing, temporally unique identifier with the attribute of the first data subject; transform the value of the first generated dynamically-changing, temporally unique identifier into a first unintelligible form, wherein a first key may be used to transform the first unintelligible form back into a first view of the first generated dynamically-changing, temporally unique identifier, wherein a second key may be used to transform the first unintelligible form back into a second view of the first generated dynamically-changing, temporally unique identifier, wherein the first key is different from the second key, and wherein the first view is different from the second view; store, in a memory, the first generated dynamically-changing, temporally unique identifier, the first key, the second key, and the first unintelligible form; and send the first unintelligible form over the network to the first data subject.

Example 95 includes the subject matter of example 94, wherein the first view provides more detail than the second view.

Example 96 includes the subject matter of example 94, wherein the unintelligible form comprises non-encrypted text.

Example 97 includes the subject matter of example 94, wherein the instructions further comprise instructions that cause the one or more processing units to also associate the first generated dynamically-changing, temporally unique identifier with an attribute of a second data subject.

Example 98 includes the subject matter of example 97, wherein the instructions that cause the one or more processing units to also associate the first generated dynamically-changing, temporally unique identifier with an attribute of a second data subject are executed in at least one of the following situations: at a different time than the first generated dynamically-changing, temporally unique identifier is associated with the attribute of the first data subject; at a different physical or virtual location than the first generated dynamically-changing, temporally unique identifier is associated with the attribute of the first data subject; and for a different purpose than the first generated dynamically-changing, temporally unique identifier is associated with the attribute of the first data subject.

Example 99 includes the subject matter of example 94, wherein the instructions further comprise instructions that cause the one or more processing units to: associate a second generated dynamically-changing, temporally unique identifier with the attribute of the first data subject.

Example 100 includes the subject matter of example 99, wherein the instructions that cause the one or more processing units to associate the second generated dynamically-changing, temporally unique identifier with the attribute of the first data subject are executed in at least one of the following situations: at a different time than the first generated dynamically-changing, temporally unique identifier is associated with the attribute of the first data subject; at a different physical or virtual location than the first generated dynamically-changing, temporally unique identifier is associated with the attribute of the first data subject; and for a different purpose than the first generated dynamically-changing, temporally unique identifier is associated with the attribute of the first data subject.

Example 101 is a computer-implemented method comprising: generating one or more dynamically-changing, temporally unique identifiers; receiving, over a network, a first request from a first data subject for a generated dynamically-changing, temporally unique identifier to be related to an attribute of the first data subject; associating, in response to the first request, a first generated dynamically-changing, temporally unique identifier with the attribute of the first data subject; transforming the value of the first generated dynamically-changing, temporally unique identifier into a first unintelligible form, wherein a first key may be used to transform the first unintelligible form back into a first view of the first generated dynamically-changing, temporally unique identifier, wherein a second key may be used to transform the first unintelligible form back into a second view of the first generated dynamically-changing, temporally unique identifier, wherein the first key is different from the second key, and wherein the first view is different from the second view; storing, in a memory, the first generated dynamically-changing, temporally unique identifier, the first key, the second key, and the first unintelligible form; and sending the first unintelligible form over the network to the first data subject.

Example 102 includes the subject matter of example 101, wherein the first view provides more detail than the second view.

Example 103 includes the subject matter of example 101, further comprising also associating the first generated dynamically-changing, temporally unique identifier with an attribute of a second data subject.

Example 104 includes the subject matter of example 103, wherein the act of also associating the first generated dynamically-changing, temporally unique identifier with an attribute of a second data subject is performed in at least one of the following situations: at a different time than the first generated dynamically-changing, temporally unique identifier is associated with the attribute of the first data subject; at a different physical or virtual location than the first generated dynamically-changing, temporally unique identifier is associated with the attribute of the first data subject; and for a different purpose than the first generated dynamically-changing, temporally unique identifier is associated with the attribute of the first data subject.

Example 105 includes the subject matter of example 101, further comprising: associating a second generated dynamically-changing, temporally unique identifier with the attribute of the first data subject.

Example 106 includes the subject matter of example 105, wherein the act of associating the second generated dynamically-changing, temporally unique identifier with the attribute of the first data subject is performed in at least one of the following situations: at a different time than the first generated dynamically-changing, temporally unique identifier is associated with the attribute of the first data subject; at a different physical or virtual location than the first generated dynamically-changing, temporally unique identifier is associated with the attribute of the first data subject; and for a different purpose than the first generated dynamically-changing, temporally unique identifier is associated with the attribute of the first data subject.

Example 107 is a system, comprising: a communication interface for sending data over a network; a memory having, stored therein, computer program code; one or more data sources; and one or more processing units operatively coupled to the memory and configured to execute instructions in the computer program code that cause the one or more processing units to: obtain data from each of the one or more data sources pertaining to a first plurality of data subjects; generate a first dynamically-changing, temporally unique identifier for a first data subject in the first plurality of data subjects, wherein the first data subject is in each of a first data source and a second data source of the one or more data sources; generate one or more second dynamically-changing, temporally unique identifiers corresponding to one or more quasi-identifiers in each of the first data source and the second data source, wherein each quasi-identifier has a value; receive, over the network, a first request for the values of the one or more quasi-identifiers in the first data source; receive, over the network, a second request for the values of the one or more quasi-identifiers in the second data source; transform the values obtained from the first request into one or more third dynamically changing temporally unique identifiers; transform the values obtained from the second request into one or more fourth dynamically changing temporally unique identifiers; store, in the memory: the first dynamically changing, temporally unique identifier; the second dynamically-changing, temporally unique identifier; the one or more third dynamically-changing, temporally unique identifiers; and the one or more fourth dynamically-changing, temporally unique identifiers; and send the first dynamically-changing, temporally unique identifier; the second dynamically-changing, temporally unique identifier; the one or more third dynamically-changing, temporally unique identifiers; and the one or more fourth dynamically-changing, temporally unique identifiers over the network.

Example 108 includes the subject matter of example 107, wherein the first dynamically-changing, temporally unique identifier comprises a Replacement DDID (R-DDID).

Example 109 includes the subject matter of example 108, wherein the one or more third dynamically-changing, temporally unique identifiers comprise Association DDIDs (A-DDIDs).

Example 110 includes the subject matter of example 107, wherein the R-DDID comprises a specific value.

Example 111 includes the subject matter of example 107, wherein each of the A-DDIDs comprises a specific value.

Example 112 includes the subject matter of example 109, wherein the instructions further cause the one or more processing units to: use a first key to transform the R-DDID into a first view of the R-DDID; and use a second key to transform the R-DDID into a second view of the R-DDID, wherein the first key is different from the second key.

Example 113 includes the subject matter of example 109, wherein the instructions further cause the one or more processing units to: use a third key to transform a first one of the A-DDIDs into a third view of the first one of the A-DDIDs; and use a fourth key to transform the first one of the A-DDIDs into a fourth view of the first one of the A-DDIDs, wherein the third key is different from the fourth key, and wherein the third view is different from the fourth view.

Example 114 includes the subject matter of example 107, wherein a first one of the second dynamically-changing, temporally unique identifiers has the same value in the first data source and the second data source.

Example 115 includes the subject matter of example 107, wherein at least one of the one or more third dynamically changing temporally unique identifiers comprises a first unintelligible form.

Example 116 includes the subject matter of example 107, wherein at least one of the one or more fourth dynamically changing temporally unique identifiers comprises a second unintelligible form.

Example 117 includes the subject matter of example 115, wherein the first unintelligible form comprises encrypted data.

Example 118 includes the subject matter of example 116, wherein the first unintelligible form comprises encrypted data.

Example 119 includes the subject matter of example 107, wherein at least one of the one or more data sources comprises a particular subset, population, or cohort of data subjects.

Example 120 includes the subject matter of example 107, wherein each of the one or more data sources pertains to a particular plurality of data subjects during a particular time period.

Example 121 includes the subject matter of example 109, wherein at least one of the one or more A-DDIDs comprises one of the following: a numerical grouping, or a categorical grouping.

Example 122 includes the subject matter of example 109, wherein at least one of the one or more A-DDIDs comprises one of the following: a discrete value, or a discrete set of values.

Example 123 is a non-transitory computer readable medium comprising computer executable instructions stored thereon to cause one or more processing units to: obtain data from each of the one or more data sources pertaining to a first plurality of data subjects; generate a first dynamically-changing, temporally unique identifier for a first data subject in the first plurality of data subjects, wherein the first data subject is in each of a first data source and a second data source of the one or more data sources; generate one or more second dynamically-changing, temporally unique identifiers corresponding to one or more quasi-identifiers in each of the first data source and the second data source, wherein each quasi-identifier has a value; receive, over a network, a first request for the values of the one or more quasi-identifiers in the first data source; receive, over the network, a second request for the values of the one or more quasi-identifiers in the second data source; transform the values obtained from the first request into one or more third dynamically changing temporally unique identifiers; transform the values obtained from the second request into one or more fourth dynamically changing temporally unique identifiers; store, in the memory: the first dynamically changing, temporally unique identifier; the second dynamically-changing, temporally unique identifier; the one or more third dynamically-changing, temporally unique identifiers; and the one or more fourth dynamically-changing, temporally unique identifiers; and send the first dynamically-changing, temporally unique identifier; the second dynamically-changing, temporally unique identifier; the one or more third dynamically-changing, temporally unique identifiers; and the one or more fourth dynamically-changing, temporally unique identifiers over the network.

Example 124 includes the subject matter of example 123, wherein the first dynamically-changing, temporally unique identifier comprises a Replacement DDID (R-DDID).

Example 125 includes the subject matter of example 124, wherein the one or more third dynamically-changing, temporally unique identifiers comprise Association DDIDs (A-DDIDs).

Example 126 includes the subject matter of example 123, wherein the R-DDID comprises a specific value.

Example 127 includes the subject matter of example 123, wherein each of the A-DDIDs comprises a specific value.

Example 128 includes the subject matter of example 125, wherein the instructions further cause the one or more processing units to: use a first key to transform the R-DDID into a first view of the R-DDID; and use a second key to transform the R-DDID into a second view of the R-DDID, wherein the first key is different from the second key.

Example 129 includes the subject matter of example 125, wherein the instructions further cause the one or more processing units to: use a third key to transform a first one of the A-DDIDs into a third view of the first one of the A-DDIDs; and use a fourth key to transform the first one of the A-DDIDs into a fourth view of the first one of the A-DDIDs, wherein the third key is different from the fourth key, and wherein the third view is different from the fourth view.

Example 130 includes the subject matter of example 123, wherein a first one of the second dynamically-changing, temporally unique identifiers has the same value in the first data source and the second data source.

Example 131 includes the subject matter of example 123, wherein at least one of the one or more third dynamically changing temporally unique identifiers comprises a first unintelligible form.

Example 132 includes the subject matter of example 123, wherein at least one of the one or more fourth dynamically changing temporally unique identifiers comprises a second unintelligible form.

Example 133 includes the subject matter of example 131, wherein the first unintelligible form comprises encrypted data.

Example 134 includes the subject matter of example 132, wherein the first unintelligible form comprises encrypted data.

Example 135 includes the subject matter of example 123, wherein at least one of the one or more data sources comprises a particular subset, population, or cohort of data subjects.

Example 136 includes the subject matter of example 123, wherein each of the one or more data sources pertains to a particular plurality of data subjects during a particular time period.

Example 137 includes the subject matter of example 125, wherein at least one of the one or more A-DDIDs comprises one of the following: a numerical grouping, or a categorical grouping.

Example 138 includes the subject matter of example 125, wherein at least one of the one or more A-DDIDs comprises one of the following: a discrete value, or a discrete set of values.

Example 139 is a computer-implemented method comprising: obtaining data from each of one or more data sources pertaining to a first plurality of data subjects; generating a first dynamically-changing, temporally unique identifier for a first data subject in the first plurality of data subjects, wherein the first data subject is in each of a first data source and a second data source of the one or more data sources; generating one or more second dynamically-changing, temporally unique identifiers corresponding to one or more quasi-identifiers in each of the first data source and the second data source, wherein each quasi-identifier has a value; receiving, over a network, a first request for the values of the one or more quasi-identifiers in the first data source; receiving, over the network, a second request for the values of the one or more quasi-identifiers in the second data source; transforming the values obtained from the first request into one or more third dynamically changing temporally unique identifiers; transforming the values obtained from the second request into one or more fourth dynamically changing temporally unique identifiers; storing, in the memory: the first dynamically changing, temporally unique identifier; the second dynamically-changing, temporally unique identifier; the one or more third dynamically-changing, temporally unique identifiers; and the one or more fourth dynamically-changing, temporally unique identifiers; and sending the first dynamically-changing, temporally unique identifier; the second dynamically-changing, temporally unique identifier; the one or more third dynamically-changing, temporally unique identifiers; and the one or more fourth dynamically-changing, temporally unique identifiers over the network.

Example 140 includes the subject matter of example 139, wherein the first dynamically-changing, temporally unique identifier comprises a Replacement DDID (R-DDID).

Example 141 includes the subject matter of example 140, wherein the one or more third dynamically-changing, temporally unique identifiers comprise Association DDIDs (A-DDIDs).

Example 142 includes the subject matter of example 139, wherein the R-DDID comprises a specific value.

Example 143 includes the subject matter of example 139, wherein each of the A-DDIDs comprises a specific value.

Example 144 includes the subject matter of example 141, further comprising the acts of: using a first key to transform the R-DDID into a first view of the R-DDID; and using a second key to transform the R-DDID into a second view of the R-DDID, wherein the first key is different from the second key.

Example 145 includes the subject matter of example 141, further comprising the acts of: using a third key to transform a first one of the A-DDIDs into a third view of the first one of the A-DDIDs; and using a fourth key to transform the first one of the A-DDIDs into a fourth view of the first one of the A-DDIDs, wherein the third key is different from the fourth key, and wherein the third view is different from the fourth view.

Example 146 includes the subject matter of example 139, wherein a first one of the second dynamically-changing, temporally unique identifiers has the same value in the first data source and the second data source.

Example 147 includes the subject matter of example 139, wherein at least one of the one or more third dynamically changing temporally unique identifiers comprises a first unintelligible form.

Example 148 includes the subject matter of example 139, wherein at least one of the one or more fourth dynamically changing temporally unique identifiers comprises a second unintelligible form.

Example 149 includes the subject matter of example 147, wherein the first unintelligible form comprises encrypted data.

Example 150 includes the subject matter of example 148, wherein the first unintelligible form comprises encrypted data.

Example 151 includes the subject matter of example 139, wherein at least one of the one or more data sources comprises a particular subset, population, or cohort of data subjects.

Example 152 includes the subject matter of example 139, wherein each of the one or more data sources pertains to a particular plurality of data subjects during a particular time period.

Example 153 includes the subject matter of example 141, wherein at least one of the one or more A-DDIDs comprises one of the following: a numerical grouping, or a categorical grouping.

Example 154 includes the subject matter of example 141, wherein at least one of the one or more A-DDIDs comprises one of the following: a discrete value, or a discrete set of values.

Example 155 is a system, comprising: a communication interface for sending data over a network; a memory having, stored therein, computer program code; one or more data stores; and one or more processing units operatively coupled to the memory and configured to execute instructions in the computer program code that cause the one or more processing units to: obtain a request from a first user for provision of a privacy policy; determine a first privacy policy based, at least in part, on the request; obtain data from the first user pertaining to a first plurality of data subjects; generate a first dynamically-changing, temporally unique identifier (DDID) for a first data subject in the first plurality of data subjects, wherein the first dynamically-changing, temporally unique identifier is configured to: replace a first value related to the first data subject; and comply with the determined first privacy policy; store the first dynamically changing, temporally unique identifier in the one or more data stores; receive, over the network, a first request for the first value related to the first data subject; send the first dynamically-changing, temporally unique identifier over the network in response to the first request when, according to the first privacy policy, the first request is not authorized to receive the first value; and send the first value over the network in response to the first request when, according to the first privacy policy, the first request is authorized to receive the first value.

Example 156 includes the subject matter of example 155, wherein the first dynamically-changing, temporally unique identifier comprises a Replacement DDID (R-DDID).

Example 157 includes the subject matter of example 155, wherein the first dynamically-changing, temporally unique identifier comprises an Association DDID (A-DDID).

Example 158 includes the subject matter of example 156, wherein the R-DDID comprises a specific value that is used to replace the first value.

Example 159 includes the subject matter of example 157, wherein the A-DDID comprises a specific value.

Example 160 includes the subject matter of example 159, wherein the specific value further comprises a class, cohort, or range of values that is used to replace the first value.

Example 161 includes the subject matter of example 155, wherein at least one of: the request from the first user for provision of a privacy policy; the data pertaining to the first plurality of data subjects; and the first request for the first value is received via a shim.

Example 162 includes the subject matter of example 155, wherein the first value comprises a quasi-identifier.

Example 163 includes the subject matter of example 162, wherein the quasi-identifier comprises unstructured data.

Example 164 includes the subject matter of example 162, wherein the quasi-identifier comprises a class, cohort, or range of values.

Example 165 includes the subject matter of example 155, wherein the privacy policy specifies the generation of synthetic data.

Example 166 includes the subject matter of example 165, wherein the privacy policy further specifies for the generation of DDIDs for synthetic data.

Example 167 includes the subject matter of example 155, wherein at least some of the data obtained from the first user comprises synthetic data.

Example 168 includes the subject matter of example 155, wherein the data obtained from the first user comprises solely synthetic data.

Example 169 is a computer-implemented method comprising: obtaining a request from a first user for provision of a privacy policy; determining a first privacy policy based, at least in part, on the request; obtaining data from the first user pertaining to a first plurality of data subjects; generating a first dynamically-changing, temporally unique identifier (DDID) for a first data subject in the first plurality of data subjects, wherein the first dynamically-changing, temporally unique identifier is configured to: replace a first value related to the first data subject; and comply with the determined first privacy policy; storing the first dynamically changing, temporally unique identifier in one or more data stores; receiving, over a network, a first request for the first value related to the first data subject; sending the first dynamically-changing, temporally unique identifier over the network in response to the first request when, according to the first privacy policy, the first request is not authorized to receive the first value; and sending the first value over the network in response to the first request when, according to the first privacy policy, the first request is authorized to receive the first value.

Example 170 includes the subject matter of example 169, wherein the first dynamically-changing, temporally unique identifier comprises a Replacement DDID (R-DDID).

Example 171 includes the subject matter of example 169, wherein the first dynamically-changing, temporally unique identifier comprises an Association DDID (A-DDID).

Example 172 includes the subject matter of example 169, wherein the R-DDID comprises a specific value that is used to replace the first value.

Example 173 includes the subject matter of example 171, wherein the A-DDID comprises a specific value.

Example 174 includes the subject matter of example 173, wherein the specific value further comprises a class, cohort, or range of values that is used to replace the first value.

Example 175 includes the subject matter of example 169, wherein at least one of: the request from the first user for provision of a privacy policy; the data pertaining to the first plurality of data subjects; and the first request for the first value is received via a shim.

Example 176 includes the subject matter of example 169, wherein the first value comprises a quasi-identifier.

Example 177 includes the subject matter of example 176, wherein the quasi-identifier comprises unstructured data.

Example 178 includes the subject matter of example 176, wherein the quasi-identifier comprises a class, cohort, or range of values.

Example 179 includes the subject matter of example 169, wherein the privacy policy specifies the generation of synthetic data.

Example 180 includes the subject matter of example 179, wherein the privacy policy further specifies for the generation of DDIDs for synthetic data.

Example 181 includes the subject matter of example 169, wherein at least some of the data obtained from the first user comprises synthetic data.

Example 182 includes the subject matter of example 169, wherein the data obtained from the first user comprises solely synthetic data.

Example 183 is a non-transitory program storage device, readable by a programmable control device, comprising instructions stored thereon that, when executed, cause the programmable control device to: obtain a request from a first user for provision of a privacy policy; determine a first privacy policy based, at least in part, on the request; obtain data from the first user pertaining to a first plurality of data subjects; generate a first dynamically-changing, temporally unique identifier (DDID) for a first data subject in the first plurality of data subjects, wherein the first dynamically-changing, temporally unique identifier is configured to: replace a first value related to the first data subject; and comply with the determined first privacy policy; store the first dynamically changing, temporally unique identifier in one or more data stores; receive, over a network, a first request for the first value related to the first data subject; send the first dynamically-changing, temporally unique identifier over the network in response to the first request when, according to the first privacy policy, the first request is not authorized to receive the first value; and send the first value over the network in response to the first request when, according to the first privacy policy, the first request is authorized to receive the first value.

Example 184 includes the subject matter of example 183, wherein the first dynamically-changing, temporally unique identifier comprises a Replacement DDID (R-DDID).

Example 185 includes the subject matter of example 183, wherein the first dynamically-changing, temporally unique identifier comprises an Association DDID (A-DDID).

Example 186 includes the subject matter of example 185, wherein the R-DDID comprises a specific value that is used to replace the first value.

Example 187 includes the subject matter of example 185, wherein the A-DDID comprises a specific value.

Example 188 includes the subject matter of example 187, wherein the specific value further comprises a class, cohort, or range of values that is used to replace the first value.

Example 189 includes the subject matter of example 183, wherein at least one of: the request from the first user for provision of a privacy policy; the data pertaining to the first plurality of data subjects; and the first request for the first value is received via a shim.

Example 190 includes the subject matter of example 183, wherein the first value comprises a quasi-identifier.

Example 191 includes the subject matter of example 190, wherein the quasi-identifier comprises unstructured data.

Example 192 includes the subject matter of example 190, wherein the quasi-identifier comprises a class, cohort, or range of values.

Example 193 includes the subject matter of example 183, wherein the privacy policy specifies the generation of synthetic data.

Example 194 includes the subject matter of example 193, wherein the privacy policy further specifies for the generation of DDIDs for synthetic data.

Example 195 includes the subject matter of example 183, wherein at least some of the data obtained from the first user comprises synthetic data.

Example 196 includes the subject matter of example 183, wherein the data obtained from the first user comprises solely synthetic data.

Example 197 is a system comprising: a communication interface for sending data over a network; a memory having, stored therein, computer program code and one or more distributed ledgers capable of recording data records; and one or more processing units operatively coupled to the memory and configured to execute instructions in the computer program code that cause the one or more processing units to: obtain data from a first user pertaining to a first data subject; generate a first dynamically-changing, temporally unique identifier (DDID) for the first data subject, wherein the first DDID is configured to replace a first value related to the first data subject; store the first DDID in a first element of a first one of the one or more distributed ledgers; receive, over the network, a first request from a first requesting party for the first value related to the first data subject; send the first DDID to the first requesting party over the network in response to the first request when the first requesting party is not authorized to receive the first value; and send the first value related to the first data subject to the first requesting party over the network in response to the first request when the first requesting party is authorized to receive the first value.

Example 198 includes the subject matter of example 197, wherein the network is decentralized, wherein the network comprises a plurality of nodes, and wherein each node in the network stores a copy of the first one of the one or more distributed ledgers.

Example 199 includes the subject matter of example 198, wherein the first one of the one or more distributed ledgers comprises a blockchain, and wherein the first element comprises a first block.

Example 200 includes the subject matter of example 197, wherein the one or more processing units are further configured to execute instructions in the computer program code that further cause the one or more processing units to: obtain a request from a first user for provision of a privacy policy; and determine a first privacy policy based, at least in part, on the request, wherein the first DDID is further configured to comply with the determined first privacy policy.

Example 201 includes the subject matter of example 197, wherein the first DDID points to a storage location containing the first value related to the first data subject.

Example 202 includes the subject matter of example 201, wherein the one or more processing units are further configured to execute instructions in the computer program code that further cause the one or more processing units to: obtain a request from the first user to modify the first value related to the data subject to be a first modified value; and store the first modified value in the storage location containing the first value related to the data subject.

Example 203 includes the subject matter of example 197, wherein the first data subject comprises a first executable term of a smart contract.

Example 204 is a computer-implemented method comprising: obtaining data from a first user pertaining to a first data subject; generating a first dynamically-changing, temporally unique identifier (DDID) for the first data subject, wherein the first DDID is configured to replace a first value related to the first data subject; storing the first DDID in a first element of a first one of one or more distributed ledgers; receiving, over a network, a first request from a first requesting party for the first value related to the first data subject; sending the first DDID to the first requesting party over the network in response to the first request when the first requesting party is not authorized to receive the first value; and sending the first value related to the first data subject to the first requesting party over the network in response to the first request when the first requesting party is authorized to receive the first value.

Example 205 includes the subject matter of example 204, wherein the network is decentralized, wherein the network comprises a plurality of nodes, wherein each node in the network stores a copy of the first one of the one or more distributed ledgers, wherein the first one of the one or more distributed ledgers comprises a blockchain, and wherein the first element comprises a first block.

Example 206 includes the subject matter of example 204, further comprising: obtaining a request from a first user for provision of a privacy policy; and determining a first privacy policy based, at least in part, on the request, wherein the first DDID is further configured to comply with the determined first privacy policy.

Example 207 includes the subject matter of example 204, wherein the first DDID points to a storage location containing the first value related to the first data subject.

Example 208 includes the subject matter of example 207, further comprising: obtaining a request from the first user to modify the first value related to the data subject to be a first modified value; and storing the first modified value in the storage location containing the first value related to the data subject.

Example 209 includes the subject matter of example 204, wherein the first data subject comprises a first executable term of a smart contract.

Example 210 is a non-transitory program storage device, readable by a programmable control device, comprising instructions stored thereon that, when executed, cause the programmable control device to: obtain data from a first user pertaining to a first data subject; generate a first dynamically-changing, temporally unique identifier (DDID) for the first data subject, wherein the first DDID is configured to replace a first value related to the first data subject; store the first DDID in a first element of a first one of one or more distributed ledgers; receive, over a network, a first request from a first requesting party for the first value related to the first data subject; send the first DDID to the first requesting party over the network in response to the first request when the first requesting party is not authorized to receive the first value; and send the first value related to the first data subject to the first requesting party over the network in response to the first request when the first requesting party is authorized to receive the first value.

Example 211 includes the subject matter of example 210, wherein the network is decentralized, wherein the network comprises a plurality of nodes, and wherein each node in the network stores a copy of the first one of the one or more distributed ledgers.

Example 212 includes the subject matter of example 210, wherein the first one of the one or more distributed ledgers comprises a blockchain, and wherein the first element comprises a first block.

Example 213 includes the subject matter of example 210, wherein the instructions further comprise instructions that, when executed, further cause the programmable control device to: obtain a request from a first user for provision of a privacy policy; and determine a first privacy policy based, at least in part, on the request, wherein the first DDID is further configured to comply with the determined first privacy policy.

Example 214 includes the subject matter of example 210, wherein the first DDID points to a storage location containing the first value related to the first data subject.

Example 215 includes the subject matter of example 214, wherein the instructions further comprise instructions that, when executed, further cause the programmable control device to: obtain a request from the first user to modify the first value related to the data subject to be a first modified value; and store the first modified value in the storage location containing the first value related to the data subject.

Example 216 includes the subject matter of example 210, wherein the first data subject comprises a first executable term of a smart contract.

While the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention. For instance, as a non-limiting example, in alternative embodiments, portions of operations described herein may be rearranged and performed in different order than as described herein.

It should be appreciated that reference throughout this specification to "one embodiment" or "an embodiment" or "one example" or "an example" means that a particular feature, structure or characteristic described in connection with the embodiment may be included, if desired, in at least one embodiment of the present invention. Therefore, it should be appreciated that two or more references to "an embodiment" or "one embodiment" or "an alternative embodiment" or "one example" or "an example" in various portions of this specification are not necessarily all referring to the same embodiment. Furthermore, the particular features, structures or characteristics may be combined as desired in one or more embodiments of the invention.

It will be understood that that the term "browser," as used herein, may refer to not only a browser for the web, but also to, e.g., a programmable display engine such as is used in X-Windows; a remote-display facility, such as is used for desktop virtualization; or a user interface for an application on a device, where such interface enables text and/or multimedia messaging with other parties (e.g., Facebook Messenger, WhatsApp, Snapchat, Wickr, Cyberdust or any other user or enterprise application providing such functionality). The term "web," as used herein, refers to not only the World Wide Web (WWW), but may also refer to, e.g., purely textually-linked documents or interconnected devices, which may be spread over multiple entities or within a single entity (such as an intranet). "Device," as used herein, may refer to a physical device or a "virtual" device, e.g., a virtual machine (VM) or even a nodeJS hosted microservice. It will also be understood that a server may be comprised of multiple components on different computers or devices, and/or multiple components within the same computer or device. Similarly, a client may be comprised of multiple components on different computers or devices, and/or multiple components within the same computer or device. While a server and client may communicate over channels such as the Internet, they may also communicate using, e.g., remote procedure calls (RPC) and/or operating system application programming interfaces (APIs).

It should be appreciated that in the foregoing description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed inventions require more features than are expressly recited in each claim. Rather, inventive aspects lie in less than all features of a single foregoing disclosed embodiment, and each embodiment described herein may contain more than one inventive feature.

While the invention has been particularly shown and described with reference to embodiments thereof, it will be understood by those skilled in the art that various other changes in the form and details may be made without departing from the spirit and scope of the invention.

The invention claimed is:

1. A system, comprising:
a communication interface for sending data over a network;
a memory having, stored therein, computer program code and one or more distributed ledgers capable of recording data records; and
one or more processing units operatively coupled to the memory and configured to execute instructions in the computer program code that cause the one or more processing units to:
obtain data from a first user pertaining to a first data subject;
generate a first dynamically-changing, temporally unique identifier (DDID) for the first data subject, wherein the first DDID is configured to replace a first value related to the first data subject;
store the first DDID in a first element of a first one of the one or more distributed ledgers;
receive, over the network, a first request from a first requesting party for the first value related to the first data subject;
send the first DDID to the first requesting party over the network in response to the first request when the first requesting party is not authorized to receive the first value; and
send the first value related to the first data subject to the first requesting party over the network in response to the first request when the first requesting party is authorized to receive the first value.

2. The system of claim 1, wherein the network is decentralized, wherein the network comprises a plurality of nodes, and wherein each node in the network stores a copy of the first one of the one or more distributed ledgers.

3. The system of claim 2, wherein the first one of the one or more distributed ledgers comprises a blockchain, and wherein the first element comprises a first block.

4. The system of claim 1, wherein the one or more processing units are further configured to execute instructions in the computer program code that further cause the one or more processing units to:
obtain a request from a first user for provision of a privacy policy; and
determine a first privacy policy based, at least in part, on the request,
wherein the first DDID is further configured to comply with the determined first privacy policy.

5. The system of claim 1, wherein the first DDID points to a storage location containing the first value related to the first data subject.

6. The system of claim 5, wherein the one or more processing units are further configured to execute instructions in the computer program code that further cause the one or more processing units to:
obtain a request from the first user to modify the first value related to the data subject to be a first modified value; and
store the first modified value in the storage location containing the first value related to the data subject.

7. The system of claim 1, wherein the first data subject comprises a first executable term of a smart contract.

8. A computer-implemented method comprising:
obtaining data from a first user pertaining to a first data subject;
generating a first dynamically-changing, temporally unique identifier (DDID) for the first data subject, wherein the first DDID is configured to replace a first value related to the first data subject;
storing the first DDID in a first element of a first one of one or more distributed ledgers;
receiving, over a network, a first request from a first requesting party for the first value related to the first data subject;
sending the first DDID to the first requesting party over the network in response to the first request when the first requesting party is not authorized to receive the first value; and
sending the first value related to the first data subject to the first requesting party over the network in response to the first request when the first requesting party is authorized to receive the first value.

9. The computer-implemented method of claim 8, wherein the network is decentralized, wherein the network comprises a plurality of nodes, wherein each node in the network stores a copy of the first one of the one or more distributed ledgers, wherein the first one of the one or more distributed ledgers comprises a blockchain, and wherein the first element comprises a first block.

10. The computer-implemented method of claim 8, further comprising:
obtaining a request from a first user for provision of a privacy policy; and
determining a first privacy policy based, at least in part, on the request,
wherein the first DDID is further configured to comply with the determined first privacy policy.

11. The computer-implemented method of claim 8, wherein the first DDID points to a storage location containing the first value related to the first data subject.

12. The computer-implemented method of claim 11, further comprising:

obtaining a request from the first user to modify the first value related to the data subject to be a first modified value; and
storing the first modified value in the storage location containing the first value related to the data subject.

13. The computer-implemented method of claim 8, wherein the first data subject comprises a first executable term of a smart contract.

14. A non-transitory program storage device, readable by a programmable control device, comprising instructions stored thereon that, when executed, cause the programmable control device to:
obtain data from a first user pertaining to a first data subject;
generate a first dynamically-changing, temporally unique identifier (DDID) for the first data subject, wherein the first DDID is configured to replace a first value related to the first data subject;
store the first DDID in a first element of a first one of one or more distributed ledgers;
receive, over a network, a first request from a first requesting party for the first value related to the first data subject;
send the first DDID to the first requesting party over the network in response to the first request when the first requesting party is not authorized to receive the first value; and
send the first value related to the first data subject to the first requesting party over the network in response to the first request when the first requesting party is authorized to receive the first value.

15. The non-transitory program storage device of claim 14, wherein the network is decentralized, wherein the network comprises a plurality of nodes, and wherein each node in the network stores a copy of the first one of the one or more distributed ledgers.

16. The non-transitory program storage device of claim 15, wherein the first one of the one or more distributed ledgers comprises a blockchain, and wherein the first element comprises a first block.

17. The non-transitory program storage device of claim 14, wherein the instructions further comprise instructions that, when executed, further cause the programmable control device to:
obtain a request from a first user for provision of a privacy policy; and
determine a first privacy policy based, at least in part, on the request,
wherein the first DDID is further configured to comply with the determined first privacy policy.

18. The non-transitory program storage device of claim 14, wherein the first DDID points to a storage location containing the first value related to the first data subject.

19. The non-transitory program storage device of claim 18, wherein the instructions further comprise instructions that, when executed, further cause the programmable control device to:
obtain a request from the first user to modify the first value related to the data subject to be a first modified value; and
store the first modified value in the storage location containing the first value related to the data subject.

20. The non-transitory program storage device of claim 14, wherein the first data subject comprises a first executable term of a smart contract.

* * * * *